(12) United States Patent
Lee et al.

(10) Patent No.: US 11,787,812 B2
(45) Date of Patent: Oct. 17, 2023

(54) SUBSTITUTED PYRAZOLO[4,3-D]PYRIMIDINES AND IMIDAZO[5,1-F][1,2,4]TRIAZINES AS ANDROGEN RECEPTOR AND PHOSPHODIESTERASE DUAL INHIBITORS

(71) Applicant: ILDONG PHARMACEUTICAL CO., LTD., Seoul (KR)

(72) Inventors: Yoonsuk Lee, Hwaseong-si (KR); Kyung Sun Kim, Hwaseong-si (KR); Jeong-Ah Kim, Hwaseong-si (KR); Anna Moon, Hwaseong-si (KR); Dongkeun Song, Hwaseong-si (KR); Juyoung Jung, Hwaseong-si (KR); Jun-Su Ban, Hwaseong-si (KR); Soo-Jin Lee, Hwaseong-si (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 17/548,279

(22) Filed: Dec. 10, 2021

(65) Prior Publication Data
US 2022/0194948 A1 Jun. 23, 2022

Related U.S. Application Data

(60) Provisional application No. 63/124,615, filed on Dec. 11, 2020.

(51) Int. Cl.
| | |
|---|---|
| *A61K 31/519* | (2006.01) |
| *A61K 31/53* | (2006.01) |
| *C07D 239/70* | (2006.01) |
| *C07D 253/08* | (2006.01) |
| *C07D 487/04* | (2006.01) |
| *G01N 33/50* | (2006.01) |
| *C07D 519/00* | (2006.01) |

(52) U.S. Cl.
CPC ......... *C07D 487/04* (2013.01); *C07D 519/00* (2013.01); *G01N 33/5041* (2013.01)

(58) Field of Classification Search
CPC .... A61K 31/519; A61K 31/53; C07D 239/70; C07D 253/08
USPC ................ 514/243, 262.1; 544/184, 262
See application file for complete search history.

(56) References Cited

U.S. PATENT DOCUMENTS

| 6,476,029 B1 | 11/2002 | Niewöhner et al. |
| 6,878,708 B2 | 4/2005 | Niewöhner et al. |

FOREIGN PATENT DOCUMENTS

| CN | 101691373 A | 4/2010 |
| JP | 2004170323 A | 6/2004 |
| JP | 2018076234 A | 5/2018 |
| KR | 10-2009-0087795 A | 8/2009 |
| WO | WO 1999/024433 A1 | 5/1999 |
| WO | WO 1999/067244 A1 | 12/1999 |
| WO | WO 2000/027848 A1 | 5/2000 |
| WO | WO 2001/098304 A1 | 12/2001 |
| WO | WO 2004/031134 A1 | 4/2004 |
| WO | WO 2004/087153 A2 | 10/2004 |
| WO | WO 2006/124118 A1 | 11/2006 |
| WO | WO 2007/056955 A1 | 5/2007 |
| WO | WO 2008/045664 A2 | 4/2008 |
| WO | WO 2010/074284 A1 | 7/2010 |
| WO | WO 2010/099238 A1 | 9/2010 |
| WO | WO 2010/118367 A2 | 10/2010 |
| WO | WO 2011/126250 A2 | 10/2011 |
| WO | WO 2012/097750 A1 | 7/2012 |
| WO | WO 2014/131855 A1 | 9/2014 |
| WO | WO 2016/020307 A1 | 2/2016 |
| WO | WO 2016/120432 A1 | 8/2016 |
| WO | WO-2022123310 A1 * | 6/2022 ........... C07D 487/04 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Iratni, R. et al. "Sildenafil in Combination Therapy Against Cancer: A Literature Review." Current Medicinal Chemistry, vol. 28, No. 11, Apr. 2021, pp. 2248-2259.
PCT International Search Report and Written Opinion, PCT Application No. PCT/IB2021/000856, dated May 2, 2022, 19 pages.
PCT International Search Report and Written Opinion, PCT Application No. PCT/IB2022/000612, dated Mar. 29, 2023, 12 pages.

* cited by examiner

*Primary Examiner* — Douglas M Willis
(74) *Attorney, Agent, or Firm* — Glenn J. Foulds; Fenwick & West LLP

(57) ABSTRACT

The present disclosure provides androgen receptor (AR) and phosphodiesterase 5 (PDE-5) inhibitor compounds of the formula (I):

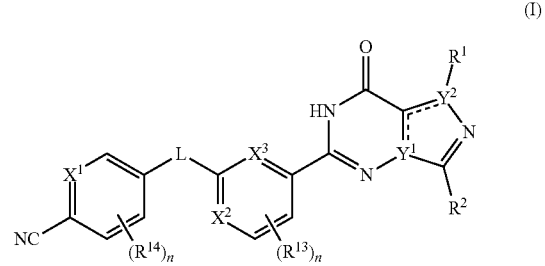

and compositions including said compounds. The compounds can provide dual functionality for inhibiting AR and inhibiting PDE-5. The present disclosure also provides methods of using said compounds and compositions for inhibiting AR and PDE-5 in a biological system or biological sample. Also provided are methods of preparing said compounds and compositions, and synthetic precursors of said compounds.

44 Claims, No Drawings

SUBSTITUTED PYRAZOLO[4,3-D]PYRIMIDINES AND IMIDAZO[5,1-F][1,2,4]TRIAZINES AS ANDROGEN RECEPTOR AND PHOSPHODIESTERASE DUAL INHIBITORS

1. CROSS REFERENCE TO RELATED APPLICATIONS

This application claims the benefit of U.S. Provisional Application No. 63/124,615, filed Dec. 11, 2020, which is hereby incorporated in its entirety by reference.

2. BACKGROUND OF THE INVENTION

The androgen receptor (AR) is a member of the steroid-hormone family involved in the regulation of normal growth and development within a broad array of target organs. AR inhibitors and antagonists find use in various therapeutic applications. Enzalutamide and apalutamide are AR antagonist compounds that find use in treating cancer.

Phosphodiesterases (PDE) encompass a large family of metallophosphohydrolases involved in regulation of cellular cAMP and/or cyclic GMP (cGMP) levels by many stimuli. Compounds that selectively inhibit the catalytic activities of PDEs (e.g., PDE5) have been developed for the treatment of a variety of diseases. PDE5 is a cGMP binding enzyme that specifically hydrolyzes cGMP to 5'-GMP. PDE5 inhibitors increase cGMP levels.

Compounds having dual activity as AR inhibitors or antagonists and PDE5 inhibitors, would find use in overlapping therapeutic indications where inhibition of both targets was of interest.

3. SUMMARY OF THE INVENTION

The present disclosure provides androgen receptor (AR) inhibitor and phosphodiesterase 5 (PDE-5) inhibitor compounds and compositions including said compounds. The compounds can provide dual functionality for inhibiting or antagonizing the androgen receptor and for inhibiting PDE-5. The present disclosure also provides methods of using said compounds and compositions for inhibiting AR and PDE-5 in a biological system or sample. Also provided are methods of preparing said compounds and compositions, and synthetic precursors of said compounds.

In a first aspect, the present disclosure provides a compound of formula (I):

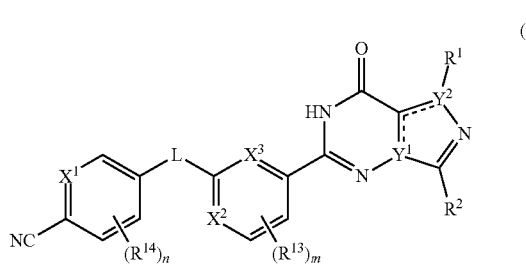

or a solvate, a hydrate, a prodrug, and/or a stereoisomer thereof, or a pharmaceutically acceptable salt thereof, or a pharmaceutically acceptable salt thereof, wherein:

L is a linking moiety;

$R^1$ and $R^2$ are independently selected from —H, optionally substituted $(C_1$-$C_6)$alkyl, optionally substituted $(C_3$-$C_6)$cycloalkyl, optionally substituted $(C_1$-$C_6)$alkoxy, and optionally substituted $(C_2$-$C_4)$alkenyl;

each $R^{13}$ is selected from —H, optionally substituted $(C_1$-$C_6)$alkyl, and optionally substituted $(C_1$-$C_6)$alkoxy;

each $R^{14}$ is selected from —H, —CN, —OH, —NH_2, —NO_2, halogen, optionally substituted $(C_1$-$C_5)$alkyl, optionally substituted $(C_1$-$C_5)$haloalkyl, optionally substituted $(C_1$-$C_5)$alkoxy, optionally substituted $(C_3$-$C_6)$cycloalkyl, and optionally substituted $(C_2$-$C_4)$alkenyl;

$X^1$ is N or $CR^{14}$;

$X^2$ and $X^3$ are independently selected from N and $CR^{13}$;

$Y^1$ and $Y^2$ are independently selected from N and C, wherein one of $Y^1$ and $Y^2$ is N;

m is 0 to 2; and n is 1 to 4.

In a second aspect, the present disclosure provides a pharmaceutical composition comprising a compound of formula (I), or a solvate, a hydrate, a prodrug, and/or a stereoisomer, or pharmaceutically acceptable salt thereof, and at least one pharmaceutically acceptable excipient.

In a third aspect, the present disclosure provides a method of modulating the androgen receptor and/or inhibiting PDE-5 activity, comprising contacting a biological system or sample comprising the androgen receptor and/or PDE-5 with an effective amount of a compound of formula (I), or a solvate, a hydrate, a prodrug, and/or a stereoisomer, or a pharmaceutically acceptable salt thereof. In some embodiments of the method of modulating, the method comprises inhibiting or antagonising the androgen receptor. In another embodiment, the method comprises inhibiting PDE-5 activity. In some embodiments of the method of modulating, the method comprises inhibiting the androgen receptor and inhibiting PDE-5 in the biological system or sample.

4. DETAILED DESCRIPTION OF THE INVENTION

4.1 AR and PDE-5 Inhibitor Compounds

As summarized above, the present disclosure provides compounds having dual activity, e.g., as androgen receptor (AR) and PDE-5 inhibiting compounds.

In general, the compounds comprising bicyclic core structures of substituted 1,6-dihydro-7H-pyrazolo[4,3-d]pyrimidin-7-one

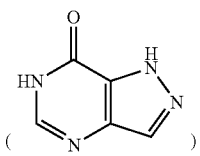

or substituted imidazo[5,1-f][1,2,4]triazin-4(3H)-one

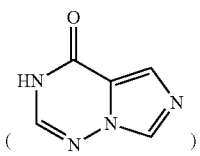

covalently attached to various cyano-substituted aryl groups via i) a 1,3-phenylene, 2,4-pyridyl or 2,6-pyridyl, and ii) a variety of linking moieties such as substituted 2-thioxoimidazolidin-4-one

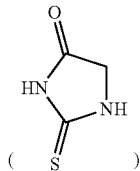

groups, urea groups, or thiourea groups.

More specifically, in a first aspect, the present disclosure provides a compound of formula (I):

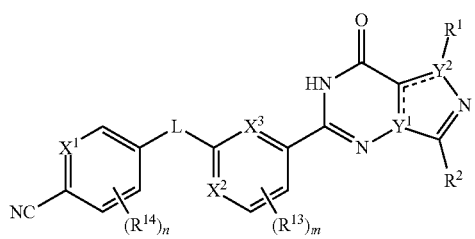

or a solvate, a hydrate, a prodrug, and/or a stereoisomer thereof, or a pharmaceutically acceptable salt thereof, wherein:

L is a linking moiety;

$R^1$ and $R^2$ are independently selected from —H, optionally substituted $(C_1-C_6)$alkyl, optionally substituted $(C_3-C_6)$cycloalkyl, optionally substituted $(C_1-C_6)$alkoxy, and optionally substituted $(C_2-C_4)$alkenyl;

each $R^{13}$ is selected from —H, optionally substituted $(C_1-C_6)$alkyl, and optionally substituted $(C_1-C_6)$alkoxy;

each $R^{14}$ is selected from —H, —CN, —OH, —NH$_2$, —NO$_2$, halogen, optionally substituted $(C_1-C_5)$alkyl, optionally substituted $(C_1-C_5)$haloalkyl, optionally substituted $(C_1-C_5)$alkoxy, optionally substituted $(C_3-C_6)$cycloalkyl, and optionally substituted $(C_2-C_4)$alkenyl;

$X^1$ is N or $CR^{14}$;

$X^2$ and $X^3$ are independently selected from N and $CR^{13}$;

$Y^1$ and $Y^2$ are independently selected from N and C, wherein one of $Y^1$ and $Y^2$ is N;

m is 0 to 2; and n is 1 to 4.

In some embodiments of formula (I), the compound is of formula (Ia):

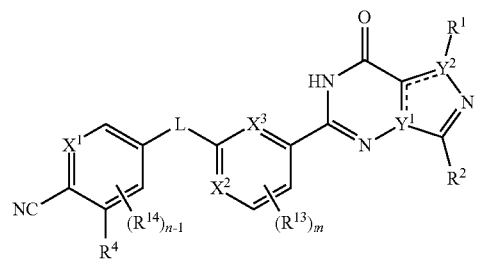

or a solvate, a hydrate, a prodrug, and/or a stereoisomer thereof, or a pharmaceutically acceptable salt thereof, wherein:

each $R^{13}$ is selected from —H, halogen and optionally substituted $(C_1-C_6)$alkoxy; and $R^4$ and each $R^{14}$ is independently selected from —H, —CN, —OH, —NH$_2$, —NO$_2$, halogen, optionally substituted $(C_1-C_5)$alkyl, and optionally substituted $(C_1-C_5)$haloalkyl.

In some embodiments of formula (I)-(Ia), -L- is -A-B—, wherein:

-A- is selected from a covalent bond, optionally substituted $(C_6-C_{12})$ aryl or $(C_3-C_{12})$ heteroaryl, optionally substituted-$(C_3-C_{12})$ heteroaryl-$(C_1-C_5)$alkylene-, optionally substituted 3- to 6-membered heterocycle, —NHC(O)R$^5$—,

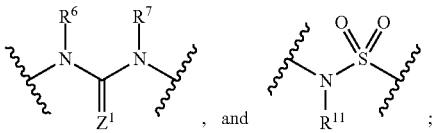

and

—B— is selected from a covalent bond, optionally substituted 3- to 6-membered heterocycle, —NHC(O)R$^5$—, —O—, —S—, —NR$^{11}$—,

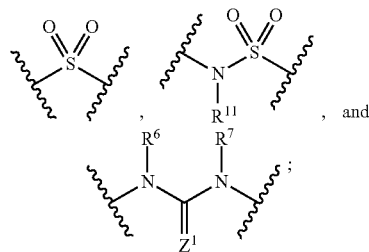

wherein:

$R^{11}$ is H or optionally substituted $(C_1-C_3)$alkyl;

$R^5$ is selected from —OH, —$(C_1-C_5)$alkyl, —$(C_1-C_5)$haloalkyl an optionally substituted $(C_1-C_5)$alkylene;

$R^6$ and $R^7$ are each independently —H or optionally substituted $(C_1-C_3)$alkyl; or $R^6$ and $R^7$ together with the nitrogen atom to which they are attached are cyclically linked to provide an optionally substituted 3- to 6-membered heterocycle;

$Z^1$ is selected from O and S; and at least one of -A- and —B— is not a covalent bond.

In some embodiments of formula (Ia), -A- is

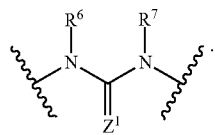

In some embodiments of formula (I)-(Ia), the compound is of formula (IIa) or (IIb):

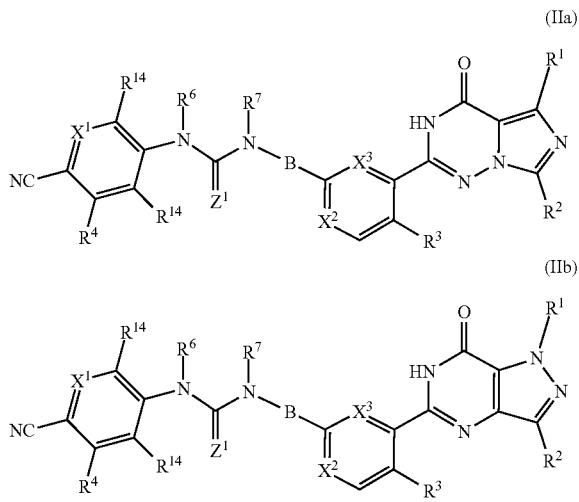

or a solvate, a hydrate, a prodrug, and/or a stereoisomer thereof, or a pharmaceutically acceptable salt thereof, wherein:

$R^3$ is selected from —H, and optionally substituted ($C_1$-$C_6$)alkoxy; and

—B— is selected from covalent bond and optionally substituted 3- to 6-membered heterocycle.

In some embodiments of formula (IIa) or (IIb), each $R^{14}$ is independently —H or halogen. In some embodiments of formula (IIa) or (IIb), each $R^{14}$ is independently —H or —F. In some embodiments of formula (IIa) or (IIb), each $R^{14}$ is —H. In some embodiments of formula (IIa) or (IIb), each $R^{14}$ is —F. In some embodiments of formula (IIa) or (IIb), at least one $R^{14}$ is —F.

In some embodiments of formula (IIa) or (IIb), $Z^1$ is S. In some embodiments of formula (IIa) or (IIb), $Z^1$ is O.

In some embodiments of formula (IIa) or (IIb), $R^6$ and $R^7$ together with the nitrogen atom to which they are attached are cyclically linked to provide an optionally substituted 3- to 6-membered heterocycle.

In some embodiments of formula (IIa) or (IIb), the compound is of formula (IIIa) or (IIIb):

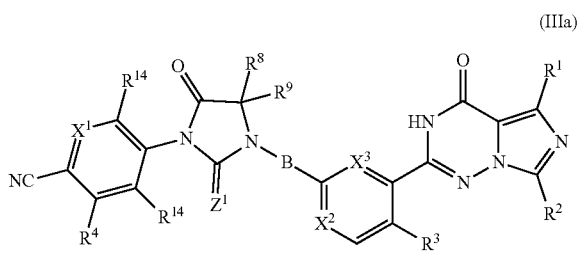

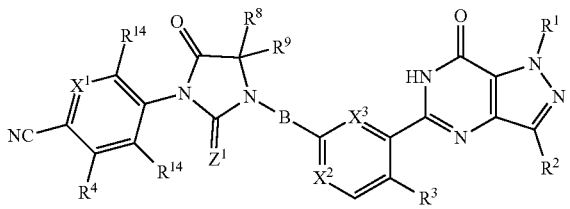

or a solvate, a hydrate, a prodrug, and/or a stereoisomer thereof, or a pharmaceutically acceptable salt thereof, wherein:

$R^8$ and $R^9$ are independently selected from —H and optionally substituted ($C_1$-$C_3$)alkyl, or $R^8$ and $R^9$ together with the carbon atom to which they are attached are cyclically linked to provide an optionally substituted 3- to 6-membered carbocycle or optionally substituted 3- to 6-membered heterocycle; and $Z^1$ is O or S.

In some embodiments of formula (IIIa) or (IIIb), each $R^{14}$ is independently —H or halogen. In some embodiments of formula (IIIa) or (IIIb), each $R^{14}$ is independently —H or —F. In some embodiments of formula (IIIa) or (IIIb), each $R^{14}$ is —H. In some embodiments of formula (IIIa) or (IIIb), each $R^{14}$ is —F. In some embodiments of formula (IIIa) or (IIIb), at least one $R^{14}$ is —F.

In some embodiments of formula (IIIa) or (IIIb), $Z^1$ is S. In some embodiments of formula (IIIa) or (IIIb), $Z^1$ is O.

In some embodiments of formula (IIIa) or (IIIb), —B— is a covalent bond and the compound is of formula (IVa) or (IVb):

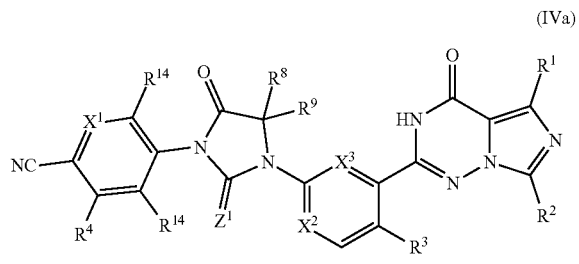

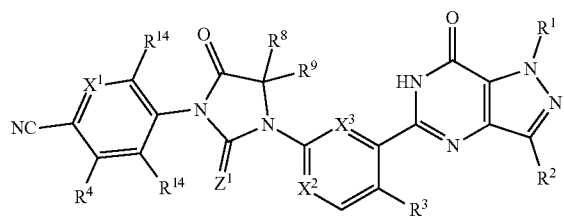

or a solvate, a hydrate, a prodrug, and/or a stereoisomer thereof, or a pharmaceutically acceptable salt thereof.

In some embodiments of formula (IVa) or (IVb), each $R^{14}$ is independently —H or halogen. In some embodiments of formula (IVa) or (IVb), each $R^{14}$ is independently —H or —F. In some embodiments of formula (IVa) or (IVb), each $R^{14}$ is —H. In some embodiments of formula (IVa) or (IVb), each $R^{14}$ is —F. In some embodiments of formula (IVa) or (IVb), at least one $R^{14}$ is —F.

In some embodiments of formula (IVa) or (IVb), $Z^1$ is S. In some embodiments of formula (IVa) or (IVb), $Z^1$ is O.

In some embodiments of formula (IIIa) or (IIIb), —B— is an optionally substituted 4- to 6-membered heterocycle.

In some embodiments of formula (IIIa) or (IIIb), the compound is of formula (Va) or (Vb):

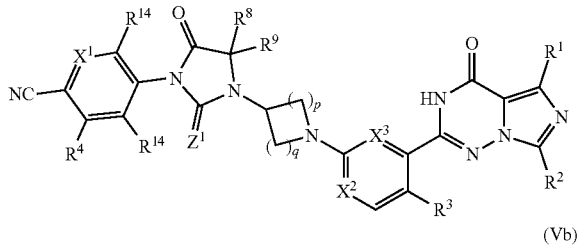

(Va)

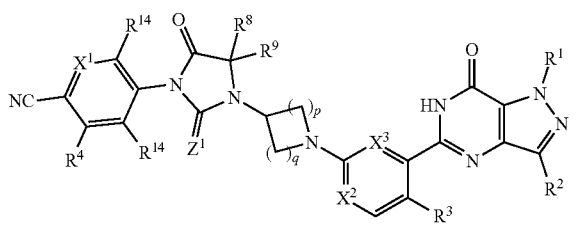

(Vb)

or a solvate, a hydrate, a prodrug, and/or a stereoisomer thereof, or a pharmaceutically acceptable salt thereof, wherein p and q are independently 1 or 2.

In some embodiments of formula (Va) or (Vb), —B— is selected from

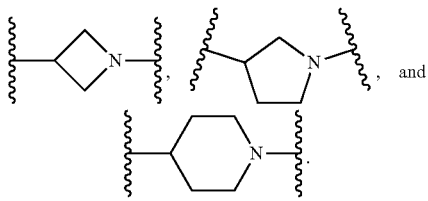

In some embodiments of formula (Va) or (Vb), $R^8$ is —H. In another embodiment of formula (Va) or (Vb), $R^9$ is —H.

In some embodiments of formula (Va) or (Vb), $R^9$ is an optionally substituted $(C_1$-$C_3)$alkyl. In another embodiment of formula (Va) or (Vb), $R^9$ is —$CH_3$.

In some embodiments of formula (Va) or (Vb), $R^8$ and $R^9$ are each independently optionally substituted $(C_1$-$C_3)$alkyl. In another embodiments of formula (Va) or (Vb), $R^8$ and $R^9$ are each —$CH_3$.

In some embodiments of formula (Va) or (Vb), $Z^1$ is S. In some embodiments of formula (Va) or (Vb), $Z^1$ is O.

In some embodiments of formula (Va) or (Vb), -A- is selected from

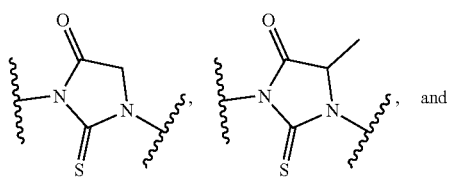

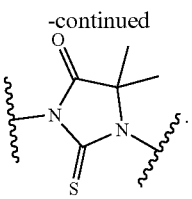

In some embodiments of formula (Va) or (Vb), $R^8$ and $R^9$ together with the carbon atom to which they are attached are cyclically linked to provide an optionally substituted 3- to 6-membered carbocycle or optionally substituted 3- to 6-membered heterocycle. In some embodiments of formula (Va) or (Vb), $R^8$ and $R^9$ together with the carbon atom to which they are attached are cyclically linked to provide an optionally substituted 4-membered or 5-membered carbocycle or heterocycle. In another embodiment of formula (Va) or (Vb), the optionally substituted 3- to 6-membered carbocycle or optionally substituted 3- to 6-membered heterocycle is selected from optionally substituted cyclobutyl, optionally substituted cyclopentyl, and optionally substituted tetrahydrofuran.

In some embodiments of formula (Va) or (Vb), -A- is selected from

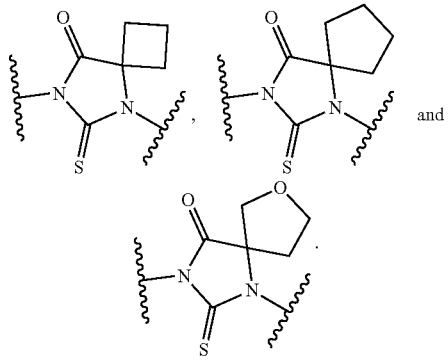

In some embodiments of formula (Va) or (Vb), each $R^4$ is independently —H or halogen. In some embodiments of formula (Va) or (Vb), each $R^{14}$ is independently —H or —F. In some embodiments of formula (Va) or (Vb), each $R^{14}$ is —H. In some embodiments of formula (Va) or (Vb), each $R^{14}$ is —F. In some embodiments of formula (Va) or (Vb), at least one $R^{14}$ is —F.

In some embodiments of formula (IIa) or (IIb), $R^6$ and $R^7$ are each independently —H or optionally substituted $(C_1$-$C_3)$alkyl. In some embodiments of formula (IIa) or (IIb), $R^6$ and $R^7$ are each —H.

In some embodiments of formula (IIa) or (IIb), the compound is of formula (VIa) or (VIb):

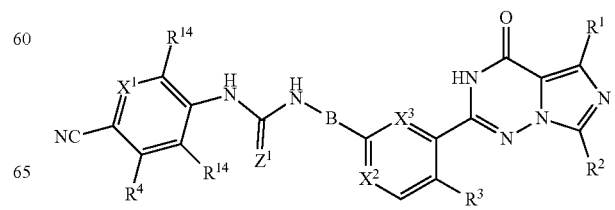

(VIa)

-continued

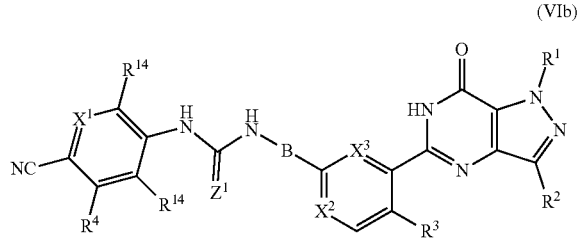
(VIb)

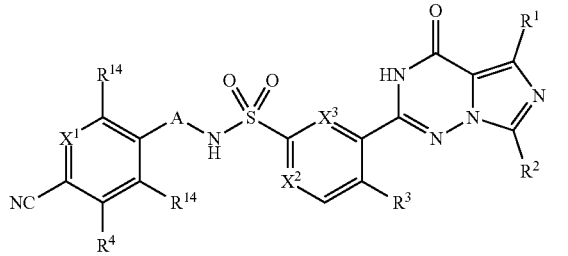
(VIIIa)

or a solvate, a hydrate, a prodrug, and/or a stereoisomer thereof, or a pharmaceutically acceptable salt thereof.

In some embodiments of formula (VIa) or (VIb), $Z^1$ is S. In some embodiments of formula (VIa) or (VIb), $Z^1$ is O.

In some embodiments of formula (VIa) or (VIb), —B— is a covalent bond.

In some embodiments of formula (VIa) or (VIb), each $R^{14}$ is independently —H or halogen. In some embodiments of formula (VIa) or (VIb), each $R^{14}$ is independently —H or —F.

In some embodiments of formula (VIa) or (VIb), each $R^{14}$ is —H. In some embodiments of formula (VIa) or (VIb), each $R^{14}$ is —F. In some embodiments of formula (VIa) or (VIb), at least one $R^{14}$ is —F.

In some embodiments of formula (VIa) or (VIb), the compound is of formula (VIIa) or (VIIb):

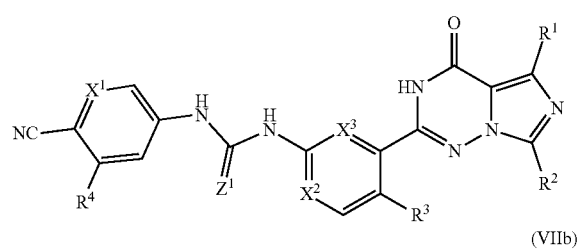
(VIIa)

(VIIb)

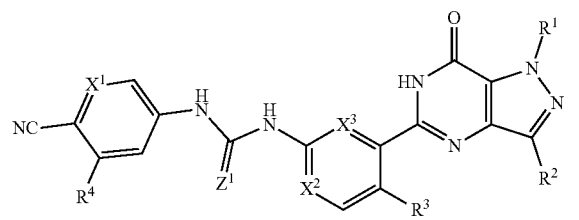

or a solvate, a hydrate, a prodrug, and/or a stereoisomer thereof, or a pharmaceutically acceptable salt thereof.

In some embodiments of formula (Ia), —B— is

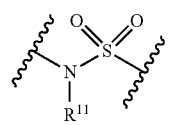

wherein $R^{11}$ is —H or optionally substituted $(C_1-C_3)$alkyl.

In some embodiments of formula (Ia), the compound is of formula (VIIIa) or (VIIIb):

(VIIIb)

or a solvate, a hydrate, a prodrug, and/or a stereoisomer thereof, or a pharmaceutically acceptable salt thereof, wherein $R^3$ is selected from —H and optionally substituted $(C_1-C_5)$alkoxy.

In some embodiments of formula (VIIIa) or (VIIIb), -A- is an optionally substituted 3- to 6-membered heterocycle. In some embodiments of formula (VIIIa) or (VIIIb), -A- is an optionally substituted azetidine, optionally substituted pyrrolidine, optionally substituted piperidine, optionally substituted piperidin-2-one or optionally substituted pyrrolidin-2-one. In some embodiments, the -A- ring is connected to the adjacent 4-cyanophenyl or 2-cyanopyrid-5-yl ring via a N atom of the optionally substituted 3- to 6-membered heterocycle (e.g., optionally substituted azetidine, pyrrolidine, piperidine, piperidin-2-one or pyrrolidin-2-one).

In some embodiments of formula (VIIIa) or (VIIIb), -A- is wherein:
R$^{12}$ is selected from —H, —OH, optionally substituted $(C_1-C_3)$alkyl, and optionally substituted $(C_1-C_5)$haloalkyl; and
r, s and t are independently is 0 or 1.

In some embodiments of formula (VIIIa) or (VIIIb), -A- is selected from:

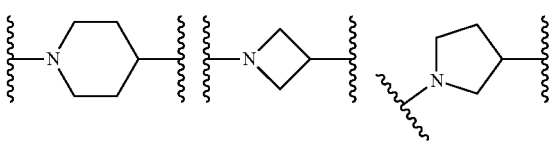

-continued

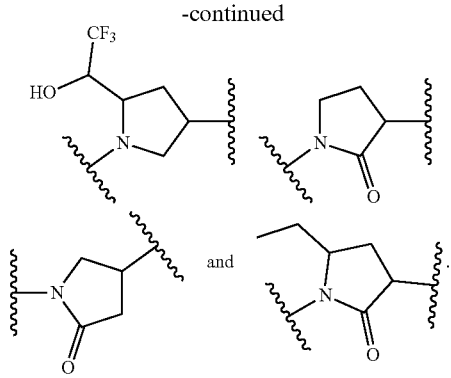

In some embodiments of formula (VIIIa) or (VIIIb), -A- is a covalent bond.

In some embodiments of formula (VIIIa) or (VIIIb), each $R^{14}$ is independently —H or halogen. In some embodiments of formula (VIIIa) or (VIIIb), each $R^{14}$ is independently —H or —F. In some embodiments of formula (VIIIa) or (VIIIb), each $R^{14}$ is —H. In some embodiments of formula (VIIIa) or (VIIIb), each $R^{14}$ is —F. In some embodiments of formula (VIIIa) or (VIIIb), at least one $R^{14}$ is —F.

In some embodiments of formula (VIIIa) or (VIIIb), the compound is of formula (IXa) or (IXb):

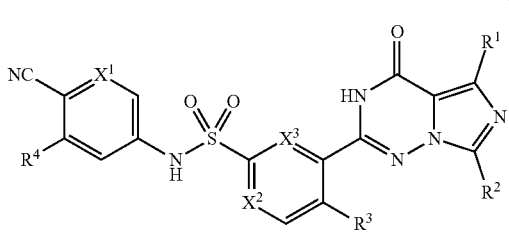
(IXa)

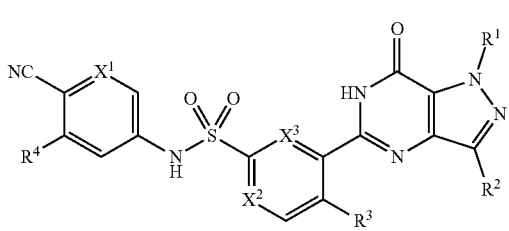
(IXb)

or a solvate, a hydrate, a prodrug, and/or a stereoisomer thereof, or a pharmaceutically acceptable salt thereof.

In some embodiments of formula (VIIIa) or (VIIIb), -A- is an optionally substituted —($C_3$-$C_{12}$)heteroaryl-($C_1$-$C_5$) alkylene- (e.g., where the —($C_3$-$C_{12}$)heteroaryl- and/or the —($C_1$-$C_5$)alkylene- of -A- are each optionally substituted).

In some embodiments of formula (VIIIa) or (VIIIb), -A- is

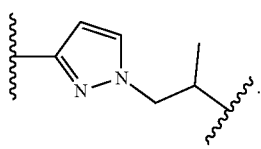 [SMILES: *c1ccn(CC(*)C)n1]

In some embodiments of formula (I)-(Ia), -L- is -A-B—, wherein -A- is an optionally substituted 3- to 6-membered heterocycle. In some embodiments, -A- is an optionally substituted pyrrolidin-2-one.

In some embodiments, -A- is selected from

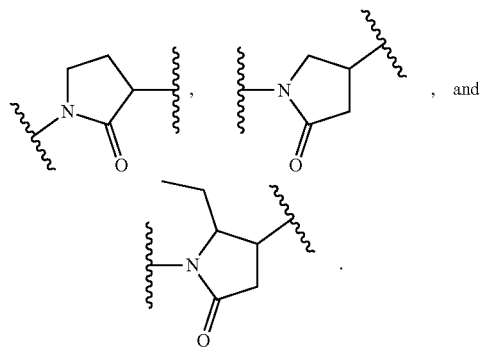

In some embodiments of formula (Ia), the compound is of formula (Xa) or (Xb):

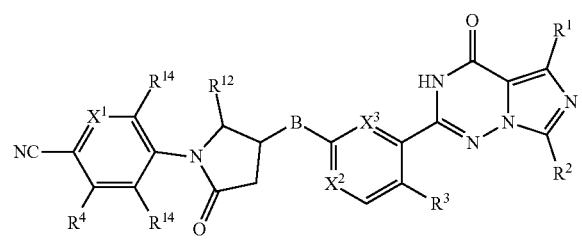
(Xa)

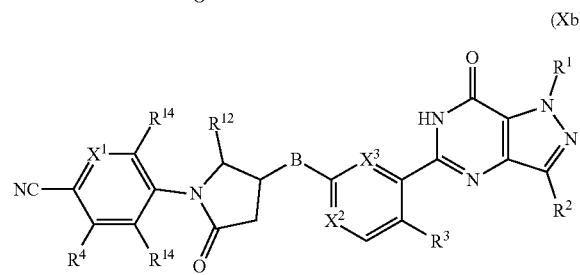
(Xb)

or a solvate, a hydrate, a prodrug, and/or a stereoisomer thereof, or a pharmaceutically acceptable salt thereof, wherein:

B is as defined above;

$R^3$ is selected from —H, and optionally substituted ($C_1$-$C_6$)alkoxy; and $R^{12}$ is selected from —H and optionally substituted ($C_1$-$C_3$)alkyl.

In some embodiments of formula (Xa) or (Xb), $R^{12}$ is —H. In some embodiments of formula (Xa) or (Xb), $R^{12}$ is optionally substituted ($C_1$-$C_3$)alkyl. In some embodiments of formula (Xa) or (Xb), $R^{12}$ is ethyl.

In some embodiments of formula (Xa) or (Xb), —B— is selected from —O—, —S—, —NH—, —$SO_2$—, and —$NHSO_2$—. In some embodiments of formula (Xa) or (Xb), —B— is —O—. In some embodiments of formula (Xa) or (Xb), —B— is —S—. In some embodiments of formula (Xa) or (Xb), —B— is —$SO_2$—. In some embodiments of formula (Xa) or (Xb), —B— is —$NHSO_2$—.

In some embodiments of formula (Xa) or (Xb), each $R^{14}$ is independently —H or halogen. In some embodiments of formula (Xa) or (Xb), each $R^{14}$ is independently —H or —F. In some embodiments of formula (Xa) or (Xb), each $R^{14}$ is —H. In some embodiments of formula (Xa) or (Xb), each $R^{14}$ is —F. In some embodiments of formula (Xa) or (Xb), at least one $R^{14}$ is —F.

In some embodiments of formula (I)-(Ia), -L- is -A-B—, wherein -A- is —NHC(O)$R^5$—. In some embodiments of -A-, $R^5$ is

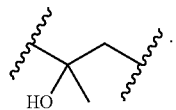 [SMILES: *CC(*)(C)O]

In some embodiments, the compound is of formula (XIa) or (XIb):

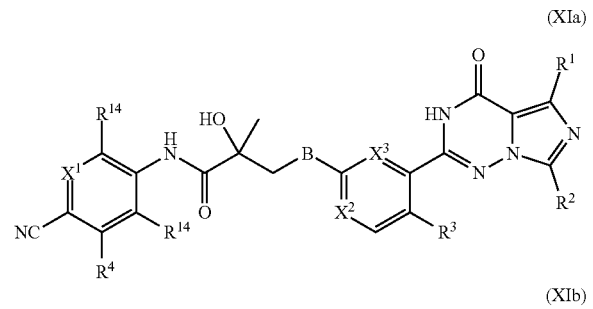

or a solvate, a hydrate, a prodrug, and/or a stereoisomer thereof, or a pharmaceutically acceptable salt thereof, wherein $R^3$ is selected from —H, and optionally substituted $(C_1-C_6)$alkoxy.

In some embodiments of formula (XIa) or (XIb), —B— is selected from —O—, —S—, —SO$_2$— and —NHSO$_2$—. In some embodiments of formula (XIa) or (XIb), —B— is —O—. In some embodiments of formula (XIa) or (XIb), —B— is —S—. In some embodiments of formula (XIa) or (XIb), —B— is —SO$_2$—. In some embodiments of formula (XIa) or (XIb), —B— is —NHSO$_2$—.

In some embodiments of formula (XIa) or (XIb), each $R^{14}$ is independently —H or halogen. In some embodiments of formula (XIa) or (XIb), each $R^{14}$ is independently —H or —F. In some embodiments of formula (XIa) or (XIb), each $R^{14}$ is —H. In some embodiments of formula (XIa) or (XIb), each $R^{14}$ is —F. In some embodiments of formula (XIa) or (XIb), at least one $R^{14}$ is —F.

In any one of the embodiments of formula (I) to (XIb) described herein, $R^1$ is optionally substituted $(C_1-C_6)$alkyl. In any one of the embodiments of formula (I) to (XIb) described herein, $R^1$ is optionally substituted $(C_1-C_3)$alkyl. In any one of the embodiments of formula (I) to (XIb) described herein, $R^1$ is —CH$_3$.

In any one of the embodiments of formula (I) to (XIb) described herein, $R^2$ is an optionally substituted $(C_1-C_6)$alkyl. In any one of the embodiments of formula (I) to (XIb) described herein, $R^2$ is an optionally substituted $(C_1-C_3)$alkyl. In any one of the embodiments of formula (I) to (XIb) described herein, $R^2$ is n-propyl.

In any one of the embodiments of formula (I) to (XIb) described herein, $R^3$ is optionally substituted $(C_1-C_3)$alkoxy. In any one of the embodiments of formula (I) to (XIb) described herein, $R^3$ is ethoxy.

In various embodiments of the compound, each $R^{14}$ and $R^4$ is an optionally substituted $(C_1-C_5)$haloalkyl or halogen. In another embodiment, $R^{14}$ and $R^4$ are each —CF$_3$, —F or —Cl.

In some embodiments of the compound, $X^1$, $X^2$, and $X^3$ are each CH.

In some embodiments of the compound, $X^1$ is N. In another embodiment, $X^2$ and $X^3$ are each CH.

In some embodiments of the compound, $X^2$ is N. In another embodiment, $X^1$ and $X^3$ are each CH.

In some embodiments of the compound, $X^3$ is N. In another embodiment, $X^1$ and $X^2$ are each CH.

In some embodiments, the compound is of formula (IVc) or (IVd):

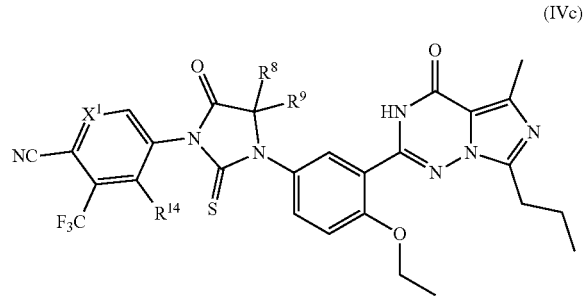

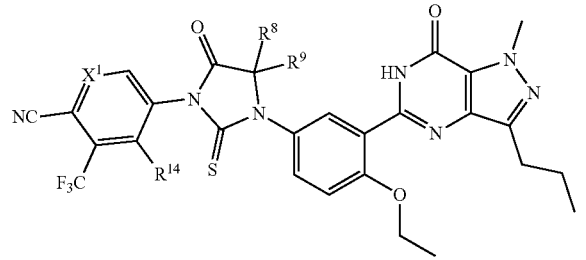

or a solvate, a hydrate, a prodrug, and/or a stereoisomer thereof, or a pharmaceutically acceptable salt thereof, wherein $R^{14}$ is —H or halogen.

In some embodiments of formula (IVc) or (IVd), $R^{14}$ is —H or —F. In some embodiments of formula (IVc) or (IVd), $R^{14}$ is —H. In some embodiments of formula (IVc) or (IVd), $R^{14}$ is —F.

In some embodiments of formula (IVc) or (IVd), $X^1$ is CH and $R^{14}$ is —F. In some embodiments of formula (IVc) or (IVd), $X^1$ is N and $R^{14}$ is —F. In some embodiments of formula (IVc) or (IVd), $X^1$ is CR$^{14}$ and each $R^{14}$ is —H. In some embodiments of formula (IVc) or (IVd), $X^1$ is N and $R^{14}$ is —H.

In some embodiments of formula (IVc) or (IVd), $R^8$ and $R^9$ are each independently —H or optionally substituted $(C_1-C_3)$alkyl. In another embodiment, $R^8$ and $R^9$ are each independently —CH$_3$.

In some embodiments of formula (IVc) or (IVd), the compound is selected from:

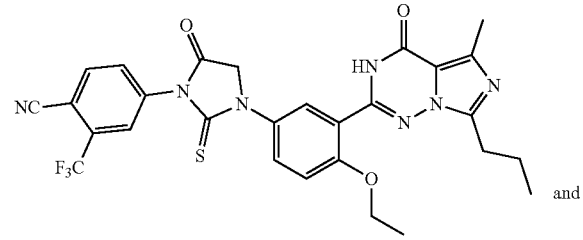

and

, or a solvate, a hydrate, a prodrug, and/or a stereoisomer thereof, or a pharmaceutically acceptable salt thereof.

In some embodiments of formula (IVc) or (IVd),

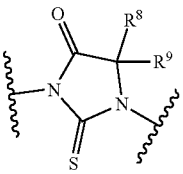

is

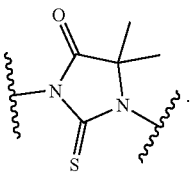 [SMILES: *N1C(=O)C(C)(C)N(*)C1=S]

.

In some embodiments, the compound is selected from

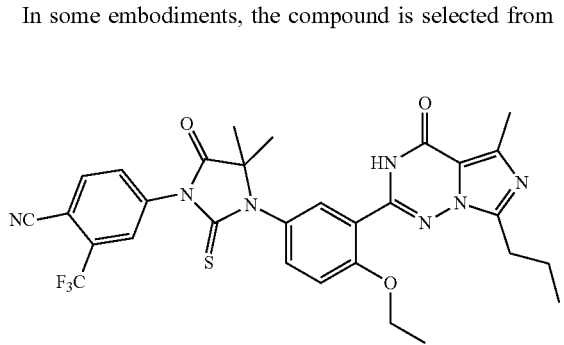

-continued

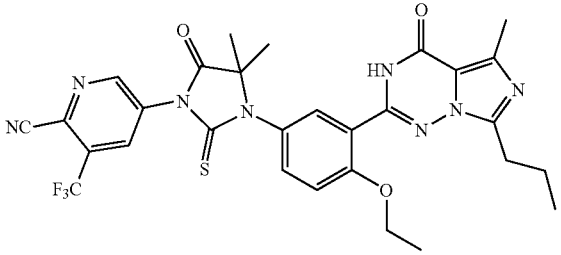

or a solvate, a hydrate, a prodrug, and/or a stereoisomer thereof, or a pharmaceutically acceptable salt thereof.

In some embodiments of formula (IVc) or (IVd), $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle that is selected from optionally substituted cyclobutyl, optionally substituted cyclopentyl, and optionally substituted tetrahydrofuran.

In some embodiments of formula (IVc) or (IVd),

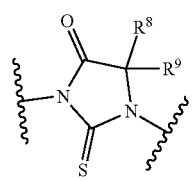

is

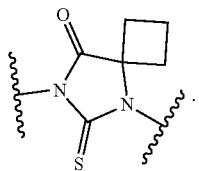 [SMILES: *N1C(=O)C2(CCC2)N(*)C1=S]

In some embodiments, the compound is selected from:

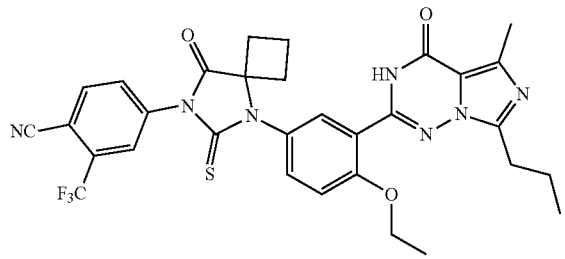

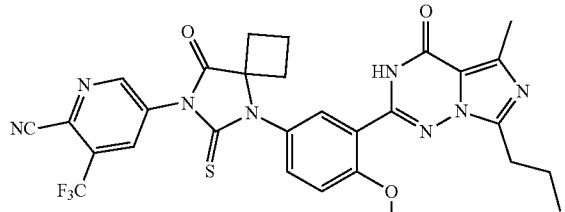

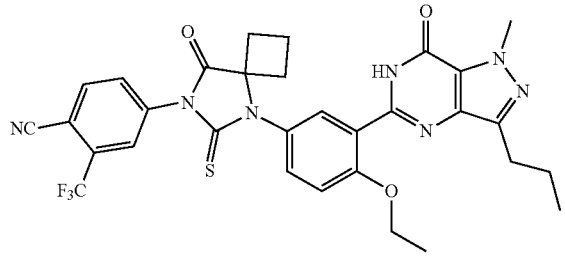

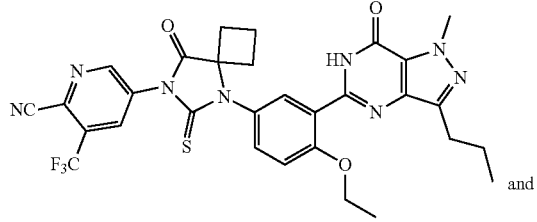

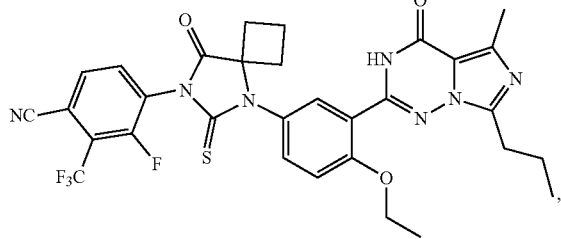

or a solvate, a hydrate, a prodrug, and/or a stereoisomer thereof, or a pharmaceutically acceptable salt thereof.

In some embodiments, the compound is of formula (IVa), or a solvate, a hydrate, a prodrug, and/or a stereoisomer thereof, or a pharmaceutically acceptable salt thereof, wherein:

X is CH or N;

each $R^{14}$ is independently —H or halogen; and $R^8$ and $R^9$ are each independently H or $(C_1$-$C_3)$alkyl (e.g., $R^8$ and $R^9$ are each —$CH_3$), or $R^8$ and $R^9$ together with the carbon atom to which they are attached are cyclically linked to provide an optionally substituted 3- to 5-membered carbocycle, or an optionally substituted 4-membered or 5-membered heterocycle (e.g., cyclopentane cyclobutane, cyclopentane, oxetane or tetrahydrofuran).

In some embodiments, the compound is of formula (IV):

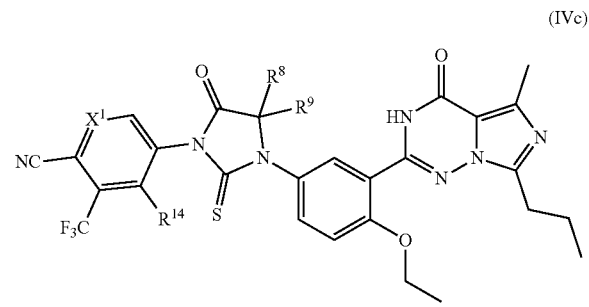

(IVc)

or a solvate, a hydrate, a prodrug, and/or a stereoisomer thereof, or a pharmaceutically acceptable salt thereof, wherein:

$X^1$ is CH or N;

$R^{14}$ is —H or halogen; and $R^8$ and $R^9$ are each independently H or $(C_1$-$C_3)$alkyl (e.g., $R^8$ and $R^9$ are each —$CH_3$), or $R^8$ and $R^9$ together with the carbon atom to which they are attached are cyclically linked to provide an optionally substituted 3- to 5-membered carbocycle, or an optionally substituted 4-membered or 5-membered heterocycle (e.g., cyclopentane cyclobutane, cyclopentane, oxetane or tetrahydrofuran).

In some embodiments, the compound is selected from:

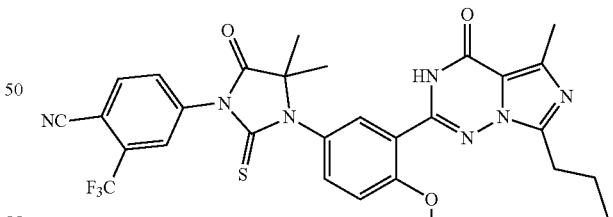

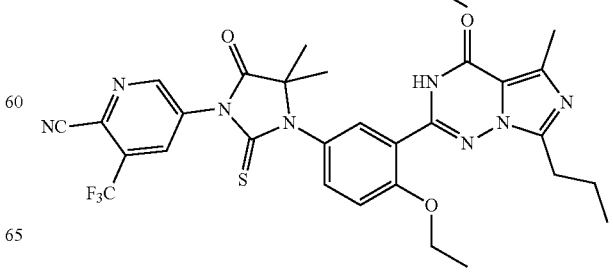

-continued

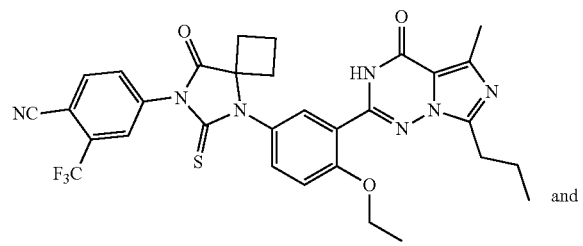

and

In some embodiments, the compound is

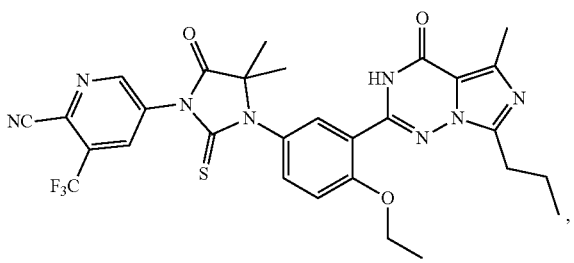

or a solvate, a hydrate, a prodrug, and/or a stereoisomer thereof, or a pharmaceutically acceptable salt thereof.

In some embodiments, the compound is

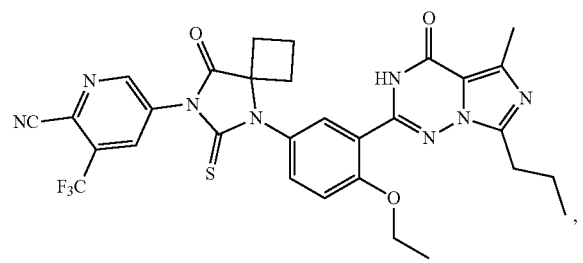

or a solvate, a hydrate, a prodrug, and/or a stereoisomer thereof, or a pharmaceutically acceptable salt thereof.

In some embodiments, the compound is

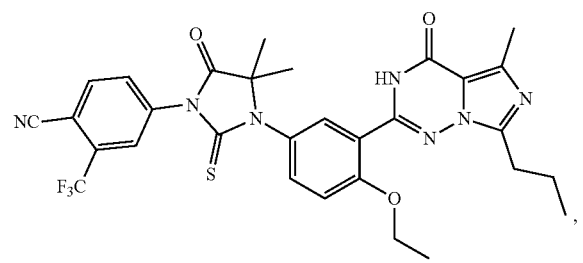 [SMILES: CCCc1nc(C)c2c(=O)[nH]c(-c3cc(N4C(=S)N(c5ccc(C#N)c(C(F)(F)F)c5)C(=O)C4(C)C)ccc3OCC)nn12]

or a solvate, a hydrate, a prodrug, and/or a stereoisomer thereof, or a pharmaceutically acceptable salt thereof.

In some embodiments, the compound is

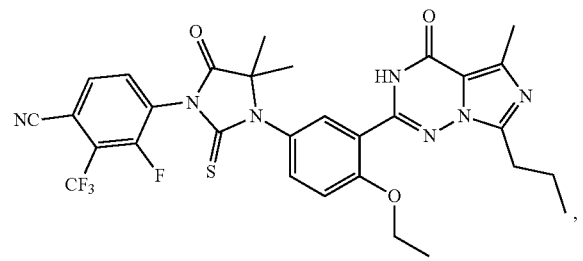 [SMILES: CCCc1nc(C)c2c(=O)[nH]c(-c3cc(N4C(=S)N(c5ccc(C#N)c(C(F)(F)F)c5F)C(=O)C4(C)C)ccc3OCC)nn12]

or a solvate, a hydrate, a prodrug, and/or a stereoisomer thereof, or a pharmaceutically acceptable salt thereof.

In some embodiments, the compound is

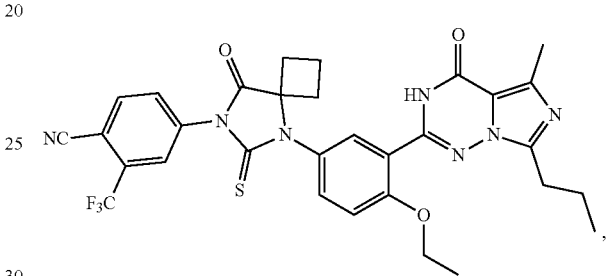

or a solvate, a hydrate, a prodrug, and/or a stereoisomer thereof, or a pharmaceutically acceptable salt thereof.

In some embodiments, the compound is

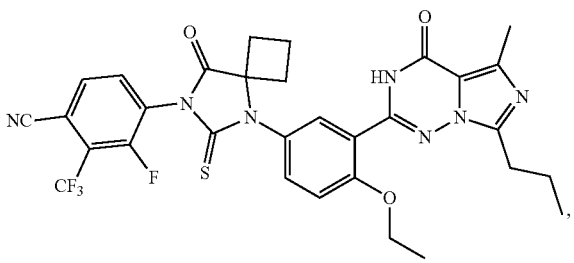 [SMILES: CCCc1nc(C)c2c(=O)[nH]c(-c3cc(N4C(=S)N(c5ccc(C#N)c(C(F)(F)F)c5F)C(=O)C45CCC5)ccc3OCC)nn12]

or a solvate, a hydrate, a prodrug, and/or a stereoisomer thereof, or a pharmaceutically acceptable salt thereof.

In some embodiments, the compound is

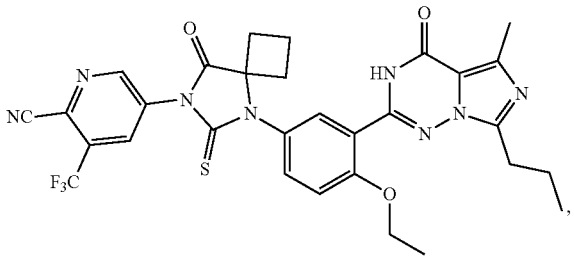 [SMILES: CCCc1nc(C)c2c(=O)[nH]c(-c3cc(N4C(=S)N(c5cnc(C#N)c(C(F)(F)F)c5)C(=O)C45CCC5)ccc3OCC)nn12]

or a solvate, a hydrate, a prodrug, and/or a stereoisomer thereof, or a pharmaceutically acceptable salt thereof.

In some embodiments of formula (IVc) or (IVd),

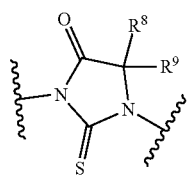

is

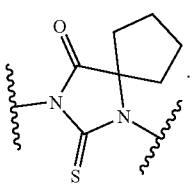 [SMILES: *N1C(=O)C2(CCCC2)N(*)C1=S]

In some embodiments, the compound is selected from:

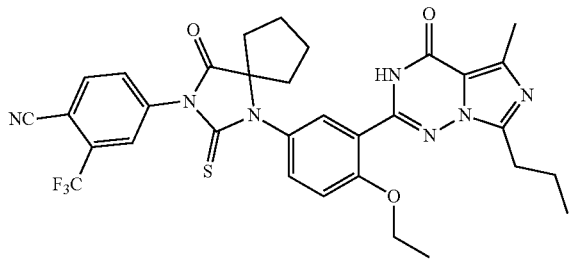

and

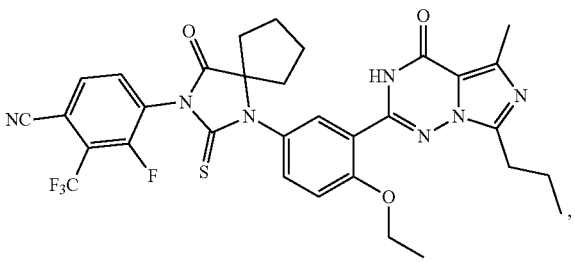

or a solvate, a hydrate, a prodrug, and/or a stereoisomer thereof, or a pharmaceutically acceptable salt thereof.

In some embodiments of formula (IVc) or (IVd),

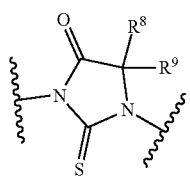

is

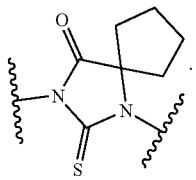 [SMILES: *N1C(=O)C2(CCCC2)N(*)C1=S]

In some embodiments, the compound is selected from:

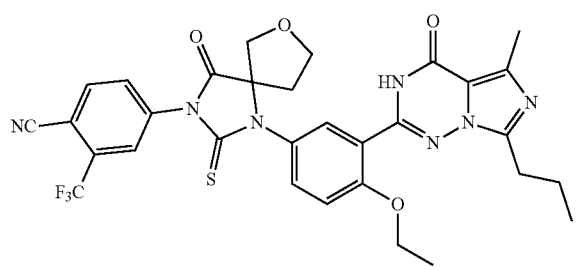

and

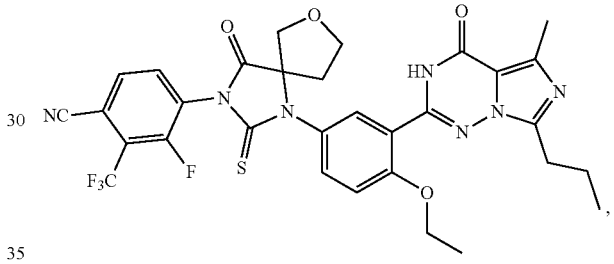

or a solvate, a hydrate, a prodrug, and/or a stereoisomer thereof, or a pharmaceutically acceptable salt thereof.

In some embodiments of formula (IVc) or (IVd), either $X^2$ is N and $X^3$ is CH, or $X^2$ is CH and $X^3$ is N. In another embodiment, $R^8$ and $R^9$ are each optionally substituted $(C_1$-$C_3)$alkyl. In another embodiment, $R^8$ and $R^9$ are each independently —$CH_3$.

In some embodiments, the compound is selected from:

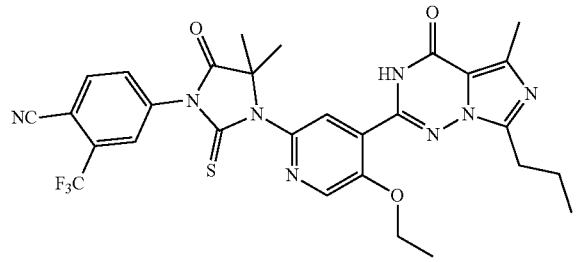

and

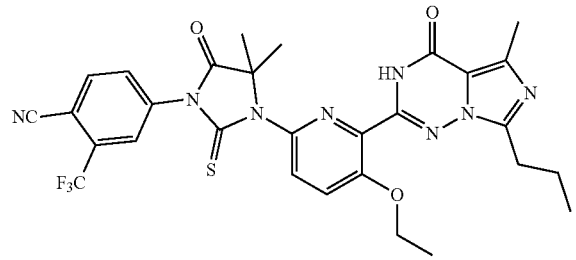

or a solvate, a hydrate, a prodrug, and/or a stereoisomer thereof, or a pharmaceutically acceptable salt thereof.

In some embodiments of formula (IVc) or (IVd), $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle) that is selected from optionally substituted cyclobutyl, optionally substituted cyclopentyl, and optionally substituted tetrahydrofuran.

In some embodiments, the compound is selected from

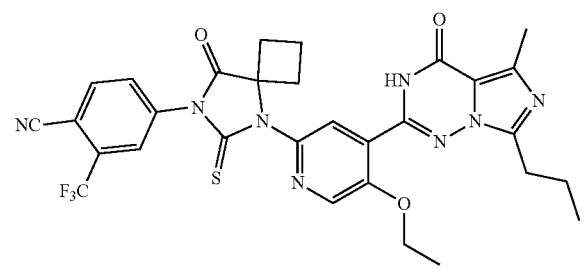

and

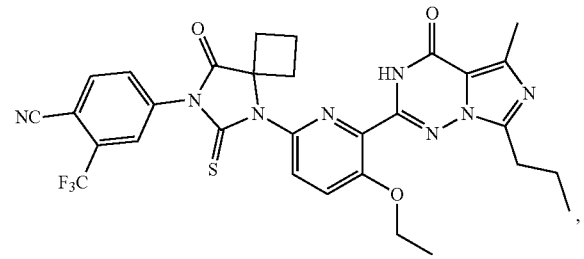

or a solvate, a hydrate, a prodrug, and/or a stereoisomer thereof, or a pharmaceutically acceptable salt thereof.

In some embodiments, the compound is of formula (Vc):

(Vc)

or a solvate, a hydrate, a prodrug, and/or a stereoisomer thereof, or a pharmaceutically acceptable salt thereof.

In some embodiments of formula (Vc), $R^8$ and $R^9$ are each independently optionally substituted $(C_1-C_3)$alkyl. In another embodiment of formula (Vc), $R^8$ and $R^9$ are each —$CH_3$.

In some embodiments of formula (Vc), the compound is selected from:

and

, or a solvate, a hydrate, a prodrug, and/or a stereoisomer thereof, or a pharmaceutically acceptable salt thereof.

In some embodiments of formula (Vc), $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle) that is selected from optionally substituted cyclobutyl, optionally substituted cyclopentyl, and optionally substituted tetrahydrofuran.

In some embodiments, the compound is selected from:

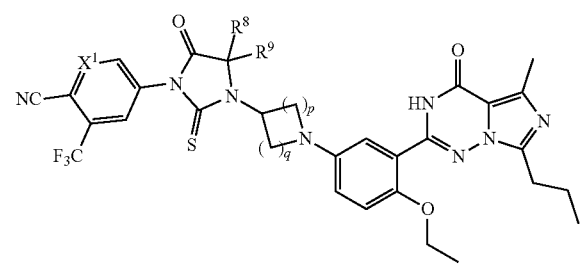

and

, or a solvate, a hydrate, a prodrug, and/or a stereoisomer thereof, or a pharmaceutically acceptable salt thereof.

In some embodiments, the compound is of formula (VIIc):

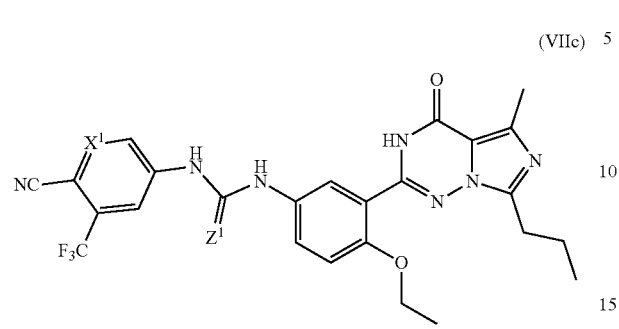
(VIIc)

or a solvate, a hydrate, a prodrug, and/or a stereoisomer thereof, or a pharmaceutically acceptable salt thereof.

In some embodiments, the compound is selected from:

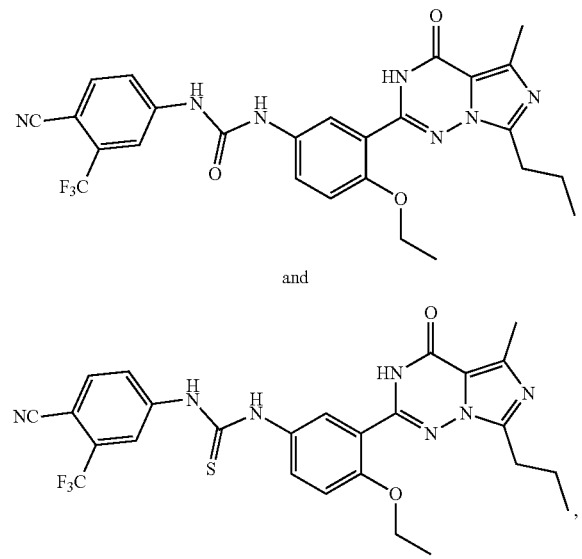

and or a solvate, a hydrate, a prodrug, and/or a stereoisomer thereof, or a pharmaceutically acceptable salt thereof.

In some embodiments, the compound is of formula (VIIIc):

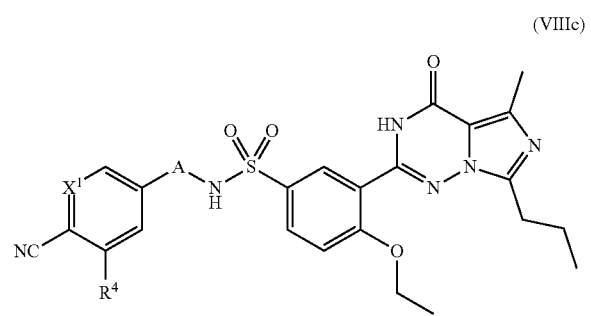
(VIIIc)

or a solvate, a hydrate, a prodrug, and/or a stereoisomer thereof, or a pharmaceutically acceptable salt thereof.

In some embodiments of formula (VIIIc), -A- is

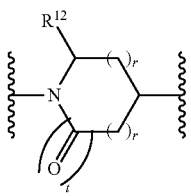

wherein:
$R^{12}$ is selected from —H, —OH, optionally substituted $(C_1-C_3)$alkyl, and optionally substituted $(C_1-C_5)$haloalkyl; and
r, s and t are independently is 0 or 1.

In some embodiments of formula (VIIIc), $R^4$ is —$CF_3$.

In some embodiments, the compound is selected from:

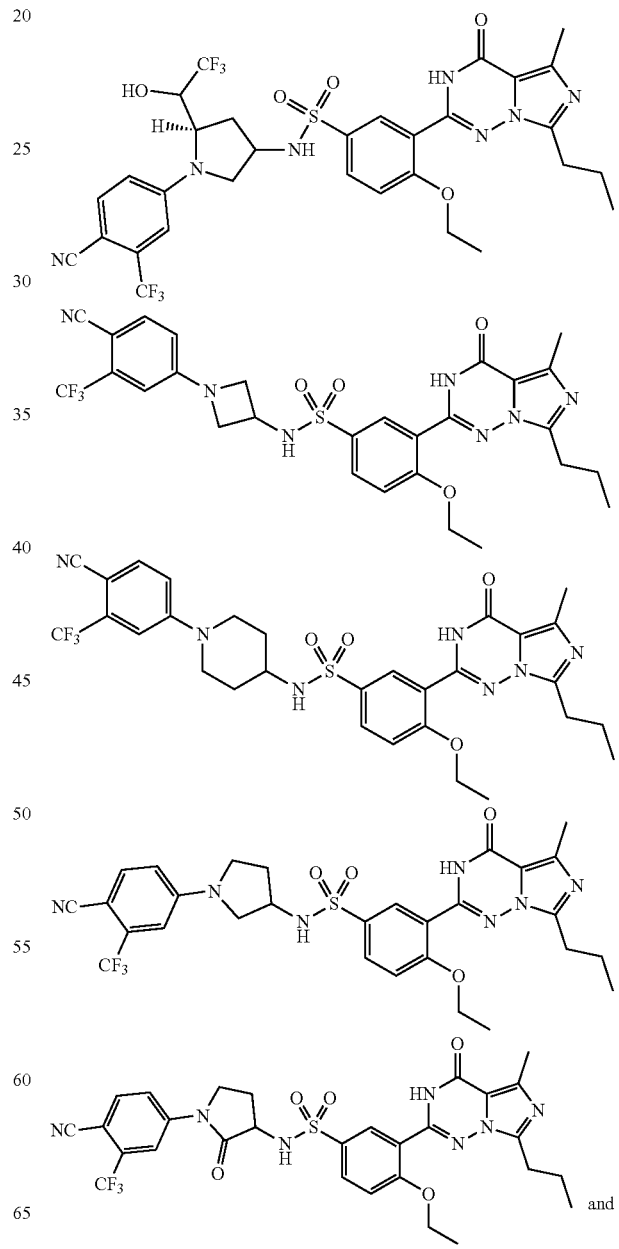

and

-continued

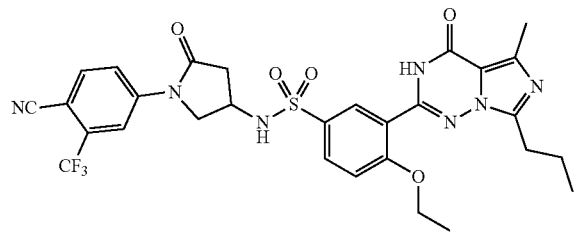

or a solvate, a hydrate, a prodrug, and/or a stereoisomer thereof, or a pharmaceutically acceptable salt thereof.

In some embodiments, the compound is of formula (IXc) or (IXd)

(IXc)

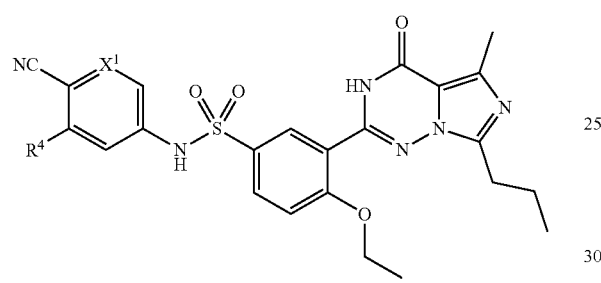

(IXd)

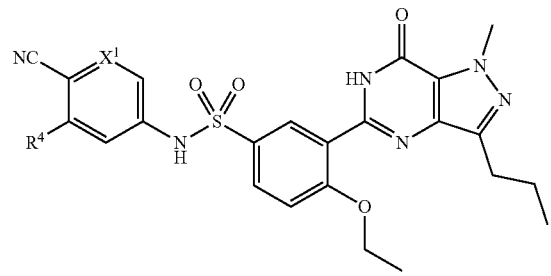

or a solvate, a hydrate, a prodrug, and/or a stereoisomer thereof, or a pharmaceutically acceptable salt thereof.

In some embodiments of formula (IXc) or (IXd), $R^4$ is —CF$_3$ or —Cl.

In some embodiments, the compound is selected from:

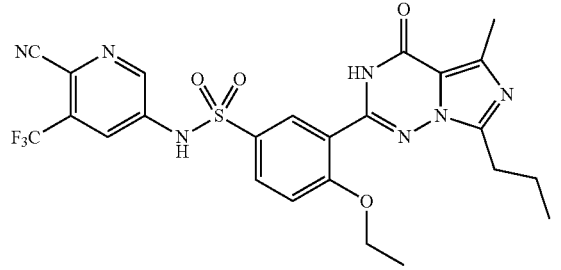

-continued

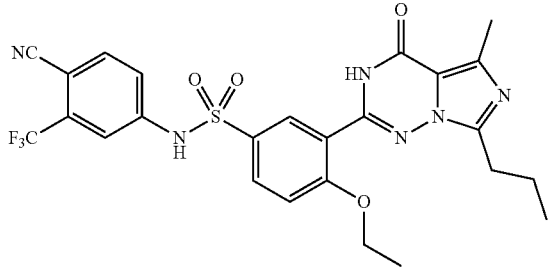

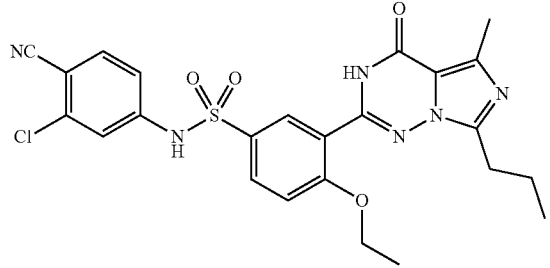

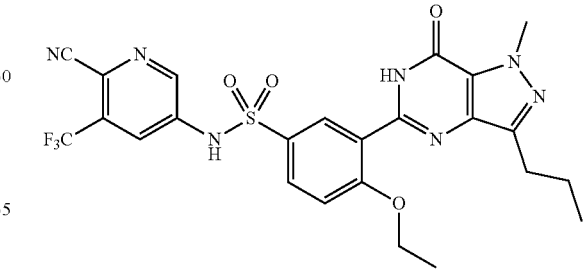

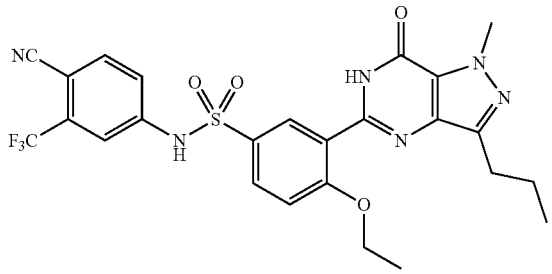

and or a solvate, a hydrate, a prodrug, and/or a stereoisomer thereof, or a pharmaceutically acceptable salt thereof.

In some embodiments, the compound is of formula (VIId):

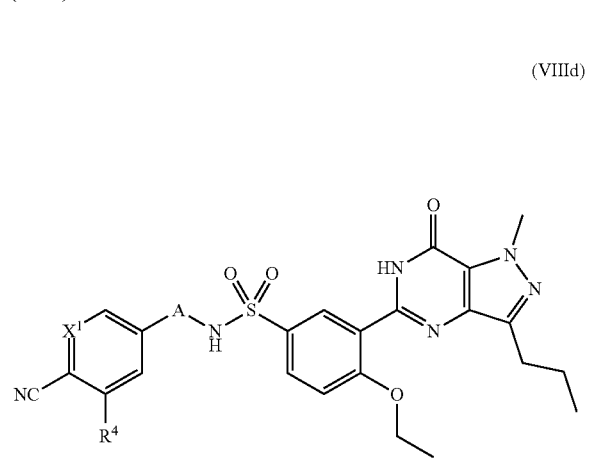
(VIIId)

or a solvate, a hydrate, a prodrug, and/or a stereoisomer thereof, or a pharmaceutically acceptable salt thereof.

In some embodiments of formula (VIIId), $R^4$ is —Cl.

In some embodiments, the compound is

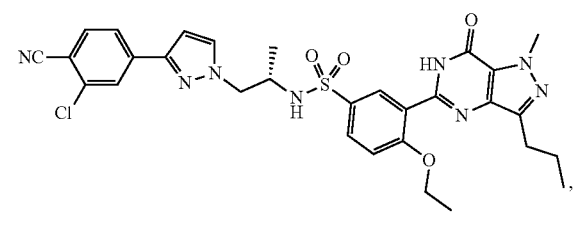 [SMILES: CCCc1nn(C)c2c(=O)[nH]c(-c3cc(S(=O)(=O)N[C@@H](C)Cn4ccc(-c5ccc(C#N)c(Cl)c5)n4)ccc3OCC)nc12]

or a solvate, a hydrate, a prodrug, and/or a stereoisomer thereof, or a pharmaceutically acceptable salt thereof.

In some embodiments, the compound is of formula (XIc):

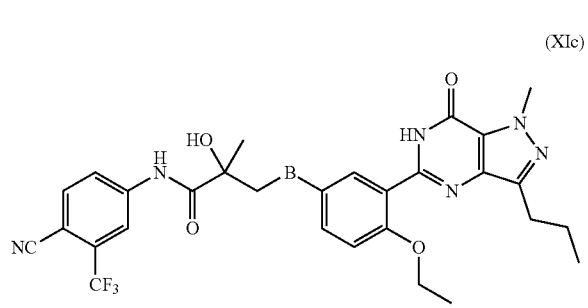
(XIc)

or a solvate, a hydrate, a prodrug, and/or a stereoisomer thereof, or a pharmaceutically acceptable salt thereof.

In some embodiments, the compound is selected from:

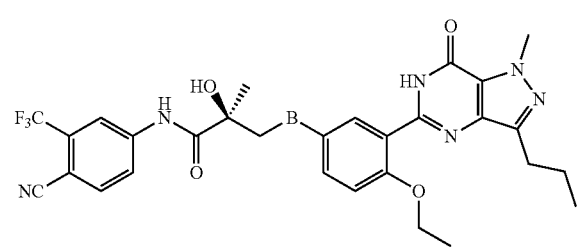

-continued

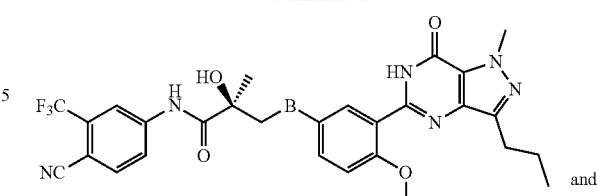
and

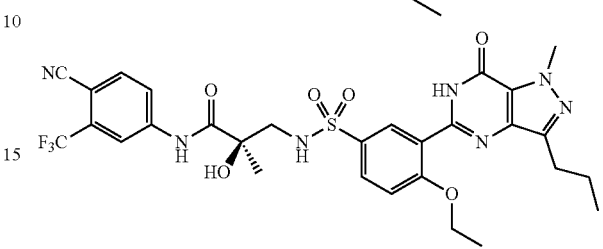

or a solvate, a hydrate, a prodrug, and/or a stereoisomer thereof, or a pharmaceutically acceptable salt thereof.

In some embodiments, the compound is of formula (Xc):

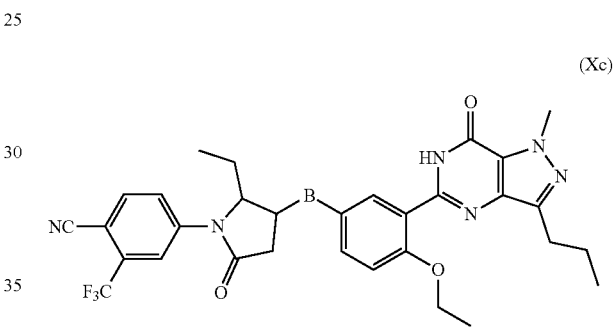
(Xc)

or a solvate, a hydrate, a prodrug, and/or a stereoisomer thereof, or a pharmaceutically acceptable salt thereof.

In some embodiments of formula (Xc), —B— is selected from —NH—, —O—, —S—, and —SO$_2$—.

In some embodiments, the compound is selected from:

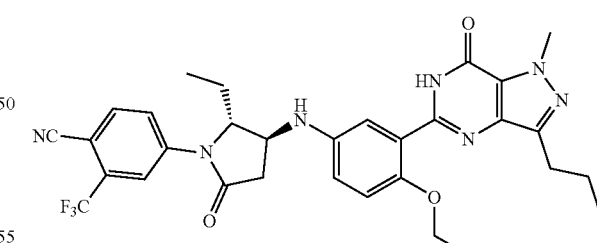

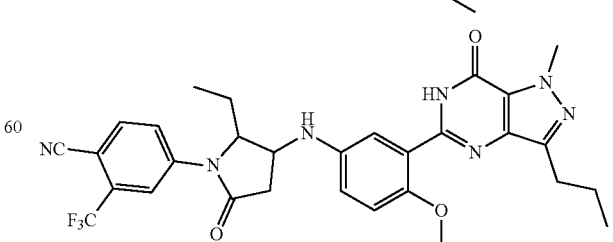

31
-continued

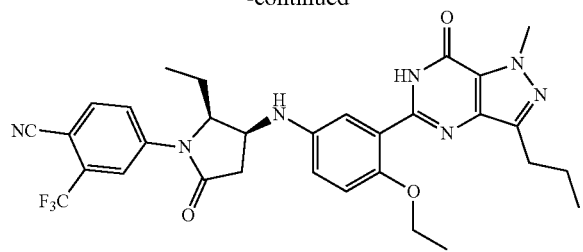

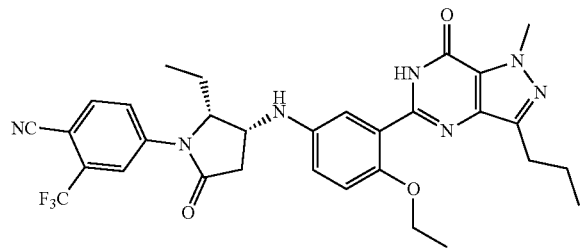

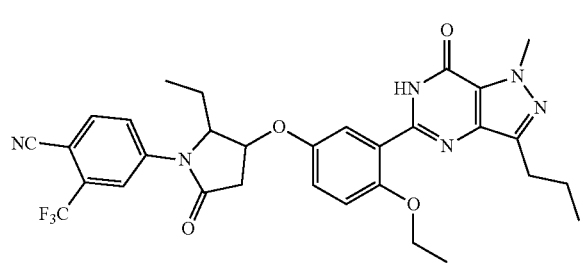

32
-continued

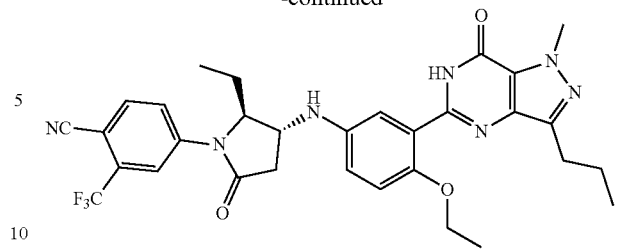

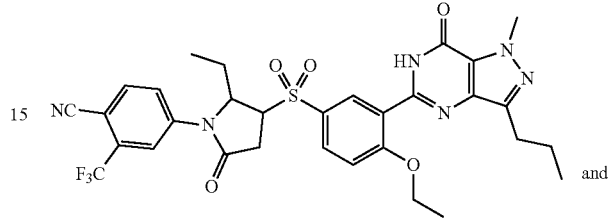

and

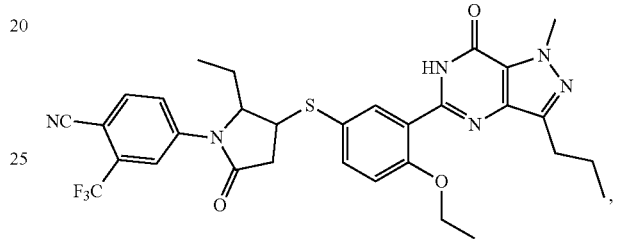

, or a solvate, a hydrate, a prodrug, and/or a stereoisomer thereof, or a pharmaceutically acceptable salt thereof.

In some embodiments, the compound is represented by the structure of one of the compounds in Table 1, or a solvate, a hydrate, a prodrug, and/or a stereoisomer thereof, or a pharmaceutically acceptable salt form thereof.

TABLE 1

Exemplary AR Antagonist and/or PDE5 Inhibitor Compounds of Formula (I)-(XIc)

| Cmpd No. | Structure | Name |
|---|---|---|
| 1 | 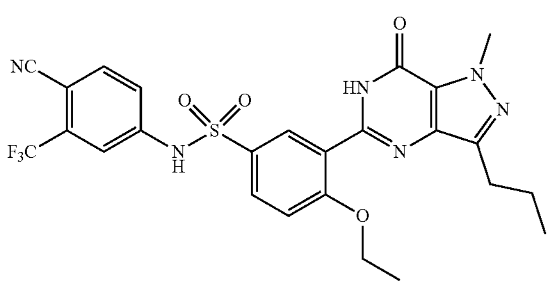 [SMILES: CCCc1nn(C)c2c(=O)[nH]c(-c3cc(S(=O)(=O)Nc4ccc(C#N)c(C(F)(F)F)c4)ccc3OCC)nc12] | N-(4-cyano-3-(trifluoromethyl)phenyl)-4-ethoxy-3-(1-methyl-7-oxo-3-propyl-6,7-dihydro-1H-pyrazolo[4,3-d]pyrimidin-5-yl)benzenesulfonamide |
| 2 | 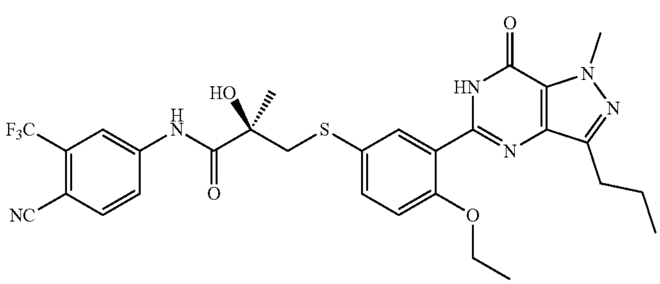 [SMILES: CCCc1nn(C)c2c(=O)[nH]c(-c3cc(SC[C@](C)(O)C(=O)Nc4ccc(C#N)c(C(F)(F)F)c4)ccc3OCC)nc12] | (R)-N-(4-cyano-3-(trifluoromethyl)phenyl)-3-((4-ethoxy-3-(1-methyl-7-oxo-3-propyl-6,7-dihydro-1H-pyrazolo[4,3-d]pyrimidin-5-yl)phenyl)thio)-2-hydroxy-2-methylpropanamide |

TABLE 1-continued

Exemplary AR Antagonist and/or PDE5 Inhibitor Compounds of Formula (I)-(XIc)

| Cmpd No. | Structure | Name |
|---|---|---|
| 3 | 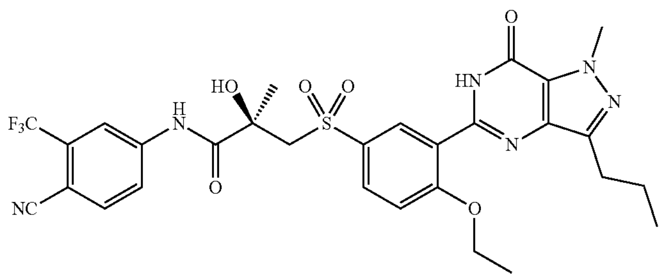 [SMILES: CCCc1nn(C)c2c(=O)[nH]c(-c3cc(S(=O)(=O)C[C@](C)(O)C(=O)Nc4ccc(C#N)c(C(F)(F)F)c4)ccc3OCC)nc12] | (R)-N-(4-cyano-3-(trifluoromethyl)phenyl)-3-((4-ethoxy-3-(1-methyl-7-oxo-3-propyl-6,7-dihydro-1H-pyrazolo[4,3-d]pyrimidin-5-yl)phenyl)sulfonyl)-2-hydroxy-2-methylpropanamide |
| 4 | 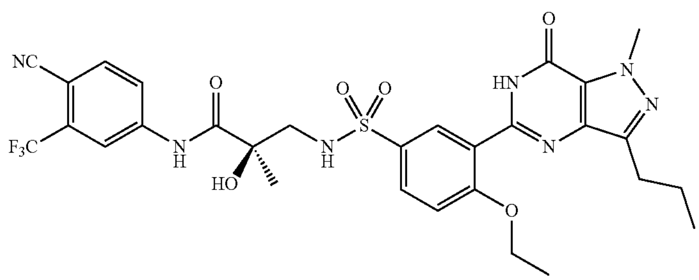 [SMILES: CCCc1nn(C)c2c(=O)[nH]c(-c3cc(S(=O)(=O)NC[C@@](C)(O)C(=O)Nc4ccc(C#N)c(C(F)(F)F)c4)ccc3OCC)nc12] | (R)-N-(4-cyano-3-(trifluoromethyl)phenyl)-3-((4-ethoxy-3-(1-methyl-7-oxo-3-propyl-6,7-dihydro-1H-pyrazolo[4,3-d]pyrimidin-5-yl)phenyl)sulfonamido)-2-hydroxy-2-methylpropanamide |
| 5 | 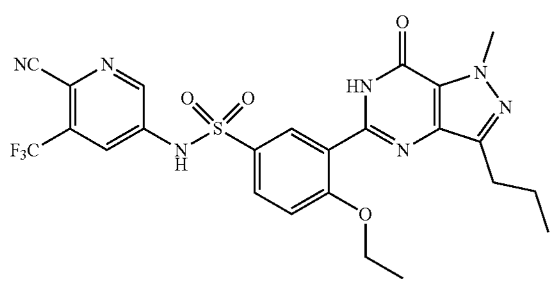 [SMILES: CCCc1nn(C)c2c(=O)[nH]c(-c3cc(S(=O)(=O)Nc4cnc(C#N)c(C(F)(F)F)c4)ccc3OCC)nc12] | N-(6-cyano-5-(trifluoromethyl)pyridin-3-yl)-4-ethoxy-3-(1-methyl-7-oxo-3-propyl-6,7-dihydro-1H-pyrazolo[4,3-d]pyrimidin-5-yl)benzenesulfonamide |
| 6 | 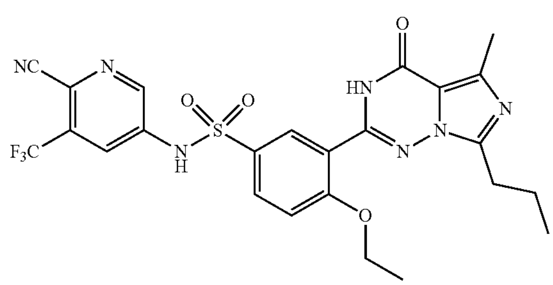 [SMILES: CCCc1nc(C)c2c(=O)[nH]c(-c3cc(S(=O)(=O)Nc4cnc(C#N)c(C(F)(F)F)c4)ccc3OCC)nn12] | N-(6-cyano-5-(trifluoromethyl)pyridin-3-yl)-4-ethoxy-3-(5-methyl-4-oxo-7-propyl-3,4-dihydroimidazo[5,1-f][1,2,4]triazin-2-yl)benzenesulfonamide |
| 7 | 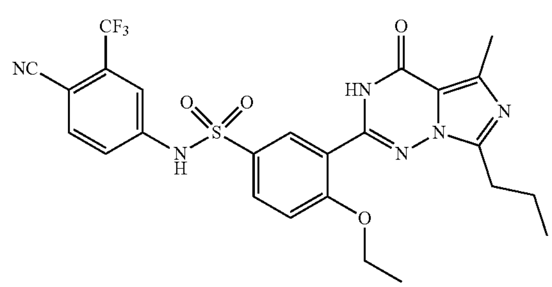 [SMILES: CCCc1nc(C)c2c(=O)[nH]c(-c3cc(S(=O)(=O)Nc4ccc(C#N)c(C(F)(F)F)c4)ccc3OCC)nn12] | N-(4-cyano-3-(trifluoromethyl)phenyl)-4-ethoxy-3-(5-methyl-4-oxo-7-propyl-3,4-dihydroimidazo[5,1-f][1,2,4]triazin-2-yl)benzenesulfonamide |

TABLE 1-continued

Exemplary AR Antagonist and/or PDE5 Inhibitor Compounds of Formula (I)-(XIc)

| Cmpd No. | Structure | Name |
| --- | --- | --- |
| 8 | 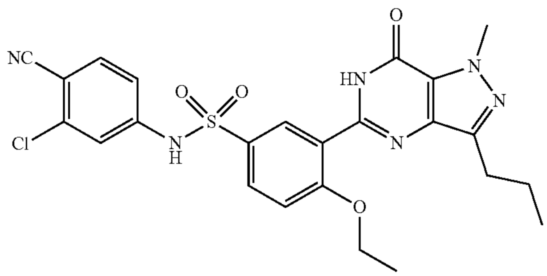 [SMILES: CCCc1nn(C)c2c(=O)[nH]c(-c3cc(S(=O)(=O)Nc4ccc(C#N)c(Cl)c4)ccc3OCC)nc12] | N-(3-chloro-4-cyanophenyl)-4-ethoxy-3-(1-methyl-7-oxo-3-propyl-6,7-dihydro-1H-pyrazolo[4,3-d]pyrimidin-5-yl)benzenesulfonamide |
| 9 | 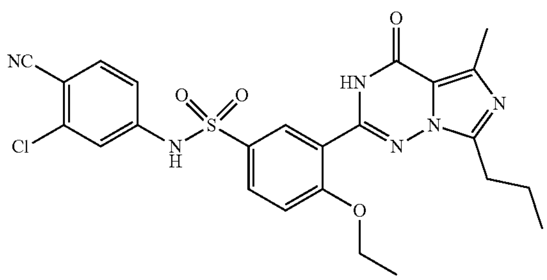 [SMILES: CCCc1nc(C)c2c(=O)[nH]c(-c3cc(S(=O)(=O)Nc4ccc(C#N)c(Cl)c4)ccc3OCC)nn12] | N-(3-chloro-4-cyanophenyl)-4-ethoxy-3-(5-methyl-4-oxo-7-propyl-3,4-dihydroimidazo[5,1-f][1,2,4]triazin-2-yl)benzenesulfonamide |
| 10 | 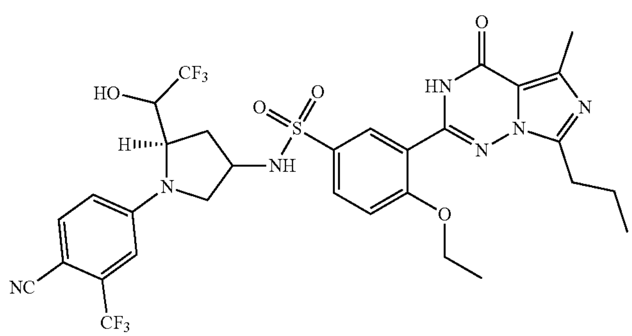 [SMILES: CCCc1nc(C)c2c(=O)[nH]c(-c3cc(S(=O)(=O)NC4C[C@H](C(O)C(F)(F)F)N(c5ccc(C#N)c(C(F)(F)F)c5)C4)ccc3OCC)nn12] | N-((3S,5R)-1-(4-cyano-3-(trifluoromethyl)phenyl)-5-(2,2,2-trifluoro-1-hydroxyethyl)pyrrolidin-3-yl)-4-ethoxy-3-(5-methyl-4-oxo-7-propyl-3,4-dihydroimidazo[5,1-f][1,2,4]triazin-2-yl)benzenesulfonamide |
| 11 | 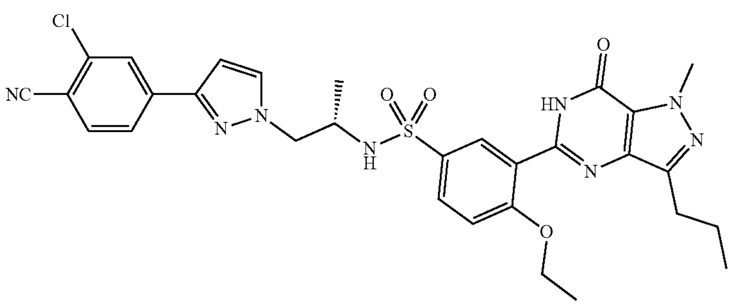 [SMILES: CCCc1nn(C)c2c(=O)[nH]c(-c3cc(S(=O)(=O)N[C@@H](C)Cn4ccc(-c5ccc(C#N)c(Cl)c5)n4)ccc3OCC)nc12] | (S)-N-(1-(3-(3-chloro-4-cyanophenyl)-1H-pyrazol-1-yl)propan-2-yl)-4-ethoxy-3-(1-methyl-7-oxo-3-propyl-6,7-dihydro-1H-pyrazolo[4,3-d]pyrimidin-5-yl)benzenesulfonamide |
| 12 | 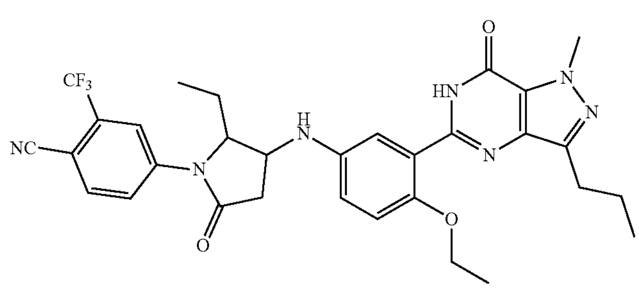 [SMILES: CCCc1nn(C)c2c(=O)[nH]c(-c3cc(NC4CC(=O)N(c5ccc(C#N)c(C(F)(F)F)c5)C4CC)ccc3OCC)nc12] | 4-(3-((4-ethoxy-3-(1-methyl-7-oxo-3-propyl-6,7-dihydro-1H-pyrazolo[4,3-d]pyrimidin-5-yl)phenyl)amino)-2-ethyl-5-oxopyrrolidin-1-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
|---|---|---|
| 13 | 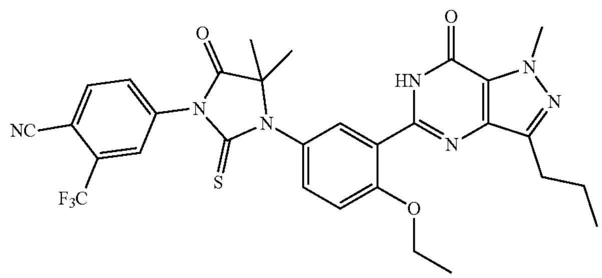 [SMILES: CCCc1nn(C)c2c(=O)[nH]c(-c3cc(N4C(=S)N(c5ccc(C#N)c(C(F)(F)F)c5)C(=O)C4(C)C)ccc3OCC)nc12] | 4-(3-(4-ethoxy-3-(1-methyl-7-oxo-3-propyl-6,7-dihydro-1H-pyrazolo[4,3-d]pyrimidin-5-yl)phenyl)-4,4-dimethyl-5-oxo-2-thioxoimidazolidin-1-yl)-2-(Influoromethyl)benzonilrile |
| 14 | 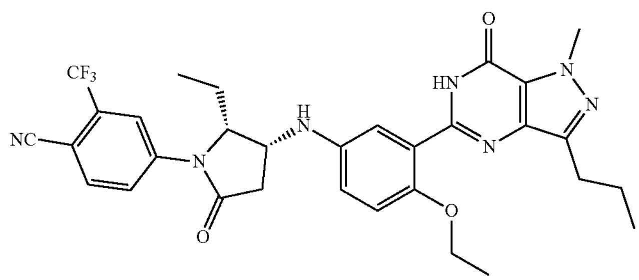 [SMILES: CCCc1nn(C)c2c(=O)[nH]c(-c3cc(N[C@@H]4CC(=O)N(c5ccc(C#N)c(C(F)(F)F)c5)[C@@H]4CC)ccc3OCC)nc12] | 4-((2R,3R)-3-((4-ethoxy-3-(1-methyl-7-oxo-3-propyl-6,7-dihydro-1H-pyrazolo[4,3-d]pyrimidin-5-yl)phenyl)amino)-2-ethyl-5-oxopyrrolidin-1-yl)-2-(trifluoromethyl)benzonitrile |
| 15 | 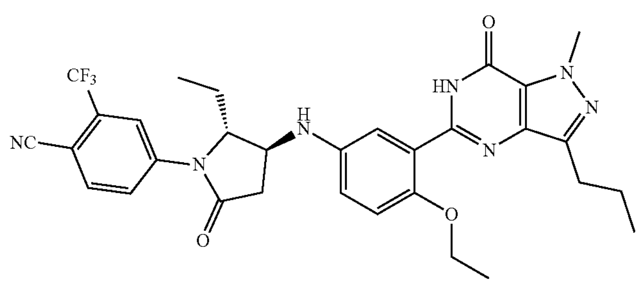 [SMILES: CCCc1nn(C)c2c(=O)[nH]c(-c3cc(N[C@H]4CC(=O)N(c5ccc(C#N)c(C(F)(F)F)c5)[C@@H]4CC)ccc3OCC)nc12] | 4-((2R,3S)-3-((4-ethoxy-3-(1-methyl-7-oxo-3-propyl-6,7-dihydro-1H-pyrazolo[4,3-d]pyrimidin-5-yl)phenyl)amino)-2-ethyl-5-oxopyrrolidin-1-yl)-2-(trifluoromethyl)benzonitrile |
| 16 | 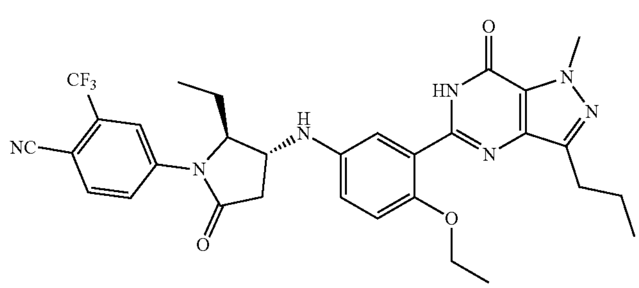 [SMILES: CCCc1nn(C)c2c(=O)[nH]c(-c3cc(N[C@@H]4CC(=O)N(c5ccc(C#N)c(C(F)(F)F)c5)[C@H]4CC)ccc3OCC)nc12] | 4-((2S,3R)-3-((4-ethoxy-3-(1-methyl-7-oxo-3-propyl-6,7-dihydro-1H-pyrazolo[4,3-d]pyrimidin-5-yl)phenyl)amino)-2-ethyl-5-oxopyrrolidin-1-yl)-2-(trifluoromethyl)benxonitrile |
| 17 | 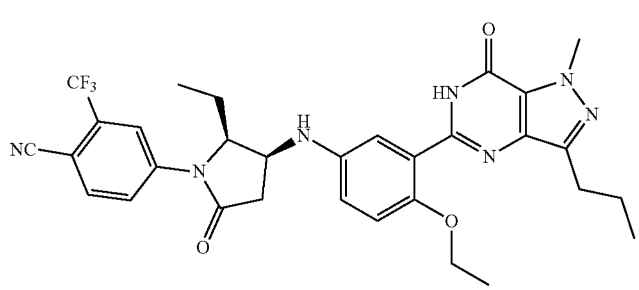 [SMILES: CCCc1nn(C)c2c(=O)[nH]c(-c3cc(N[C@H]4CC(=O)N(c5ccc(C#N)c(C(F)(F)F)c5)[C@H]4CC)ccc3OCC)nc12] | 4-((2S,3S)-3-((4-ethoxy-3-(1-methyl-7-oxo-3-propyl-6,7-dihydro-1H-pyrazolo[4,3-d]pyrimidin-5-yl)phenyl)amino)-2-ethyl-5-oxopyrrolidin-1-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
|---|---|---|
| 18 | 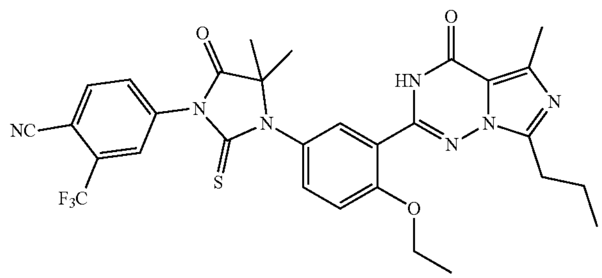 [SMILES: CCCc1nc(C)c2c(=O)[nH]c(-c3cc(N4C(=S)N(c5ccc(C#N)c(C(F)(F)F)c5)C(=O)C4(C)C)ccc3OCC)nn12] | 4-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-2-(trifluoromethyl)benzonitrile |
| 19 | 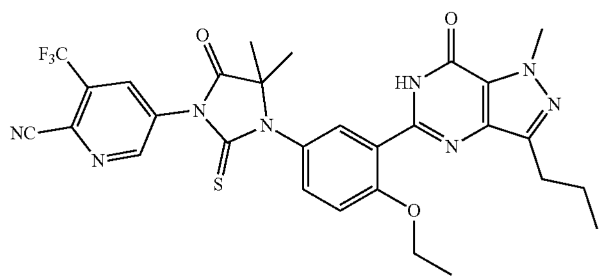 [SMILES: CCCc1nn(C)c2c(=O)[nH]c(-c3cc(N4C(=S)N(c5cnc(C#N)c(C(F)(F)F)c5)C(=O)C4(C)C)ccc3OCC)nc12] | 5-(3-(4-ethoxy-3-(1-methyl-7-oxo-3-propyl-6,7-dihydro-1H-pyrazolo[4,3-d]pyrimidin-5-yl)phenyl)-4,4-dimethyl-5-oxo-2-thioxoimidazolidin-1-yl)-3-(trifluoromethyl)picolinonitrile |
| 20 | 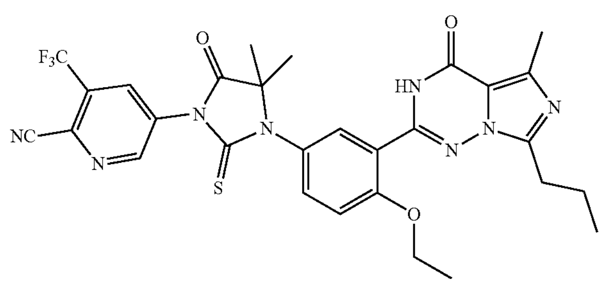 [SMILES: CCCc1nc(C)c2c(=O)[nH]c(-c3cc(N4C(=S)N(c5cnc(C#N)c(C(F)(F)F)c5)C(=O)C4(C)C)ccc3OCC)nn12] | 5-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-3-(trifluoromethyl)picolinonitrile |
| 21 | 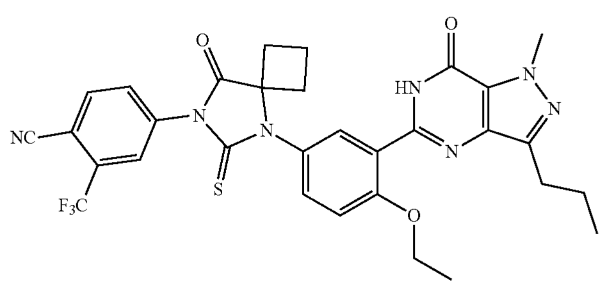 [SMILES: CCCc1nn(C)c2c(=O)[nH]c(-c3cc(N4C(=S)N(c5ccc(C#N)c(C(F)(F)F)c5)C(=O)C45CCC5)ccc3OCC)nc12] | 4-(5-(4-ethoxy-3-(1-methyl-7-oxo-3-propyl-6,7-dihydro-1H-pyrazolo[4,3-d]pyrimidin-5-yl)phenyl)-8-oxo-6-thioxo-5,7-diazaspiro[3.4]octan-7-yl)-2-(trifluoromethyl)benzonitrile |
| 22 | 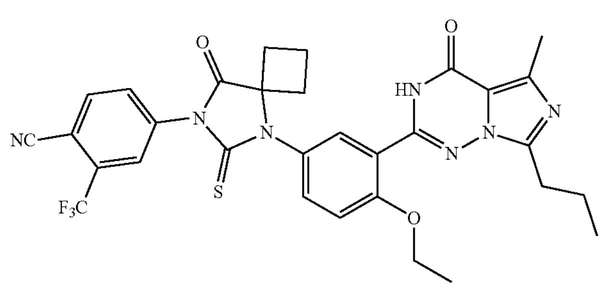 [SMILES: CCCc1nc(C)c2c(=O)[nH]c(-c3cc(N4C(=S)N(c5ccc(C#N)c(C(F)(F)F)c5)C(=O)C45CCC5)ccc3OCC)nn12] | 4-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
|---|---|---|
| 23 | 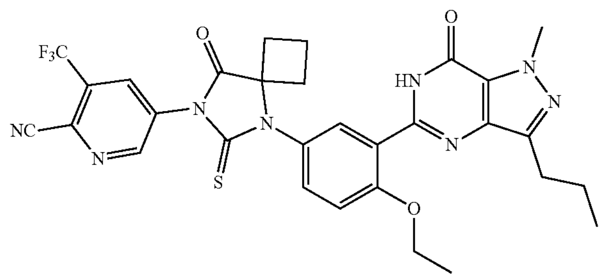 [SMILES: CCCc1nn(C)c2c(=O)[nH]c(-c3cc(N4C(=S)N(c5cnc(C#N)c(C(F)(F)F)c5)C(=O)C45CCC5)ccc3OCC)nc12] | 5-(5-(4-ethoxy-3-(1-methyl-7-oxo-3-propyl-6,7-dihydro-1H-pyrazolo[4,3-d]pyrimidin-5-yl)phenyl)-8-oxo-6-thioxo-5,7-diazaspiro[3.4]octan-7-yl)-3-(trifluoromethyl)picolinonitrile |
| 24 | 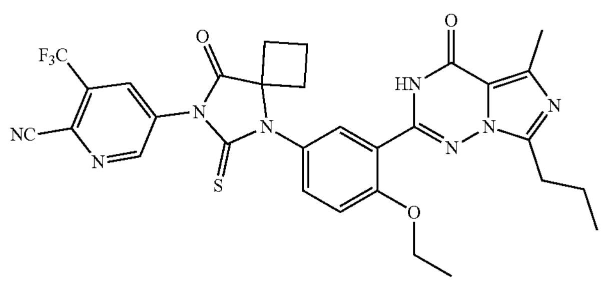 [SMILES: CCCc1nc(C)c2c(=O)[nH]c(-c3cc(N4C(=S)N(c5cnc(C#N)c(C(F)(F)F)c5)C(=O)C45CCC5)ccc3OCC)nn12] | 5-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-3-(trifluoromethyl)picolinonitrile |
| 25 | 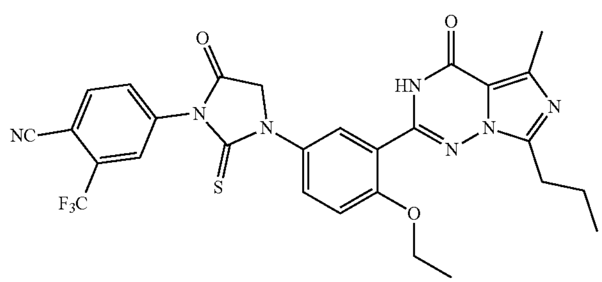 [SMILES: CCCc1nc(C)c2c(=O)[nH]c(-c3cc(N4CC(=O)N(c5ccc(C#N)c(C(F)(F)F)c5)C4=S)ccc3OCC)nn12] | 4-(3-(4-ethoxy-3-(5-methyl-4-oxo-7-propyl-3,4-dihydroimidazo[5,1-f][1,2,4]triazin-2-yl)phenyl)-5-oxo-2-thioxoimidazolidin-1-yl)-2-(trifluoromethyl)benzonitrile |
| 26 | 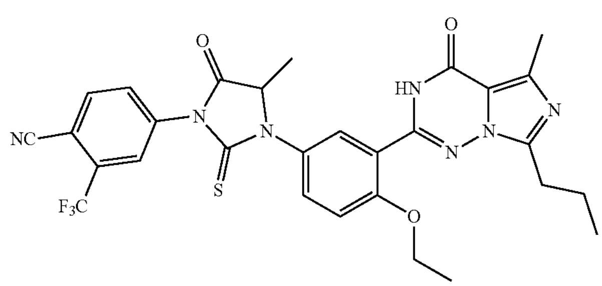 [SMILES: CCCc1nc(C)c2c(=O)[nH]c(-c3cc(N4C(=S)N(c5ccc(C#N)c(C(F)(F)F)c5)C(=O)C4C)ccc3OCC)nn12] | 4-(3-(4-ethoxy-3-(5-methyl-4-oxo-7-propyl-3,4-dihydroimidazo[5,1-f][1,2,4]triazin-2-yl)phenyl)-4-methyl-5-oxo-2-thioxoimidazolidin-1-yl)-2-(trifluoromethyl)benzonitrile |
| 27 | 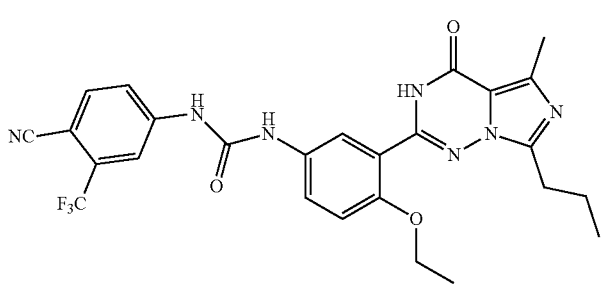 | 1-(4-cyano-3-(trifluoromethyl)phenyl)-3-(4-ethoxy-3-(5-methyl-4-oxo-7-propyl-3,4-dihydroimidazo[5,1-f][1,2,4]triazin-2-yl)phenyl)urea |

TABLE 1-continued

Exemplary AR Antagonist and/or PDE5 Inhibitor Compounds of Formula (I)-(XIc)

| Cmpd No. | Structure | Name |
|---|---|---|
| 28 | 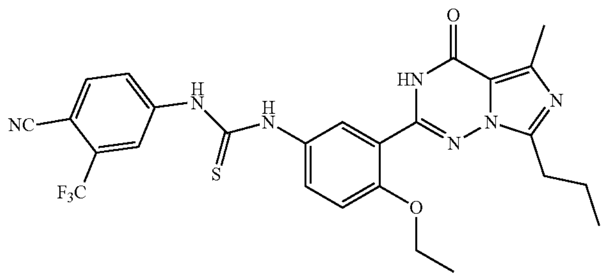 [SMILES: CCCc1nc(C)c2c(=O)[nH]c(-c3cc(NC(=O)Nc4ccc(C#N)c(C(F)(F)F)c4)ccc3OCC)nn12] | 1-(4-cyano-3-(trifluoromethyl)phenyl)-3-(4-ethoxy-3-(5-methyl-4-oxo-7-propyl-3,4-dihydroimidazo[5,1-f][1,2,4] triazin-2-yl)phenyl)thiourea |
| 29 | 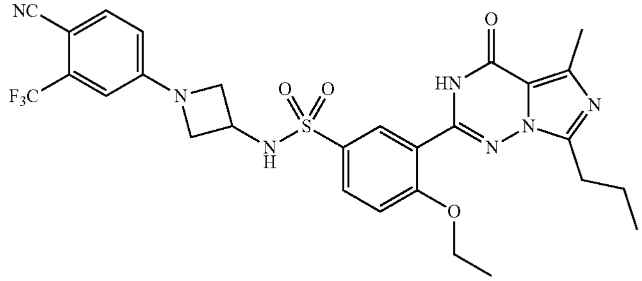 [SMILES: CCCc1nc(C)c2c(=O)[nH]c(-c3cc(S(=O)(=O)NC4CN(c5ccc(C#N)c(C(F)(F)F)c5)C4)ccc3OCC)nn12] | N-(1-(4-cyano-3-(trifluoromethyl)phenyl)azetidin-3-yl)-4-ethoxy-3-(5-methyl-4-oxo-7-propyl-3,4-dihydroimidazo[5,1-f][1,2,4]triazin-2-yl)benzenesulfonamide |
| 30 | 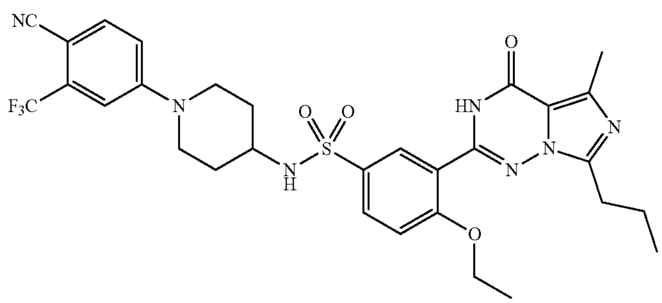 [SMILES: CCCc1nc(C)c2c(=O)[nH]c(-c3cc(S(=O)(=O)NC4CCN(c5ccc(C#N)c(C(F)(F)F)c5)CC4)ccc3OCC)nn12] | N-(1-(4-cyano-3-(trifluoromethyl)phenyl)piperidin-4-yl)-4-ethoxy-3-(5-methyl-4-oxo-7-propyl-3,4-dihydroimidazo[5,1-f][1,2,4]triazin-2-yl)benzenesulfonamide |
| 31 | 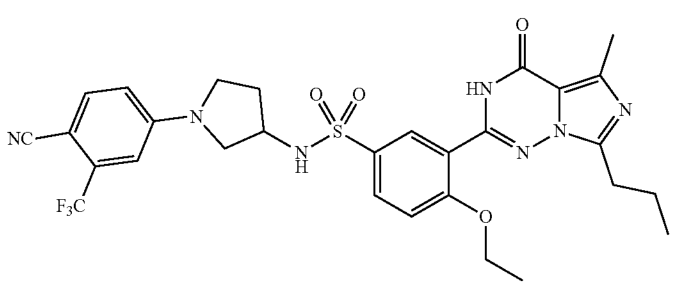 [SMILES: CCCc1nc(C)c2c(=O)[nH]c(-c3cc(S(=O)(=O)NC4CCN(c5ccc(C#N)c(C(F)(F)F)c5)C4)ccc3OCC)nn12] | N-(1-(4-cyano-3-(trifluoromethyl)phenyl)pyrrolidin-3-yl)-4-ethoxy-3-(5-methyl-4-oxo-7-propyl-3,4-dihydroimidazo[5,1-f][1,2,4]triazin-2-yl)benzenesulfonamide |
| 32 | 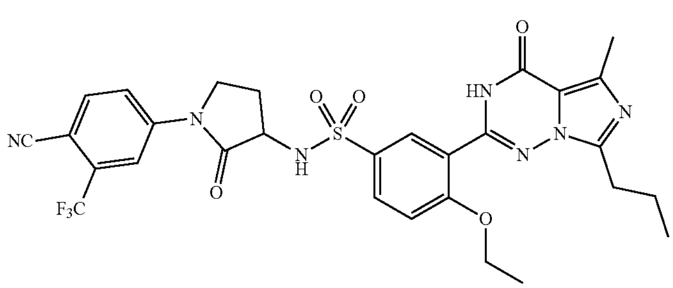 [SMILES: CCCc1nc(C)c2c(=O)[nH]c(-c3cc(S(=O)(=O)NC4CCN(c5ccc(C#N)c(C(F)(F)F)c5)C4=O)ccc3OCC)nn12] | N-(1-(4-cyano-3-(trifluoromethyl)phenyl)-2-oxopyrrolidin-3-yl)-4-ethoxy-3-(5-methyl-4-oxo-7-propyl-3,4-dihydroimidazo[5,1-f][1,2,4]triazin-2-yl)benzenesulfonamide |

TABLE 1-continued

Exemplary AR Antagonist and/or PDE5 Inhibitor Compounds of Formula (I)-(XIc)

| Cmpd No. | Structure | Name |
|---|---|---|
| 33 | 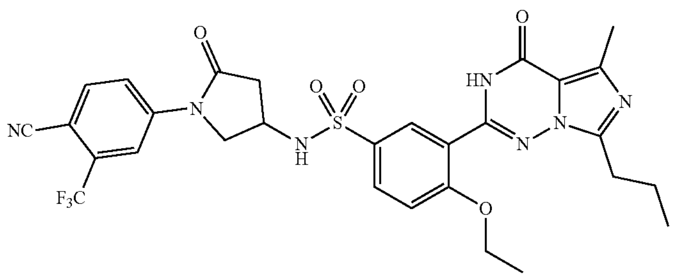 [SMILES: CCCc1nc(C)c2c(=O)[nH]c(-c3cc(S(=O)(=O)NC4CC(=O)N(c5ccc(C#N)c(C(F)(F)F)c5)C4)ccc3OCC)nn12] | N-(1-(4-cyano-3-(trifluoromethyl)phenyl)-5-oxopyrrolidin-3-yl)-4-ethoxy-3-(5-methyl-4-oxo-7-propyl-3,4-dihydroimidazo[5,1-f][1,2,4]triazin-2-yl)benzenesulfonamide |
| 34 | 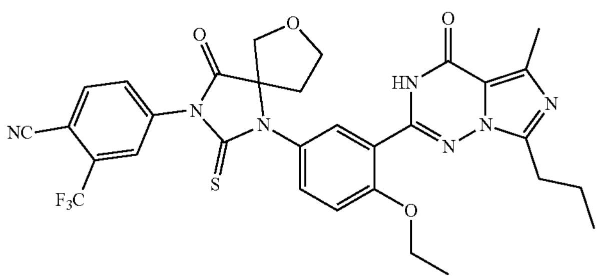 [SMILES: CCCc1nc(C)c2c(=O)[nH]c(-c3cc(N4C(=S)N(c5ccc(C#N)c(C(F)(F)F)c5)C(=O)C45CCOC5)ccc3OCC)nn12] | 4-(1-(4-ethoxy-3-(5-methyl-4-oxo-7-propyl-3,4-dihydroimidazo[5,1-f][1,2,4]triazin-2-yl)phenyl)-4-oxo-2-thioxo-7-oxa-1,3-diazaspiro[4.4]nonan-3-yl)-2-(trifluoromethyl)benzonitrile |
| 35 | 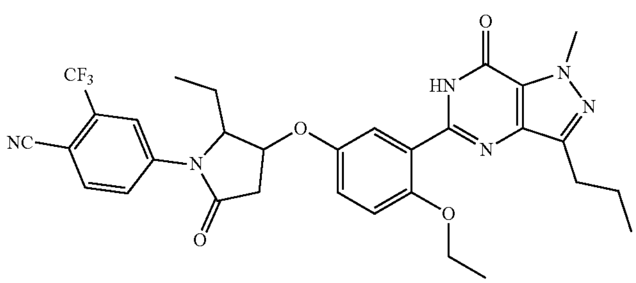 [SMILES: CCCc1nn(C)c2c(=O)[nH]c(-c3cc(OC4CC(=O)N(c5ccc(C#N)c(C(F)(F)F)c5)C4CC)ccc3OCC)nc12] | 4-(3-(4-ethoxy-3-(1-methyl-7-oxo-3-propyl-6,7-dihydro-1H-pyrazolo[4,3-d]pyrimidin-5-yl)phenoxy)-2-ethyl-5-oxopyrrolidin-1-yl)-2-(trifluoromethyl)benzonitrile |
| 36 | 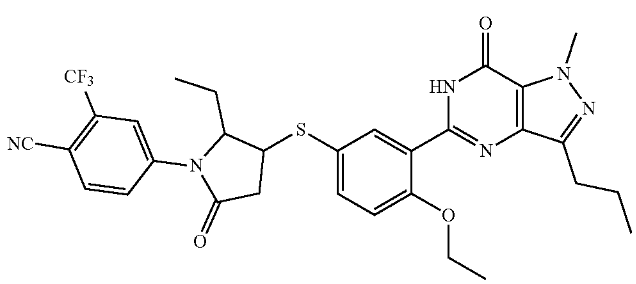 [SMILES: CCCc1nn(C)c2c(=O)[nH]c(-c3cc(SC4CC(=O)N(c5ccc(C#N)c(C(F)(F)F)c5)C4CC)ccc3OCC)nc12] | 4-(3-((4-ethoxy-3-(1-methyl-7-oxo-3-propyl-6,7-dihydro-1H-pyrazolo[4,3-d]pyrimidin-5-yl)phenyl)thio)-2-ethyl-5-oxopyrrolidin-1-yl)-2-(trifluoromethyl)benzonitrile |
| 37 | 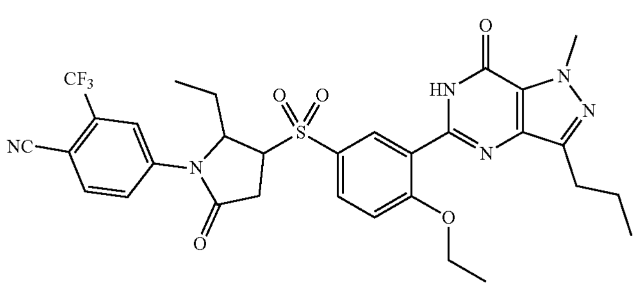 [SMILES: CCCc1nn(C)c2c(=O)[nH]c(-c3cc(S(=O)(=O)C4CC(=O)N(c5ccc(C#N)c(C(F)(F)F)c5)C4CC)ccc3OCC)nc12] | 4-(3-((4-ethoxy-3-(1-methyl-7-oxo-3-propyl-6,7-dihydro-1H-pyrazolo[4,3-d]pyrimidin-5-yl)phenyl)sulfonyl)-2-ethyl-5-oxopyrrolidin-1-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
|---|---|---|
| 38 | 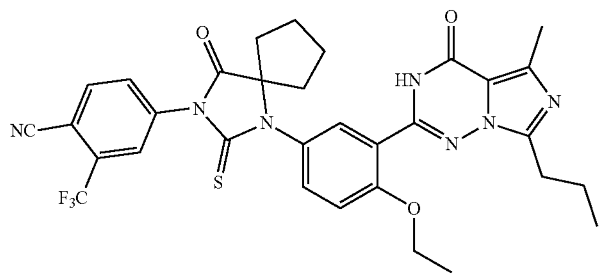 [SMILES: CCCc1nc(C)c2c(=O)[nH]c(-c3cc(N4C(=S)N(c5ccc(C#N)c(C(F)(F)F)c5)C(=O)C45CCCC5)ccc3OCC)nn12] | 4-(1-(4-ethoxy-3-(5-methyl-4-oxo-7-propyl-3,4-dihydroimidazo[5,1-f][1,2,4]triazin-2-yl)phenyl)-4-oxo-2-thioxo-1,3-diazaspiro[4.4]nonan-3-yl)-2-(trifluoromethyl)benzonitrile |
| 39 | 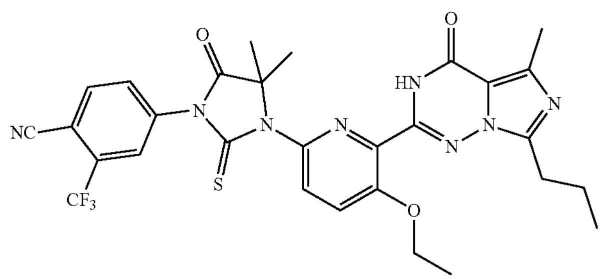 [SMILES: CCCc1nc(C)c2c(=O)[nH]c(-c3nc(N4C(=S)N(c5ccc(C#N)c(C(F)(F)F)c5)C(=O)C4(C)C)ccc3OCC)nn12] | 4-(3-(5-ethoxy-6-(5-methyl-4-oxo-7-propyl-3,4-dihydroimidazo[5,1-f][1,2,4]triazin-2-yl)pyridin-2-yl)-4,4-dimethyl-5-oxo-2-thioxoimidazolidin-1-yl)-2-(trifluoromethyl)benzonitrile |
| 40 | 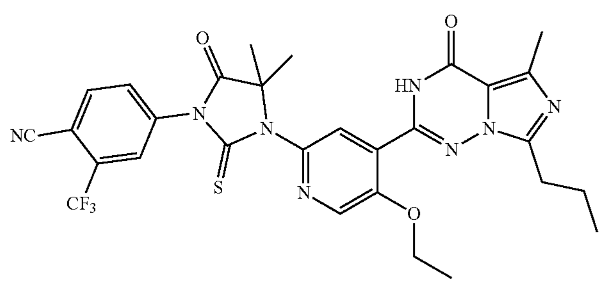 [SMILES: CCCc1nc(C)c2c(=O)[nH]c(-c3cc(N4C(=S)N(c5ccc(C#N)c(C(F)(F)F)c5)C(=O)C4(C)C)ncc3OCC)nn12] | 4-(3-(5-ethoxy-4-(5-methyl-4-oxo-7-propyl-3,4-dihydroimidazo[5,1-f][1,2,4]triazin-2-yl)pyridin-2-yl)-4,4-dimethyl-5-oxo-2-thioxoimidazolidin-1-yl)-2-(trifluoromethyl)benzonitrile |
| 41 | 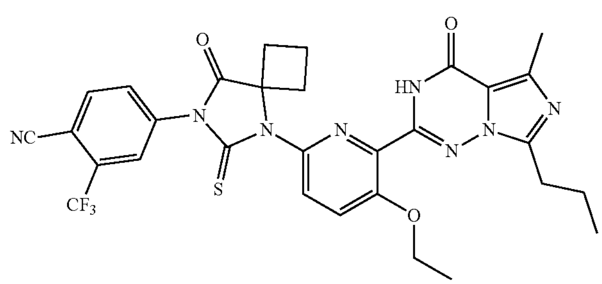 [SMILES: CCCc1nc(C)c2c(=O)[nH]c(-c3nc(N4C(=S)N(c5ccc(C#N)c(C(F)(F)F)c5)C(=O)C45CCC5)ccc3OCC)nn12] | 4-(5-(5-ethoxy-6-(5-methyl-4-oxo-7-propyl-3,4-dihydroimidazo[5,1-f][1,2,4]triazin-2-yl)pyridin-2-yl)-8-oxo-6-thioxo-5,7-diazaspiro[3.4]octan-7-yl)-2-(trifluoromethyl)benzonitrile |
| 42 | 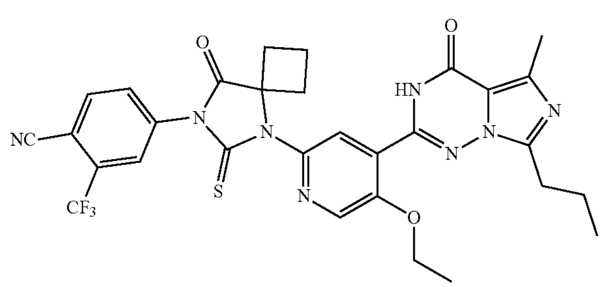 [SMILES: CCCc1nc(C)c2c(=O)[nH]c(-c3cc(N4C(=S)N(c5ccc(C#N)c(C(F)(F)F)c5)C(=O)C45CCC5)ncc3OCC)nn12] | 4-(5-(5-ethoxy-4-(5-methyl-4-oxo-7-propyl-3,4-dihydroimidazo[5,1-f][1,2,4]triazin-2-yl)pyridin-2-yl)-8-oxo-6-thioxo-5,7-diazaspiro[3.4]octan-7-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
| --- | --- | --- |
| 43 | 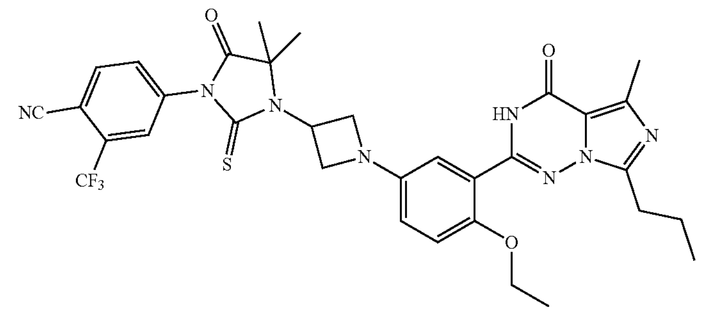 [SMILES: CCCc1nc(C)c2c(=O)[nH]c(-c3cc(N4CC(N5C(=S)N(c6ccc(C#N)c(C(F)(F)F)c6)C(=O)C5(C)C)C4)ccc3OCC)nn12] | 4-(3-(1-(4-ethoxy-3-(5-methyl-4-oxo-7-propyl-3,4-dihydroimidazo[5,1-f][1,2,4]triazin-2-yl)phenyl)azetidin-3-yl)-4,4-dimethyl-5-oxo-2-thioxoimidazolidin-1-yl)-2-(trifluoromethyl)benzonilrile |
| 44 | 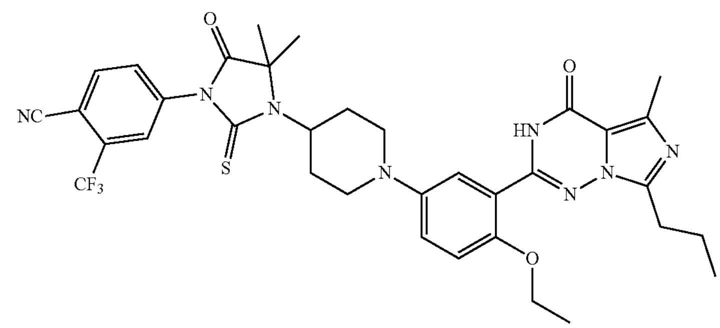 [SMILES: CCCc1nc(C)c2c(=O)[nH]c(-c3cc(N4CCC(N5C(=S)N(c6ccc(C#N)c(C(F)(F)F)c6)C(=O)C5(C)C)CC4)ccc3OCC)nn12] | 4-(3-(1-(4-ethoxy-3-(5-methyl-4-oxo-7-propyl-3,4-dihydroimidazo[5,1-f][1,2,4]triazin-2-yl)phenyl)piperidin-4-yl)-4,4-dimethyl-5-oxo-2-thioxoimidazolidin-1-yl)-2-(trifluoromethyl)benxonitrile |
| 45 | 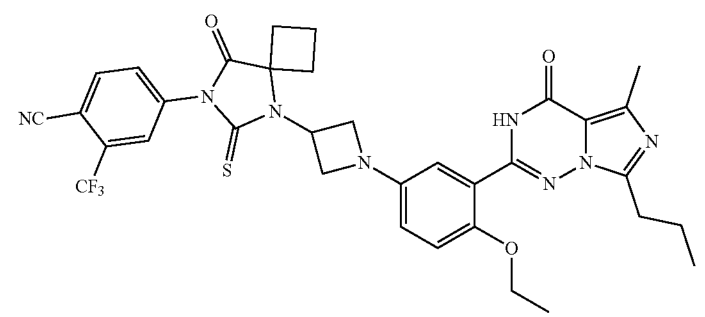 [SMILES: CCCc1nc(C)c2c(=O)[nH]c(-c3cc(N4CC(N5C(=S)N(c6ccc(C#N)c(C(F)(F)F)c6)C(=O)C56CCC6)C4)ccc3OCC)nn12] | 4-(5-(1-(4-ethoxy-3-(5-methyl-4-oxo-7-propyl-3,4-dihydroimidazo[5,1-f][1,2,4]triazin-2-yl)phenyl)azetidin-3-yl)-8-oxo-6-thioxo-5,7-diazaspiro[3.4]octan-7-yl)-2-(trifluoromethyl)benzonitrile |
| 46 | 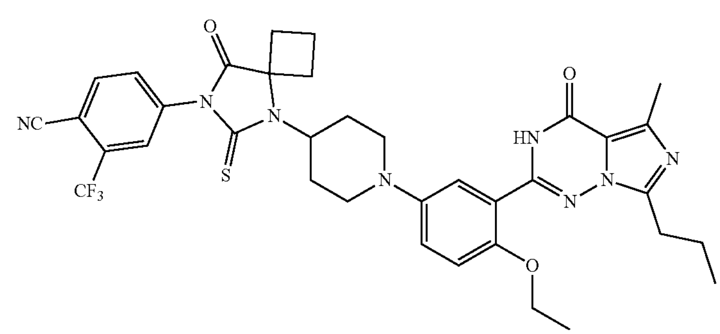 [SMILES: CCCc1nc(C)c2c(=O)[nH]c(-c3cc(N4CCC(N5C(=S)N(c6ccc(C#N)c(C(F)(F)F)c6)C(=O)C56CCC6)CC4)ccc3OCC)nn12] | 4-(5-(1-(4-ethoxy-3-(5-methyl-4-oxo-7-propyl-3,4-dihydroimidazo[5,1-f][1,2,4]triazin-2-yl)phenyl)piperidin-4-yl)-8-oxo-6-thioxo-5,7-diazaspiro[3.4]octan-7-yl)-2-(trifluoromethyl)benzonitrile |

TABLE 1-continued

Exemplary AR Antagonist and/or PDE5 Inhibitor Compounds of Formula (I)-(XIc)

| Cmpd No. | Structure | Name |
|---|---|---|
| 47 | 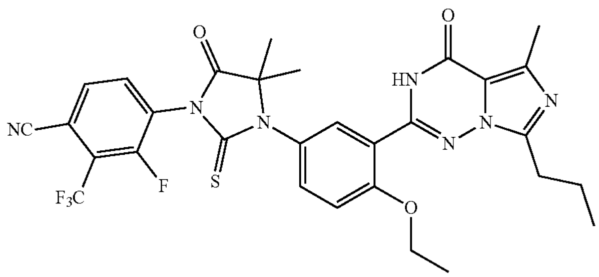 [SMILES: CCCc1nc(C)c2c(=O)[nH]c(-c3cc(N4C(=S)N(c5ccc(C#N)c(C(F)(F)F)c5F)C(=O)C4(C)C)ccc3OCC)nn12] | 4-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-3-fluoro-2-(trifluoromethyl)benzonitrile |
| 48 | 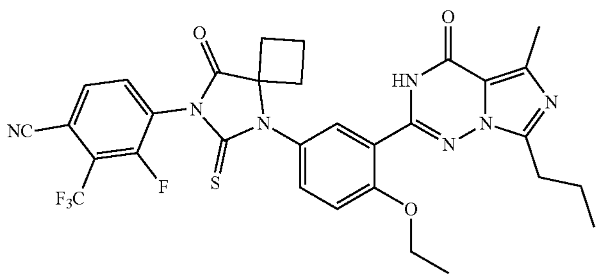 [SMILES: CCCc1nc(C)c2c(=O)[nH]c(-c3cc(N4C(=S)N(c5ccc(C#N)c(C(F)(F)F)c5F)C(=O)C45CCC5)ccc3OCC)nn12] | 4-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-3-fluoro-2-(trifluoromethyl)benzonitrile |
| 49 | 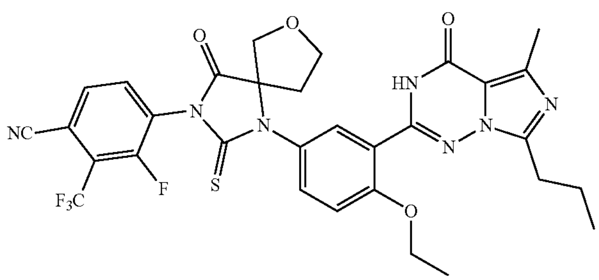 [SMILES: CCCc1nc(C)c2c(=O)[nH]c(-c3cc(N4C(=S)N(c5ccc(C#N)c(C(F)(F)F)c5F)C(=O)C45CCOC5)ccc3OCC)nn12] | 4-(1-(4-ethoxy-3-(5-methyl-4-oxo-7-propyl-3,4-dihydroimidazo[5,1-f][1,2,4]triazin-2-yl)phenyl)-4-oxo-2-thioxo-7-oxa-1,3-diazaspiro[4.4]nonan-3-yl)-3-fluoro-2-(trifluoromethyl)benzonitrile |
| 50 | 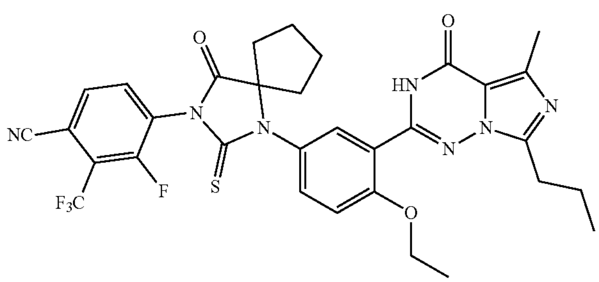 [SMILES: CCCc1nc(C)c2c(=O)[nH]c(-c3cc(N4C(=S)N(c5ccc(C#N)c(C(F)(F)F)c5F)C(=O)C45CCCC5)ccc3OCC)nn12] | 4-(1-(4-ethoxy-3-(5-methyl-4-oxo-7-propyl-3,4-dihydroimidazo[5,1-f][1,2,4]triazin-2-yl)phenyl)-4-oxo-2-thioxo-1,3-diazaspiro[4.4]nonan-3-yl)-3-fluoro-2-(trifluoromethyl)benzonitrile |

It is understood that all variations of salts, solvates, hydrates, prodrugs and/or stereoisomers of the compounds described herein (e.g., of Formula (I)-(XIc), such as a compound of Table 1) are meant to be encompassed by the present disclosure.

4.1.1 Isotopically Labelled Analogs

The present disclosure also encompasses isotopically-labeled compounds which are identical to those compounds as described herein, except that one or more atoms are replaced by an atom having an atomic mass or mass number different from the atomic mass or mass number usually found in nature ("isotopologues"). The compounds of the present disclosure may also contain unnatural proportions of atomic isotopes at one or more atoms that constituted such compounds. Examples of isotopes that can be incorporated into compounds described herein include isotopes of hydrogen, carbon, nitrogen, oxygen, phosphorus, fluorine and chlorine, such as $^{2}$H ("D"), $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound described herein can have one or more H atoms replaced with deuterium.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

In some embodiments, certain isotopically-labeled compounds, such as those labeled with $^{3}$H and $^{14}$C, can be useful in compound and/or substrate tissue distribution assays. Tritiated ($^3$H) and carbon-14 ($^{14}$C) isotopes can be particularly preferred for their ease of preparation and detectability. Further, substitution with heavier isotopes such as deuterium can afford certain therapeutic advantages resulting from greater metabolic stability, such as increased in vivo half-life or reduced dosage requirements, and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

In some embodiments, the compounds disclosed in the present disclosure are deuterated analogs of any of the compounds, or a salt thereof, as described herein. A deuterated analog of a compound of any one of formulae (I)-(XIc) is a compound where one or more hydrogen atoms are substituted with a deuterium. In some embodiments, the deuterated analog is a compound of any one of formulae (I)-(XIc) that includes a deuterated $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ group. In certain embodiments of a deuterated analog of a compound of any one of formulae (I)-(XIc), $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from optionally substituted ($C_1$-$C_6$)alkyl, optionally substituted ($C_1$-$C_6$)alkoxy, optionally substituted ($C_1$-$C_6$)alkylene-heterocycloalkyl, optionally substituted monocyclic or bicyclic carbocycle, and optionally substituted monocyclic or bicyclic heterocycle including at least one deuterium atom.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

4.1.2 Fluorinated Analogs

In some embodiments, the compounds disclosed in the present disclosure are fluorinated analogs of any of the compounds, or a salt thereof, as described herein. A fluorinated analog of a compound of any one of formulae (I)-(XIc) is a compound where one or more hydrogen atoms or substituents are substituted with a fluorine atom. In some embodiments, the fluorinated analog is a compound of any one of formulae (I)-(XIc) that includes a fluorinated $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ group. In some embodiments of a fluorinated analog of a compound of any one of formulae (I)-(XIc), $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ group are independently selected from optionally substituted ($C_1$-$C_6$)alkyl, optionally substituted ($C_1$-$C_6$)alkoxy, optionally substituted ($C_1$-$C_6$) alkylene-heterocycloalkyl, optionally substituted monocyclic or bicyclic carbocycle, optionally substituted monocyclic or bicyclic heterocycle, optionally substituted aryl, and optionally substituted heteroaryl including at least one fluorine atom. In some embodiments of a fluorinated analog of a compound of any one of formulae (I)-(XIc), the hydrogen atom of an aliphatic or an aromatic C—H bond is replaced by a fluorine atom. In some embodiments of a fluorinated analog of a compound of any one of formulae (I)-(XIc), at least one hydrogen of an optionally substituted aryl or an optionally substituted heteroaryl is replaced by a fluorine atom. In some embodiments of a fluorinated analog of a compound of formula (I), a hydroxyl substituent (—OH) or an amino substituent (—NH$_2$) is replaced by a fluorine atom.

4.1.3 Salt, Solvate, Hydrate, Prodrug and/or Stereoisomer Forms

In some embodiments, the compounds described herein also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

In some embodiments, the compounds described herein are present in a prodrug form. Any convenient prodrug forms of the subject compounds can be prepared, for example, according to the strategies and methods described by Rautio et al. ("Prodrugs: design and clinical applications", Nature Reviews Drug Discovery 7, 255-270 (February 2008)).

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

In some embodiments, the compounds described herein are present in a solvate form.

In some embodiments, the compounds described herein are present in a hydrate form when the solvent component of the solvate is water.

In some embodiments, the compounds described herein have one or more chiral centers. It is understood that if an absolute stereochemistry is not expressly indicated, then each chiral center may independently be of the R-configuration or the S-configuration or a mixture thereof.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures of R-enantiomer and S-enantiomer, and enantio-enriched stereometric mixtures comprising of R- and S-enantiomers, as well as the individual optical isomers can be isolated or synthesized so as to be substantially free of their enantiomeric or diastereomeric partners, and these stereoisomers are all within the scope of the present technology.

In some embodiments, the compounds described herein are present in a salt form.

In some embodiments, the compounds, or a prodrug form thereof, are provided in the form of pharmaceutically acceptable salts.

The term "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts.

For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Compounds containing an amine functional group or a nitrogen-containing heteroaryl group may be basic in nature and may react with any number of inorganic and organic acids to from the corresponding pharmaceutically acceptable salts. In some embodiments, the salt is an acid addition salt form of the compound (e.g., as described herein). In some embodiments, the acid addition salt is an inorganic acid salt. In some embodiments, the acid addition salt is an organic acid salt.

Compounds included in the present compositions that are acidic in nature are capable of forming base salts with various pharmacologically acceptable cations.

Compounds included in the present compositions that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

It is understood that all variations of salts, solvates, hydrates, prodrugs and stereoisomers are meant to be encompassed by the present disclosure.

4.1.4 Prodrugs

Aspects of this disclosure include prodrug forms of any of the compounds described herein. Any convenient prodrug forms of the subject compounds can be prepared, for example, according to the strategies and methods described by Rautio et al. ("Prodrugs: design and clinical applications", Nature Reviews Drug Discovery 7, 255-270 (February 2008)).

The term "prodrug" refers to an agent which is converted into a biologically active drug in vivo by some physiological or chemical process. In some embodiments, a prodrug is converted to the desired drug form, when subjected to a biological system at physiological pH. In some embodiments, a prodrug is enzymatically converted to the desired drug form, when subjected to a biological system.

Prodrugs forms of any of the compounds described herein can be useful, for example, to provide particular therapeutic benefits as a consequence of an extension of the half-life of the resulting compound in the body, or a reduction in the active dose required.

Pro-drugs can also be useful in some situations, as they may be easier to administer than the parent drug. They may, for instance, be bioavailable by oral administration whereas the parent drug is not. The pro-drug may also have improved solubility in pharmacological compositions over the parent drug.

Prodrug forms or derivatives of a compound of this disclosure generally include a promoiety substituent at a suitable labile site of the compound. The promoiety refers to the group that can be removed by enzymatic or chemical reactions, when a prodrug is converted to the drug in vivo.

In some embodiments, the promoiety is a group (e.g., a optionally substituted $C_{1-6}$ alkanoyl, or an optionally substituted $C_{1-6}$ alkyl) attached via an ester linkage to a hydroxyl group or a carboxylic acid group of the compound or drug.

4.2 Compound Synthesis

Compounds of the present disclosure may be synthesized according to standard methods known in the art [see, e.g. Morrison and Boyd in "Organic Chemistry", $6^{th}$ edition, Prentice Hall (1992)]. Some compounds and/or intermediates of the present disclosure may be commercially available, known in the literature, or readily obtainable by those skilled in the art using standard procedures. Some compounds of the present disclosure may be synthesized using schemes, examples, or intermediates described herein. Where the synthesis of a compound, intermediate or variant thereof is not fully described, those skilled in the art can recognize that the reaction time, number of equivalents of reagents and/or temperature may be modified from reactions described herein to prepare compounds presented or intermediates or variants thereof and that different work-up and/or purification techniques may be necessary or desirable to prepare such compounds, intermediates, or variants.

Synthesized compounds may be validated for proper structure by methods known to those skilled in the art, for example by nuclear magnetic resonance (NMR) spectroscopy and/or mass spectrometry.

In various embodiments, the compound as described herein is represented by the structure of one of the compounds in Table 1. The present disclosure is meant to encompass a compound of any one of Table 1, or a salt, a single stereoisomer, a mixture of stereoisomers and/or an isotopically labelled form thereof.

4.3 Pharmaceutical Compositions

Compounds of the present disclosure may be included in a composition that includes one or more such compounds and at least one excipient (e.g., a pharmaceutically acceptable excipient). Such compositions may include an inhibitor compound of PDE-5, and/or the androgen receptor (e.g., as described herein).

The compounds described herein can find use in pharmaceutical compositions for administration to a subject in need thereof in a variety of therapeutic applications where inhibition of PDE-5 and/or the androgen receptor are desirable. In some embodiments, compounds of the present disclosure may be formulated as pharmaceutical compositions.

Accordingly, in a second aspect, the present disclosure provides pharmaceutical compositions comprising at least one compound described herein, a pharmaceutically acceptable salt thereof, or a prodrug thereof, and at least one pharmaceutically acceptable excipient.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

The terms "pharmaceutically acceptable excipient," "pharmaceutically acceptable diluent," "pharmaceutically acceptable carrier," and "pharmaceutically acceptable adjuvant" are used interchangeably and refer to any ingredient other than the inventive compounds described herein (for example, a vehicle capable of suspending or dissolving the active compound, or any other convenient pharmaceutically acceptable carriers, excipients, diluent, adjuvant or additives) and having the properties of being substantially non-toxic and non-inflammatory in a patient. The phrase "pharmaceutically acceptable excipient" includes both one and more than one such excipient, diluent, carrier, and/or adjuvant. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing, or dispersing agents, sweeteners, and waters of hydration. In some embodiments, the pharmaceutical composition comprises a compound as described herein, a pharmaceutically acceptable salt thereof, or a prodrug thereof in a therapeutically effective amount.

The pharmaceutical composition may be formulated according to any convenient methods, and may be prepared in various forms for oral administration such as tablets, pills, powders, capsules, syrups, emulsions and microemulsions, or in forms for non-oral administration such as eye drops or preparations for intramuscular, intravenous or subcutaneous administration. In one example, the pharmaceutical composition may be administered through the eyes in the form of eyedrops. In one example, the pharmaceutical composition may be an ophthalmic composition, such as an eye drop composition.

In some embodiments, the pharmaceutical compositions are formulated for oral delivery. In a case wherein the pharmaceutical composition is prepared in a form for oral administration, examples of additives or carriers which may be used include cellulose, calcium silicate, corn starch, lactose, sucrose, dextrose, calcium phosphate, magnesium stearate, stearic acid, stearate, talc, surfactant, suspending agent, emulsifier and diluent. Examples of additives or carriers which may be used in a case wherein the pharmaceutical composition of the present invention is prepared as an injection include water, saline solution, glucose aqueous solution, pseudosugar solution, alcohol, glycol, ether (e.g., polyethylene glycol 400), oil, fatty acid, fatty acid ester, glyceride, surfactants, suspending agents and emulsifiers.

In some embodiments, the pharmaceutical compositions are formulated for parenteral administration to a subject in need thereof. In some parenteral embodiments, the pharmaceutical compositions are formulated for intravenous administration to a subject in need thereof. In some parenteral embodiments, the pharmaceutical compositions are formulated for subcutaneous administration to a subject in need thereof.

4.4 Methods of Modulating the Androgen Receptor (AR) and Phosphodiesterase 5 (PDE-5)

Aspects of the present disclosure include methods of modulating the androgen receptor and/or PDE-5 in a biological system or sample by contacting with compounds which exhibit dual functionality by: i) modulating the androgen receptor, and ii) modulating PDE-5. In some embodiments, the compound as described herein inhibits the androgen receptor in the biological system or sample. In another embodiment, the compound as described herein inhibits the PDE-5 in the biological system or sample.

In certain embodiments, the biological system or sample is in vitro. In some instances, the sample is a cellular sample.

"Androgen receptor" or "nuclear receptor subfamily 3, group c, member 4" or "NR3C4" is a type of nuclear receptor that is activated by binding any of the androgenic hormones, including testosterone and dihydrotestosterone in the cytoplasm and then translocating into the nucleus.

Phosphodiesterase 5 (PDE-5) is a phosphodiesterase. Inhibition of PDE-5 suppresses the decomposition of cGMP, which can then lead to increased activity of PKG along with increasing the concentration of cGMP. Increasing the activity of PKG can then cause phosphorylation of numerous biologically important targets, relaxation of the smooth muscles, and increase in the flow of blood.

The present disclosure provides compounds having potent PDE-5 inhibitory activity. The compounds can be assessed using in vitro enzyme assays. For example, Table 3 of Example 3 in the experimental section shows the $IC_{50}$ values for exemplary compounds in as in vitro PDE-5 assay.

The present disclosure also provides compounds having inhibitory and antagonistic activity against the androgen receptor (AR). The compounds can be assessed using cellular assays. For example, Table 4 of Example 4 in the experimental section shows the $IC_{50}$ values for exemplary compounds in an in vitro AR reporter assay. As illustrated in Example 4, tested compounds exhibited superior antagonistic activity against AR with comparable or more potent $IC_{50}$ values as compared to enzalutamide and apalutamide. Further, Table 5 of Example 5 in the experimental section shows the binding affinity for exemplary compounds in an in vitro radioligand binding assay. As illustrated in Example 5, exemplary compounds exhibited superior or comparable binding affinity and AR inhibition as compared to enzalutamide and apalutamide.

Aspects of the present disclosure include methods of inhibiting both PDE-5 and AR using PDE-5 and AR inhibitor compounds described herein. Such methods may include methods of inhibiting AR and PDE-5 in biological systems by contacting such systems with compounds of this disclosure (e.g., AR and PDE-5 inhibitor compounds having structures according to any of those of Table 1 or a pharmaceutically acceptable salt thereof).

In some embodiments, the method of inhibiting AR and PDE-5 comprises contacting a biological system or sample comprising AR and PDE-5 with an effective amount of any of the compounds or a pharmaceutically acceptable salt thereof as described herein, or a pharmaceutical composition as described herein to inhibit AR and PDE-5. In certain embodiments, the biological system or sample is in vitro. Biological systems may include, but are not limited to, cells, tissues, organs, bodily fluids, organisms, non-mammalian subjects, and mammalian subjects (e.g., humans).

The AR and PDE-5 inhibitors may inhibit the activity of AR and PDE-5 in a sample, e.g., as assessed by a AR or PDE-5 inhibition assay described in Examples 3 and 4. AR and PDE-5 inhibitors according to such methods may each have $IC_{50}$ values for AR and PDE-5 inhibition, (e.g., as assessed by the assays of Example 3-4) of less than 5000 nM, such as 1000 nM or less, 200 nM or less, 100 nM or less, or 20 nM or less. Biological systems may include subjects (e.g., human subjects).

In some embodiments of the method, the AR and PDE-5 inhibitors (e.g. the compound of formula (I) exhibit dual functionality. In some embodiment, the dual functionality of the compounds as describe herein are to inhibit AR and to inhibit PDE-5.

In some embodiments, the present disclosure provides methods of inhibiting AR and PDE-5 activity in a biological system (e.g., a subject). In some cases, the percentage of AR activity inhibited in a biological system (e.g., a subject) may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%. In some cases, the percentage of PDE-5 activity inhibited in a biological system (e.g., a subject) may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%.

In some cases, this level of inhibition and/or maximum inhibition of AR and PDE-5 activities may be achieved by from about 1 hour after administration to about 3 hours after administration, from about 2 hours after administration to about 4 hours after administration, from about 3 hours after administration to about 10 hours after administration, from about 5 hours after administration to about 20 hours after administration, or from about 12 hours after administration to about 24 hours after administration. Inhibition of AR and/or PDE-5 activity may continue throughout a period of at least 1 day, of at least 2 days, of at least 3 days, of at least 4 days, of at least 5 days, of at least 6 days, of at least 7 days, of at least 2 weeks, of at least 3 weeks, of at least 4 weeks, of at least 8 weeks, of at least 3 months, of at least 6 months, or at least 1 year. In some cases, this level of inhibition may be achieved through daily administration. Such daily administration may include administration for at least 2 days, for at least 3 days, for at least 4 days, for at least 5 days, for at least 6 days, for at least 7 days, for at least 2 weeks, for at least 3 weeks, for at least 4 weeks, for at least 2 months, for at least 4 months, for at least 6 months, for at least 1 year, or for at least 5 years. In some cases, subjects may be administered compounds or compositions of the present disclosure for the life of such subjects.

In some embodiments, compounds of the present disclosure may be used in assays to assess AR and PDE-5 inhibition. In some cases, compounds may be included in methods of drug discovery. In some embodiments, methods of the present disclosure include use of AR and PDE-5 inhibiting compounds of the present disclosure to assess AR and PDE-5 inhibition by other compounds. Such methods may include conjugating AR and PDE-5 inhibiting compounds with one or more detectable labels (e.g., fluorescent dyes) and measuring both AR and PDE-5 dissociation (via detectable label detection) in the presence of the other compounds. The detectable labels may include fluorescent compounds.

4.5 Therapeutic Indications

Aspects of the present disclosure include methods of treating therapeutic indications of interest using compounds and/or compositions disclosed herein. The term "therapeutic indication" refers to any symptom, condition, disorder, or disease that may be alleviated, stabilized, improved, cured, or otherwise addressed by some form of treatment or other therapeutic intervention (e.g., through AR and PDE-5 inhibitor administration). Therapeutic indications associated with aberrant AR and/or PDE-5 biological activity are referred to herein as "AR and/or PDE-5 related indications." In some embodiments, methods of the present disclosure may include treating AR and/or PDE-5 related indications by administering compounds and/or compositions disclosed herein (e.g., AR and PDE-5 inhibitor compounds).

In one embodiment, the methods of the present invention comprise administering an AR and PDE-5 inhibitor as the sole active ingredient or as a composition. The AR and PDE-5 inhibitors of the present invention are useful for a) benign prostate hyperplasia, prostate cancer; b) breast cancer, uterine cancer and ovarian cancer; and/or c) decreasing the incidence of, halting or causing a regression of prostate cancer.

Also encompassed within the scope of the present invention are methods for treating breast cancer, for delaying the progression of breast cancer, and for preventing and treating the recurrence of breast cancer and/or breast cancer metastasis, which comprise administering the selective androgen receptor modulators in combination with one or more therapeutic agents.

The terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

The terms "individual" and "subject" are used interchangeably and refer to a subject requiring treatment of a disease. More specifically, what is referred to is a human or non-human primate, mouse, dog, cat, horse, cow, rabbit, rat, or other mammal.

In some embodiments, one or more symptoms of the therapeutic indication of interest are reduced or alleviated in the subject after administration of the composition or compound as described herein.

In some embodiments, the method includes oral administration of the subject compound or composition. The administration dose may be administrated orally or non-orally depending on the purpose, in an amount effective at prevention or therapy in the individual or patient in question. When administering orally, the compound may be administered so that 0.01 to 1000 mg, more specifically 0.1 to 300 mg of the active agent is administered per 1 kg body weight, and when administering non-orally, the compound may be administered so that 0.01 to 100 mg, more specifically 0.1 to 50 mg of the active ingredient is administered per 1 kg body weight. The dose may be administered at one time or over multiple administrations. The administration dose for a specific individual or patient should be decided based on various related factors such as the body weight, age, sex, health, diet, administration intervals, method of administration and severity of the illness, and may be appropriately increased or reduced by an expert. The administration doses stated above are not intended to limit the scope of the present invention in any manner. A physician or veterinarian have ordinary skill in related art may readily decide and prescribe an effective required dose for the pharmaceutical composition. For example, a physician or veterinarian may, beginning at levels less than that required for achieving the target therapeutic effect, gradually increase the dose of the compound of the present invention in a pharmaceutical composition until the intended effect is achieved.

The compounds and compositions of the present disclosure may be administered alone, in combination with a compound according to another example of the present disclosure, or in simultaneous, separate or sequential concomitant administration with at least one other therapeutic agent.

4.5.1 AR-Related Indications

Therapeutic indications associated with AR activity and/or dysfunction are referred to herein as "AR-related indications." In some embodiments, methods of the present disclosure may include treating AR-related indications by administering compounds and/or compositions disclosed herein (e.g., AR and PDE5 modulator compounds).

In some embodiments, the administration of the compounds of the present disclosure can cause significant changes in AR activity as illustrated by Examples 4 and 5.

4.5.2 PDE-5-Related Indications

Aspects of the present disclosure include methods of treating therapeutic indications of interest using compounds and/or compositions disclosed herein. Therapeutic indications associated with PDE5 activity and/or dysfunction are referred to herein as "PDE5-related indications." In some embodiments, methods of the present disclosure may include treating PDE5-related indications by administering compounds and/or compositions disclosed herein (e.g., PDE5 and AR inhibitor compounds).

PDE5 inhibitors are a well characterized class of agent having a variety of activities. A human phosphodiesterase5 (PDE5) inhibition assay in host cells can be used to assess the abilities of the compounds of the present disclosure to inhibit target PDE5. In some embodiments, the administration of the compounds of the present disclosure can cause significant changes in PDE5 activity as illustrated by Example 3.

4.6 Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

As used herein, the symbol " ⁓⁓⁓⁓⁓ " refers to a covalent bond comprising a single or a double bond.

The term "$C_x$-$C_y$" when used in conjunction with a chemical moiety, such as alkyl, alkenyl, or alkynyl is meant to include groups that contain from x to y carbons in the chain. For example, the term "$C_1$-$C_6$ alkyl" refers to substituted or unsubstituted saturated hydrocarbon groups, including straight-chain alkyl and branched-chain alkyl groups that contain from 1 to 6 carbons. In some embodiments, the term "($C_x$-$C_y$)alkylene" refers to a substituted or unsubstituted alkylene chain with from x to y carbons in the alkylene chain. For example "($C_x$-$C_y$)alkylene may be selected from methylene, ethylene, propylene, butylene, pentylene, and hexylene, any one of which is optionally substituted.

The term "alkyl" refers to an unbranched or branched saturated hydrocarbon chain. In some embodiments, alkyl as used herein has 1 to 20 carbon atoms (($C_1$-$C_{20}$)alkyl), 1 to 10 carbon atoms (($C_1$-$C_{10}$)alkyl), 1 to 8 carbon atoms (($C_1$-$C_8$)alkyl), 1 to 6 carbon atoms (($C_1$-$C_6$)alkyl), or 1 to 5 carbon atoms (($C_1$-$C_5$)alkyl). Examples include, but are not limited to, methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. For example, "butyl" can include n-butyl, sec-butyl, isobutyl and t-butyl, and "propyl" can include n-propyl and isopropyl. Unless stated otherwise specifically in the specification, an alkyl chain is optionally substituted by one or more substituents such as those substituents described herein.

The term "alkylene" refers to a straight divalent hydrocarbon chain linking the rest of the molecule to a radical group, consisting solely of carbon and hydrogen, containing no unsaturation, and preferably having from 1 to 20 carbon atoms (($C_1$-$C_{20}$)alkylene), 1 to 10 carbon atoms (($C_1$-$C_{10}$) alkylene), 1 to 6 carbon atoms (($C_1$-$C_6$)alkylene), or 1 to 5 carbon atoms (($C_1$-$C_5$)alkylene). Examples include, but are not limited to, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Unless stated otherwise specifically in the specification, an alkylene chain is optionally substituted by one or more substituents such as those substituents described herein. Examples include, methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—($CH_2$)$_6$—) and the like.

The term "alkenyl" refers to an aliphatic hydrocarbon group containing at least one carbon-carbon double bond including straight-chain, branched-chain and cyclic alkenyl groups. In some embodiments, the alkenyl group has 2-10 carbon atoms (a $C_{2-10}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl The term "alkynyl" refers to straight or branched monovalent hydrocarbyl groups having from 2 to 6 carbon atoms and preferably 2 to 3 carbon atoms and having at least 1 and preferably from 1 to 2 sites of acetylenic (C≡C—) unsaturation. Examples of such alkynyl groups include, but are not limited to, acetylenyl (C≡CH), and propargyl ($CH_2$C≡CH).

The term "aryl" refers to a monocyclic or polycyclic group having at least one hydrocarbon aromatic ring, wherein all of the ring atoms of the at least one hydrocarbon aromatic ring is carbon. Aryl may include groups with a single aromatic ring (e.g., phenyl) and multiple fused aromatic rings (e.g., naphthyl, anthryl). Aryl may further include groups with one or more aromatic hydrocarbon rings fused to one or more non-aromatic hydrocarbon rings (e.g., fluorenyl; 2,3-dihydro-1H-indene; 1,2,3,4-tetrahydronaphthalene). In certain embodiments, aryl includes groups with an aromatic hydrocarbon ring fused to a non-aromatic ring, wherein the non-aromatic ring comprises at least one ring heteroatom independently selected from the group consisting of N, O, and S. For example, in some embodiments, aryl includes groups with a phenyl ring fused to a non-aromatic ring, wherein the non-aromatic ring comprises at least one ring heteroatom independently selected from the group consisting of N, O, and S (e.g., chromane; thiochromane; 2,3-dihydrobenzofuran; indoline). In some embodiments, aryl as used herein has from 6 to 14 carbon atoms (($C_6$-$C_{14}$) aryl), or 6 to 10 carbon atoms (($C_6$-$C_{10}$)aryl). Where the aryl includes fused rings, the aryl may connect to one or more substituents or moieties of the formulae described herein through any atom of the fused ring for which valency permits.

The term "cycloalkyl" refers to a monocyclic or polycyclic saturated hydrocarbon. In some embodiments, cycloalkyl has 3 to 20 carbon atoms (($C_3$-$C_{20}$)cycloalkyl), 3 to 8 carbon atoms (($C_3$-$C_5$)cycloalkyl), 3 to 6 carbon atoms (($C_3$-$C_6$)cycloalkyl), or 3 to 5 carbon atoms (($C_3$-$C_5$)cycloalkyl). In some embodiments, cycloalkyl has 3 to 8 carbon atoms having single or multiple cyclic rings including fused, bridged, and spiro ring systems. Examples of suitable cycloalkyl groups include, but are not limited to, adamantyl, cyclopropyl, cyclobutyl, cyclopentyl, cyclooctyl, octahydropentalenyl, octahydro-1H-indene, decahydronaphthalene, cubane, bicyclo[3.1.0]hexane, and bicyclo[1.1.1]pentane, and the like.

The term "carbocycle" refers to a saturated, unsaturated or aromatic ring in which each atom of the ring is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl.

The term "heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems.

The term "heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (i.e., pyridinyl or furyl) or multiple condensed rings (i.e., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N—O), sulfinyl, or sulfonyl moieties. Preferred heteroaryls include 5 or 6 membered heteroaryls such as pyridinyl, pyrrolyl, indolyl, thiophenyl, and furanyl.

The term "heteroalkyl" refers to an alkyl substituent in which one or more of the carbon atoms and any attached hydrogen atoms are independently replaced with the same or different heteroatomic group. For example, 1, 2, or 3 carbon atoms may be independently replaced with the same or different heteroatomic substituent.

The term "substituted" refers to moieties having substituents replacing a hydrogen on one or more carbons or substitutable heteroatoms, e.g., an NH or NH2 of a compound. It will be understood that "substitution" or "substituted with" includes the implicit proviso that such substitution is in accordance with permitted valence of the substituted atom and the substituent, and that the substitution results in a stable compound. For example, stable compounds include, but is not limited to, compounds which do not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. The permissible substituents can be one or more and the same or different for appropriate organic compounds.

It will be understood by those skilled in the art that substituents can themselves be substituted, if appropriate.

The phrase "optionally substituted" refers to when a non-hydrogen substituent may or may not be present on a given atom, and, thus, the description includes structures wherein a non-hydrogen substituent is present and structures wherein a non-hydrogen substituent is not present.

Substituents are selected from:
(i) halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), and —$R^b$—S(O)$_t$N($R^a$)$_2$ (where t is 1 or 2); and (ii) alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo, thioxo, cyano, nitro, imino, oximo, hydrazine, —$R^b$$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); and wherein:
each $R^a$, $R^b$, and $R^c$ are independently selected from hydrogen, alkyl, cycloalkyl, cycloalkylalkyl, aryl, aralkyl, heterocycloalkyl, heterocycloalkylalkyl, heteroaryl, and heteroarylalkyl; and each $R^a$, $R^b$, and $R^c$, valence permitting, may be optionally substituted with alkyl, alkenyl, alkynyl, halogen, haloalkyl, haloalkenyl, haloalkynyl, oxo, thioxo, cyano, nitro, imino, oximo, hydrazine, and hydroxyl.

The term "isomers" refers to two or more compounds comprising the same numbers and types of atoms, groups or components, but with different structural arrangement and connectivity of the atoms.

The term "tautomer" refers to one of two or more structural isomers which readily convert from one isomeric form to another and which exist in equilibrium.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their respective enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaemo, Classics in Stereoselective Synthesis, Wiley-VCH: Weinheim, 2009.

Geometric isomers, resulting from the arrangement of substituents around a carbon-carbon double bond or arrangement of substituents around a cycloalkyl or heterocyclic ring, can also exist in the compounds of the present disclosure. The symbol = denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituent on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compound wherein the substituents are disposed on both the same and opposite sides of the plane of the ring are designated "cis/trans."

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a 10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

A dash ("-") symbol that is not between two letters or symbols refers to a point of bonding or attachment for a substituent. For example, —NH$_2$ is attached through the nitrogen atom.

The terms "active agent," "drug," "pharmacologically active agent," and "active pharmaceutical ingredient" are used interchangeably to refer to a compound or composition which, when administered to a subject, induces a desired pharmacologic or physiologic effect by local or systemic action or both.

The terms "individual," "host," and "subject," are used interchangeably, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines, felines, equines, bovines, ovines, rodentia, etc. and primates, i.e., non-human primates, and humans. Non-human animal models, i.e., mammals, non-human primates, murines, lagomorpha, etc. may be used for experimental investigations.

"Patient" refers to a human subject.

The terms "treating," "treatment," and the like, refer to obtaining a desired pharmacologic and/or physiologic effect, such as reduction of one or more symptoms of the disease or disorder. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (i.e., including diseases that may be associated with or caused by a primary disease); (b) inhibiting the disease, i.e., arresting its development; and (c) relieving the disease, i.e., causing regression of the disease (i.e., reduction in pain or other symptom).

The term "amelioration" or any grammatical variation thereof (e.g., ameliorate, ameliorating, and amelioration etc.), includes, but is not limited to, delaying the onset, or reducing the severity of a disease or condition (e.g., diarrhea, bacteremia and/or endotoxemia). Amelioration, as used herein, does not require the complete absence of symptoms.

The phrase "therapeutically effective amount" refers to the amount of a compound that, when administered to a mammal or other subject for treating a disease, condition, or disorder, is sufficient to affect such treatment for the disease, condition, or disorder. The "therapeutically effective amount" will vary depending on the compound, the disease and its severity and the age, weight, etc., of the subject to be treated.

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the present technology. Procedures for inserting such labels into the compounds of the present technology will be readily apparent to those skilled in the art based on the disclosure herein.

4.7 Exemplary Embodiments

As described herein, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Notwithstanding the appended claims, aspects of the present disclosure are illustrated by the following clauses.

Clause 1. A compound of formula (I):

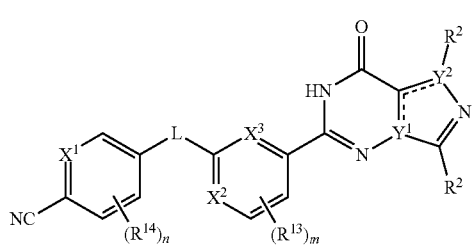

(I)

or a solvate, a hydrate, a prodrug, and/or a stereoisomer thereof, or a pharmaceutically acceptable salt thereof, wherein:

L is a linking moiety;

$R^1$ and $R^2$ are independently selected from —H, optionally substituted $(C_1-C_6)$alkyl, optionally substituted $(C_3-C_6)$cycloalkyl, optionally substituted $(C_1-C_6)$alkoxy, and optionally substituted $(C_2-C_4)$alkenyl;

each $R^{13}$ is selected from —H, optionally substituted $(C_1-C_6)$alkyl, and optionally substituted $(C_1-C_6)$alkoxy;

each $R^{14}$ is independently selected from —H, —CN, —OH, —NH$_2$, —NO$_2$, halogen, optionally substituted $(C_1-C_5)$alkyl, optionally substituted $(C_1-C_5)$haloalkyl, optionally substituted $(C_1-C_5)$alkoxy, optionally substituted $(C_3-C_6)$cycloalkyl, and optionally substituted $(C_2-C_4)$alkenyl;

$X^1$ is N or $CR^{14}$;

$X^2$ and $X^3$ are independently selected from N and $CR^{13}$;

$Y^1$ and $Y^2$ are independently selected from N and C, wherein one of $Y^1$ and $Y^2$ is N;

m is 0 to 2; and n is 1 to 4.

Clause 2. The compound of clause 1, wherein the compound is of formula (Ia):

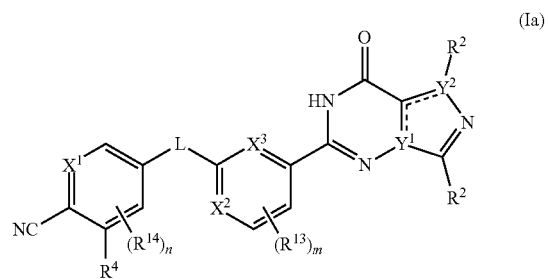

(Ia)

or a solvate, a hydrate, a prodrug, and/or a stereoisomer thereof, or a pharmaceutically acceptable salt thereof, wherein:

each $R^{13}$ is selected from —H, halogen and optionally substituted $(C_1-C_6)$alkoxy; and $R^4$ and each $R^{14}$ is independently selected from —H, —CN, —OH, —NH$_2$, —NO$_2$, halogen, optionally substituted $(C_1-C_5)$alkyl, and optionally substituted $(C_1-C_5)$haloalkyl.

Clause 3. The compound of clause 1 or 2, or a solvate, a hydrate, a prodrug, and/or a stereoisomer thereof, or a pharmaceutically acceptable salt thereof, wherein -L- is -A-B—, wherein:

A- is selected from a covalent bond, optionally substituted $(C_6-C_{12})$ aryl or $(C_3-C_{12})$ heteroaryl, optionally substituted-$(C_3-C_{12})$ heteroaryl-$(C_1-C_5)$alkylene-, optionally substituted 3- to 6-membered heterocycle, —NHC(O)R$^5$—,

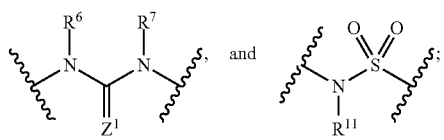

and

—B— is selected from a covalent bond, optionally substituted 3- to 6-membered heterocycle, —NHC(O)R$^5$—, —O—, —S—, —NR$^{11}$—,

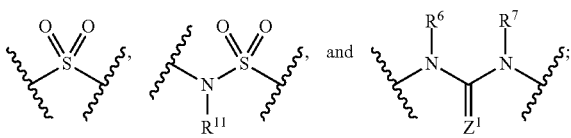

wherein:
R[11] is H or optionally substituted (C$_1$-C$_3$)alkyl;
R[5] is selected from —OH, —(C$_1$-C$_5$)alkyl, —(C$_1$-C$_5$) haloalkyl and optionally substituted (C$_1$-C$_5$)alkylene;
R[6] and R[7] are each independently —H or optionally substituted (C$_1$-C$_3$)alkyl; or R[6] and R[7] together with the nitrogen atom to which they are attached are cyclically linked to provide an optionally substituted 3- to 6-membered heterocycle;
Z[1] is selected from O and S; and
at least one of -A- and —B— is not a covalent bond.

Clause 4. The compound of clause 3, or a solvate, a hydrate, a prodrug, and/or a stereoisomer thereof, or a pharmaceutically acceptable salt thereof, wherein -A- is

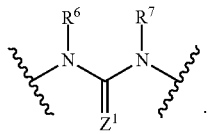

Clause 5. The compound of clause 4, wherein the compound is of formula (IIa) or (IIb):

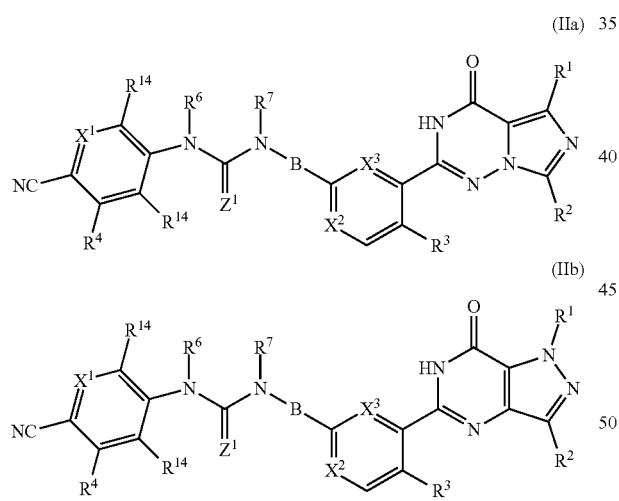

or a solvate, a hydrate, a prodrug, and/or a stereoisomer thereof, or a pharmaceutically acceptable salt thereof, wherein:
R[3] is selected from —H, and optionally substituted (C$_1$-C$_6$)alkoxy; and
—B— is selected from covalent bond and optionally substituted 3- to 6-membered heterocycle.

Clause 6. The compound of clause 5, or a solvate, a hydrate, a prodrug, and/or a stereoisomer thereof, or a pharmaceutically acceptable salt thereof, wherein R[6] and R[7] together with the nitrogen atom to which they are attached are cyclically linked to provide an optionally substituted 3- to 6-membered heterocycle.

Clause 7. The compound of clause 6, wherein the compound is of formula (IIIa) or (IIIb):

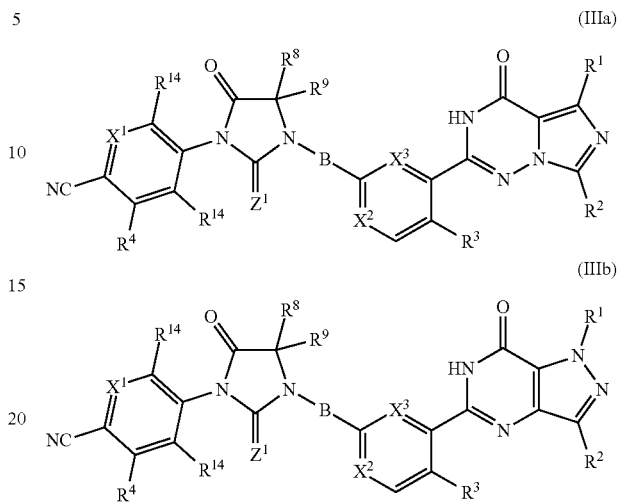

or a solvate, a hydrate, a prodrug, and/or a stereoisomer thereof, or a pharmaceutically acceptable salt thereof, wherein:
R[8] and R[9] are independently selected from —H and optionally substituted (C$_1$-C$_3$)alkyl, or R[8] and R[9] together with the carbon atom to which they are attached are cyclically linked to provide an optionally substituted 3- to 6-membered carbocycle or optionally substituted 3- to 6-membered heterocycle; and
Z[1] is O or S.

Clause 8. The compound of clause 7, wherein B is a covalent bond and the compound is of formula (IVa) or (IVb):

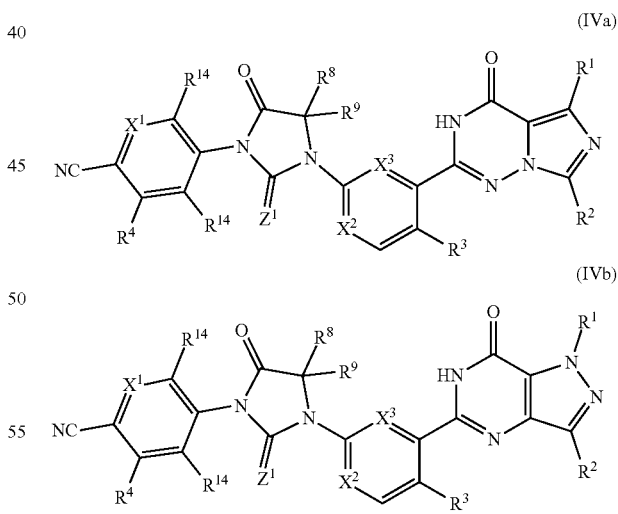

or a solvate, a hydrate, a prodrug, and/or a stereoisomer thereof, or a pharmaceutically acceptable salt thereof.

Clause 9. The compound of clause 7, or a solvate, a hydrate, a prodrug, and/or a stereoisomer thereof, or a pharmaceutically acceptable salt thereof, wherein —B— is an optionally substituted 4- to 6-membered heterocycle.

Clause 10. The compound of clause 9, wherein the compound is of formula (Va) or (Vb):

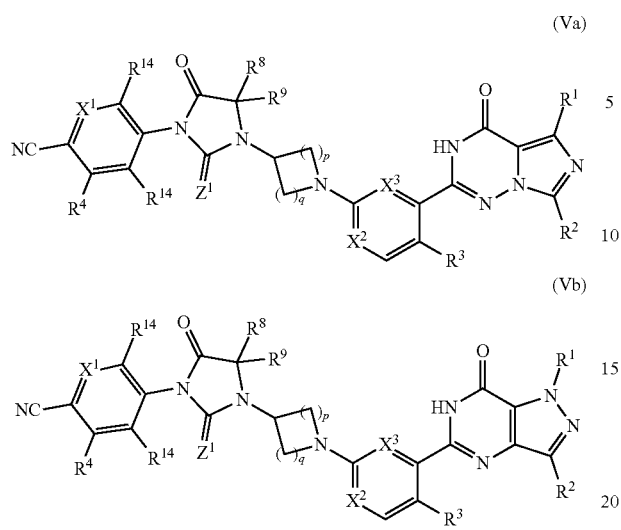

(Va)

(Vb)

or a solvate, a hydrate, a prodrug, and/or a stereoisomer thereof, or a pharmaceutically acceptable salt thereof, wherein p and q are independently 1 or 2.

Clause 11. The compound of any one of clauses 9 to 10, or a solvate, a hydrate, a prodrug, and/or a stereoisomer thereof, or a pharmaceutically acceptable salt thereof, wherein —B— is

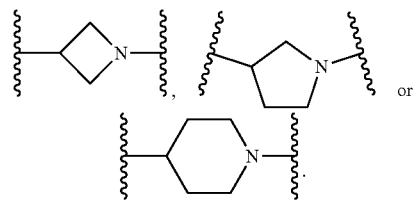

or.

Clause 12. The compound of any one of clauses 7 to 11, or a solvate, a hydrate, a prodrug, and/or a stereoisomer thereof, or a pharmaceutically acceptable salt thereof, wherein $R^8$ is —H.

Clause 13. The compound of any one of clauses 7 to 12, or a solvate, a hydrate, a prodrug, and/or a stereoisomer thereof, or a pharmaceutically acceptable salt thereof, wherein $R^9$ is —H.

Clause 14. The compound of any one of clauses 7 to 12, or a solvate, a hydrate, a prodrug, and/or a stereoisomer thereof, or a pharmaceutically acceptable salt thereof, wherein $R^9$ is optionally substituted $(C_1\text{-}C_3)$alkyl.

Clause 15. The compound of any one of clauses 7 to 11, or a solvate, a hydrate, a prodrug, and/or a stereoisomer thereof, or a pharmaceutically acceptable salt thereof, wherein $R^8$ and $R^9$ are each independently optionally substituted $(C_1\text{-}C_3)$alkyl.

Clause 16. The compound of any one of clauses 7 to 15, or a solvate, a hydrate, a prodrug, and/or a stereoisomer thereof, or a pharmaceutically acceptable salt thereof, wherein $Z^1$ is S.

Clause 17. The compound of clause 16, or a solvate, a hydrate, a prodrug, and/or a stereoisomer thereof, or a pharmaceutically acceptable salt thereof, wherein -A- is selected from:

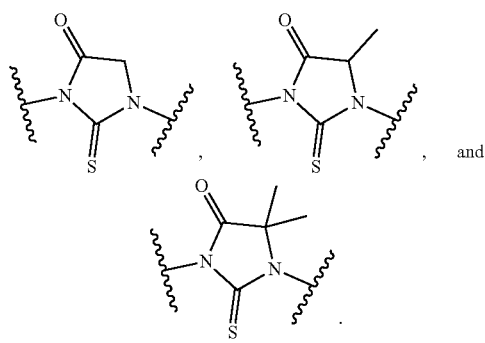

, and

.

Clause 18. The compound of any one of clauses 7 to 11, or a solvate, a hydrate, a prodrug, and/or a stereoisomer thereof, or a pharmaceutically acceptable salt thereof, wherein $R^8$ and $R^9$ together with the carbon atom to which they are attached are cyclically linked to provide an optionally substituted 3- to 6-membered carbocycle or optionally substituted 3- to 6-membered heterocycle.

Clause 19. The compound of clause 18, or a solvate, a hydrate, a prodrug, and/or a stereoisomer thereof, or a pharmaceutically acceptable salt thereof, wherein the optionally substituted 3- to 6-membered carbocycle or optionally substituted 3- to 6-membered heterocycle is selected from optionally substituted cyclobutyl, optionally substituted cyclopentyl, and optionally substituted tetrahydrofuran.

Clause 20. The compound of clause 18, or a solvate, a hydrate, a prodrug, and/or a stereoisomer thereof, or a pharmaceutically acceptable salt thereof, wherein -A- is selected from

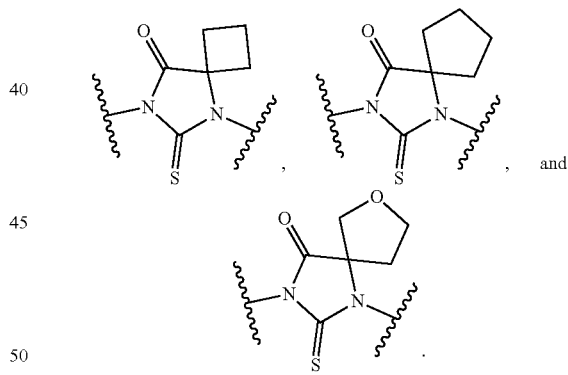

, and

.

Clause 21. The compound of clause 5, wherein $R^6$ and $R^7$ are each —H and the compound is of formula (VIa) or (VIb):

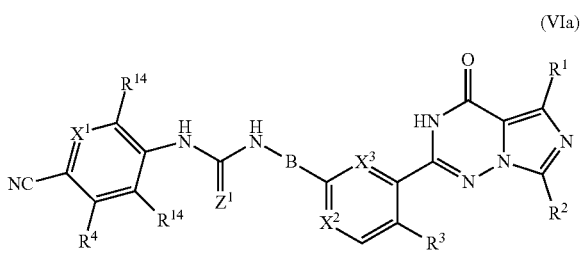

(VIa)

(VIb)

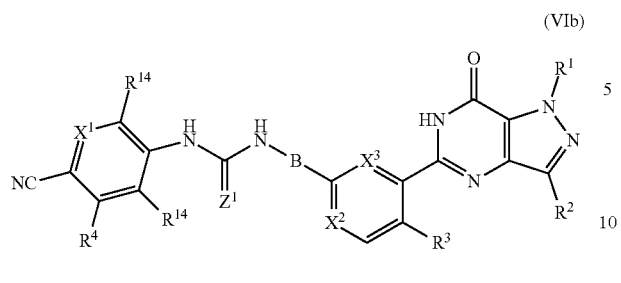

or a solvate, a hydrate, a prodrug, and/or a stereoisomer thereof, or a pharmaceutically acceptable salt thereof.

Clause 22. The compound of clause 21, wherein —B— is a bond and the compound is of formula (VIIa) or (VIIb):

(VIIa)

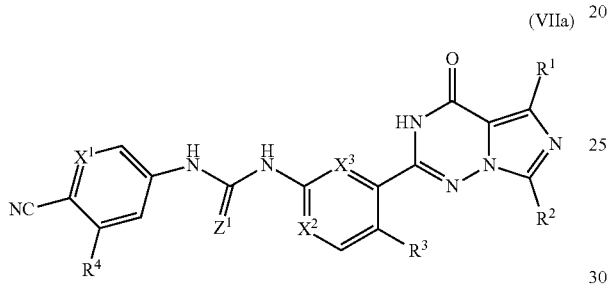

(VIIb)

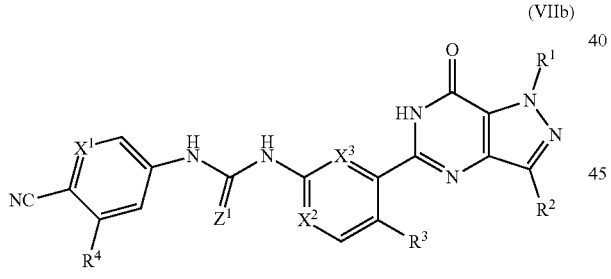

or a solvate, a hydrate, a prodrug, and/or a stereoisomer thereof, or a pharmaceutically acceptable salt thereof.

Clause 23. The compound of clause 3, or a solvate, a hydrate, a prodrug, and/or a stereoisomer thereof, or a pharmaceutically acceptable salt thereof, wherein —B— is

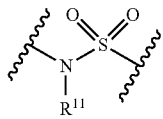

and $R^{11}$ is —H or optionally substituted $(C_1-C_3)$alkyl.

Clause 24. The compound of clause 23, wherein the compound is of formula (VIIIa) or (VIIIb):

(VIIIa)

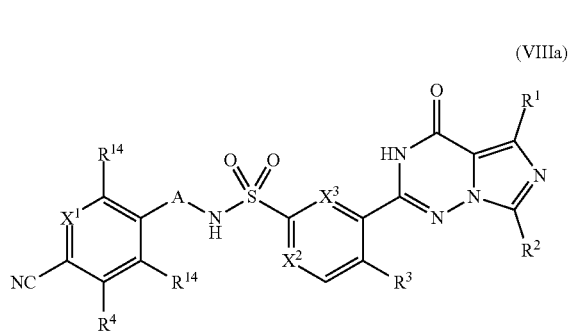

(VIIIb)

or a solvate, a hydrate, a prodrug, and/or a stereoisomer thereof, or a pharmaceutically acceptable salt thereof, wherein $R^3$ is selected from —H, and optionally substituted $(C_1-C_5)$alkoxy.

Clause 25 The compound of clause 23 or 24, or a solvate, a hydrate, a prodrug, and/or a stereoisomer thereof, or a pharmaceutically acceptable salt thereof, wherein -A- is an optionally substituted 3- to 6-membered heterocycle.

Clause 26. The compound of clause 25, or a solvate, a hydrate, a prodrug, and/or a stereoisomer thereof, or a pharmaceutically acceptable salt thereof, wherein -A- is

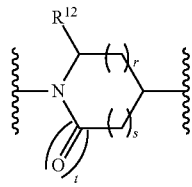

wherein:

$R^{12}$ is selected from —H, —OH, optionally substituted $(C_1-C_3)$alkyl, and optionally substituted $(C_1-C_5)$haloalkyl; and r, s and t are independently is 0 or 1.

Clause 27. The compound of clause 26, or a solvate, a hydrate, a prodrug, and/or a stereoisomer thereof, or a pharmaceutically acceptable salt thereof, wherein -A- is selected from:

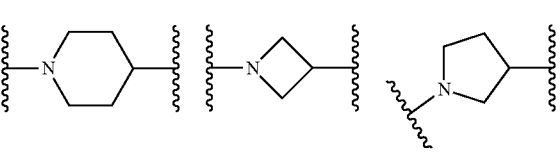

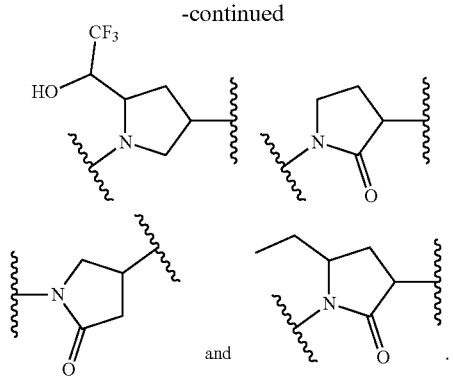

Clause 28. The compound of clause 23 or 24, or a solvate, a hydrate, a prodrug, and/or a stereoisomer thereof, or a pharmaceutically acceptable salt thereof, wherein -A- is a covalent bond.

Clause 29. The compound of clause 28, wherein the compound is of formula (IXa) or (IXb):

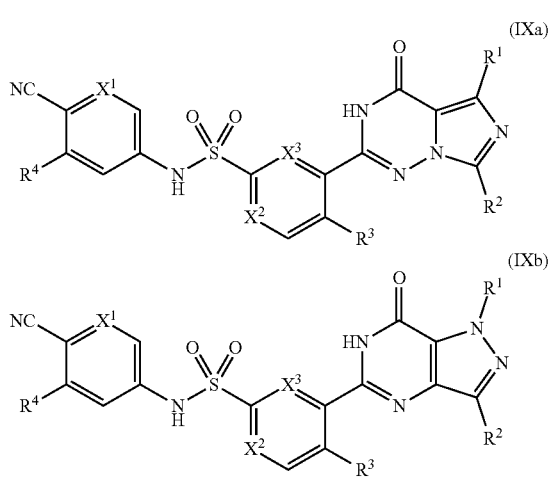

or a solvate, a hydrate, a prodrug, and/or a stereoisomer thereof, or a pharmaceutically acceptable salt thereof.

Clause 30. The compound of clause 23 or 24, or a solvate, a hydrate, a prodrug, and/or a stereoisomer thereof, or a pharmaceutically acceptable salt thereof, wherein -A- is an optionally substituted —($C_3$-$C_{12}$)heteroaryl-($C_1$-$C_5$)alkylene-.

Clause 31. The compound of clause 30, or a solvate, a hydrate, a prodrug, and/or a stereoisomer thereof, or a pharmaceutically acceptable salt thereof, wherein -A- is

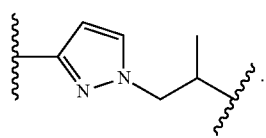 [SMILES: *c1ccn(CC(*)C)n1]

Clause 32. The compound of clause 3, or a solvate, a hydrate, a prodrug, and/or a stereoisomer thereof, or a pharmaceutically acceptable salt thereof, wherein -A- is an optionally substituted 3- to 6-membered heterocycle.

Clause 33. The compound of clause 32, or a solvate, a hydrate, a prodrug, and/or a stereoisomer thereof, or a pharmaceutically acceptable salt thereof, wherein -A- is

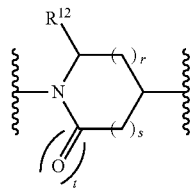

wherein:

$R^{12}$ is selected from —H, —OH, optionally substituted ($C_1$-$C_3$)alkyl and optionally substituted ($C_1$-$C_5$)haloalkyl; and r, s and t are independently is 0 or 1.

Clause 34. The compound of clause 33, or a solvate, a hydrate, a prodrug, and/or a stereoisomer thereof, or a pharmaceutically acceptable salt thereof, wherein -A- is selected from

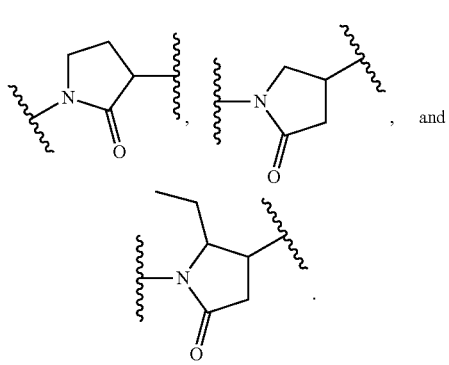

Clause 35. The compound of clause 33, wherein the compound is of formula (Xa) or (Xb);

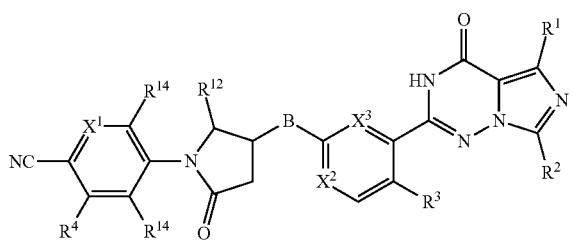

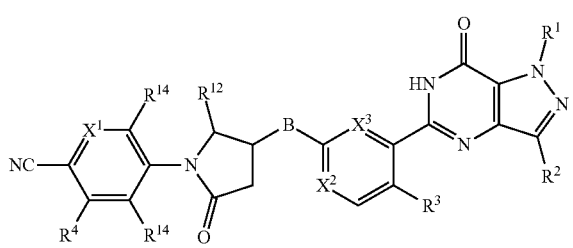

or a solvate, a hydrate, a prodrug, and/or a stereoisomer thereof, or a pharmaceutically acceptable salt thereof, wherein:

$R^3$ is selected from —H, and optionally substituted $(C_1-C_6)$alkoxy; and $R^{12}$ is —H, or optionally substituted $(C_1-C_3)$alkyl.

Clause 36. The compound of clause 35, or a solvate, a hydrate, a prodrug, and/or a stereoisomer thereof, or a pharmaceutically acceptable salt thereof, wherein $R^{12}$ is ethyl.

Clause 37. The compound of any one of clauses 32 to 36, or a solvate, a hydrate, a prodrug, and/or a stereoisomer thereof, or a pharmaceutically acceptable salt thereof, wherein —B— is —O—, —S—, —NH—, —SO$_2$—, or —NHSO$_2$—.

Clause 38. The compound of clause 3, or a solvate, a hydrate, a prodrug, and/or a stereoisomer thereof, or a pharmaceutically acceptable salt thereof, wherein -A- is —NHC(O)R$^5$—.

Clause 39. The compound of clause 38, or a solvate, a hydrate, a prodrug, and/or a stereoisomer thereof, or a pharmaceutically acceptable salt thereof, wherein $R^5$ is

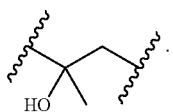

Clause 40. The compound of clause 39, wherein the compound is of formula (XIa) or (XIb):

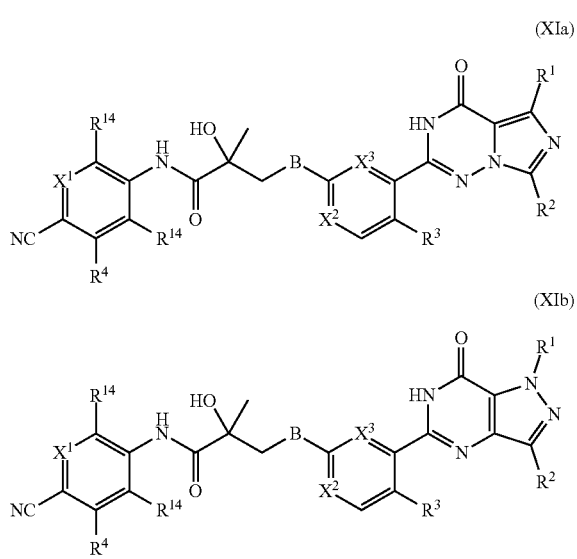

or a solvate, a hydrate, a prodrug, and/or a stereoisomer thereof, or a pharmaceutically acceptable salt thereof, wherein $R^3$ is selected from —H, and optionally substituted $(C_1-C_6)$alkoxy.

Clause 41. The compound of any one of clauses 38 to 40, or a solvate, a hydrate, a prodrug, and/or a stereoisomer thereof, or a pharmaceutically acceptable salt thereof, wherein —B— is selected from —O—, —S—, —SO$_2$— and —NHSO$_2$—.

Clause 42. The compound of any one of clauses 1 to 41, or a solvate, a hydrate, a prodrug, and/or a stereoisomer thereof, or a pharmaceutically acceptable salt thereof, wherein $R^1$ is optionally substituted $(C_1-C_6)$alkyl.

Clause 43. The compound of clause 42, or a solvate, a hydrate, a prodrug, and/or a stereoisomer thereof, or a pharmaceutically acceptable salt thereof, wherein $R^1$ is —CH$_3$.

Clause 44. The compound of any one of clauses 1 to 43, wherein $R^2$ is optionally substituted $(C_1-C_6)$alkyl.

Clause 45. The compound of clause 44, or a solvate, a hydrate, a prodrug, and/or a stereoisomer thereof, or a pharmaceutically acceptable salt thereof, wherein $R^2$ is n-propyl.

Clause 46. The compound of any one of clauses 1 to 45, or a solvate, a hydrate, a prodrug, and/or a stereoisomer thereof, or a pharmaceutically acceptable salt thereof, wherein $R^3$ is optionally substituted $(C_1-C_3)$alkoxy.

Clause 47. The compound of clause 46, or a solvate, a hydrate, a prodrug, and/or a stereoisomer thereof, or a pharmaceutically acceptable salt thereof, wherein $R^3$ is ethoxy.

Clause 48. The compound of any one of clauses 1 to 47, or a solvate, a hydrate, a prodrug, and/or a stereoisomer thereof, or a pharmaceutically acceptable salt thereof, wherein each $R^{14}$ and $R^4$ is optionally substituted $(C_1-C_5)$haloalkyl or halogen.

Clause 49. The compound of clause 48, or a solvate, a hydrate, a prodrug, and/or a stereoisomer thereof, or a pharmaceutically acceptable salt thereof, wherein each $R^{14}$ and $R^4$ is —CF$_3$, F or —Cl.

Clause 50. The compound of any one of clauses 1 to 49, or a solvate, a hydrate, a prodrug, and/or a stereoisomer thereof, or a pharmaceutically acceptable salt thereof, wherein $X^1$, $X^2$, and $X^3$ are each CH.

Clause 51. The compound of any one of clauses 1 to 49, or a solvate, a hydrate, a prodrug, and/or a stereoisomer thereof, or a pharmaceutically acceptable salt thereof, wherein $X^1$ is N.

Clause 52. The compound of clause 51, or a solvate, a hydrate, a prodrug, and/or a stereoisomer thereof, or a pharmaceutically acceptable salt thereof, wherein $X^2$ and $X^3$ are each CH.

Clause 53. The compound of any one of clauses 1 to 49, or a solvate, a hydrate, a prodrug, and/or a stereoisomer thereof, or a pharmaceutically acceptable salt thereof, wherein $X^2$ is N.

Clause 54. The compound of clause 53, or a solvate, a hydrate, a prodrug, and/or a stereoisomer thereof, or a pharmaceutically acceptable salt thereof, wherein $X^1$ and $X^3$ are each CH.

Clause 55. The compound of any one of clauses 1 to 49, or a solvate, a hydrate, a prodrug, and/or a stereoisomer thereof, or a pharmaceutically acceptable salt thereof, wherein $X^3$ is N.

Clause 56. The compound of clause 55, or a solvate, a hydrate, a prodrug, and/or a stereoisomer thereof, or a pharmaceutically acceptable salt thereof, wherein $X^1$ and $X^2$ are each CH.

Clause 57. The compound of clause 8, wherein the compound is of formula (IVc) or (IVd):

(IVc)

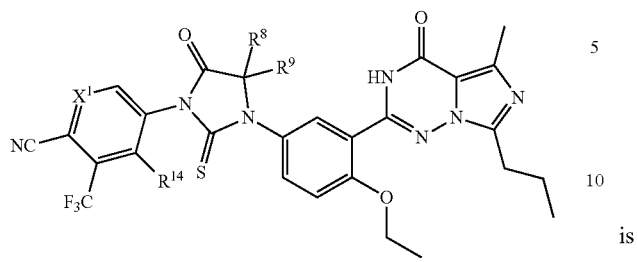

(IVd)

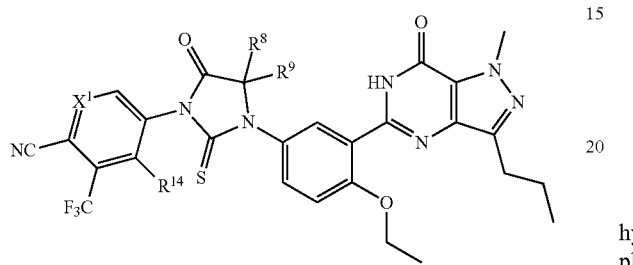

or a solvate, a hydrate, a prodrug, and/or a stereoisomer thereof, or a pharmaceutically acceptable salt thereof; wherein $R^{14}$ is —H or halogen (e.g., —F).

Clause 58. The compound of clause 57, or a solvate, a hydrate, a prodrug, and/or a stereoisomer thereof, or a pharmaceutically acceptable salt thereof, wherein $R^8$ and $R^9$ are each independently H or optionally substituted ($C_1$-$C_3$) alkyl (e.g., —$CH_3$).

Clause 59. The compound of clause 58, wherein the compound is selected from

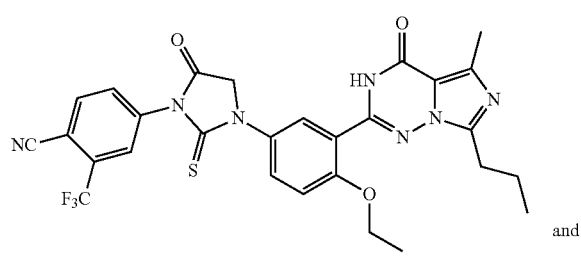

and

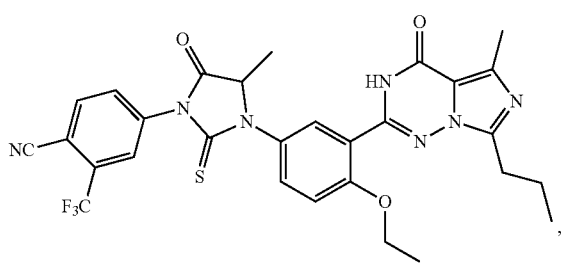

or a solvate, a hydrate, a prodrug, and/or a stereoisomer thereof, or a pharmaceutically acceptable salt thereof.

Clause 60. The compound of clause 58, wherein

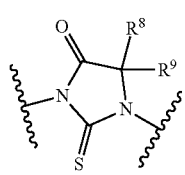

is

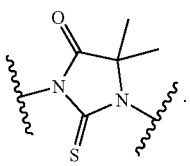 [SMILES: *N1C(=O)C(C)(C)N(*)C1=S]

Clause 61. The compound of clause 60, or a solvate, a hydrate, a prodrug, and/or a stereoisomer thereof, or a pharmaceutically acceptable salt thereof, wherein the compound is selected from

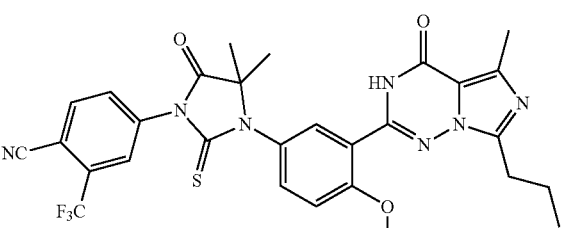

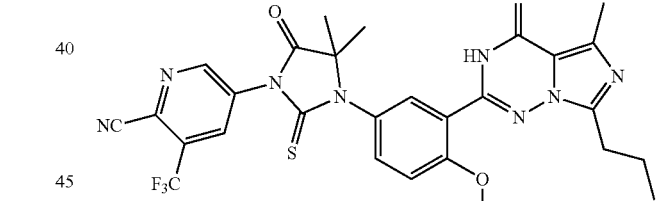

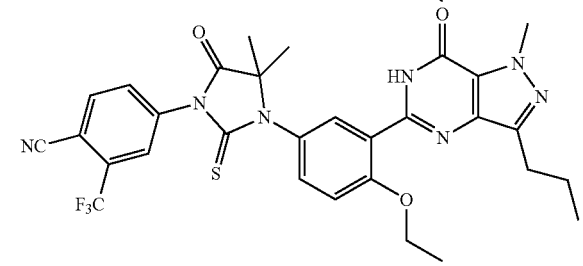

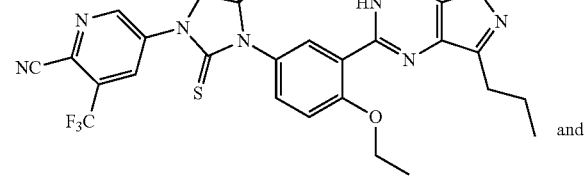

and

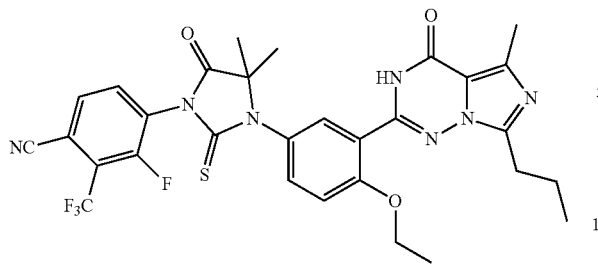

or a solvate, a hydrate, a prodrug, and/or a stereoisomer thereof, or a pharmaceutically acceptable salt thereof.

Clause 62. The compound of clause 57, or a solvate, a hydrate, a prodrug, and/or a stereoisomer thereof, or a pharmaceutically acceptable salt thereof, wherein $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle) that is selected from optionally substituted cyclobutyl, optionally substituted cyclopentyl, and optionally substituted tetrahydrofuran.

Clause 63. The compound of clause 62, or a solvate, a hydrate, a prodrug, and/or a stereoisomer thereof, or a pharmaceutically acceptable salt thereof, wherein

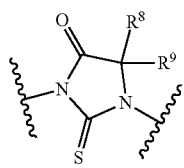

is

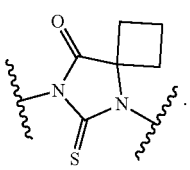 [SMILES: *N1C(=O)C2(CCC2)N(*)C1=S]

Clause 64. The compound of clause 63, wherein the compound is selected from:

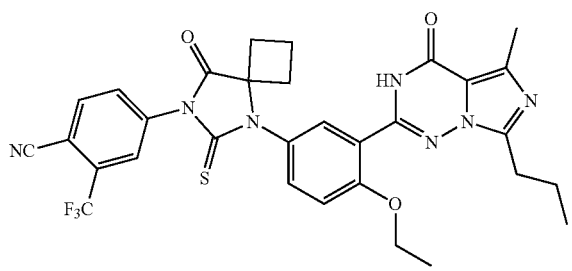

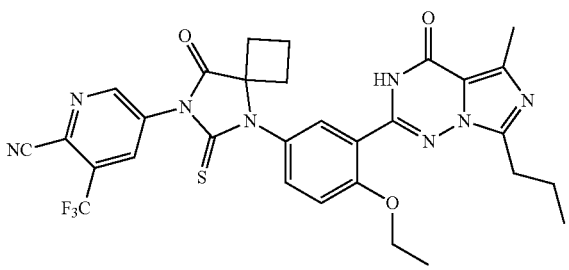

or a solvate, a hydrate, a prodrug, and/or a stereoisomer thereof, or a pharmaceutically acceptable salt thereof.

Clause 65. The compound of any one of clauses 60 to 64, wherein the compound is selected from:

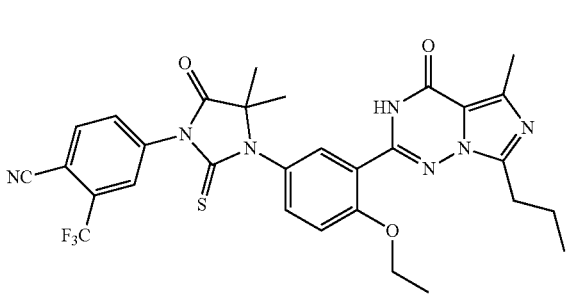

-continued

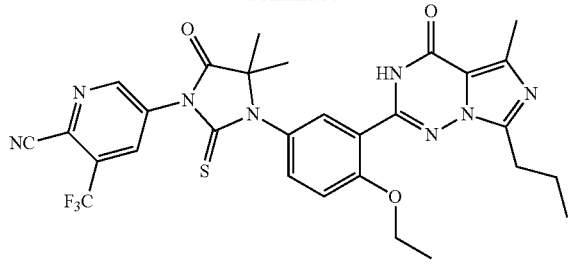

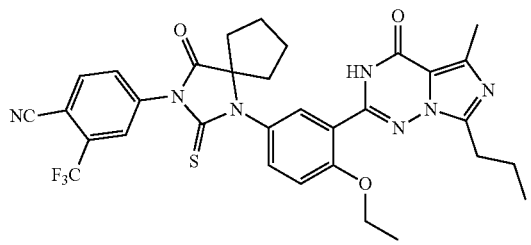

and

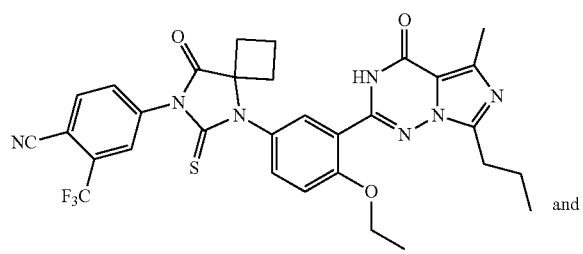

and

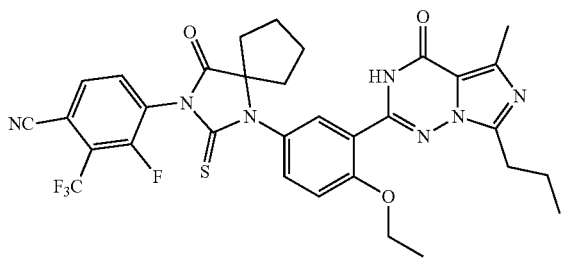

, or a solvate, a hydrate, a prodrug, and/or a stereoisomer thereof, or a pharmaceutically acceptable salt thereof.

Clause 68. The compound of clause 62, or a solvate, a hydrate, a prodrug, and/or a stereoisomer thereof, or a pharmaceutically acceptable salt thereof, wherein

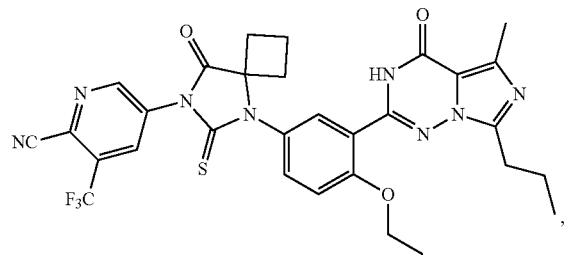

, or a solvate, a hydrate, a prodrug, and/or a stereoisomer thereof, or a pharmaceutically acceptable salt thereof.

Clause 66. The compound of clause 62, or a solvate, a hydrate, a prodrug, and/or a stereoisomer thereof, or a pharmaceutically acceptable salt thereof, wherein

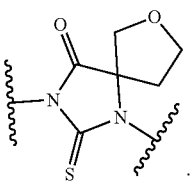

is

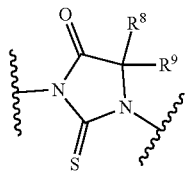

is

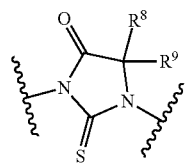

.

Clause 69. The compound of clause 68, wherein the compound is selected from:

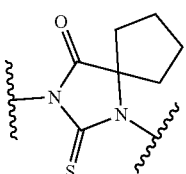

.

Clause 67. The compound of clause 66, wherein the compound is selected from:

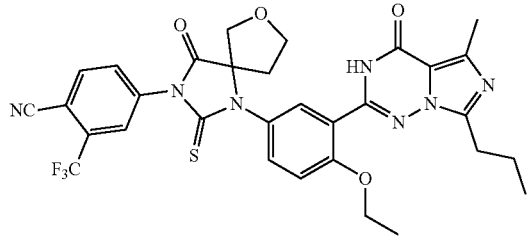

and

-continued

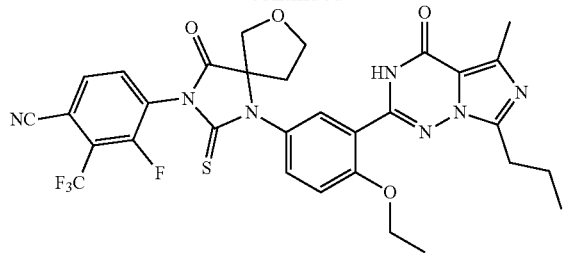

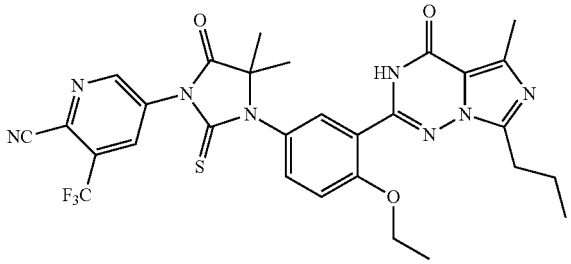

or a solvate, a hydrate, a prodrug, and/or a stereoisomer thereof, or a pharmaceutically acceptable salt thereof.

Clause 70. The compound of clause 8, wherein the compound is of formula (IVc):

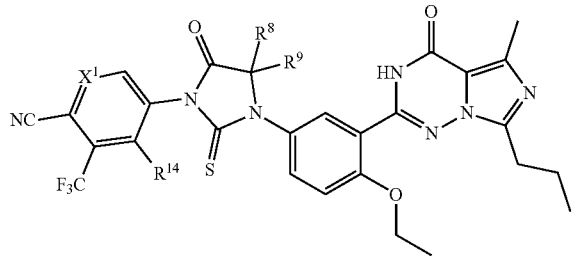

(IVc)

or a pharmaceutically acceptable salt thereof, wherein:
$X^1$ is CH or N;
$R^{14}$ is —H or halogen; and
$R^8$ and $R^9$ are each independently H or $(C_1-C_3)$alkyl (e.g., $R^8$ and $R^9$ are each —$CH_3$), or $R^8$ and $R^9$ together with the carbon atom to which they are attached are cyclically linked to provide an optionally substituted 3- to 5-membered carbocycle, or an optionally substituted 4-membered or 5-membered heterocycle (e.g., cyclopentane cyclobutane, cyclopentane, oxetane or tetrahydrofuran).

Clause 71. The compound of clause 70, wherein the compound is selected from:

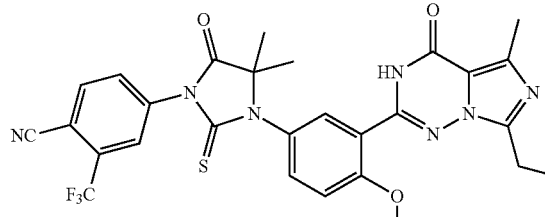

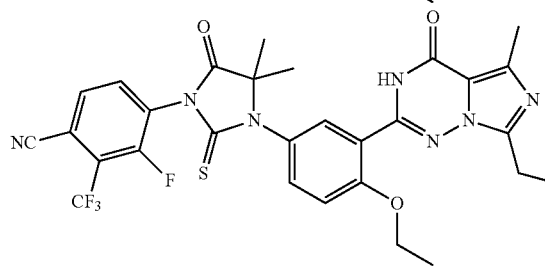

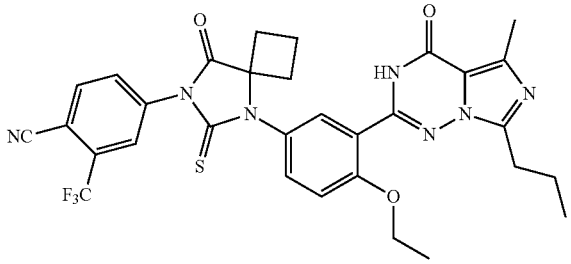

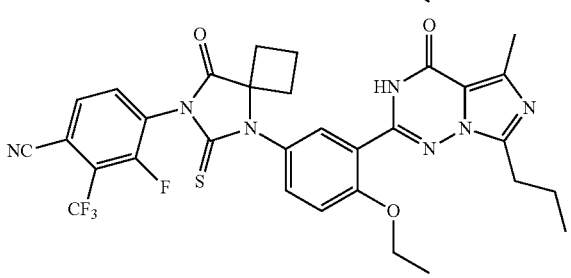

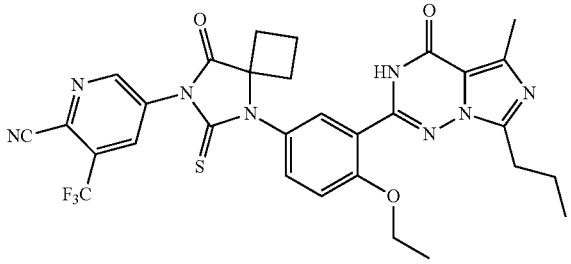

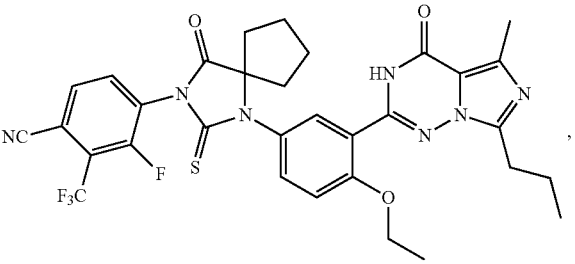

-continued

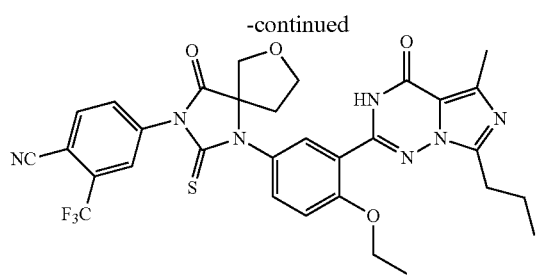

and

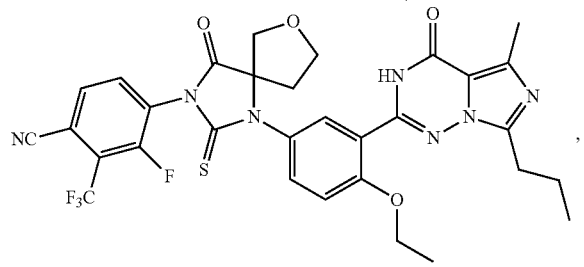

, or a pharmaceutically acceptable salt thereof.

Clause 72. The compound of clause 8, or a solvate, a hydrate, a prodrug, and/or a stereoisomer thereof, or a pharmaceutically acceptable salt thereof, wherein either $X^2$ is N and $X^3$ is CH, or $X^2$ is CH and $X^3$ is N.

Clause 73. The compound of clause 72, or a solvate, a hydrate, a prodrug, and/or a stereoisomer thereof, or a pharmaceutically acceptable salt thereof, wherein $R^8$ and $R^9$ are each optionally substituted $(C_1$-$C_3)$alkyl (e.g., —$CH_3$).

Clause 74. The compound of clause 73, wherein the compound is selected from:

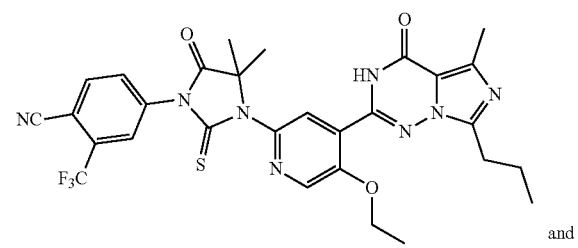

and

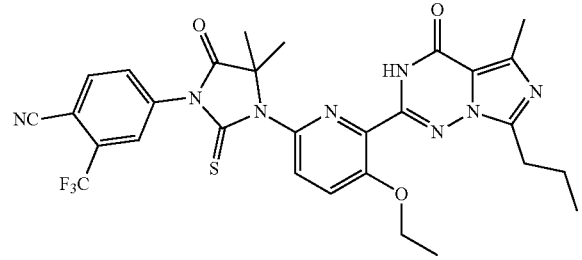

or a solvate, a hydrate, a prodrug, and/or a stereoisomer thereof, or a pharmaceutically acceptable salt thereof.

Clause 75. The compound of clause 72, or a solvate, a hydrate, a prodrug, and/or a stereoisomer thereof, or a pharmaceutically acceptable salt thereof, wherein $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle) that is selected from optionally substituted cyclobutyl, optionally substituted cyclopentyl, and optionally substituted tetrahydrofuran.

Clause 76. The compound of clause 75, wherein the compound is

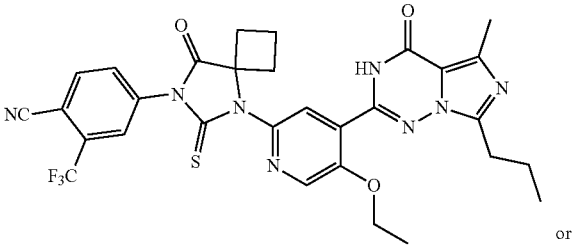

or

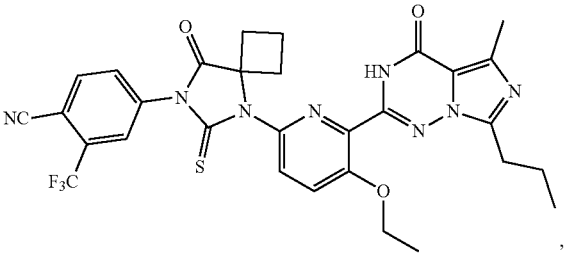

, or a solvate, a hydrate, a prodrug, and/or a stereoisomer thereof, or a pharmaceutically acceptable salt thereof.

Clause 77. The compound of clause 10, wherein the compound is of formula (Vc):

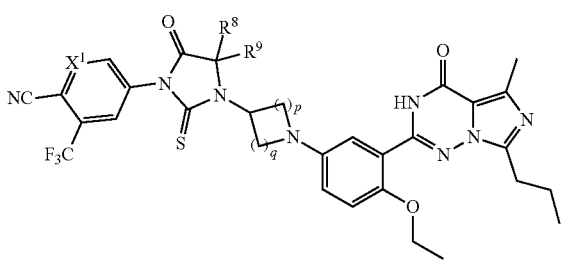

(Vc)

or a solvate, a hydrate, a prodrug, and/or a stereoisomer thereof, or a pharmaceutically acceptable salt thereof.

Clause 78. The compound of clause 77, or a solvate, a hydrate, a prodrug, and/or a stereoisomer thereof, or a pharmaceutically acceptable salt thereof, wherein $R^8$ and $R^9$ are each optionally substituted $(C_1$-$C_3)$alkyl (e.g., —$CH_3$).

Clause 79. The compound of clause 78, wherein the compound is selected from:

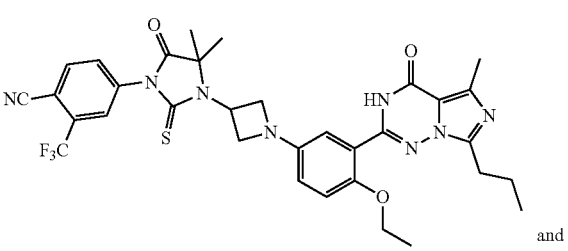

and

-continued

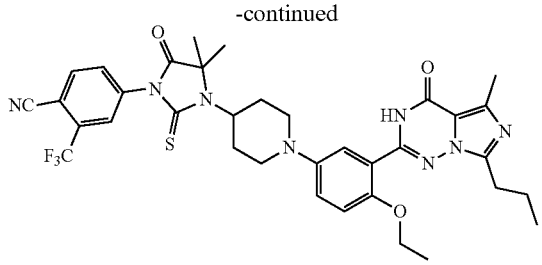

or a solvate, a hydrate, a prodrug, and/or a stereoisomer thereof, or a pharmaceutically acceptable salt thereof.

Clause 80. The compound of clause 77, or a solvate, a hydrate, a prodrug, and/or a stereoisomer thereof, or a pharmaceutically acceptable salt thereof, wherein $R^8$ and $R^9$ together with the carbon atom to which they are attached are cyclically linked to provide an optionally substituted 3- to 6-membered carbocycle or optionally substituted 3- to 6-membered heterocycle (e.g., 4-membered or 5-membered carbocycle or heterocycle) that is selected from optionally substituted cyclobutyl, optionally substituted cyclopentyl, and optionally substituted tetrahydrofuran.

Clause 81. The compound of clause 80, wherein the compound is selected from:

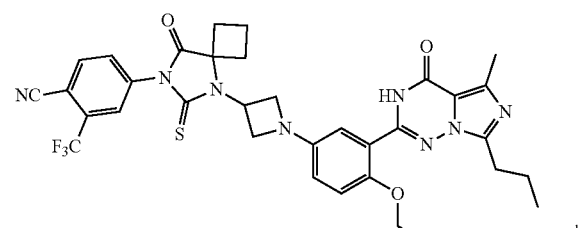

and

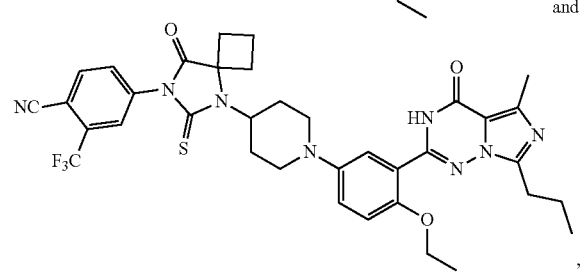

, or a solvate, a hydrate, a prodrug, and/or a stereoisomer thereof, or a pharmaceutically acceptable salt thereof.

Clause 82. The compound of clause 22, wherein the compound is of formula (VIIc):

(VIIc)

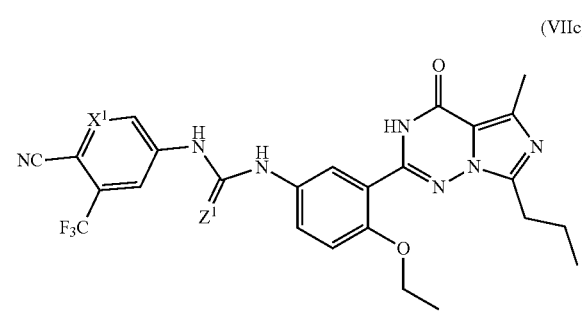

or a solvate, a hydrate, a prodrug, and/or a stereoisomer thereof, or a pharmaceutically acceptable salt thereof.

Clause 83. The compound of clause 82, wherein the compound is selected from:

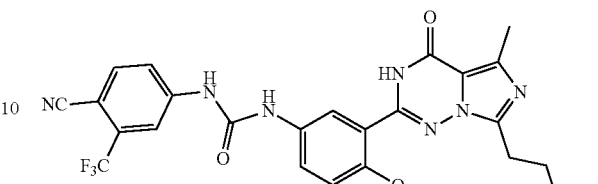

and

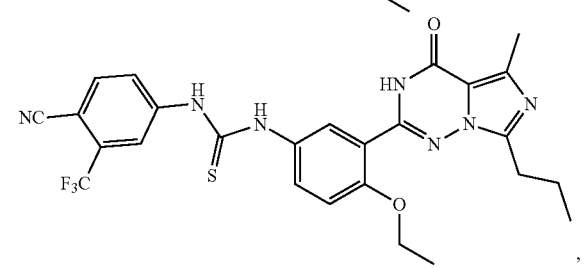

, or a solvate, a hydrate, a prodrug, and/or a stereoisomer thereof, or a pharmaceutically acceptable salt thereof.

Clause 84. The compound of clause 24, wherein the compound is of formula (VIIIc):

(VIIIc)

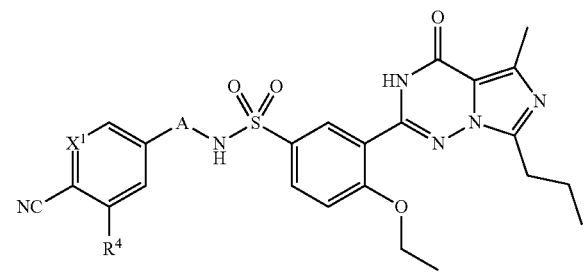

or a solvate, a hydrate, a prodrug, and/or a stereoisomer thereof, or a pharmaceutically acceptable salt thereof.

Clause 85. The compound of clause 84, or a solvate, a hydrate, a prodrug, and/or a stereoisomer thereof, or a pharmaceutically acceptable salt thereof, wherein -A- is

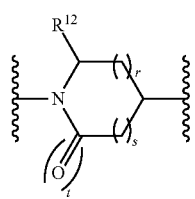

wherein:
$R^{12}$ is selected from —H, —OH, optionally substituted $(C_1-C_3)$alkyl, and optionally substituted $(C_1-C_5)$haloalkyl; and
r, s and t are independently is 0 or 1.

Clause 86. The compound of clause 85, wherein -A- is selected from:

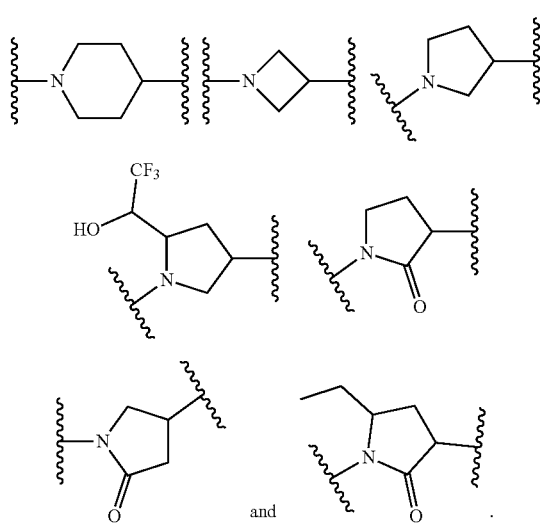

Clause 87. The compound of clause 85 or 86, or a solvate, a hydrate, a prodrug, and/or a stereoisomer thereof, or a pharmaceutically acceptable salt thereof, wherein R⁴ is —CF₃.

Clause 88. The compound of clause 87, wherein the compound is selected from:

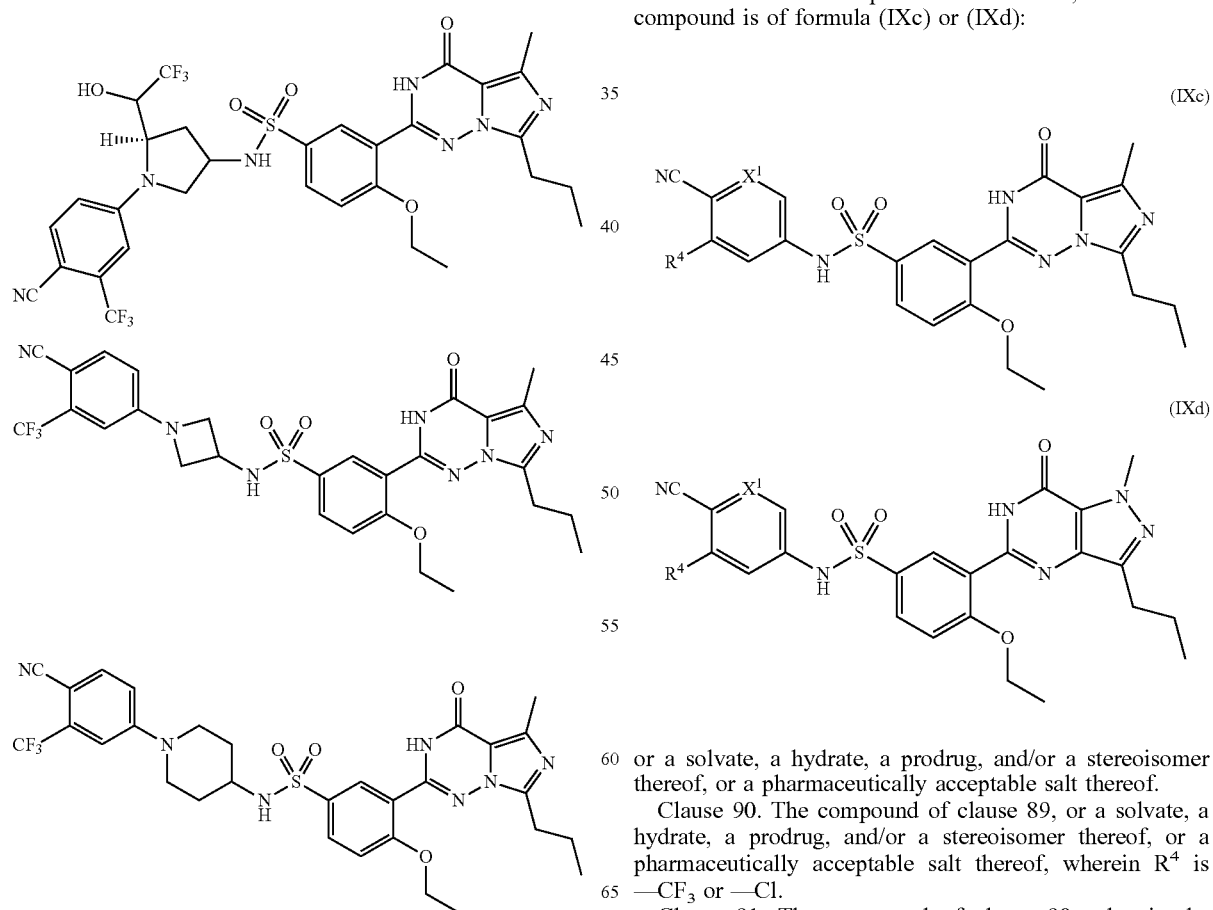

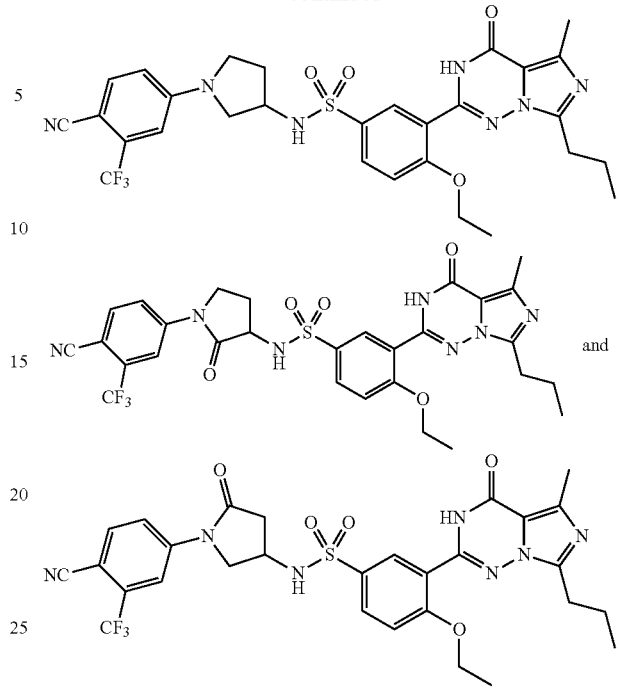

or a solvate, a hydrate, a prodrug, and/or a stereoisomer thereof, or a pharmaceutically acceptable salt thereof.

Clause 89. The compound of clause 29, wherein the compound is of formula (IXc) or (IXd):

(IXc)

(IXd)

or a solvate, a hydrate, a prodrug, and/or a stereoisomer thereof, or a pharmaceutically acceptable salt thereof.

Clause 90. The compound of clause 89, or a solvate, a hydrate, a prodrug, and/or a stereoisomer thereof, or a pharmaceutically acceptable salt thereof, wherein R⁴ is —CF₃ or —Cl.

Clause 91. The compound of clause 90, wherein the compound is selected from:

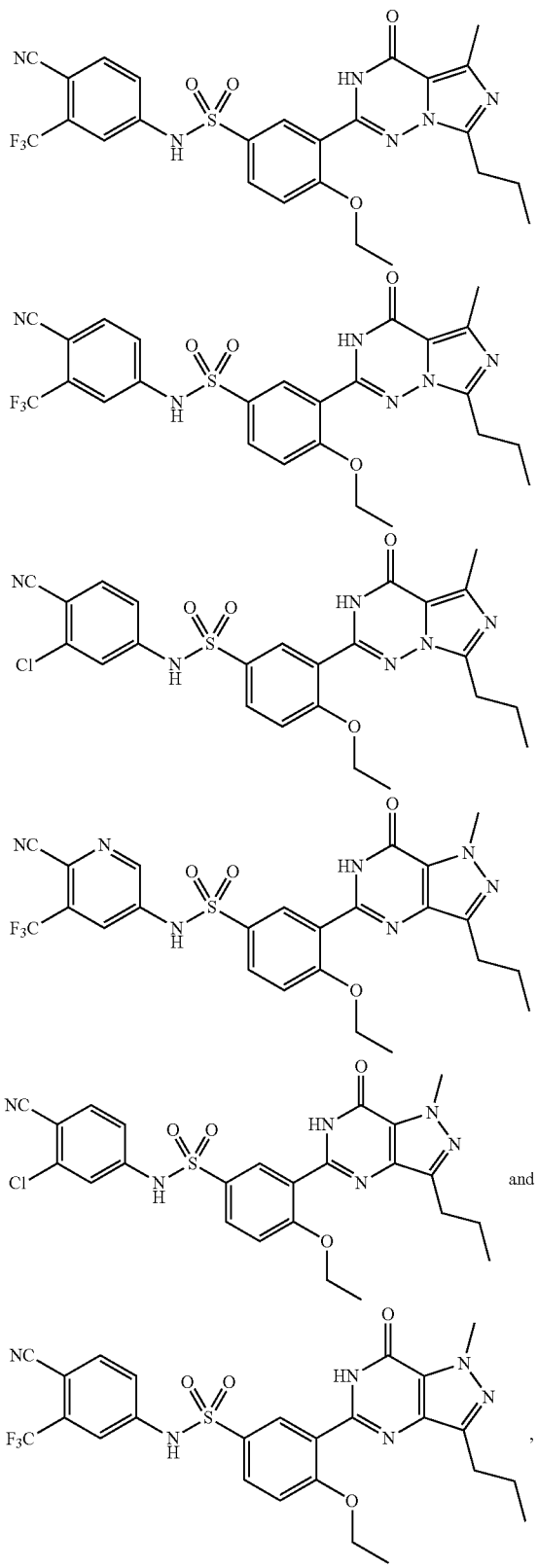

and or a solvate, a hydrate, a prodrug, and/or a stereoisomer thereof, or a pharmaceutically acceptable salt thereof.

Clause 92. The compound of clause 24, wherein the compound is of formula (VIIId):

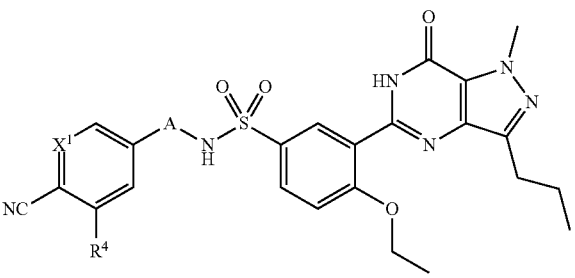

(VIIId)

or a solvate, a hydrate, a prodrug, and/or a stereoisomer thereof, or a pharmaceutically acceptable salt thereof.

Clause 93. The compound of clause 92, or a solvate, a hydrate, a prodrug, and/or a stereoisomer thereof, or a pharmaceutically acceptable salt thereof, wherein $R^4$ is —Cl.

Clause 94. The compound of clause 92 or 93, wherein -A- is an optionally substituted —($C_3$-$C_{12}$)heteroaryl-($C_1$-$C_5$)alkylene-.

Clause 95. The compound of clause 94, wherein the compound is

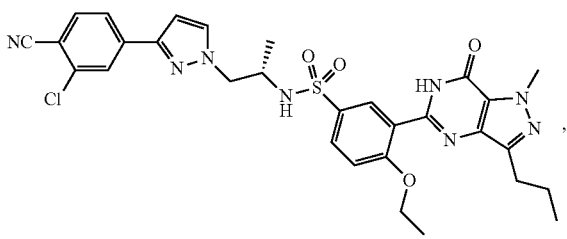 [SMILES: CCCc1nn(C)c2c(=O)[nH]c(-c3cc(S(=O)(=O)N[C@@H](C)Cn4ccc(-c5ccc(C#N)c(Cl)c5)n4)ccc3OCC)nc12]

or a solvate, a hydrate, a prodrug, and/or a stereoisomer thereof, or a pharmaceutically acceptable salt thereof.

Clause 96. The compound of clause 41, wherein the compound is of formula (XIc):

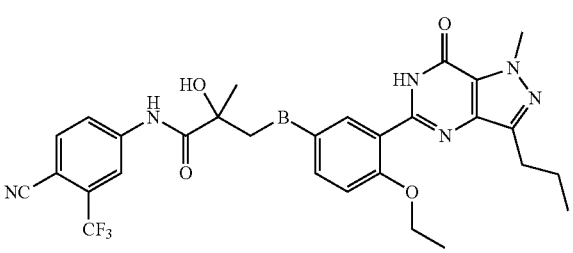

(XIc)

or a solvate, a hydrate, a prodrug, and/or a stereoisomer thereof, or a pharmaceutically acceptable salt thereof.

Clause 97. The compound of clause 96, wherein the compound is selected from:

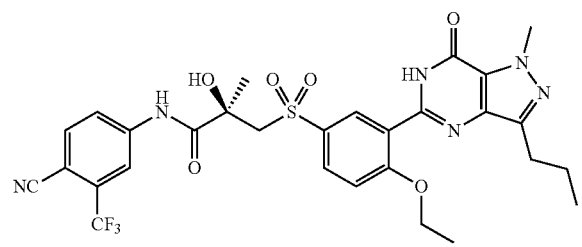

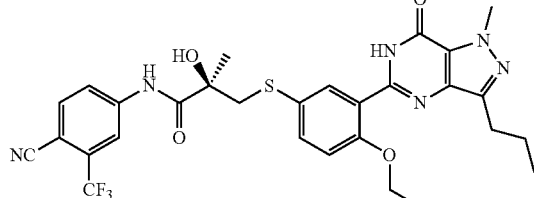

and

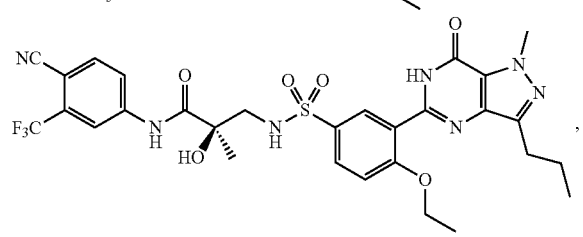

, or a solvate, a hydrate, a prodrug, and/or a stereoisomer thereof, or a pharmaceutically acceptable salt thereof.

Clause 98. The compound of clause 36, wherein the compound is of formula (Xc):

(Xc)

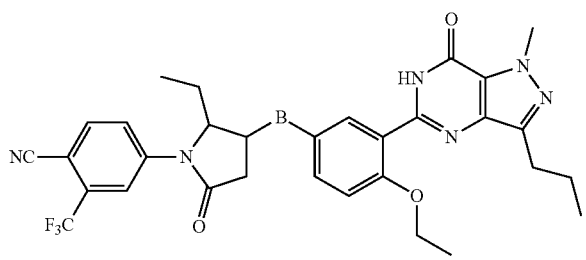

or a solvate, a hydrate, a prodrug, and/or a stereoisomer thereof, or a pharmaceutically acceptable salt thereof.

Clause 99. The compound of clause 98, or a solvate, a hydrate, a prodrug, and/or a stereoisomer thereof, or a pharmaceutically acceptable salt thereof, wherein —B— is selected from —NH—, —O—, —S—, and —SO$_2$—.

Clause 100. The compound of clause 99, wherein the compound is selected from:

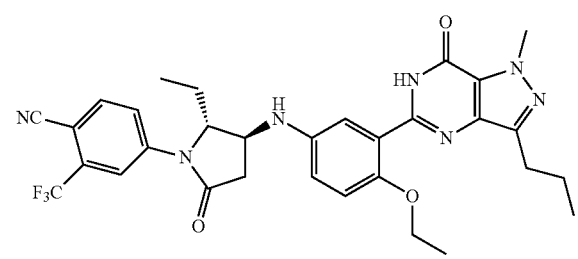

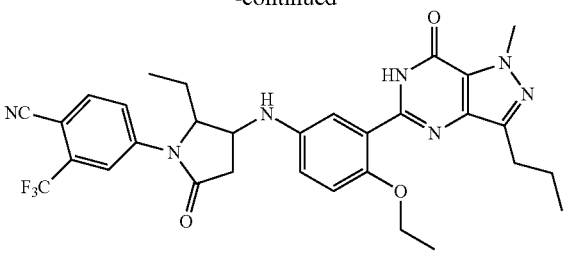

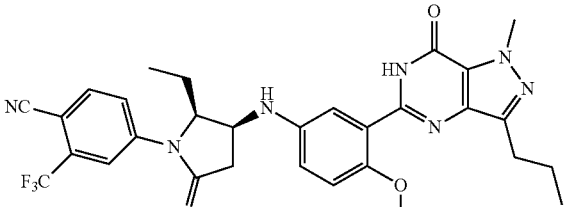

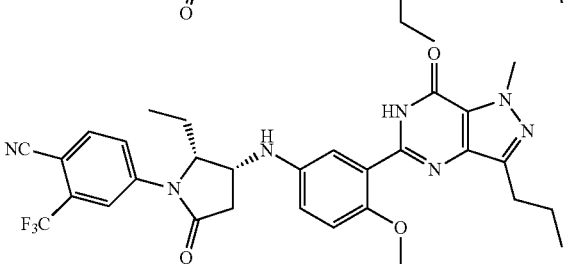

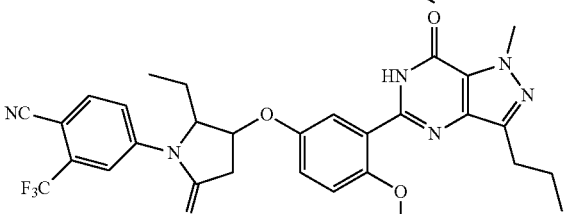

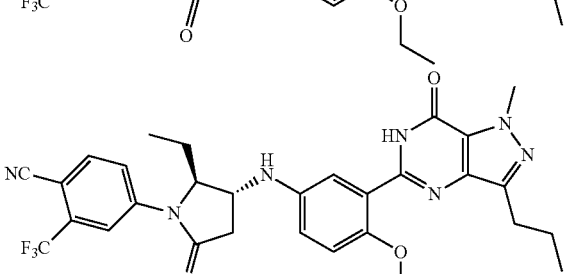

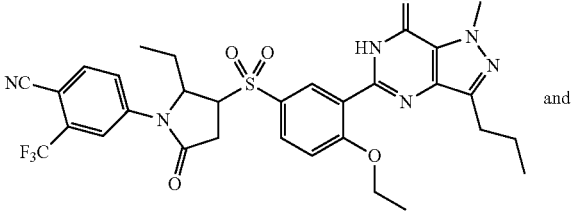

and

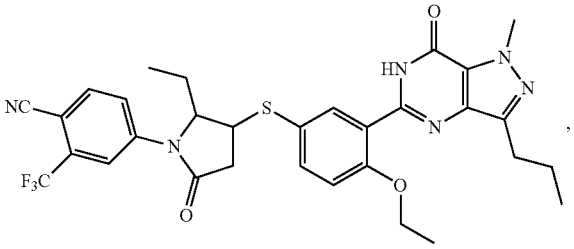

, or a solvate, a hydrate, a prodrug, and/or a stereoisomer thereof, or a pharmaceutically acceptable salt thereof.

Clause 101. The compound of clause 1, wherein the compound is a compound of Table 1, or a pharmaceutically acceptable salt thereof.

Clause 102. A pharmaceutical composition comprising: a compound or a solvate, a hydrate, a prodrug, and/or a stereoisomer thereof, or a pharmaceutically acceptable salt thereof, according to any one of clauses 1 to 101; and at least one pharmaceutically acceptable excipient.

Clause 103. A compound for use in modulating androgen receptor and/or inhibiting PDE-5, wherein the compound is a compound or a solvate, a hydrate, a prodrug, and/or a stereoisomer thereof, or a pharmaceutically acceptable salt thereof, according to any one of clauses 1 to 101.

Clause 104. A pharmaceutical composition for use in modulating androgen receptor and/or inhibiting PDE-5, wherein the pharmaceutical composition is according to clause 102.

Clause 105. A method of modulating androgen receptor and/or inhibiting PDE-5, the method comprising contacting a biological system comprising the androgen receptor and/or the PDE-5 with an effective amount of a compound, or a solvate, a hydrate, a prodrug, and/or a stereoisomer thereof, or a pharmaceutically acceptable salt thereof, according to any one of clauses 1 to 100.

Clause 106. The method of clause 105, wherein the biological system is comprised in a sample in vitro.

Clause 107. The method of clause 105 or 106, wherein the method comprises inhibiting androgen receptor.

Clause 108. The method of any one of clauses 105 to 107, wherein the method comprises inhibiting PDE-5.

5. EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description and accompanying FIGURES. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

In the examples below, if an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
$Cs_2CO_3$=cesium carbonate
NaH=sodium hydride
o/n=overnight
HATU=1-[bis(dimethylamino)methylene]-1H-1,2,3-triazolo[4,5-b]pyridinium 3-oxide hexafluorophosphate
r.t.=room temperature
LAH=lithium aluminum hydride
DCM=dichloromethane
DMF=dimethylformamide
DMSO=dimethyl sulfoxide
DIEA=diisopropylethylamine
equiv.=equivalent
EtOAc or EA=ethyl acetate
EtOH=ethanol
EDCI=1-ethyl-3-(3-dimethylaminopropyl)carbodiimide
g=gram
h=hours
HCl=hydrochloric acid
HPLC=high-performance liquid chromatography
HOAc=acetic acid
HOBT=hydroxybenzotriazole
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
ppm=parts per million
TFA=trifluoroacetic acid
TLC=thin layer chromatography
TsOH=p-Toluenesulfonic acid
UV=ultraviolet
wt %=weight percent
µM=micromolar General Synthetic Methods Final compounds were confirmed by HPLC/MS analysis and determined to be >90% pure by weight. $^1H$ and $^{13}C$ NMR spectra were recorded in $CDCl_3$ (residual internal standard $CHCl_3$=δ 7.26), DMSO-$d_6$ (residual internal standard $CD_3SOCD_2H$=δ 2.50), methanol-$d_4$ (residual internal standard $CD_2HOD$=δ 3.31), or acetone-$d_6$ (residual internal standard $CD_3COCD_2H$=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Example 1—Synthesis of Intermediate Compounds

Described herein are details of the synthesis and characterization of several exemplary intermediate compounds or synthons that can be used to prepare a variety of final compounds of this disclosure. It is understood that the synthetic methods and intermediate compounds described, in combination with generally available starting materials, may readily be adapted to synthesize a variety of compounds of formula (I)-(XIc), including any of the compounds of Table 1.

Synthesis of Intermediate Compound 51

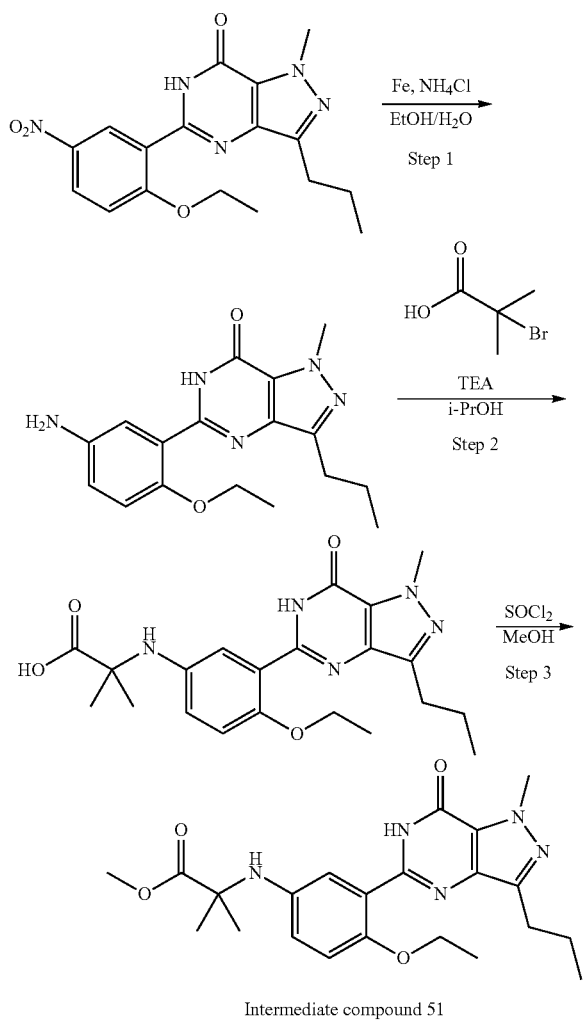

Intermediate compound 51

Step 1:

To a solution of 5-(2-ethoxy-5-nitrophenyl)-1-methyl-3-propyl-1,6-dihydro-7H-pyrazolo[4,3-d] pyrimidin-7-one (500 mg, 1.40 mmol) in EtOH (10 mL) and $H_2O$ (2 mL) was added Fe (391 mg, 7.00 mmol) and $NH_4Cl$ (748 mg, 13.99 mmol), the reaction mixture was stirred at 60° C. for 1 h. The reaction mixture was filtered and the filtrate was concentrated under reduced pressure. The residue was purified by column chromatography to afford 5-(5-amino-2-ethoxyphenyl)-1-methyl-3-propyl-1,6-dihydro-7H-pyrazolo[4,3-d]pyrimidin-7-one (430 mg, 93.88% yield) as a yellow solid. MS: m/z=328.2 (M+1, ESI+).

Step 2:

To a solution of 5-(5-amino-2-ethoxyphenyl)-1-methyl-3-propyl-1,6-dihydro-7H-pyrazolo[4,3-d] pyrimidin-7-one (430 mg, 1.31 mmol) and 2-bromo-2-methylpropanoic acid (658 mg, 3.94 mmol) in i-PrOH (10 mL) was added TEA (399 mg, 3.94 mmol), the reaction mixture was stirred at 80° C. for 16 h. The reaction mixture was poured into water (100 mL) and extracted with EA (30 mL×3), the combined organic layers were dried over $Na_2SO_4$ and concentrated under reduced pressure. The residue was purified by column chromatography to afford 2-((4-ethoxy-3-(1-methyl-7-oxo-3-propyl-6,7-dihydro-1H-pyrazolo[4,3-d]pyrimidin-5-yl) phenyl)amino)-2-methylpropanoic acid (400 mg, 73.65% yield) as a white solid. MS: m/z=414.3 (M+1, ESI+).

Step 3:

To a solution of 2-((4-ethoxy-3-(1-methyl-7-oxo-3-propyl-6,7-dihydro-1H-pyrazolo[4,3-d]pyrimidin-5-yl)phenyl) amino)-2-methylpropanoic acid (370 mg, 894.87 umol) in MeOH (10 mL) was added $SOCl_2$ (1 g, 8.41 mmol), the reaction mixture was stirred at 60° C. for 16 h. The reaction mixture was concentrated and the residue was poured into water (30 mL) and extracted with EA (10 mL×3), the combined organic layers were dried over $Na_2SO_4$ and concentrated under reduced pressure. The residue was purified by column chromatography to afford intermediate compound 51, methyl 2-((4-ethoxy-3-(1-methyl-7-oxo-3-propyl-6,7-dihydro-1H-pyrazolo[4,3-d]pyrimidin-5-yl)phenyl) amino)-2-methylpropanoate (150 mg, 39.27% yield) as a white solid. MS: m/z=428.4 (M+1, ESI+).

Synthesis of Intermediate Compound 52

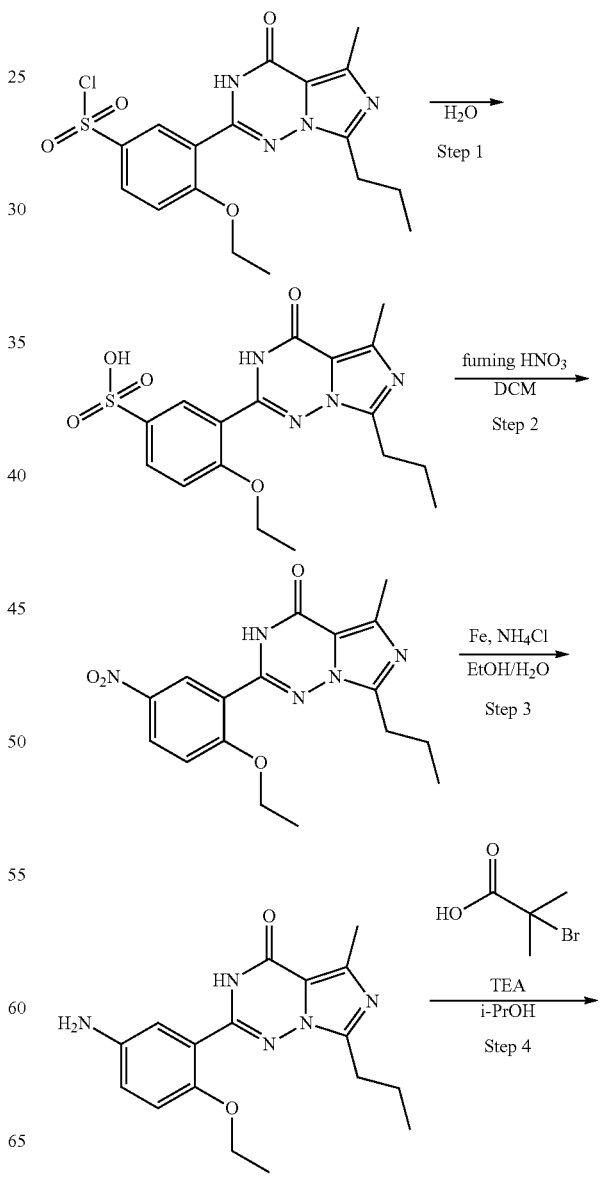

-continued

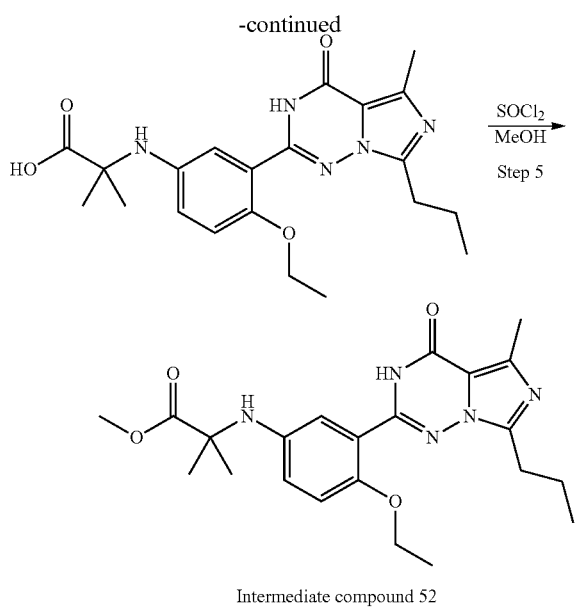

Intermediate compound 52

Step 1:
A mixture of 4-ethoxy-3-(5-methyl-4-oxo-7-propyl-3,4-dihydroimidazo[5,1-f][1,2,4]triazin-2-yl) benzenesulfonyl chloride (5 g, 12.17 mmol) in H₂O (50 mL) was stirred at 70° C. for 3 h. The reaction mixture was filtered and the filter cake was dried under reduced pressure to afford 4-ethoxy-3-(5-methyl-4-oxo-7-propyl-3,4-dihydroimidazo[5,1-f][1,2,4]triazin-2-yl)benzenesulfonic acid (4.45 g, 93.18% yield) as a white solid. MS: m/z=393.1 (M+1, ESI+).

Step 2:
A mixture of 4-ethoxy-3-(5-methyl-4-oxo-7-propyl-3,4-dihydroimidazo[5,1-f][1,2,4]triazin-2-yl) benzenesulfonic acid (4.45 g, 11.34 mmol) was added to fuming nitric acid (20 mL) and DCM (20 mL) at −50° C. in portions, the reaction mixture was allowed to warm to room temperature and stirred for 2 h. The reaction mixture was poured into ice water (100 mL) and extracted with DCM (20 mL×3), the combined organic layers were washed with water (100 mL) and brine (100 mL), then dried over Na₂SO₄ and concentrated under reduced pressure. The residue was purified by column chromatography to afford 2-(2-ethoxy-5-nitrophenyl)-5-methyl-7-propylimidazo[5,1-f][1,2,4] triazin-4(3H)-one (1.05 g, 25.91% yield) as a yellow solid. MS: m/z=358.2 (M+1, ESI+).

Step 3:
To a solution of 2-(2-ethoxy-5-nitrophenyl)-5-methyl-7-propylimidazo[5,1-f][1,2,4]triazin-4(3H)-one (1.10 g, 3.08 mmol) in EtOH (10 mL) and H₂O (2 mL) was added Fe (516 mg, 9.23 mmol) and NH₄Cl (540 mg, 9.23 mmol), the reaction mixture was stirred at 70° C. for 3 h. The reaction mixture was filtered and the filtrate was concentrated under reduced pressure. The residue was purified by column chromatography to afford 2-(5-amino-2-ethoxyphenyl)-5-methyl-7-propyl imidazo[5,1-f][1,2,4]triazin-4(3H)-one (980 mg, 97.25% yield) as a yellow solid. MS: m/z=328.2 (M+1, ESI+).

Step 4:
To a solution of 2-(5-amino-2-ethoxyphenyl)-5-methyl-7-propylimidazo[5,1-f][1,2,4]triazin-4(3H)-one (980 mg, 2.99 mmol) and 2-bromo-2-methylpropanoic acid (1 g, 5.99 mmol) in i-PrOH (10 mL) was added TEA (909 mg, 8.98 mmol), the reaction mixture was stirred at 80° C. for 16 h. The reaction mixture was poured into water (100 mL) and extracted with EtOAc (30 mL×3), the combined organic layers were dried over Na₂SO₄ and concentrated under reduced pressure. The residue was purified by column chromatography to afford 2-((4-ethoxy-3-(5-methyl-4-oxo-7-propyl-3,4-dihydroimidazo[5,1-f][1,2,4]triazin-2-yl)phenyl)amino)-2-methylpropanoic acid (430 mg, 34.74% yield) as a yellow solid. MS: m/z=414.2 (M+1, ESI+).

Step 5:
To a solution of 2-((4-ethoxy-3-(5-methyl-4-oxo-7-propyl-3,4-dihydroimidazo[5,1-f][1,2,4]triazin-2-yl)phenyl)amino)-2-methylpropanoic acid (300 mg, 725.57 umol) in MeOH (10 mL) was added SOCl₂ (259 mg, 2.18 mmol), the reaction mixture was stirred at 70° C. for 16 h. The reaction mixture was concentrated and the residue was poured into water (30 mL) and extracted with EA (10 mL×3), the combined organic layers were dried over Na₂SO₄ and concentrated under reduced pressure. The residue was purified by column chromatography to afford intermediate compound 52, methyl 2-((4-ethoxy-3-(5-methyl-4-oxo-7-propyl-3,4-dihydroimidazo[5,1-f][1,2,4]triazin-2-yl)phenyl)amino)-2-methyl propanoate (278 mg, 89.63% yield) as a yellow solid. MS: m/z=428.3 (M+1, ESI+).

Synthesis of Intermediate Compound 53

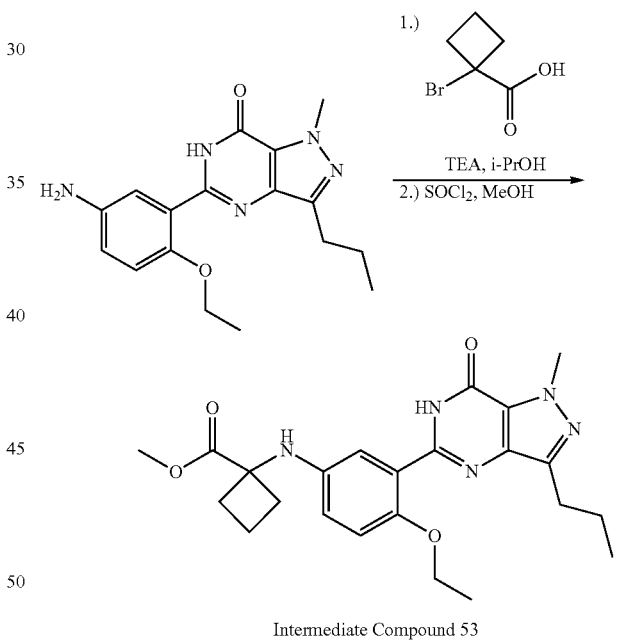

Intermediate Compound 53

Step 1:
To a solution of 5-(5-amino-2-ethoxyphenyl)-1-methyl-3-propyl-1,6-dihydro-7H-pyrazolo[4,3-d] pyrimidin-7-one (2.5 g, 7.64 mmol) and 1-bromocyclobutane-1-carboxylic acid (2.05 g, 11.45 mmol) in i-PrOH (30 mL) was added TEA (2.32 g, 22.91 mmol), the reaction mixture was stirred at 80° C. for 16 h. The reaction mixture was concentrated under reduced pressure and the residue was purified by column chromatography to afford 1-((4-ethoxy-3-(1-methyl-7-oxo-3-propyl-6,7-dihydro-1H-pyrazolo[4,3-d]pyrimidin-5-yl)phenyl)amino)cyclobutane-1-carboxylic acid (1.5 g, 46.17% yield) as a yellow solid. MS: m/z=426.2 (M+1, ESI+).

Step 2:

To a solution of 1-((4-ethoxy-3-(1-methyl-7-oxo-3-propyl-6,7-dihydro-TH-pyrazolo[4,3-d]pyrimidin-5-yl)phenyl)amino)cyclobutane-1-carboxylic acid (1.5 g, 3.53 mmol) in MeOH (30 mL) was added $SOCl_2$ (2.10 g, 17.63 mmol), the reaction mixture was stirred at 80° C. for 16 h. The reaction mixture was concentrated and the residue was poured into water (30 mL) and extracted with EA (10 mL×3), the combined organic layers were dried over $Na_2SO_4$ and concentrated under reduced pressure. The residue was purified by column chromatography to afford intermediate compound 53 methyl 1-((4-ethoxy-3-(1-methyl-7-oxo-3-propyl-6,7-dihydro-TH-pyrazolo[4,3-d]pyrimidin-5-yl)phenyl)amino) cyclobutane-1-carboxylate (1 g, 64.51% yield) as a yellow solid. MS: m/z=440.2 (M+1, ESI+).

Synthesis of Intermediate Compound 54

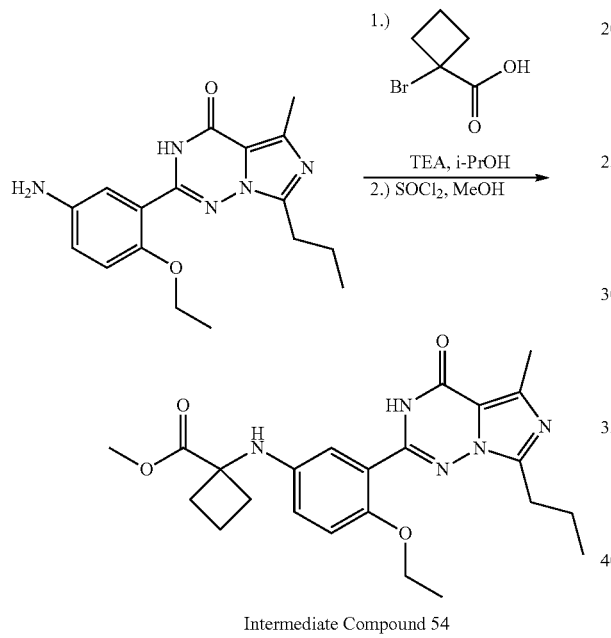

Intermediate Compound 54

Step 1:

To a solution of 2-(5-amino-2-ethoxyphenyl)-5-methyl-7-propylimidazo[5,1-f][1,2,4]triazin-4(3H)-one (3.2 g, 9.77 mmol) and 1-bromocyclobutane-1-carboxylic acid (3.5 g, 19.55 mmol) in i-PrOH (40 mL) was added TEA (2.97 g, 29.32 mmol), the reaction mixture was stirred at 90° C. for 16 h. The reaction mixture was concentrated under reduced pressure and the residue was purified by column chromatography to afford 1-((4-ethoxy-3-(5-methyl-4-oxo-7-propyl-3,4-dihydroimidazo [5,1-f][1,2,4]triazin-2-yl)phenyl)amino)cyclobutane-1-carboxylic acid (2 g, 48.09% yield) as a white solid. MS: m/z=426.1 (M+1, ESI+).

Step 2:

To a solution of 1-((4-ethoxy-3-(5-methyl-4-oxo-7-propyl-3,4-dihydroimidazo[5,1-f][1,2,4]triazin-2-yl)phenyl)amino)cyclobutane-1-carboxylic acid (2 g, 4.70 mmol) in MeOH (30 mL) was added $SOCl_2$ (1.68 g, 14.10 mmol), the reaction mixture was stirred at 80° C. for 16 h. The reaction mixture was concentrated and the residue was poured into water (30 mL) and extracted with EA (10 mL×3), the combined organic layers were dried over $Na_2SO_4$ and concentrated under reduced pressure. The residue was purified by column chromatography to afford intermediate compound 54, methyl 1-((4-ethoxy-3-(5-methyl-4-oxo-7-propyl-3,4-dihydroimidazo[5,1-f][1,2,4]triazin-2-yl)phenyl)amino)cyclobutane-1-carboxylate (1 g, 48.40% yield) as a white solid. MS: m/z=440.2 (M+1, ESI+).

Synthesis of Intermediate Compound 55

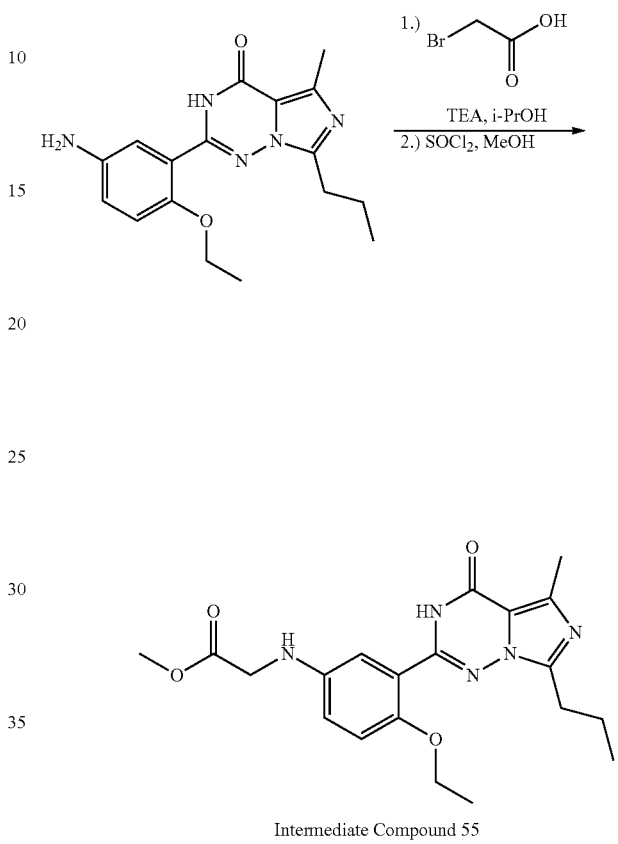

Intermediate Compound 55

Step 1:

To a solution of 2-(5-amino-2-ethoxyphenyl)-5-methyl-7-propylimidazo[5,1-f][1,2,4]triazin-4(3H)-one (500 mg, 1.53 mmol) and 2-bromoacetic acid (255 mg, 1.83 mmol) in i-PrOH (10 mL) was added TEA (464 mg, 4.58 mmol), the reaction mixture was stirred at 80° C. for 16 h. The reaction mixture was cooled to room temperature and concentrated under reduced pressure, the residue was purified by column chromatography to afford (4-ethoxy-3-(5-methyl-4-oxo-7-propyl-3,4-dihydroimidazo[5,1-f][1,2,4]triazin-2-yl)phenyl) glycine (400 mg, 67.95% yield) as a yellow solid. MS: m/z=386.1 (M+1, ESI+).

Step 2:

To a solution of (4-ethoxy-3-(5-methyl-4-oxo-7-propyl-3,4-dihydroimidazo[5,1-f][1,2,4]triazin-2-yl)phenyl)glycine (400 mg, 1.04 mmol) in MeOH (10 mL) was added $SOCl_2$ (617.36 mg, 5.19 mmol), the reaction mixture was stirred at 80° C. for 16 h. The reaction mixture was cooled to room temperature and concentrated under reduced pressure, the residue was purified by column chromatography to afford intermediate compound 55, methyl (4-ethoxy-3-(5-methyl-4-oxo-7-propyl-3,4-dihydroimidazo[5,1-f][1,2,4]triazin-2-yl)phenyl)glycinate (350 mg, 84.43% yield) as a yellow oil. MS: m/z=400.1 (M+1, ESI+).

Synthesis of Intermediate Compound 56

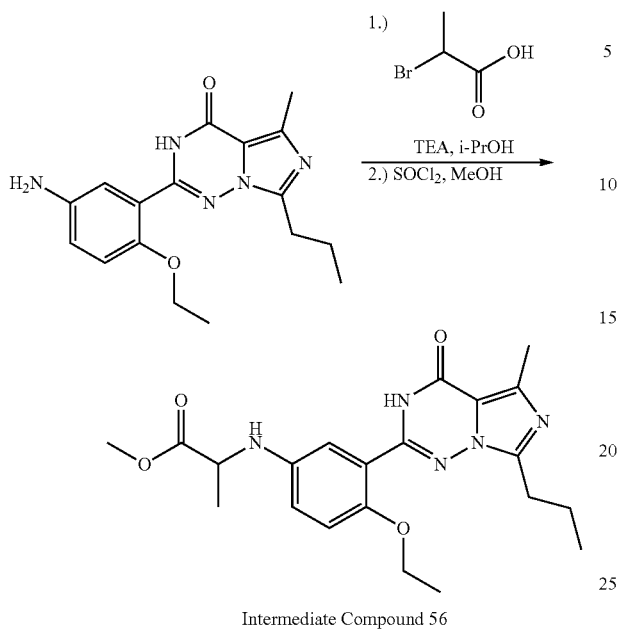

Intermediate Compound 56

Step 1:
To a solution of 2-(5-amino-2-ethoxyphenyl)-5-methyl-7-propylimidazo[5,1-f][1,2,4]triazin-4(3H)-one (500 mg, 1.53 mmol) and 2-bromopropanoic acid (280 mg, 1.83 mmol) in i-PrOH (10 mL) was added TEA (464 mg, 4.58 mmol), the reaction mixture was stirred at 80° C. for 16 h. The reaction mixture was cooled to room temperature and concentrated under reduced pressure, the residue was purified by column chromatography to afford (4-ethoxy-3-(5-methyl-4-oxo-7-propyl-3,4-dihydroimidazo[5,1-f][1,2,4]triazin-2-yl)phenyl)alanine (360 mg, 59.01% yield) as a yellow solid. MS: m/z=400.1 (M+1, ESI+).

Step 2:
To a solution of (4-ethoxy-3-(5-methyl-4-oxo-7-propyl-3,4-dihydroimidazo[5,1-f][1,2,4]triazin-2-yl)phenyl)alanine (360 mg, 901 umol) in MeOH (8 mL) was added SOCl$_2$ (536 mg, 4.51 mmol), the reaction mixture was stirred at 80° C. for 16 h. The reaction mixture was cooled to room temperature and concentrated under reduced pressure, the residue was purified by column chromatography to afford intermediate compound 56, methyl (4-ethoxy-3-(5-methyl-4-oxo-7-propyl-3,4-dihydroimidazo[5,1-f][1,2,4]triazin-2-yl)phenyl)alaninate (310 mg, 83.19% yield) as a yellow oil. MS: m/z=414.1 (M+1, ESI+).

Synthesis of Intermediate Compound 57

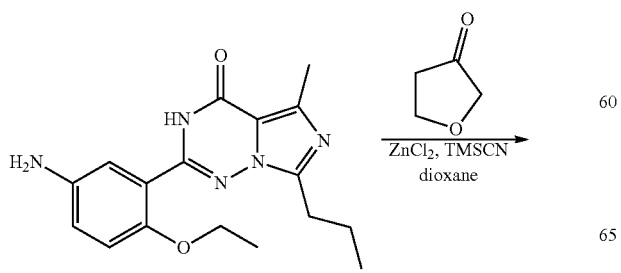

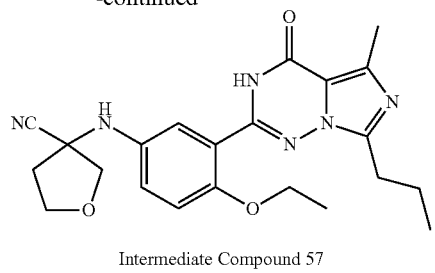

Intermediate Compound 57

To a solution of 2-(5-amino-2-ethoxyphenyl)-5-methyl-7-propylimidazo[5,1-f][1,2,4]triazin-4(3H)-one (1 g, 3.05 mmol) and dihydrofuran-3(2H)-one (525.93 mg, 6.11 mmol) in dioxane (30 mL) was added TMSCN (453.60 mg, 4.58 mmol) and ZnCl$_2$ (83.08 mg, 610.91 umol), the reaction mixture was stirred at 50° C. for 16 h. The reaction mixture was cooled to room temperature and poured into water (80 mL), extracted with EA (30 mL×3), washed by brine (80 mL), dried over Na$_2$SO$_4$ and concentrated. The residue was purified by column chromatography to afford intermediate compound 57, 3-((4-ethoxy-3-(5-methyl-4-oxo-7-propyl-3,4-dihydroimidazo[5,1-f][1,2,4]triazin-2-yl)phenyl)amino)tetrahydrofuran-3-carbonitrile (1.09 g, 84.46% yield) as a yellow solid. MS: m/z=423.2 (M+1, ESI+).

Synthesis of Intermediate Compound 58

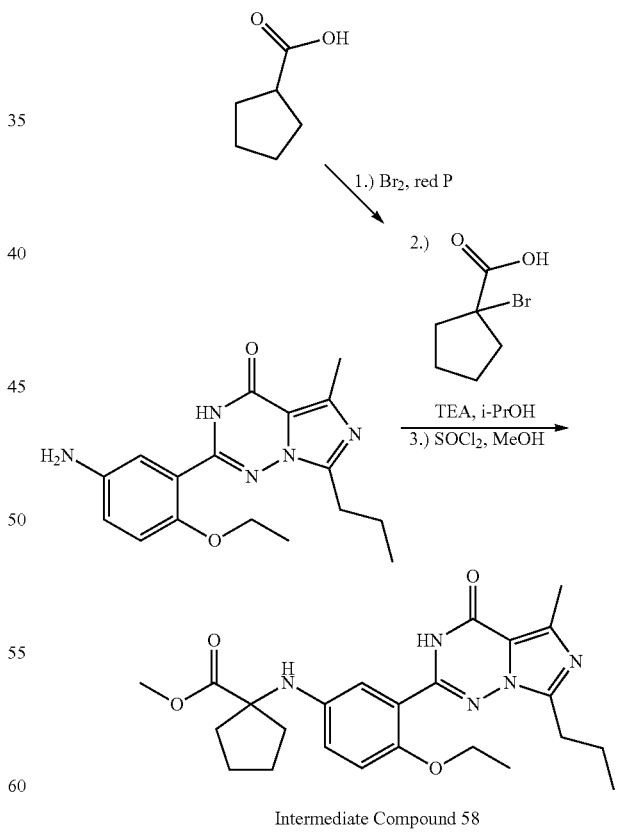

Intermediate Compound 58

Step 1:
A mixture of cyclopentanecarboxylic acid (10 g, 86.12 mmol) and red P (1.33 g, 43.06 mmol) at 0° C. was added Br$_2$ (27.56 g, 172.24 mmol) in portions, after that, the reaction mixture was stirred at 60° C. for 6 h. The reaction mixture was diluted with EA (200 mL) and washed with brine (100 mL×2), the organic layer was dried over Na₂SO₄ and concentrated under reduced pressure, the residue was purified by column chromatography to afford 1-bromocyclopentane-1-carboxylic acid (12 g, crude) as a yellow oil. ¹H NMR (400 MHz, DMSO-d₆) δ 12.91 (s, 1H), 2.31-2.22 (m, 2H), 2.21-2.11 (m, 2H), 1.89-1.83 (m, 2H), 1.78-1.72 (m, 2H).

Step 2:

To a solution of 2-(5-amino-2-ethoxyphenyl)-5-methyl-7-propylimidazo[5,1-f][1,2,4]triazin-4(3H)-one (800 mg, 2.44 mmol) and 1-bromocyclopentane-1-carboxylic acid (943.43 mg, 4.89 mmol) in i-PrOH (15 mL) was added TEA (741.82 mg, 7.33 mmol), the reaction mixture was stirred at 80° C. for 16 h. The reaction mixture was cooled to room temperature and poured into water (100 mL) and extracted with EA (40 mL×3), washed by brine (100 mL), dried over Na₂SO₄ and concentrated. The residue was purified by column chromatography to afford 1-((4-ethoxy-3-(5-methyl-4-oxo-7-propyl-3,4-dihydroimidazo[5,1-f][1,2,4]triazin-2-yl)phenyl)amino)cyclopentane-1-carboxylic acid (336 mg, 31.29% yield) as a yellow solid. MS: m/z=440.1 (M+1, ESI+).

Step 3:

To a solution of 1-((4-ethoxy-3-(5-methyl-4-oxo-7-propyl-3,4-dihydroimidazo[5,1-f][1,2,4]triazin-2-yl)phenyl)amino)cyclopentane-1-carboxylic acid (336 mg, 764.49 umol) in MeOH (8 mL) was added SOCl₂ (2 mL) in portions, the reaction mixture was stirred at 70° C. for 16 h. The reaction mixture was concentrated and the residue was poured into water (30 mL) and extracted with EA (10 mL×3), the combined organic layers were dried over Na₂SO₄ and concentrated under reduced pressure. The residue was purified by column chromatography to afford intermediate compound 58, methyl 1-((4-ethoxy-3-(5-methyl-4-oxo-7-propyl-3,4-dihydroimidazo[5,1-f][1,2,4]triazin-2-yl)phenyl)amino) cyclopentane-1-carboxylate (140 mg, 40.38% yield) as a yellow solid. MS: m/z=454.2 (M+1, ESI+).

Synthesis of Intermediate Compound 59

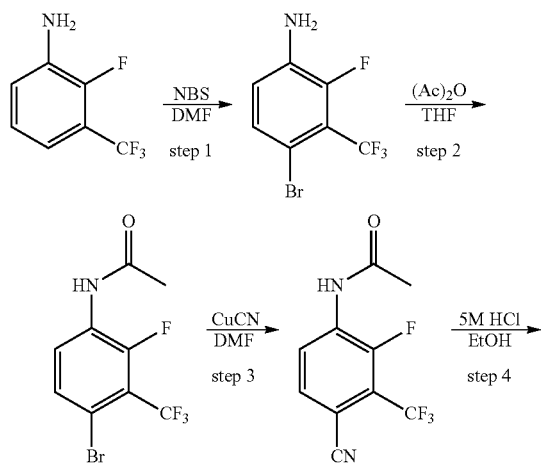

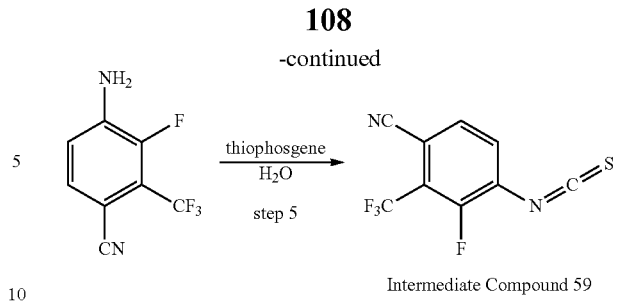

Intermediate Compound 59

Step 1:

To a solution of 2-fluoro-3-(trifluoromethyl)aniline (25 g, 139.6 mmol) in DMF (200 mL) was added NBS (27.3 g, 153.5 mmol) in portions, the resulting mixture was stirred at 25° C. for 16 h. The reaction mixture was poured into water (800 mL) and extracted with EA (200 mL×3), the combined organic layers were washed with water (800 mL) and brine (800 mL), then dried over Na₂SO₄ and concentrated under reduced pressure. The residue was purified by column chromatography to afford 4-bromo-2-fluoro-3-(trifluoromethyl)aniline (27.5 g, 76.6% yield) as a yellow solid. ¹H NMR (400 MHz, DMSO-d₆) δ 7.32 (dd, 1H), 6.94 (t, 1H), 5.81 (br s, 2H).

Step 2:

To a solution of 4-bromo-2-fluoro-3-(trifluoromethyl)aniline (27.5 g, 107 mmol) in THF (200 mL) was added Ac₂O (30 g, 294 mmol), the resulting mixture was stirred at 60° C. for 16 h. The reaction mixture was cooled to room temperature and concentrated under reduce pressure. The residue was purified by column chromatography to afford N-(4-bromo-2-fluoro-3-(trifluoromethyl)phenyl) acetamide (30 g, 93.4% yield) as a yellow solid. MS: m/z=301.8 (M+1, ESI+).

Step 3:

To a solution of N-(4-bromo-2-fluoro-3-(trifluoromethyl)phenyl)acetamide (30 g, 100 mmol) in DMF (100 mL) was added CuCN (17.8 g, 200 mmol), the resulting mixture was stirred at 150° C. for 16 h. The reaction mixture cooled to room temperature and poured into water (800 mL) and extracted with EA (200 mL×3), the combined organic layers were washed with water (800 mL) and brine (800 mL), then dried over Na₂SO₄ and concentrated under reduced pressure. The residue was purified by column chromatography to afford N-(4-cyano-2-fluoro-3-(trifluoromethyl)phenyl)acetamide (19 g, 77% yield) as a yellow solid. MS: m/z=246.9 (M+1, ESI+).

Step 4:

To a solution of N-(4-cyano-2-fluoro-3-(trifluoromethyl)phenyl)acetamide (19 g, 77 mmol) in EtOH (100 ml) was added 5 M HCl (100 mL), the resulting mixture was stirred at 80° C. for 2 h. The reaction mixture was cooled to room temperature and concentrated under reduce pressure. The residue was purified by column chromatography to afford 4-amino-3-fluoro-2-(trifluoromethyl) benzonitrile (12.8 g, 80% yield) as a yellow solid. MS: m/z=205.1 (M+1, ESI+).

Step 5:

To a solution of triphosgene (20.3 g, 176.5 mmol) in H₂O (200 mL) was added 4-amino-3-fluoro-2-(trifluoromethyl) benzonitrile (7.2 g, 35.3 mmol) in portions, the resulting mixture was stirred at 25° C. for 16 h. The reaction mixture was poured into ice water (200 mL) and extracted with DCM (100 mL×3), the combined organic layers were washed with water (200 mL) and brine (200 mL), then dried over Na₂SO₄ and concentrated under reduced pressure. The residue was purified by column chromatography to afford intermediate compound 59, 3-fluoro-4-isothiocyanato-2-(trifluoromethyl)benzonitrile (5.5 g, 62.8% yield) as a colorless oil.

Example 2—Synthesis of Final Compounds

Described herein are details of the synthesis and characterization of several exemplary compounds of this disclosure. It is understood that the synthetic methods and materials described may readily be adapted to synthesize a variety of compounds of formula (I)-(XIc), including any of the compounds of Table 1.

Synthesis of Compound 1

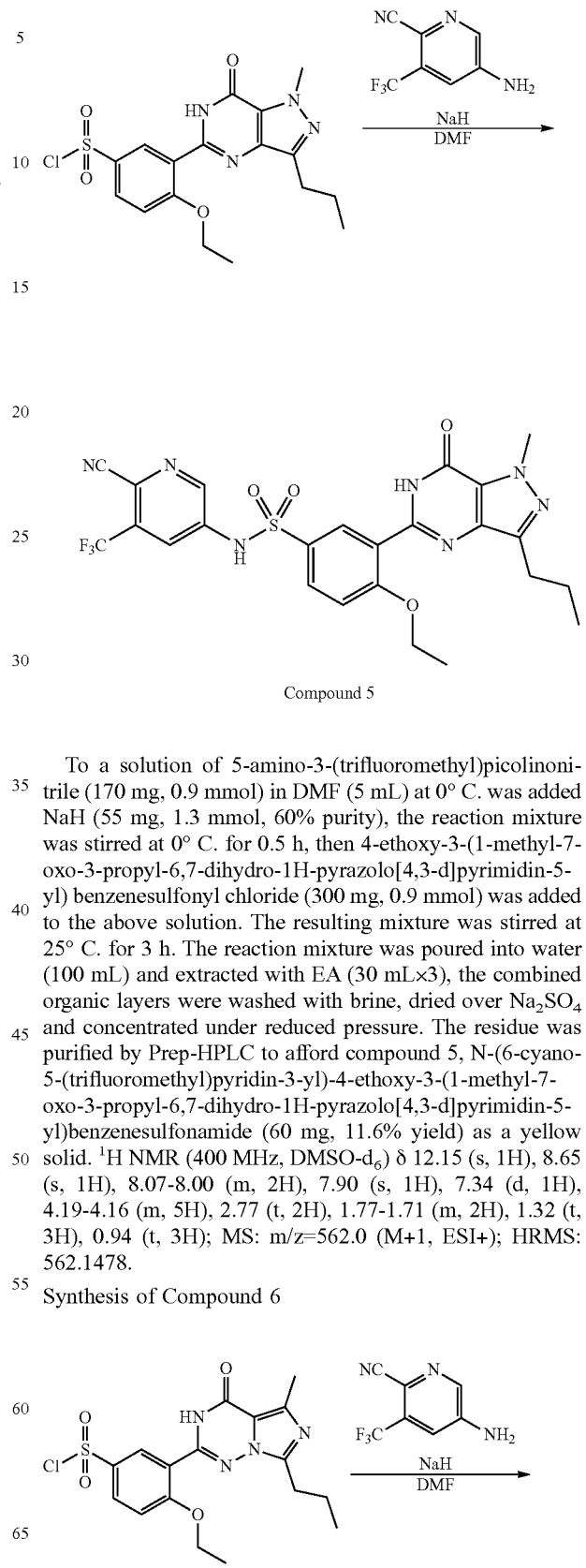

Compound 1

To a solution of 4-amino-2-(trifluoromethyl)benzonitrile (68 mg, 365 umol) in DMF (10 mL) at 0° C. was added NaH (29 mg, 730 umol, 60% purity), the reaction mixture was stirred at 0° C. for 0.5 h, then 4-ethoxy-3-(1-methyl-7-oxo-3-propyl-6,7-dihydro-1H-pyrazolo[4,3-d]pyrimidin-5-yl) benzenesulfonyl chloride (100 mg, 243 umol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 1, N-(4-cyano-3-(trifluoromethyl)phenyl)-4-ethoxy-3-(1-methyl-7-oxo-3-propyl-6,7-dihydro-1H-pyrazolo[4,3-d]pyrimidin-5-yl)benzenesulfonamide, (75 mg, 54.97% yield) as a white solid. 1H NMR (400 MHz, DMSO-$d_6$) δ 12.12 (s, 1H), 8.07-7.97 (m, 3H), 7.62-7.53 (m, 2H), 7.34 (d, 1H), 4.19-4.14 (m, 5H), 2.76 (t, 2H), 1.77-1.68 (m, 2H), 1.31 (t, 3H), 0.92 (t, 3H); MS: m/z=561.4 (M+1, ESI+); HRMS: 561.1527.

Synthesis of Compound 5

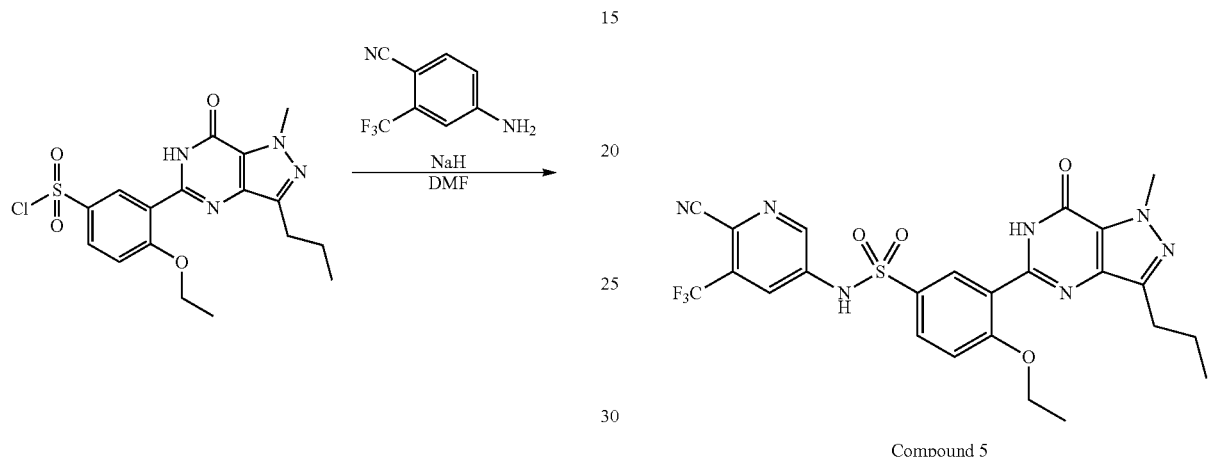

Compound 5

To a solution of 5-amino-3-(trifluoromethyl)picolinonitrile (170 mg, 0.9 mmol) in DMF (5 mL) at 0° C. was added NaH (55 mg, 1.3 mmol, 60% purity), the reaction mixture was stirred at 0° C. for 0.5 h, then 4-ethoxy-3-(1-methyl-7-oxo-3-propyl-6,7-dihydro-1H-pyrazolo[4,3-d]pyrimidin-5-yl) benzenesulfonyl chloride (300 mg, 0.9 mmol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 5, N-(6-cyano-5-(trifluoromethyl)pyridin-3-yl)-4-ethoxy-3-(1-methyl-7-oxo-3-propyl-6,7-dihydro-1H-pyrazolo[4,3-d]pyrimidin-5-yl)benzenesulfonamide (60 mg, 11.6% yield) as a yellow solid. 1H NMR (400 MHz, DMSO-$d_6$) δ 12.15 (s, 1H), 8.65 (s, 1H), 8.07-8.00 (m, 2H), 7.90 (s, 1H), 7.34 (d, 1H), 4.19-4.16 (m, 5H), 2.77 (t, 2H), 1.77-1.71 (m, 2H), 1.32 (t, 3H), 0.94 (t, 3H); MS: m/z=562.0 (M+1, ESI+); HRMS: 562.1478.

Synthesis of Compound 6

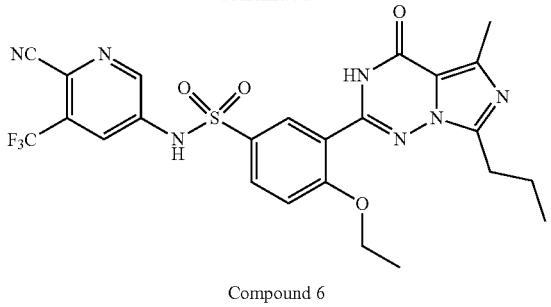

Compound 6

To a solution of 5-amino-3-(trifluoromethyl)picolinonitrile (170 mg, 0.9 mmol) in DMF (10 mL) at 0° C. was added NaH (55 mg, 1.3 mmol, 60% purity), the reaction mixture was stirred at 0° C. for 0.5 h, then 4-ethoxy-3-(5-methyl-4-oxo-7-propyl-3,4-dihydroimidazo[5,1-f][1,2,4]triazin-2-yl)benzenesulfonyl chloride (300 mg, 0.9 mmol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 6, N-(6-cyano-5-(trifluoromethyl)pyridin-3-yl)-4-ethoxy-3-(5-methyl-4-oxo-7-propyl-3,4-dihydroimidazo[5,1-f][1,2,4]triazin-2-yl)benzenesulfonamide (50 mg, 10.0% yield) as a white solid. 1H NMR (400 MHz, DMSO-$d_6$) δ 11.68 (s, 1H), 8.68 (d, 1H), 8.08-8.05 (m, 2H), 7.90 (s, 1H), 7.37 (d, 1H), 4.19 (q, 2H), 2.83 (t, 2H), 2.49 (s, 2H), 1.77-1.71 (m, 2H), 1.31 (t, 3H), 0.93 (t, 3H); MS: m/z=562.0 (M+1, ESI+); HRMS: 562.1478.

Synthesis of Compound 7

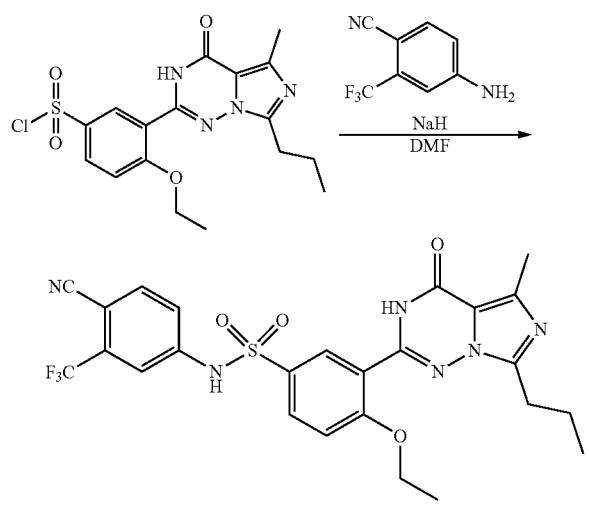

Compound 7

To a solution of 4-amino-2-(trifluoromethyl)benzonitrile (68 mg, 365 umol) in DMF (10 mL) at 0° C. was added NaH (29 mg, 730 umol, 60% purity), the reaction mixture was stirred at 0° C. for 0.5 h, then 4-ethoxy-3-(5-methyl-4-oxo-7-propyl-3,4-dihydroimidazo[5,1-f][1,2,4]triazin-2-yl) benzenesulfonyl chloride (100 mg, 243 umol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 7 N-(4-cyano-3-(trifluoromethyl)phenyl)-4-ethoxy-3-(5-methyl-4-oxo-7-propyl-3,4-dihydroimidazo[5,1-f][1,2,4]triazin-2-yl)benzenesulfonamide (60 mg, 43.98% yield) as a white solid. 1H NMR (400 MHz, DMSO-$d_6$) δ 11.77 (s, 1H), 8.10-8.06 (m, 3H), 7.71-7.63 (m, 2H), 7.41 (d, 1H), 4.21 (q, 2H), 2.87 (t, 2H), 2.52 (s, 3H), 1.80-1.74 (m, 2H), 1.33 (t, 3H), 0.95 (t, 3H); MS: m/z=561.3 (M+1, ESI+); HRMS: 561.1525.

Synthesis of Compound 8

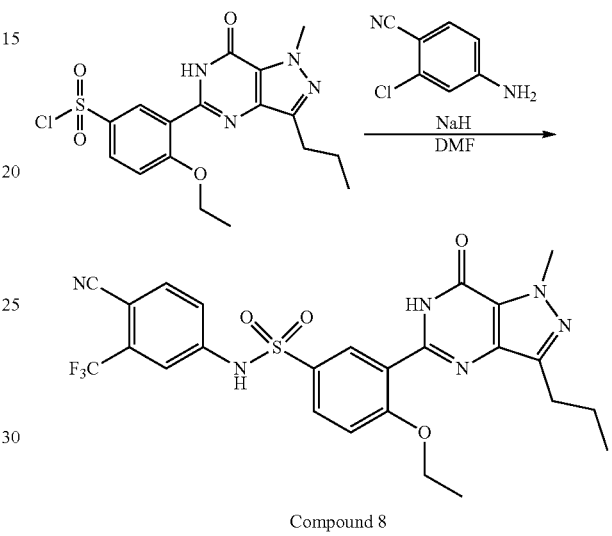

Compound 8

To a solution of 4-amino-2-chlorobenzonitrile (84 mg, 548 umol) in DMF (10 mL) at 0° C. was added NaH (44 mg, 1.10 mmol, 60% purity), the reaction mixture was stirred at 0° C. for 0.5 h, then 4-ethoxy-3-(1-methyl-7-oxo-3-propyl-6,7-dihydro-1H-pyrazolo[4,3-d]pyrimidin-5-yl) benzenesulfonyl chloride (150 mg, 365 umol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 8, N-(3-chloro-4-cyanophenyl)-4-ethoxy-3-(1-methyl-7-oxo-3-propyl-6,7-dihydro-1H-pyrazolo [4,3-d]pyrimidin-5-yl)benzenesulfonamide (90 mg, 46.78% yield) as a white solid. 1H NMR (400 MHz, DMSO-$d_6$) δ 12.14 (s, 1H), 11.33 (s, 1H), 8.04-7.97 (m, 2H), 7.85 (d, 1H), 7.37-7.33 (m, 2H), 7.26 (dd, 1H), 4.21-4.16 (m, 5H), 2.78 (t, 2H), 1.80-1.70 (m, 2H), 1.32 (t, 3H), 0.95 (t, 3H); MS: m/z=527.3 (M+1, ESI+); HRMS: 527.1263.

Synthesis of Compound 9

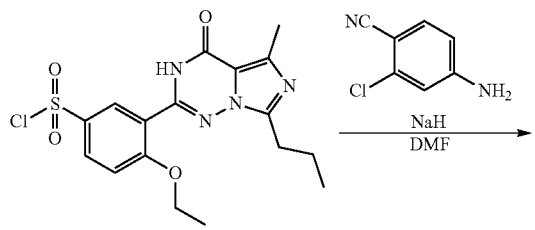

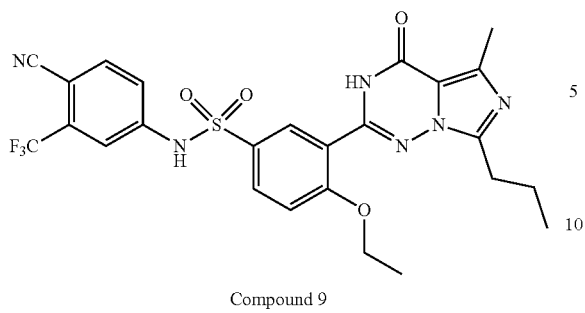

Compound 9

To a solution of 4-amino-2-chlorobenzonitrile (84 mg, 548 umol) in DMF (10 mL) at 0° C. was added NaH (44 mg, 1.10 mmol, 60% purity), the reaction mixture was stirred at 0° C. for 0.5 h, then 4-ethoxy-3-(5-methyl-4-oxo-7-propyl-3,4-dihydroimidazo[5,1-f][1,2,4]triazin-2-yl) benzenesulfonyl chloride (150 mg, 365 umol) was added to the above solution. The resulting mixture was stirred at 25° C. for 3 h. The reaction mixture was poured into water (100 mL) and extracted with EA (30 mL×3), the combined organic layers were washed with brine, dried over $Na_2SO_4$ and concentrated under reduced pressure. The residue was purified by Prep-HPLC to afford compound 9, N-(3-chloro-4-cyanophenyl)-4-ethoxy-3-(5-methyl-4-oxo-7-propyl-3,4-dihydroimidazo[5,1-f][1,2,4]triazin-2-yl)benzenesulfonamide (85 mg, 44.18% yield) as a white solid. $^1$H NMR (400 MHz, DMSO-$d_6$) δ 11.64 (s, 1H), 8.03-8.00 (m, 2H), 7.85 (d, 1H), 7.38-7.35 (m, 2H), 7.26 (d, 1H), 4.18 (q, 2H), 2.83 (t, 2H), 2.48 (s, 3H), 1.77-1.72 (m, 2H), 1.31 (t, 3H), 0.94 (t, 3H); MS: m/z=527.3 (M+1, ESI+); HRMS: 527.1262.

Synthesis of Compound 10

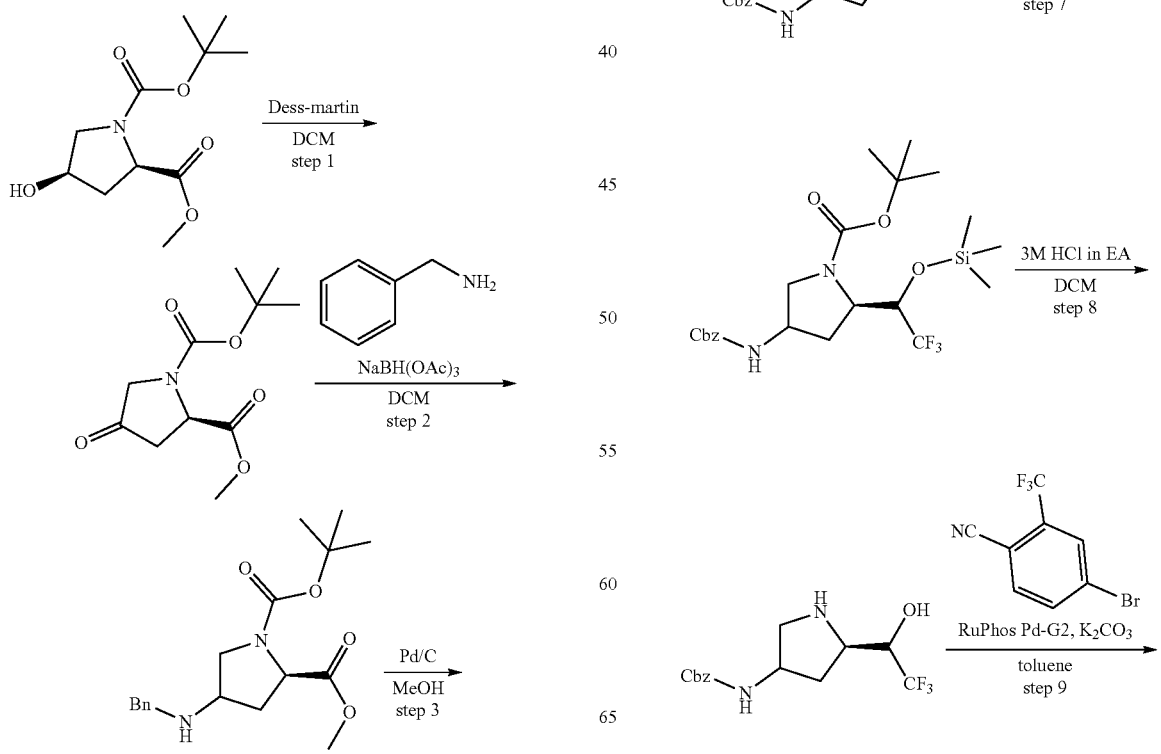

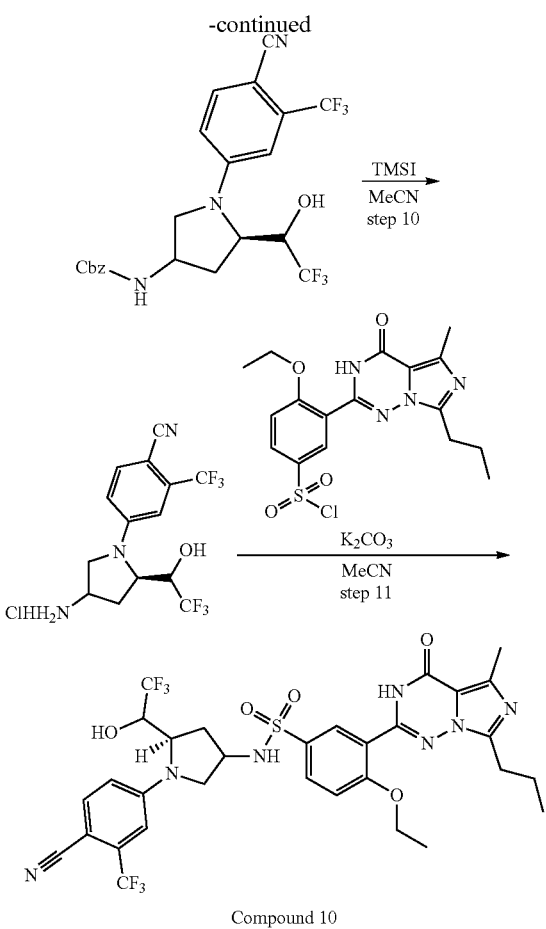

Compound 10

Step 1:
To a solution of 1-(tert-butyl) 2-methyl (2R,4R)-4-hydroxypyrrolidine-1,2-dicarboxylate (12.5 g, 50.96 mmol) in DCM (300 mL) was added Dess-martin (32.42 g, 76.45 mmol), the reaction mixture was stirred at 25° C. for 3 h. The reaction mixture was poured into water (500 mL) and extracted with DCM (100 mL×3), the combined organic layers were dried over Na₂SO₄ and concentrated under reduced pressure. The residue was purified by column chromatography to afford 1-(tert-butyl) 2-methyl (R)-4-oxopyrrolidine-1,2-dicarboxylate (10 g, 80.66% yield) as a white solid. MS: m/z=144.2 (M−100+1, ESI+).

Step 2:
To a solution of 1-(tert-butyl) 2-methyl (R)-4-oxopyrrolidine-1,2-dicarboxylate (10 g, 41.11 mmol) in DCM (300 mL) was added phenylmethanamine (5.29 g, 49.33 mmol), the reaction mixture was stirred at 25° C. for 0.5 h. Then NaBH(OAc)₃ (13.07 g, 61.66 mmol) was added to the above reaction mixture, the resulting mixture was stirred at 25° C. for another 3 h. The reaction mixture was poured into water (500 mL) and extracted with DCM (100 mL×3), the combined organic layers were dried over Na₂SO₄ and concentrated under reduced pressure. The residue was purified by column chromatography to afford 1-(tert-butyl) 2-methyl (2R)-4-(benzylamino)pyrrolidine-1,2-dicarboxylate (10.5 g, 76.38% yield) as a yellow oil. MS: m/z=335.1 (M+1, ESI+).

Step 3:
To a solution of 1-(tert-butyl) 2-methyl (2R)-4-(benzylamino)pyrrolidine-1,2-dicarboxylate (7.5 g, 22.46 mmol) in MeOH (80 mL) was added Pd/C (0.8 g), the reaction mixture was stirred at 25° C. under H₂ for 6 h. The reaction mixture was filtered and the filtrate was concentrated under reduced pressure to afford 1-(tert-butyl) 2-methyl (2R)-4-aminopyrrolidine-1,2-dicarboxylate (4.0 g, 76.38% yield) as a yellow oil. MS: m/z=245.2 (M+1, ESI+).

Step 4:
To a solution of 1-(tert-butyl) 2-methyl (2R)-4-aminopyrrolidine-1,2-dicarboxylate (4 g, 16.37 mmol) and CbzCl (4.90 g, 19.65 mmol) in DCM (100 mL) was added TEA (6.35 g, 49.12 mmol), the reaction mixture was stirred at 25° C. for 5 h. The reaction mixture was poured into water (150 mL) and extracted with DCM (50 mL×3), the combined organic layers were dried over Na₂SO₄ and concentrated under reduced pressure. The residue was purified by column chromatography to afford 1-(tert-butyl) 2-methyl (2R)-4-(((benzyloxy)carbonyl)amino)pyrrolidine-1,2-dicarboxylate (5.4 g, 87.15% yield) as a yellow oil. MS: m/z=279.1 (M−100+1, ESI+).

Step 5:
To a solution of 1-(tert-butyl) 2-methyl (2R)-4-(((benzyloxy)carbonyl)amino)pyrrolidine-1,2-dicarboxylate (5.4 g, 14.27 mmol) in THF (80 mL) at 0° C. was added LAH (813 mg, 21.40 mmol) in portions, then the reaction mixture was stirred at 25° C. for 3 h. The reaction mixture was poured into ice water (150 mL) slowly and extracted with EA (100 mL×3), the combined organic layers were dried over Na₂SO₄ and concentrated under reduced pressure. The residue was purified by column chromatography to afford tert-butyl (2R)-4-(((benzyloxy)carbonyl)amino)-2-(hydroxyl methyl)pyrrolidine-1-carboxylate (2.9 g, 58.00% yield) as a colorless oil. MS: m/z=251.1 (M−100+1, ESI+).

Step 6:
To a solution of tert-butyl (2R)-4-(((benzyloxy)carbonyl)amino)-2-(hydroxymethyl)pyrrolidine-1-carboxylate (4.5 g, 12.84 mmol) in DCM (30 mL) was added Dess-martin (5.45 g, 12.84 mmol), the reaction mixture was stirred at 25° C. for 2 h. The reaction mixture was poured into water (100 mL) and extracted with DCM (30 mL×3). The combined organic layers were dried over Na₂SO₄ and concentrated under reduced pressure.

The residue was purified by column chromatography to afford tert-butyl (2R)-4-(((benzyloxy)carbonyl)amino)-2-formylpyrrolidine-1-carboxylate (2.9 g, 64.82% yield) as a colorless oil. MS: m/z=249.2 (M−100+1, ESI+).

Step 7:
To a solution of tert-butyl (2R)-4-(((benzyloxy)carbonyl)amino)-2-formylpyrrolidine-1-carboxylate (2.9 g, 8.32 mmol) in THF (20 mL) was added TMSCF₃ (1.54 g, 10.82 mmol) and CsF (127 mg, 832 umol), the reaction mixture was stirred at 25° C. for 2 h. The reaction mixture was poured into water (100 mL) and extracted with EA (30 mL×3), the combined organic layers were dried over Na₂SO₄ and concentrated under reduced pressure. The residue was purified by column chromatography to afford tert-butyl (2R)-4-(((benzyloxy)carbonyl)amino)-2-((S)-2,2,2-trifluoro-1-((trimethylsilyl)oxy)ethyl)pyrrolidine-1-carboxylate (2.35 g, 57.55% yield) as a yellow oil. MS: m/z=391.2 (M−100+1, ESI+).

Step 8:
To a solution of tert-butyl (2R)-4-(((benzyloxy)carbonyl)amino)-2-((S)-2,2,2-trifluoro-1-((trimethylsilyl)oxy)ethyl)pyrrolidine-1-carboxylate (2.35 g, 4.79 mmol) in DCM (5 mL) was added 3M HCl in EA (5 mL), the reaction mixture was stirred at 25° C. for 2 h. The reaction mixture was poured into aq. NaHCO₃ (40 mL) and extracted with EA (10 mL×3), the combined organic layers were dried over Na₂SO₄ and concentrated under reduced pressure. The residue was purified by column chromatography to afford benzyl ((5R)-5-((S)-2,2,2-trifluoro-1-hydroxyethyl)pyrrolidin-3-yl)carbamate (1.50 g, 4.71 mmol, 98.38% yield) as a brown oil. MS: m/z=319.0 (M+1, ESI+).

Step 9:

To a solution of benzyl ((5R)-5-((S)-2,2,2-trifluoro-1-hydroxyethyl)pyrrolidin-3-yl)carbamate (1.50 g, 4.71 mmol) and 4-bromo-2-(trifluoromethyl)benzonitrile (1.77 g, 7.07 mmol) in toluene (25 mL) was added $K_2CO_3$ (1.95 g, 14.14 mmol) and RuPhosPd-$G_2$ (183.02 mg, 235.63 umol), the reaction mixture was stirred at 110° C. under $N_2$ for 16 h. The reaction mixture was cooled to room temperature and poured into water (100 mL) and extracted with EA (40 mL×3), the combined organic layers were dried over $Na_2SO_4$ and concentrated under reduced pressure. The residue was purified by column chromatography to afford benzyl ((5R)-1-(4-cyano-3-(trifluoromethyl) phenyl)-5-((S)-2,2,2-trifluoro-1-hydroxyethyl)pyrrolidin-3-yl)carbamate (869 mg, 37.83% yield) as a yellow oil. MS: m/z=488.1 (M+1, ESI+).

Step 10:

To a solution of benzyl ((5R)-1-(4-cyano-3-(trifluoromethyl)phenyl)-5-((S)-2,2,2-trifluoro-1-hydroxyethyl)pyrrolidin-3-yl)carbamate (869 mg, 1.78 mmol) in MeCN (10 mL) was added TMSI (1.07 g, 5.35 mmol), the reaction mixture was stirred at 25° C. for 1 h. The reaction mixture was poured into water (100 mL) and extracted with EA (40 mL×3), the combined organic layers were dried over $Na_2SO_4$ and concentrated under reduced pressure. The residue was purified by prep-HPLC to afford 4-((2R)-4-amino-2-((S)-2,2,2-trifluoro-1-hydroxyethyl)pyrrolidin-1-yl)-2-(trifluoro methyl)benzonitrile hydrochloride (70 mg, 11.11% yield) as an off-white solid. $^1$H NMR (400 MHz, MeOD) δ 7.81 (d, 1H), 7.03 (d, 1H), 6.97 (dd, 1H), 4.59 (d, 1H), 4.38 (q, 1H), 4.12 (t, 1H), 3.88-3.83 (m, 1H), 3.72 (dd, 1H), 2.73-2.65 (m, 1H), 2.48 (d, 1H); MS: m/z=354.0 (M+1, ESI+).

Step 11:

To a solution of 4-ethoxy-3-(5-methyl-4-oxo-7-propyl-3,4-dihydroimidazo[5,1-f][1,2,4]triazin-2-yl)benzenesulfonyl chloride (70 mg, 170 umol) in THF (5 mL) was added 4-((2R)-4-amino-2-((S)-2,2,2-trifluoro-1-hydroxyethyl)pyrrolidin-1-yl)-2-(trifluoromethyl)benzonitrile hydrochloride (60 mg, 170 umol) and TEA (51.50 mg, 508.91 umol), the reaction mixture was stirred at 25° C. for 5 h. The reaction mixture was poured into water (20 mL) and extracted with EA (10 mL×3), the combined organic layers were dried over $Na_2SO_4$ and concentrated under reduced pressure. The residue was purified by prep-HPLC to afford compound 10, N-((5R)-1-(4-cyano-3-(trifluoromethyl)phenyl)-5-(2,2,2-trifluoro-1-hydroxyethyl)pyrrolidin-3-yl)-4-ethoxy-3-(5-methyl-4-oxo-7-propyl-3,4-dihydro imidazo[5,1-f][1,2,4]triazin-2-yl)benzenesulfonamide (15 mg, 12.15% yield) as a white solid. $^1$H NMR (400 MHz, DMSO-$d_6$) δ 7.98-7.95 (m, 2H), 7.83 (d, 1H), 7.36 (d, 1H), 6.86-6.83 (m, 2H), 4.34-4.26 (m, 2H), 4.19 (q, 2H), 3.74-3.64 (m, 2H), 3.17 (t, 1H), 2.78 (t, 2H), 2.47 (s, 3H), 2.23-2.18 (m, 1H), 2.12-2.07 (m, 1H), 1.75-1.65 (m, 2H), 1.32 (t, 3H), 0.88 (t, 3H); MS: m/z=728.3 (M+1, ESI+).

Synthesis of Compound 11

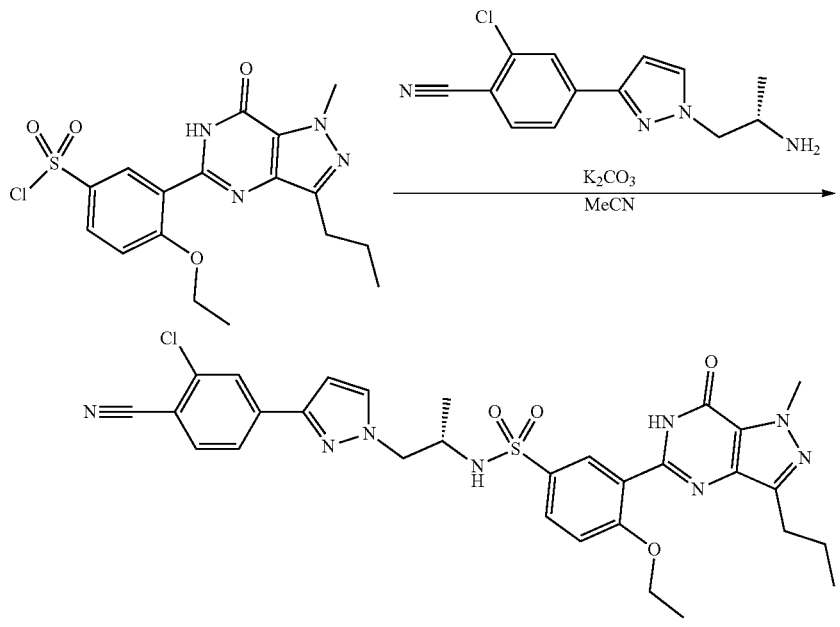

Compound 11

To a solution of 4-ethoxy-3-(1-methyl-7-oxo-3-propyl-6,7-dihydro-1H-pyrazolo[4,3-d]pyrimidin-5-yl)benzenesulfonyl chloride (250 mg, 608.46 umol) and (S)-4-(1-(2-aminopropyl)-1H-pyrazol-3-yl)-2-chlorobenzonitrile (190 mg, 730.15 umol) in MeCN (10 mL) was added $K_2CO_3$ (168 mg, 1.22 mmol), the reaction mixture was stirred at 25° C. for 16 h. Filtered and concentrated under reduced pressure, the residue was purified by prep-HPLC to afford compound 11, (S)—N-(1-(3-(3-chloro-4-cyanophenyl)-1H-pyrazol-1-yl)propan-2-yl)-4-ethoxy-3-(1-methyl-7-oxo-3-propyl-6,7-dihydro-1H-pyrazolo[4,3-d] pyrimidin-5-yl)benzenesulfonamide (102 mg, 26.35% yield) as a white solid. $^1$H NMR (400 MHz, DMSO-$d_6$) δ 11.84 (s, 1H), 7.94-7.90 (m, 3H), 7.82-7.76 (m, 2H), 7.68 (s, 2H), 7.11 (d, 1H), 6.76 (s, 1H), 4.17-4.06 (m, 7H), 3.71 (s, 1H), 2.78 (s, 2H), 1.76-1.75 (m, 2H), 1.34 (s, 3H), 1.07 (s, 3H), 0.95 (s, 3H); MS: m/z=635.2 (M+1, ESI+); HRMS: 635.1952.

Synthesis of Compound 13

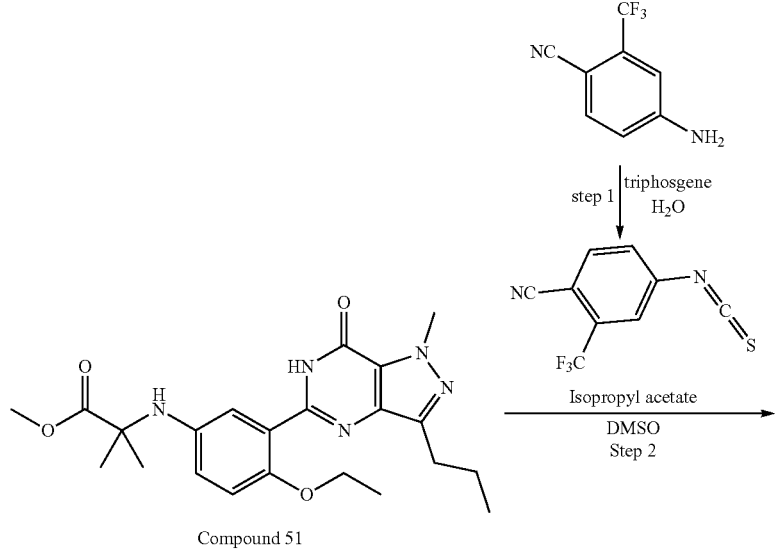

Compound 51

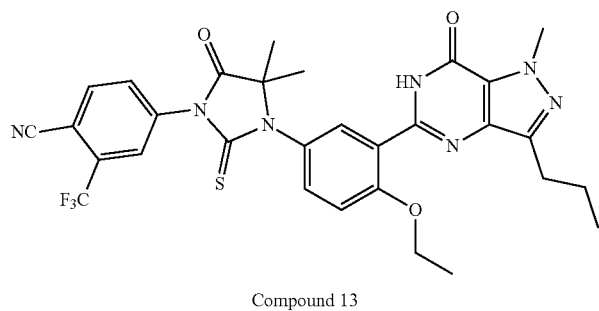

Compound 13

Step 1:

To a solution of triphosgene (8.34 g, 72.53 mmol) in H₂O (50 mL) was added 4-amino-2-(trifluoromethyl)benzonitrile (4.5 g, 24.18 mmol) in portions, the reaction mixture was stirred at 25° C. for 5 h. The reaction mixture was poured into ice water (100 mL) and extracted with DCM (40 mL×3), the combined organic layers were washed with water (100 mL) and brine (100 mL), then dried over Na₂SO₄ and concentrated under reduced pressure. The residue was purified by column chromatography to afford 4-isothiocyanato-2-(trifluoromethyl)benzonitrile (1.02 g, 18.49% yield) as a white solid.

Step 2:

To a solution of compound 51, methyl 2-((4-ethoxy-3-(1-methyl-7-oxo-3-propyl-6,7-dihydro-1H-pyrazolo[4,3-d]pyrimidin-5-yl)phenyl)amino)-2-methylpropanoate (150 mg, 350.88 umol) and 4-isothiocyanato-2-(trifluoromethyl)benzonitrile (160 mg, 702 umol) in DMSO (10 mL) was added isopropyl acetate (3 g, 29.37 mmol), the reaction mixture was stirred at 85° C. for 16 h. The reaction mixture was poured into water (150 mL) and extracted with DCM (20 mL×3), the combined organic layers were washed with water (100 mL) and brine (100 mL), then dried over Na₂SO₄ and concentrated under reduced pressure. The residue was purified by prep-HPLC to afford compound 13, 4-(3-(4-ethoxy-3-(1-methyl-7-oxo-3-propyl-6,7-dihydro-1H-pyrazolo[4,3-d]pyrimidin-5-yl)phenyl)-4,4-dimethyl-5-oxo-2-thioxoimidazolidin-1-yl)-2-(trifluoromethyl)benzonitrile (110 mg, 50.27% yield) as a white solid. ¹H NMR (400 MHz, DMSO-$d_6$) δ 12.11 (s, 1H), 8.40 (d, 1H), 8.31 (s, 1H), 8.10 (dd, 1H), 7.62 (d, 1H), 7.50 (dd, 1H), 7.34 (d, 1H), 4.20 (q, 2H), 4.16 (s, 3H), 2.77 (t, 2H), 1.77-1.71 (m, 2H), 1.54 (s, 6H), 1.36 (t, 3H), 0.93 (t, 3H); MS: m/z=624.2 (M+1, ESI+); HRMS: 624.1998.

Synthesis of Compound 18

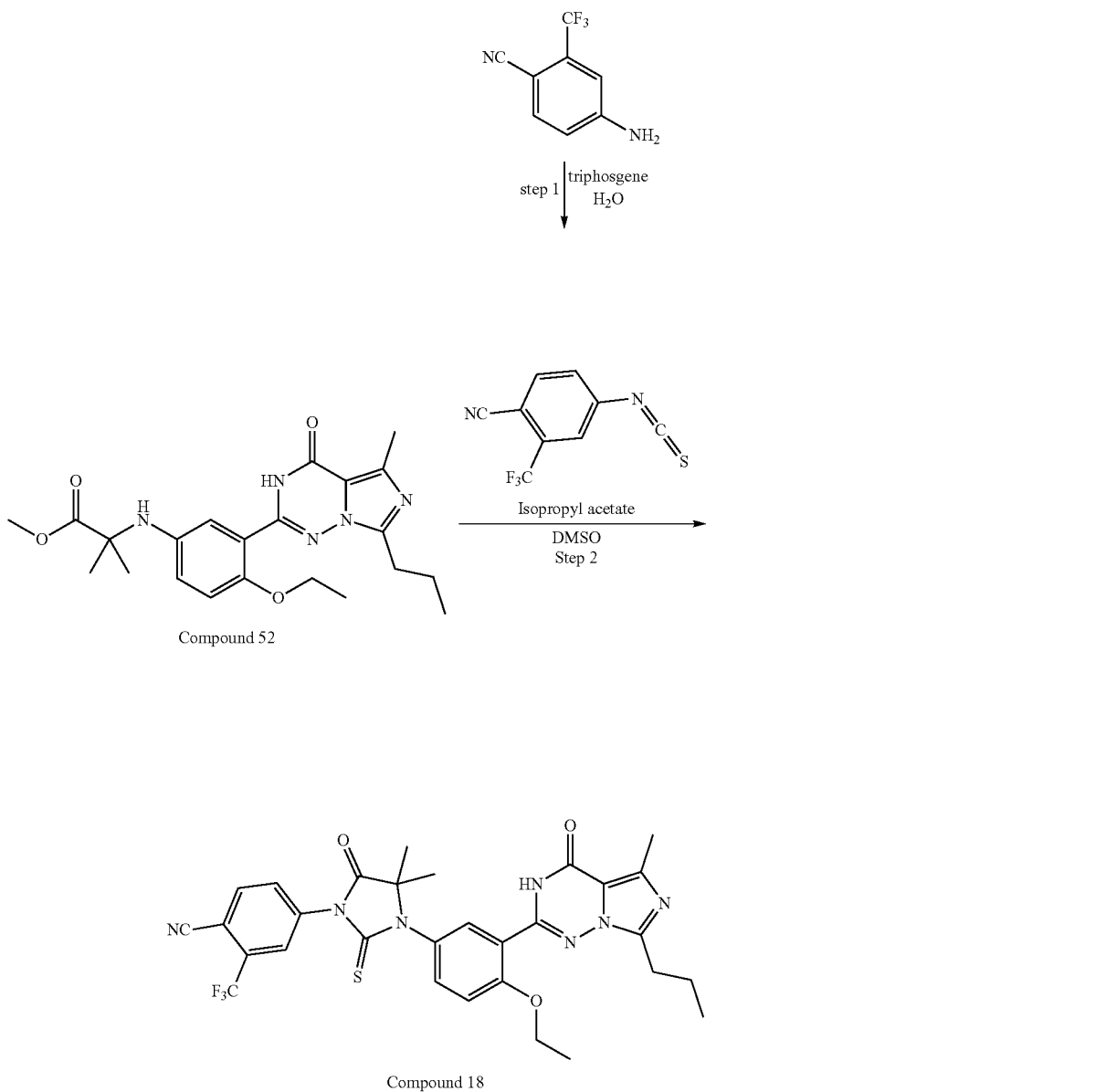

Step 1:

To a solution of triphosgene (8.34 g, 72.53 mmol) in H₂O (50 mL) was added 4-amino-2-(trifluoromethyl)benzonitrile (4.5 g, 24.18 mmol) in portions, the reaction mixture was stirred at 25° C. for 5 h. The reaction mixture was poured into ice water (100 mL) and extracted with DCM (40 mL×3), the combined organic layers were washed with water (100 mL) and brine (100 mL), then dried over Na₂SO₄ and concentrated under reduced pressure. The residue was purified by column chromatography to afford 4-isothiocyanato-2-(trifluoromethyl)benzonitrile (1.02 g, 18.49% yield) as a white solid.

Step 2:

To a solution of compound 52, methyl 2-((4-ethoxy-3-(5-methyl-4-oxo-7-propyl-3,4-dihydroimidazo[5,1-f][1,2,4]triazin-2-yl)phenyl)amino)-2-methylpropanoate (278 mg, 650.30 umol) and 4-isothiocyanato-2-(trifluoromethyl)benzonitrile (178 mg, 780.36 umol) in DMSO (15 mL) was added isopropyl acetate (1.33 g, 13 mmol), the reaction mixture was stirred at 85° C. for 16 h. The reaction mixture was poured into water (150 mL) and extracted with DCM (20 mL×3), the combined organic layers were washed with water (100 mL) and brine (100 mL), then dried over Na₂SO₄ and concentrated under reduced pressure. The residue was purified by prep-HPLC to afford compound 18, 4-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-2-(trifluoromethyl)benzonitrile (100 mg, 24.66% yield) as a white solid. $^1$H NMR (400 MHz, DMSO-d₆) δ 11.63 (s, 1H), 8.39 (d, 1H), 8.30 (s, 1H), 8.08 (dd, 1H), 7.55-7.53 (m, 2H), 7.34 (d, 1H), 4.18 (q, 2H), 2.82 (t, 2H), 2.48 (s, 3H), 1.76-1.70 (m, 2H), 1.53 (s, 6H), 1.34 (t, 3H), 0.91 (t, 3H); MS: m/z=624.1 (M+1, ESI+); HRMS: 624.1996.

Synthesis of Compound 19

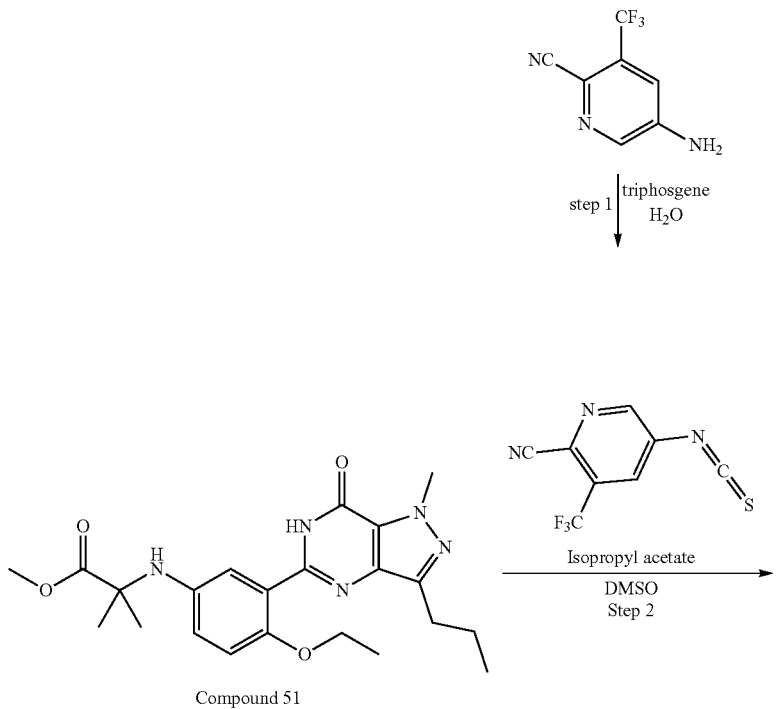

Step 1:

To a solution of triphosgene (6.14 g, 53.44 mmol) in H₂O (15 mL) was added 5-amino-3-(trifluoromethyl)picolinonitrile (2.00 g, 10.69 mmol) in portions, the reaction mixture was stirred at 25° C. for 5 h. The reaction mixture was poured into ice water (100 mL) and extracted with DCM (40 mL×3), the combined organic layers were washed with water (100 mL) and brine (100 mL), then dried over Na₂SO₄ and concentrated under reduced pressure. The residue was purified by column chromatography to afford 5-isothiocyanato-3-(trifluoromethyl)picolinonitrile (1.0 g, 40.81% yield) as a yellow oil.

Step 2:

To a solution of compound 51, methyl 2-((4-ethoxy-3-(5-methyl-4-oxo-7-propyl-3,4-dihydroimidazo[5,1-f][1,2,4]triazin-2-yl)phenyl)amino)-2-methylpropanoate (350 mg, 818.72 umol) and 5-isothiocyanato-3-(trifluoromethyl)picolinonitrile (225 mg, 982.47 umol) in DMSO (5 mL) was added isopropyl acetate (1.67 g, 16.37 mmol), the reaction mixture was stirred at 85° C. for 3 h. The reaction mixture was poured into water (50 mL) and extracted with DCM (10 mL×3), the combined organic layers were washed with water (50 mL) and brine (50 mL), then dried over Na₂SO₄ and concentrated under reduced pressure. The residue was purified by prep-HPLC to afford compound 19, 5-(3-(4-ethoxy-3-(1-methyl-7-oxo-3-propyl-6,7-dihydro-1H-pyrazolo[4,3-d]pyrimidin-5-yl)phenyl)-4,4-dimethyl-5-oxo-2-thioxoimidazolidin-1-yl)-3-(trifluoromethyl)picolinonitrile (158 mg, 30.90% yield) as a white solid. $^1$H NMR (400 MHz, DMSO-d₆) δ 12.11 (s, 1H), 9.25 (d, 1H), 8.83 (d, 1H), 7.63 (d, 1H), 7.50 (dd, 1H), 7.35 (d, 1H), 4.20 (q, 2H), 4.16 (s, 3H), 2.77 (t, 2H), 1.77-1.72 (m, 2H), 1.56 (s, 6H), 1.37 (t, 3H), 0.93 (t, 3H); MS: m/z=625.2 (M+1, ESI+); HRMS: 625.1951.

Synthesis of Compound 20

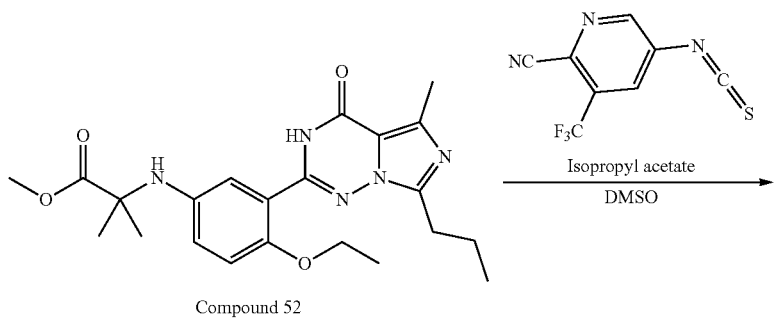

Compound 52

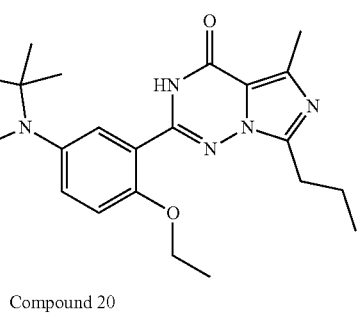

Compound 20

To a solution of compound 52, methyl 2-((4-ethoxy-3-(5-methyl-4-oxo-7-propyl-3,4-dihydroimidazo[5,1-f][1,2,4]triazin-2-yl)phenyl)amino)-2-methylpropanoate (200 mg, 467.84 umol) and 5-isothiocyanato-3-(trifluoromethyl)picolinonitrile (161 mg, 702 umol) in NMP (10 mL) was added isopropyl acetate (5 mL), the reaction mixture was stirred at 115° C. for 16 h. The reaction mixture was poured into water (150 mL) and extracted with DCM (30 mL×3), the combined organic layers were washed with water (100 mL) and brine (100 mL), then dried over $Na_2SO_4$ and concentrated under reduced pressure. The residue was purified by prep-HPLC to afford compound 20, 5-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-3-(trifluoromethyl)picolinonitrile (105 mg, 35.93% yield) as a white solid. $^1$H NMR (400 MHz, DMSO-$d_6$) δ 11.64 (s, 1H), 9.25 (s, 1H), 8.82 (s, 1H), 7.54-7.53 (m, 2H), 7.35 (d, 1H), 4.18 (q, 2H), 2.82 (t, 2H), 2.48 (s, 3H), 1.73 (q, 2H), 1.55 (s, 6H), 1.34 (t, 3H), 0.93-0.91 (t, 3H); MS: m/z=625.2 (M+1, ESI+); HRMS: 625.1944.

Synthesis of Compound 21

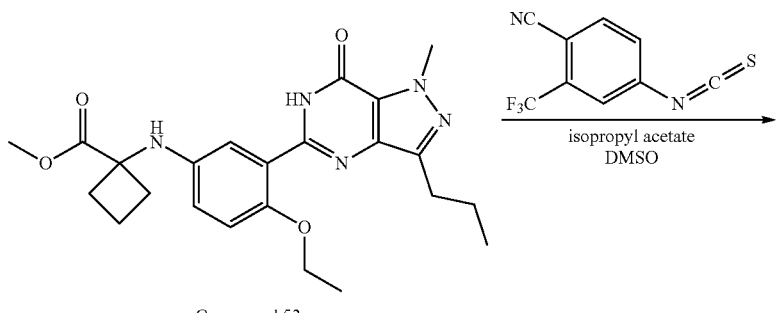

Compound 53

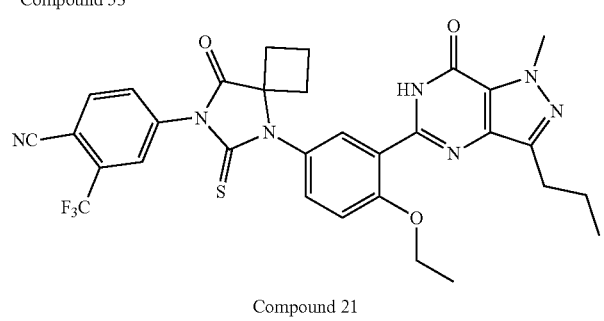

Compound 21

To a solution of compound 53, methyl 1-((4-ethoxy-3-(1-methyl-7-oxo-3-propyl-6,7-dihydro-1H-pyrazolo[4,3-d]pyrimidin-5-yl)phenyl)amino)cyclobutane-1-carboxylate (280 mg, 637 umol) and 4-isothiocyanato-2-(trifluoromethyl)benzonitrile (175 mg, 764 umol) in DMSO (5 mL) was added isopropyl acetate (1.30 g, 12.74 mmol), the reaction mixture was stirred at 85° C. for 3 h. The reaction mixture was poured into water (50 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 21, 4-(5-(4-ethoxy-3-(1-methyl-7-oxo-3-propyl-6,7-dihydro-1H-pyrazolo[4,3-d]pyrimidin-5-yl)phenyl)-8-oxo-6-thioxo-5,7-diazaspiro[3.4]octan-7-yl)-2-(trifluoromethyl)benzonitrile (80 mg, 19.75% yield) as a white solid. $^1$H NMR (400 MHz, DMSO-$d_6$) δ 12.13 (s, 1H), 8.38 (d, 1H), 8.25 (s, 1H), 8.06 (dd, 1H), 7.65 (d, 1H), 7.52 (dd, 1H), 7.36 (d, 1H), 4.21 (q, 2H), 4.12 (s, 3H), 2.76 (t, 2H), 2.67-2.61 (m, 2H), 2.45-2.38 (m, 2H), 2.00-1.94 (m, 1H), 1.76-1.69 (m, 2H), 1.58-1.53 (m, 1H), 1.36 (t, 3H), 0.92 (t, 3H); MS: m/z=636.2 (M+1, ESI+); HRMS: 636.1998.

Synthesis of Compound 22

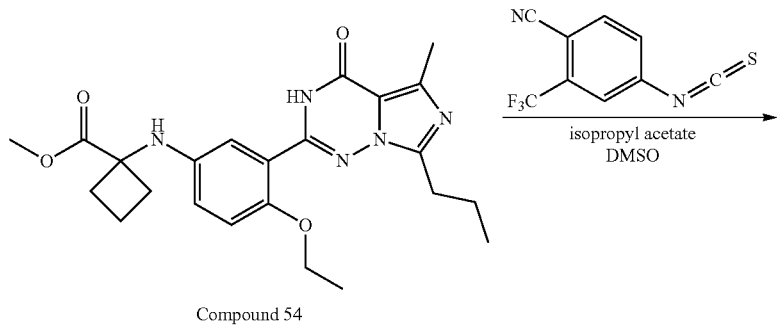

Compound 54

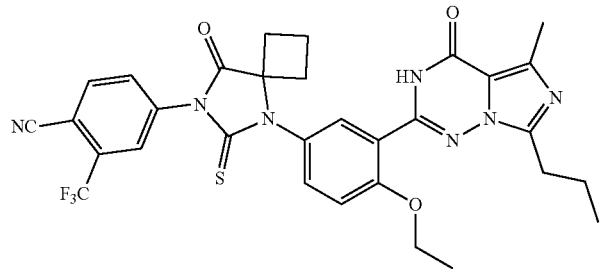

Compound 22

To a solution of compound 54, methyl 1-((4-ethoxy-3-(5-methyl-4-oxo-7-propyl-3,4-dihydroimidazo[5,1-f][1,2,4]triazin-2-yl)phenyl)amino)cyclobutane-1-carboxylate (500 mg, 1.14 mmol) and 4-isothiocyanato-2-(trifluoromethyl)benzonitrile (260 mg, 1.14 mmol) in DMSO (20 mL) was added isopropyl acetate (10 mL), the reaction mixture was stirred at 85° C. for 16 h. The reaction mixture was poured into water (200 mL) and extracted with DCM (40 mL×3), the combined organic layers were washed with water (200 mL) and brine (200 mL), then dried over $Na_2SO_4$ and concentrated under reduced pressure. The residue was purified by prep-HPLC to afford compound 22, 4-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-2-(trifluoromethyl)benzonitrile (100 mg, 13.83% yield) as a white solid. $^1$H NMR (400 MHz, CDCl$_3$) δ 9.90 (s, 1H), 8.09 (d, 1H), 8.00-7.98 (m, 2H), 7.88 (dd, 1H), 7.48 (dd, 1H), 7.27 (d, 1H), 4.36 (q, 2H), 2.97 (t, 2H), 2.76-2.71 (m, 2H), 2.64-2.54 (m, 5H), 2.31-2.24 (m, 1H), 1.90-1.81 (m, 2H), 1.78-1.70 (m, 1H), 1.62 (t, 3H), 0.99 (t, 3H); MS: m/z=636.1 (M+1, ESI+); HRMS: 636.1992.

Synthesis of Compound 23

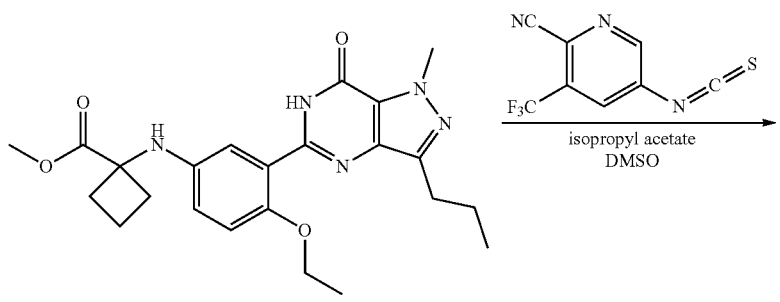
Compound 53

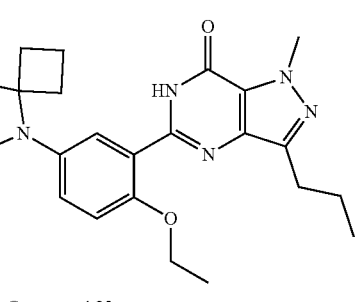
Compound 23

To a solution of methyl 1-((4-ethoxy-3-(1-methyl-7-oxo-3-propyl-6,7-dihydro-1H-pyrazolo[4,3-d] pyrimidin-5-yl)phenyl)amino)cyclobutane-1-carboxylate (700 mg, 1.59 mmol) and 5-isothiocyanato-3-(trifluoromethyl)picolinonitrile (438 mg, 1.91 mmol) in DMSO (10 mL) was added isopropyl acetate (3.25 g, 31.85 mmol)), the reaction mixture was stirred at 85° C. for 3 h. The reaction mixture was poured into water (100 mL) and extracted with DCM (20 mL×3), the combined organic layers were washed with water (100 mL) and brine (100 mL), then dried over $Na_2SO_4$ and concentrated under reduced pressure. The residue was purified by prep-HPLC to afford 5-(5-(4-ethoxy-3-(1-methyl-7-oxo-3-propyl-6,7-dihydro-1H-pyrazolo[4,3-d]pyrimidin-5-yl) phenyl)-8-oxo-6-thioxo-5,7-diazaspiro[3.4]octan-7-yl)-3-(trifluoromethyl)picolinonitrile (200 mg, 19.72% yield) as a white solid. $^1$H NMR (400 MHz, DMSO-$d_6$) δ 12.15 (s, 1H), 9.22 (d, 1H), 8.76 (d, 1H), 7.67 (d, 1H), 7.53 (dd, 1H), 7.38 (d, 1H), 4.25-4.14 (m, 5H), 2.76 (t, 2H), 2.68-2.64 (m, 2H), 2.54-2.46 (m, 2H), 2.04-1.97 (m, 1H), 1.79-1.69 (m, 2H), 1.61-1.56 (m, 1H), 1.38 (t, 3H), 0.92 (t, 3H); MS: m/z=637.0 (M+1, ESI+); HRMS: 637.1949.

Synthesis of Compound 24

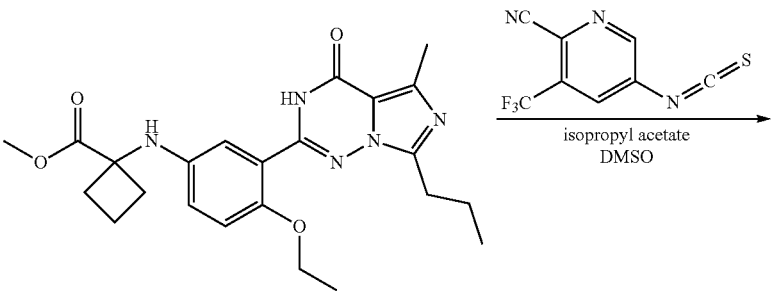
Compound 54

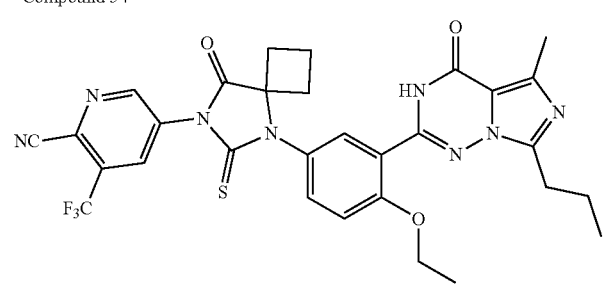
Compound 24

To a solution of compound 54, methyl 1-((4-ethoxy-3-(5-methyl-4-oxo-7-propyl-3,4-dihydroimidazo[5,1-f][1,2,4]triazin-2-yl)phenyl)amino)cyclobutane-1-carboxylate (500 mg, 1.14 mmol) and 5-isothiocyanato-3-(trifluoromethyl) picolinonitrile (261 mg, 1.14 mmol) in DMSO (5 mL) was added isopropyl acetate (5 mL), the reaction mixture was stirred at 85° C. for 16 h. The reaction mixture was poured into water (50 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 24, 5-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-3-(trifluoromethyl)picolinonitrile (95 mg, 13.12% yield) as a white solid. $^1$H NMR (400 MHz, $CDCl_3$) δ 9.89 (s, 1H), 9.13 (d, 1H), 8.41 (d, 1H), 8.07 (d, 1H), 7.48 (dd, 1H), 7.27 (s, 1H), 4.36 (dd, 2H), 2.96 (t, 2H), 2.79-2.73 (m, 2H), 2.64-2.57 (m, 5H), 2.33-2.25 (m, 1H), 1.90-1.72 (m, 3H), 1.62 (t, 3H), 0.99 (t, 3H); MS: m/z=637.1 (M+1, ESI+); HRMS: 637.1945.

Synthesis of Compound 25

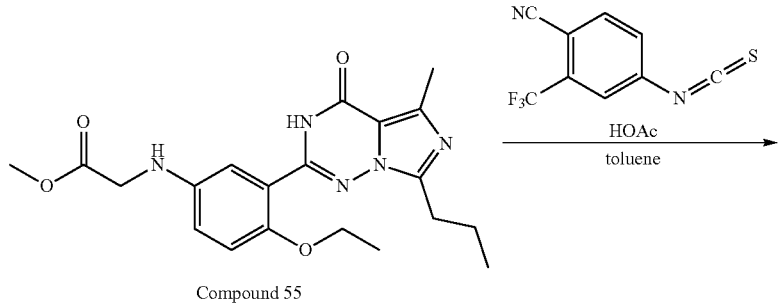

Compound 55

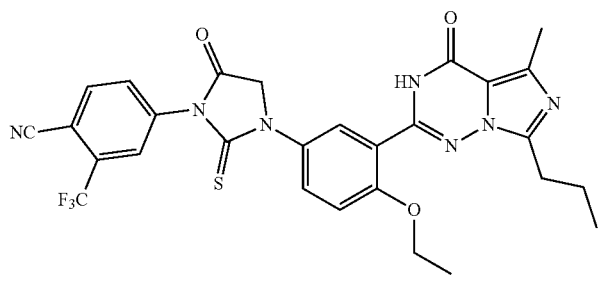

Compound 25

To a solution of compound 56 methyl (4-ethoxy-3-(5-methyl-4-oxo-7-propyl-3,4-dihydroimidazo[5,1-f][1,2,4]triazin-2-yl)phenyl)alaninate (310 mg, 749.75 umol) and 4-isothiocyanato-2-(trifluoromethyl) benzonitrile (205 mg, 900 umol) in toluene (10 mL) was added AcOH (450 mg, 7.50 mmol), the reaction mixture was stirred at 120° C. for 1 h. The reaction mixture was poured into water (50 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 26, 4-(3-(4-ethoxy-3-(5-methyl-4-oxo-7-propyl-3,4-dihydroimidazo[5,1f][1,2,4]triazin-2-yl)phenyl)-5-oxo-2-thioxoimidazolidin-1-yl)-2-(trifluoromethyl) benzonitrile (86 mg, 16.48% yield) as a white solid. $^1$H NMR (400 MHz, DMSO-$d_6$) δ 11.60 (s, 1H), 8.39 (d, 1H), 8.17 (s, 1H), 8.00 (dd, 1H), 7.88 (d, 1H), 7.82 (dd, 1H), 7.30 (d, 1H), 4.88 (s, 2H), 4.15 (q, 2H), 2.84 (t, 2H), 2.48 (s, 3H), 1.77-1.71 (m, 2H), 1.34 (t, 3H), 0.92 (t, 3H); MS: m/z=596.3 (M+1, ESI+); HRMS: 596.1689.

Synthesis of Compound 26

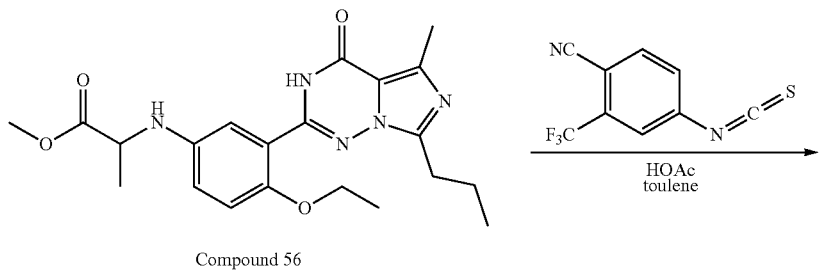

Compound 56

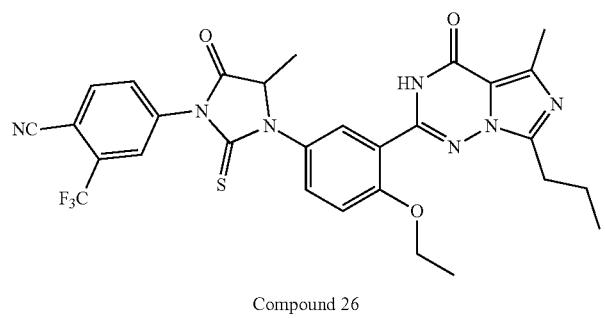

Compound 26

To a solution of compound 56 methyl (4-ethoxy-3-(5-methyl-4-oxo-7-propyl-3,4-dihydroimidazo[5,1-f][1,2,4]triazin-2-yl)phenyl)alaninate (310 mg, 749.75 umol) and 4-isothiocyanato-2-(trifluoromethyl) benzonitrile (205 mg, 900 umol) in toluene (10 mL) was added AcOH (450 mg, 7.50 mmol), the reaction mixture was stirred at 120° C. for 1 h. The reaction mixture was poured into water (50 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 26, 4-(3-(4-ethoxy-3-(5-methyl-4-oxo-7-propyl-3,4-dihydroimidazo[5,1-f][1,2,4]triazin-2-yl)phenyl)-4-methyl-5-oxo-2-thioxoimidazolidin-1-yl)-2-(trifluoromethyl)benzonitrile (80 mg, 17.50% yield) as a white solid. $^1$H NMR (400 MHz, DMSO-$d_6$) δ 11.63 (s, 1H), 8.39 (d, 1H), 8.23 (d, 1H), 8.04 (dd, 1H), 7.75-7.69 (m, 2H), 7.32 (d, 1H), 5.10 (q, 2H), 4.20-4.14 (m, 2H), 2.84 (t, 2H), 2.49 (s, 3H), 1.77-1.72 (m, 2H), 1.43 (d, 2H), 1.34 (t, 3H), 0.92 (t, 3H); MS: m/z=610.2 (M+1, ESI+); HRMS: 610.1841.

Synthesis of Compound 27

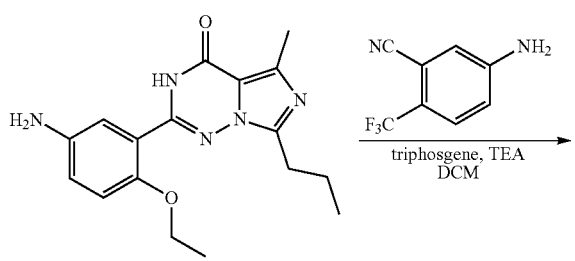

-continued

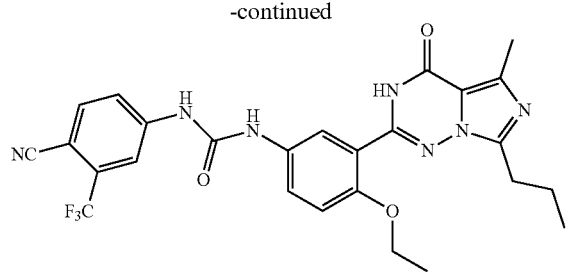

Compound 27

To a solution of 5-amino-2-(trifluoromethyl)benzonitrile (341.13 mg, 1.83 mmol) in DCM (15 mL) was added triphosgene (272 mg, 916 umol) at −10° C. in portions and stirred at this temperature for 0.5 h, then TEA (232 mg, 2.29 mmol) was added stirred for another 15 min. After that, a solution of 2-(5-amino-2-ethoxyphenyl)-5-methyl-7-propylimidazo[5,1-f][1,2,4]triazin-4(3H)-one (500 mg, 1.53 mmol) in DCM (15 mL) was added to the above mixture and stirred at −10° C. for 1 h. The resulting mixture was evaporated and the residue was purified by prep-HPLC to afford compound 27, 1-(4-cyano-3-(trifluoromethyl)phenyl)-3-(4-ethoxy-3-(5-methyl-4-oxo-7-propyl-3,4-dihydroimidazo [5,1-f][1,2,4]triazin-2-yl)phenyl)urea (85 mg, 10.32% yield) as a white solid. $^1$H NMR (400 MHz, DMSO-$d_6$) δ 11.50 (s, 1H), 10.08 (s, 1H), 9.42 (s, 1H), 8.22 (d, 1H), 8.00 (d, 1H), 7.77 (dd, 1H), 7.65 (d, 1H), 7.60 (dd, 1H), 7.11 (d, 1H), 4.08 (dd, 2H), 2.83 (t, 2H), 2.48 (s, 3H), 1.77-1.71 (m, 2H), 1.29 (t, 3H), 0.92 (t, 3H); MS: m/z=540.1 (M+1, ESI+); HRMS: 540.1967.

Synthesis of Compound 28

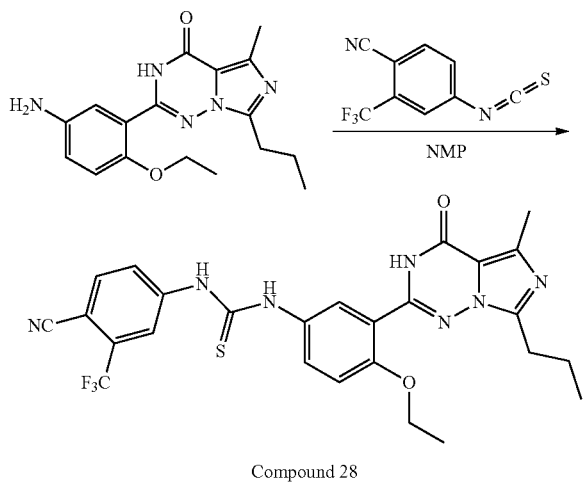

Compound 28

A mixture of 2-(5-amino-2-ethoxyphenyl)-5-methyl-7-propylimidazo[5,1-f][1,2,4]triazin-4(3H)-one (350 mg, 1.07 mmol) and 4-isothiocyanato-2-(trifluoromethyl)benzonitrile (293 mg, 1.28 mmol) in NMP (6 mL) was stirred at 80° C. for 3 h. The resulting mixture was cooled to room temperature and poured into water (60 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 28, 1-(4-cyano-3-(trifluoromethyl)phenyl)-3-(4-ethoxy-3-(5-methyl-4-oxo-7-propyl-3,4-dihydroimidazo[5,1-f][1,2,4] triazin-2-yl)phenyl)thiourea (140 mg, 23.57% yield) as a white solid. $^1$H NMR (400 MHz, DMSO-$d_6$) δ 11.53 (s, 1H), 10.47 (s, 1H), 10.37 (s, 1H), 8.33 (d, 1H), 8.10-8.01 (m, 2H), 7.65-7.59 (m, 2H), 7.19 (d, 1H), 4.13 (dd, 2H), 2.81 (t, 2H), 2.48 (s, 3H), 1.75-1.69 (m, 2H), 1.33 (t, 3H), 0.90 (t, 3H); MS: m/z=556.1 (M+1, ESI+); HRMS: 556.1739.

Synthesis of Compound 29

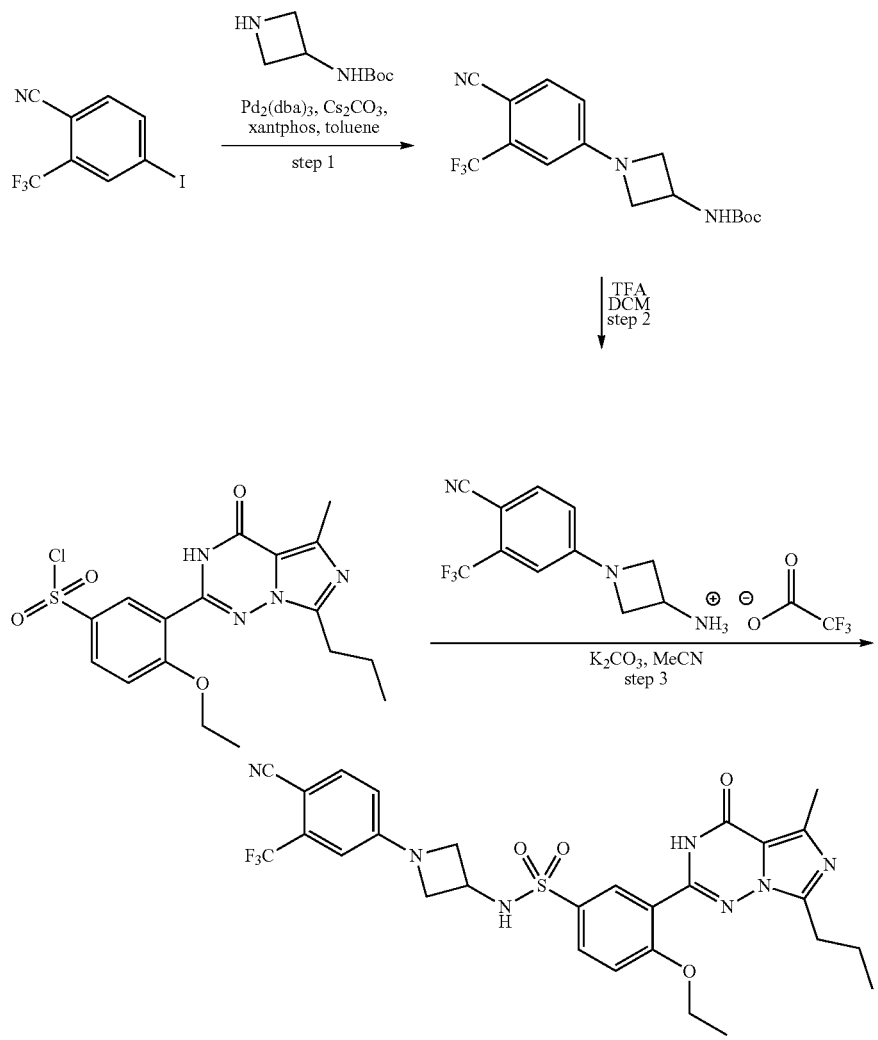

Compound 29

Step 1:

To a solution of 4-iodo-2-(trifluoromethyl)benzonitrile (500 mg, 1.68 mmol) and tert-butyl azetidin-3-ylcarbamate (319 mg, 1.85 mmol) in toluene (10 mL) was added Pd$_2$(dba)$_3$ (154 mg, 168 umol), xantphos (49 mg, 84 umol) and Cs$_2$CO$_3$ (1.10 g, 3.37 mmol), the reaction mixture was stirred at 80° C. for 1 h. The resulting mixture was cooled to room temperature and poured into water (60 mL) and extracted with EA (10 mL×3), the combined organic layers were washed with water (50 mL) and brine (50 mL), then dried over Na$_2$SO$_4$ and concentrated under reduced pressure. The residue was purified by column chromatography to afford tert-butyl (1-(4-cyano-3-(trifluoromethyl)phenyl)azetidin-3-yl)carbamate (330 mg, 57.43% yield) as a yellow solid. MS: m/z=342.1 (M+1, ESI+).

Step 2:

To a solution of tert-butyl (1-(4-cyano-3-(trifluoromethyl)phenyl)azetidin-3-yl)carbamate (330 mg, 967 umol) in DCM (6 mL) was added TFA (1.10 g, 9.67 mmol), the reaction mixture was stirred at 25° C. for 16 h. The mixture was evaporated under reduced pressure to afford 4-(3-aminoazetidin-1-yl)-2-(trifluoromethyl)benzonitrile 2,2,2-trifluoroacetate salt (230 mg, 98.71% yield) as a yellow oil. MS: m/z=242.2 (M+1, ESI+).

Step 3:

To a solution of 4-(3-aminoazetidin-1-yl)-2-(trifluoromethyl)benzonitrile 2,2,2-trifluoroacetate salt (230 mg, 954 umol) and 4-ethoxy-3-(5-methyl-4-oxo-7-propyl-3,4-dihydroimidazo[5,1-f][1,2,4]triazin-2-yl) benzenesulfonyl chloride (411 mg, 1.00 mmol) in MeCN (10 mL) was added K$_2$CO$_3$ (527 mg, 3.81 mmol), the reaction mixture was stirred at 25° C. for 1 h. The mixture was filtered and the filtrate was evaporated under reduce pressure, the residue was purified by prep-HPLC to afford compound 29 N-(1-(4-cyano-3-(trifluoromethyl)phenyl)azetidin-3-yl)-4-ethoxy-3-(5-methyl-4-oxo-7-propyl-3,4-dihydroimidazo[5,1-f][1,2,4]triazin-2-yl)benzenesulfonamide (140 mg, 99.2% purity) as a white solid. $^1$H NMR (400 MHz, DMSO-d$_6$) δ 11.73 (s, 1H), 8.56 (s, 1H), 7.96-7.94 (m, 2H), 7.78 (d, 1H), 7.38 (dd, 1H), 6.73 (d, 1H), 6.63 (dd, 1H), 4.30-4.18 (m, 5H), 3.74-3.70 (m, 2H), 2.82 (t, 2H), 2.48 (s, 3H), 1.75-1.69 (m, 2H), 1.34 (t, 3H), 0.89 (t, 3H); MS: m/z=616.1 (M+1, ESI+); HRMS: 616.1950.

Synthesis of Compound 30

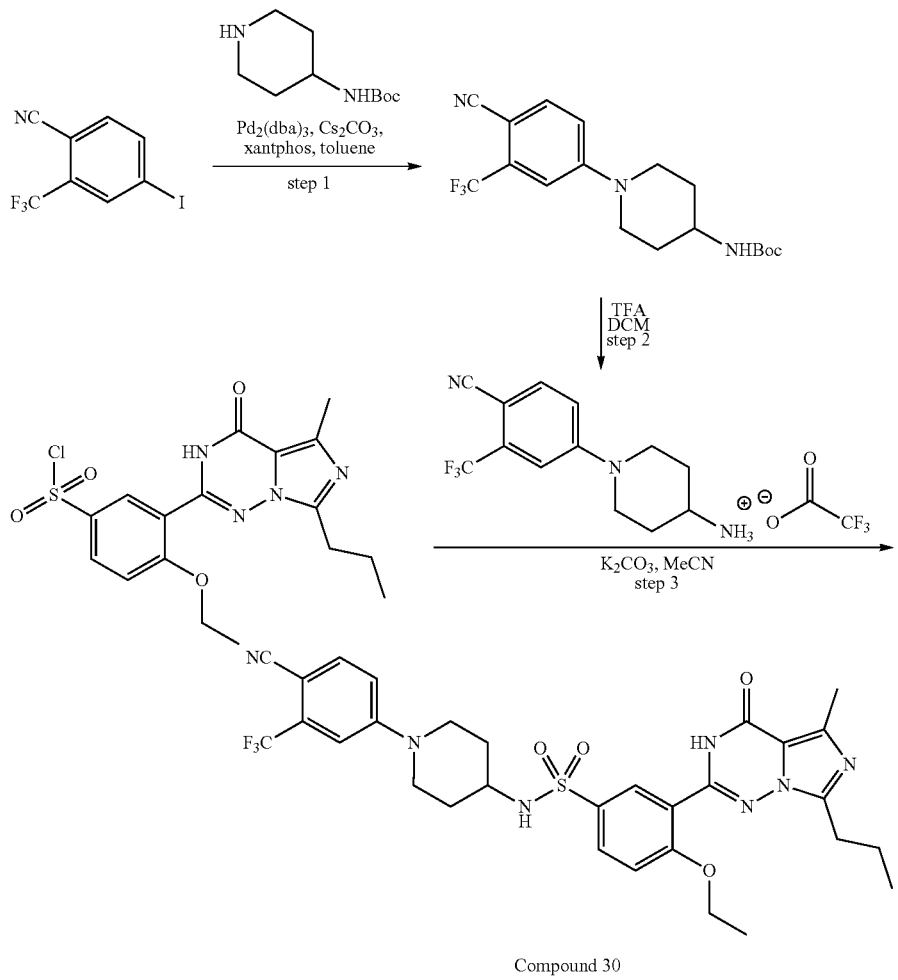

Compound 30

Step 1:

To a solution of 4-iodo-2-(trifluoromethyl)benzonitrile (500 mg, 1.68 mmol) and tert-butyl piperidin-4-ylcarbamate (405 mg, 2.02 mmol) in toluene (10 mL) was added Pd$_2$(dba)$_3$ (154 mg, 168 umol), xantphos (49 mg, 84 umol) and Cs$_2$CO$_3$ (1.10 g, 3.37 mmol), the reaction mixture was stirred at 80° C. for 2 h. The resulting mixture was cooled to room temperature and poured into water (60 mL) and extracted with EA (10 mL×3), the combined organic layers were washed with water (50 mL) and brine (50 mL), then dried over $Na_2SO_4$ and concentrated under reduced pressure. The residue was purified by column chromatography to afford tert-butyl (1-(4-cyano-3-(trifluoromethyl) phenyl)piperidin-4-yl)carbamate (390 mg, 62.72% yield) as a yellow solid. MS: m/z=370.2 (M+1, ESI+).

Step 2:

To a solution of tert-butyl (1-(4-cyano-3-(trifluoromethyl) phenyl)piperidin-4-yl)carbamate (390 mg, 1.06 mmol) in DCM (8 mL) was added TFA (1.20 g, 10.56 mmol), the reaction mixture was stirred at 25° C. for 16 h. The mixture was evaporated under reduced pressure to afford 4-(4-aminopiperidin-1-yl)-2-(trifluoromethyl)benzonitrile 2,2,2-trifluoroacetate salt (270 mg, 94.97% yield) as a yellow oil. MS: m/z=270.2 (M+1, ESI+).

Step 3:

To a solution of 4-(4-aminopiperidin-1-yl)-2-(trifluoromethyl)benzonitrile 2,2,2-trifluoroacetate salt (270 mg, 1.00 mmol) and 4-ethoxy-3-(5-methyl-4-oxo-7-propyl-3,4-dihydroimidazo[5,1-f][1,2,4]triazin-2-yl) benzenesulfonyl chloride (411 mg, 1.00 mmol) in MeCN (10 mL) was added $K_2CO_3$ (554 mg, 4.01 mmol), the reaction mixture was stirred at 25° C. for 1 h. The mixture was filtered and the filtrate was evaporated under reduce pressure, the residue was purified by prep-HPLC to afford compound 30, N-(1-(4-cyano-3-(trifluoromethyl)phenyl)piperidin-4-yl)-4-ethoxy-3-(5-methyl-4-oxo-7-propyl-3,4-dihydroimidazo[5,1-f][1,2,4]triazin-2-yl)benzenesulfonamide (185 mg, 28.58% yield) as a white solid. $^1$H NMR (400 MHz, DMSO-$d_6$) δ 11.70 (s, 1H), 7.99-7.96 (m, 2H), 7.86-7.78 (m, 2H), 7.36 (dd, 1H), 7.25 (d, 1H), 7.19 (dd, 1H), 4.20 (q, 2H), 3.89 (d, 2H), 3.36 (s, 1H), 3.06 (t, 2H), 2.83 (t, 2H), 2.49 (s, 3H), 1.76-1.68 (m, 4H), 1.44-1.32 (m, 5H), 0.90 (t, 3H); MS: m/z=644.1 (M+1, ESI+); HRMS: 644.2261.

Synthesis of Compound 31

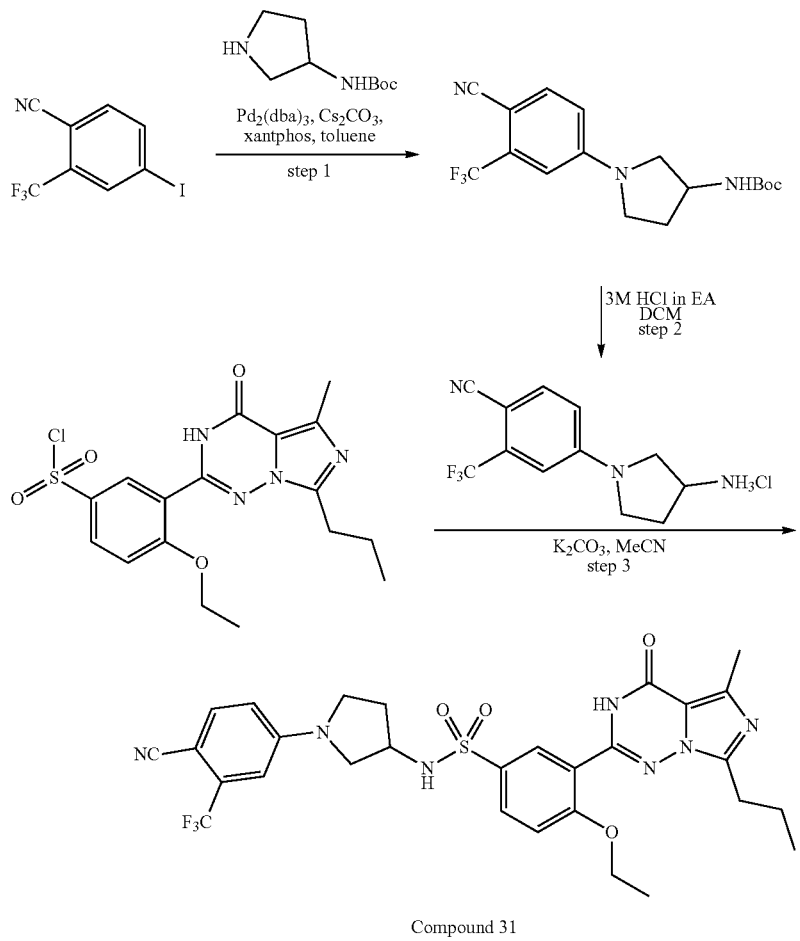

Compound 31

Step 1:

To a solution of 4-iodo-2-(trifluoromethyl)benzonitrile (500 mg, 1.68 mmol) and tert-butyl pyrrolidin-3-ylcarbamate (408 mg, 2.19 mmol) in toluene (20 mL) was added $Pd_2(dba)_3$ (77 mg, 84 umol), xantphos (146 mg, 253 umol) and $Cs_2CO_3$ (1.65 g, 5.05 mmol), the reaction mixture was stirred at 80° C. for 3 h. The resulting mixture was cooled to room temperature and poured into water (60 mL) and extracted with EA (10 mL×3), the combined organic layers were washed with water (50 mL) and brine (50 mL), then dried over $Na_2SO_4$ and concentrated under reduced pressure. The residue was purified by column chromatography to afford tert-butyl (1-(4-cyano-3-(trifluoromethyl)phenyl)pyrrolidin-3-yl)carbamate (531 mg, 88.76% yield) as a yellow solid. MS: m/z=356.1 (M+1, ESI+).

Step 2:

To a solution of tert-butyl (1-(4-cyano-3-(trifluoromethyl)phenyl)pyrrolidin-3-yl)carbamate (531 mg, 1.49 mmol) in DCM (8 mL) was added 3 M HCl in EA (4 mL), the reaction mixture was stirred at 25° C. for 2 h. The mixture was evaporated under reduced pressure to afford 4-(3-aminopyrrolidin-1-yl)-2-(trifluoromethyl)benzonitrile hydrochloride (300 mg, 78.66% yield) as a yellow solid. MS: m/z=256.1 (M+1, ESI+).

Step 3:

To a solution of 4-(3-aminopyrrolidin-1-yl)-2-(trifluoromethyl)benzonitrile hydrochloride (100 mg, 391.79 umol) and 4-ethoxy-3-(5-methyl-4-oxo-7-propyl-3,4-dihydroimidazo[5,1-f][1,2,4]triazin-2-yl) benzenesulfonyl chloride (161 mg, 392 umol) in DCM (10 mL) was added TEA (119 mg, 1.18 mmol), the reaction mixture was stirred at 25° C. for 3 h. The resulting mixture poured into water (60 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford N-(1-(4-cyano-3-(trifluoromethyl)phenyl) pyrrolidin-3-yl)-4-ethoxy-3-(5-methyl-4-oxo-7-propyl-3,4-dihydroimidazo[5,1-f][1,2,4]triazin-2-yl) benzenesulfonamide (130 mg, 52.70% yield) as a white solid. $^1$H NMR (400 MHz, DMSO-$d_6$) δ 11.69 (s, 1H), 8.13 (d, 1H), 7.99-7.97 (m, 2H), 7.76 (d, 1H), 7.36 (d, 1H), 6.80-6.75 (m, 2H), 4.21 (q, 2H), 3.94-3.90 (m, 1H), 3.54-3.46 (m, 2H), 3.39-3.33 (m, 1H), 3.25 (dd, 1H), 2.83 (t, 2H), 2.49 (s, 3H), 2.14-2.06 (m, 1H), 1.97-1.89 (m, 1H), 1.78-1.69 (m, 2H), 1.36 (t, 3H), 0.91 (t, 3H); MS: m/z=630.1 (M+1, ESI+); HRMS: 630.2106.

Synthesis of Compound 32

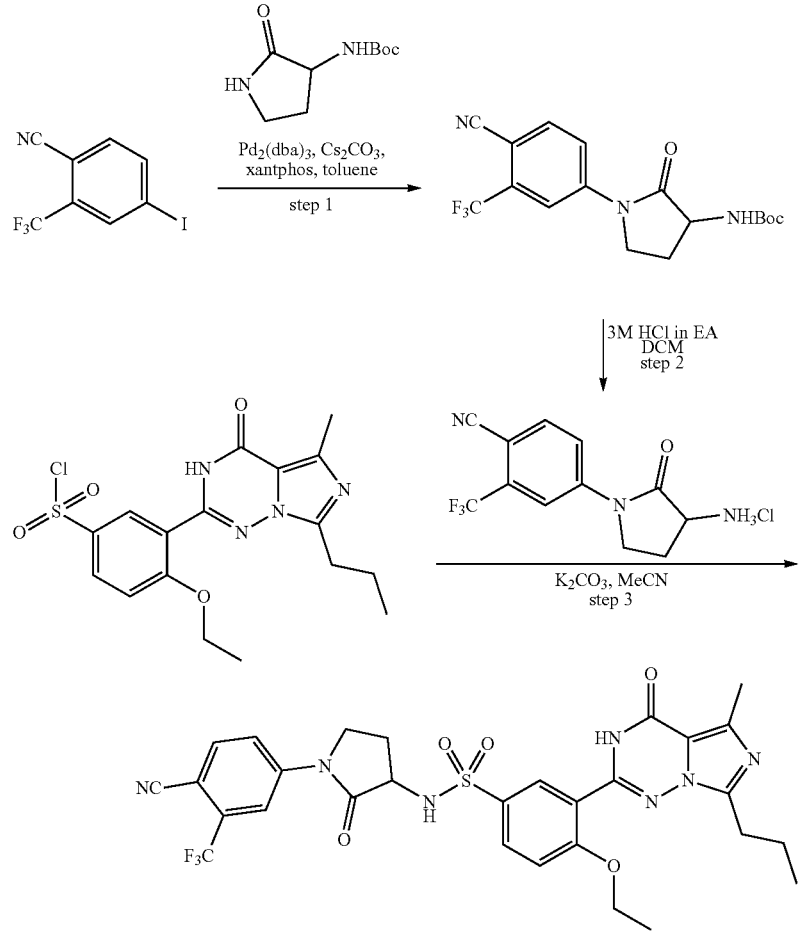

Compound 32

Step 1:

To a solution of 4-iodo-2-(trifluoromethyl)benzonitrile (300 mg, 1.01 mmol) and tert-butyl (2-oxopyrrolidin-3-yl)carbamate (263 mg, 1.31 mmol) in toluene (20 mL) was added $Pd_2(dba)_3$ (46 mg, 51 umol), xantphos (88 mg, 152 umol) and $Cs_2CO_3$ (987 mg, 3.03 mmol), the reaction mixture was stirred at 80° C. for 3 h. The resulting mixture was cooled to room temperature and poured into water (60 mL) and extracted with EA (10 mL×3), the combined organic layers were washed with water (50 mL) and brine (50 mL), then dried over $Na_2SO_4$ and concentrated under reduced pressure. The residue was purified by column chromatography to afford tert-butyl (1-(4-cyano-3-(trifluoromethyl)phenyl)-2-oxopyrrolidin-3-yl)carbamate (315 mg, 84.44% yield) as a yellow solid. MS: m/z=314.0 (M−56+1, ESI+).

Step 2:

To a solution of tert-butyl (1-(4-cyano-3-(trifluoromethyl)phenyl)-2-oxopyrrolidin-3-yl)carbamate (310 mg, 839 umol) in DCM (8 mL) was added 3 M HCl in EA (4 mL), the reaction mixture was stirred at 25° C. for 2 h. The mixture was evaporated under reduced pressure to afford 4-(3-amino-2-oxopyrrolidin-1-yl)-2-(trifluoromethyl)benzonitrile hydrochloride (220 mg, 97.36% yield) as a yellow solid. MS: m/z=270.0 (M+1, ESI+).

Step 3:

To a solution of 4-(3-amino-2-oxopyrrolidin-1-yl)-2-(trifluoromethyl)benzonitrile hydrochloride (220 mg, 817 umol) and 4-ethoxy-3-(5-methyl-4-oxo-7-propyl-3,4-dihydroimidazo[5,1-f][1,2,4]triazin-2-yl) benzenesulfonyl chloride (336 mg, 817 umol) in DCM (10 mL) was added TEA (248 mg, 2.45 mmol), the reaction mixture was stirred at 25° C. for 3 h. The resulting mixture poured into water (60 mL) and extracted with DCM (10 mL×3), the combined organic layers were washed with water (50 mL) and brine (50 mL), then dried over $Na_2SO_4$ and concentrated under reduced pressure. The residue was purified by prep-HPLC to afford compound 32, N-(1-(4-cyano-3-(trifluoromethyl)phenyl)-2-oxopyrrolidin-3-yl)-4-ethoxy-3-(5-methyl-4-oxo-7-propyl-3,4-dihydroimidazo[5,1-f][1,2,4]triazin-2-yl)benzenesulfonamide (150 mg, 28.52% yield) as a white solid. $^1$H NMR (400 MHz, DMSO-$d_6$) δ 11.69 (s, 1H), 8.40-8.36 (m, 2H), 8.19 (d, 1H), 8.03-7.97 (m, 3H), 7.37 (d, 1H), 4.44-4.37 (m, 1H), 4.21 (q, 2H), 3.88 (t, 1H), 3.78-3.71 (m, 1H), 2.83 (t, 2H), 2.48 (s, 3H), 2.34-2.27 (m, 1H), 1.86-1.68 (m, 3H), 1.34 (t, 3H), 0.90 (t, 3H); MS: m/z=644.1 (M+1, ESI+); HRMS: 644.1901.

Synthesis of Compound 33

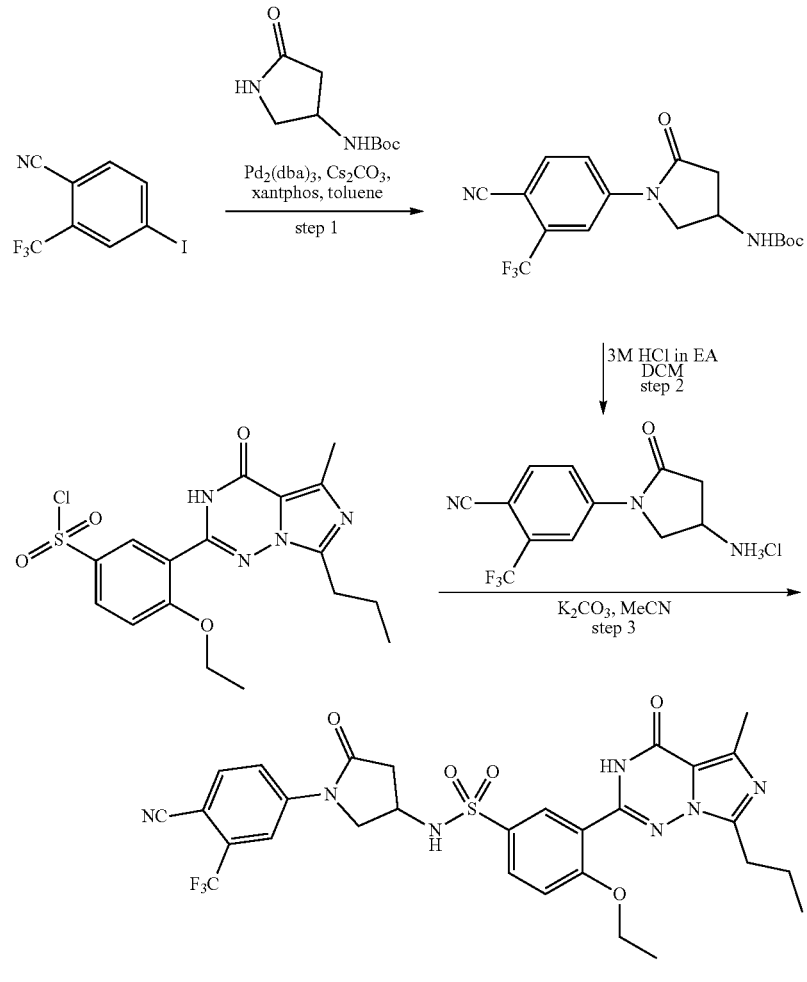

Compound 33

Step 1:

To a solution of 4-iodo-2-(trifluoromethyl)benzonitrile (500 mg, 1.68 mmol) and tert-butyl (5-oxopyrrolidin-3-yl)carbamate (438 mg, 2.19 mmol) in toluene (20 mL) was added $Pd_2(dba)_3$ (77 mg, 84 umol), xantphos (146 mg, 253 umol) and $Cs_2CO_3$ (1.65 g, 5.05 mmol), the reaction mixture was stirred at 80° C. for 3 h. The resulting mixture was cooled to room temperature and poured into water (60 mL) and extracted with EA (10 mL×3), the combined organic layers were washed with water (50 mL) and brine (50 mL), then dried over $Na_2SO_4$ and concentrated under reduced pressure. The residue was purified by column chromatography to afford tert-butyl (1-(4-cyano-3-(trifluoromethyl)phenyl)-5-oxopyrrolidin-3-yl)carbamate (522 mg, 83.96% yield) as a yellow solid. MS: m/z=370.1 (M+1, ESI+).

Step 2:

To a solution of tert-butyl (1-(4-cyano-3-(trifluoromethyl)phenyl)-5-oxopyrrolidin-3-yl)carbamate (522 mg, 1.41 mmol) in DCM (10 mL) was added 3 M HCl in EA (5 mL), the reaction mixture was stirred at 25° C. for 2 h. The mixture was evaporated under reduced pressure to afford 4-(4-amino-2-oxopyrrolidin-1-yl)-2-(trifluoromethyl)benzonitrile hydrochloride (378 mg, 99.34% yield) as a yellow solid. MS: m/z=270.1 (M+1, ESI+).

Step 3:

To a solution of 4-(4-amino-2-oxopyrrolidin-1-yl)-2-(trifluoromethyl)benzonitrile hydrochloride (378 mg, 1.40 mmol) and 4-ethoxy-3-(5-methyl-4-oxo-7-propyl-3,4-dihydroimidazo[5,1-f][1,2,4]triazin-2-yl) benzenesulfonyl chloride (577 mg, 1.40 mmol) in DCM (20 mL) was added TEA (426 mg, 4.21 mmol), the reaction mixture was stirred at 25° C. for 3 h. The resulting mixture poured into water (60 mL) and extracted with DCM (10 mL×3), the combined organic layers were washed with water (50 mL) and brine (50 mL), then dried over Na$_2$SO$_4$ and concentrated under reduced pressure. The residue was purified by prep-HPLC to afford compound 33, N-(1-(4-cyano-3-(trifluoromethyl) phenyl)-5-oxopyrrolidin-3-yl)-4-ethoxy-3-(5-methyl-4-oxo-7-propyl-3,4-dihydroimidazo[5,1-f][1,2,4]triazin-2-yl)benzenesulfonamide (170 mg, 18.81% yield) as a white solid. $^1$H NMR (400 MHz, DMSO-d$_6$) δ 11.70 (s, 1H), 8.37-8.31 (m, 2H), 8.15 (d, 1H), 7.98-7.96 (m, 2H), 7.89 (dd, 1H), 7.36 (dd, 1H), 4.23-4.05 (m, 4H), 3.77 (dd, 1H), 2.84-2.77 (m, 3H), 2.49 (s, 3H), 2.41 (dd, 1H), 1.77-1.68 (m, 2H), 1.34 (t, 3H), 0.91 (t, 3H); MS: m/z=644.2 (M+1, ESI+); HRMS: 644.1899.

Synthesis of Compound 34

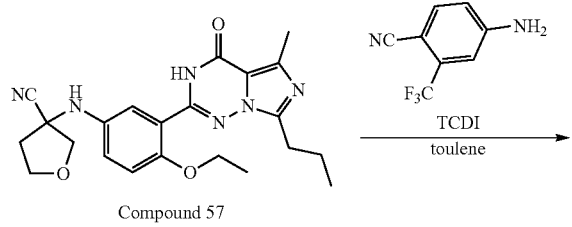

Compound 57

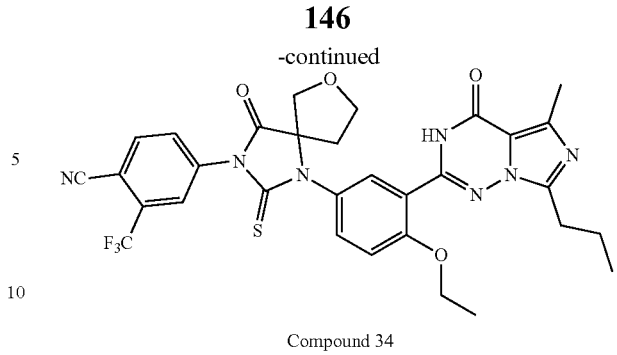

Compound 34

To a solution of compound 57, 3-((4-ethoxy-3-(5-methyl-4-oxo-7-propyl-3,4-dihydroimidazo[5,1-f][1,2,4]triazin-2-yl)phenyl)amino)tetrahydrofuran-3-carbonitrile (1.09 g, 2.58 mmol) and 4-amino-2-(trifluoromethyl)benzonitrile (576.27 mg, 3.10 mmol) in toluene (20 mL) was added TCDI (551.74 mg, 3.10 mmol), The reaction mixture was stirred at 105° C. for 22 h. The reaction solution was cooled to room temperature and concentrated under reduced pressure, DMA (2 mL) and EtOH (20 mL) was added to the residue. The mixture was heated to 70° C. and hydrogen chloride (2 M, 4 mL) was added, then stirred at this temperature for 2 h. The resulting mixture was poured into water (200 mL) and extracted with EA (50 mL×3), washed by brine (200 mL), dried over Na$_2$SO$_4$ and concentrated. The residue was purified by Prep-HPLC to afford compound 34, 4-(1-(4-ethoxy-3-(5-methyl-4-oxo-7-propyl-3,4-dihydroimidazo[5,1-f][1,2,4]triazin-2-yl)phenyl)-4-oxo-2-thioxo-7-oxa-1,3-diazaspiro[4.4]nonan-3-yl)-2-(trifluoromethyl)benzonitrile (60 mg, 3.57% yield) as a white solid. $^1$H NMR (400 MHz, DMSO-d$_6$) δ 11.67 (s, 1H), 8.39 (d, 1H), 8.26 (s, 1H), 8.07 (dd, 1H), 7.63-7.61 (m, 2H), 7.32 (d, 1H), 4.33 (d, 1H), 4.17 (q, 2H), 4.00 (d, 1H), 3.78 (dd, 1H), 3.54 (dd, 1H), 2.82 (t, 2H), 2.58 (t, 2H), 2.48 (s, 3H), 1.76-1.71 (m, 2H), 1.34 (t, 3H), 0.91 (t, 3H); MS: m/z=652.4 (M+1, ESI+); HRMS: 652.1942.

Synthesis of Compound 38

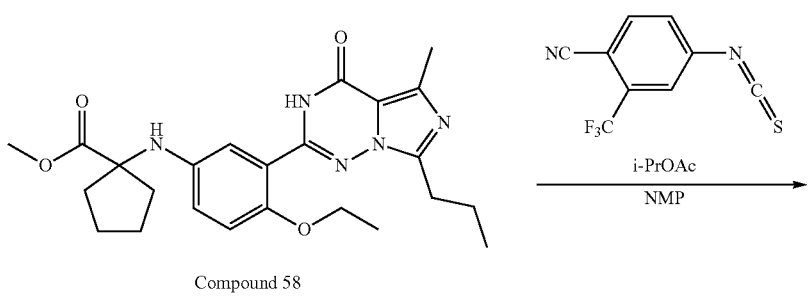

Compound 58

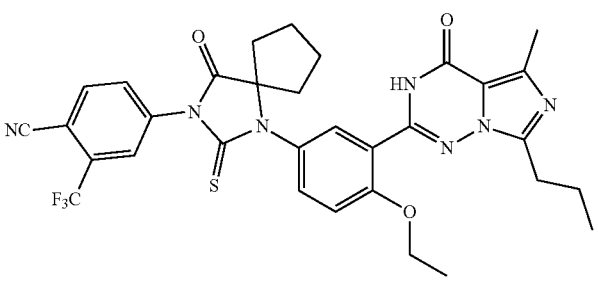

Compound 38

To a solution of compound 58, methyl 1-((4-ethoxy-3-(5-methyl-4-oxo-7-propyl-3,4-dihydroimidazo[5,1-f][1,2,4]triazin-2-yl)phenyl)amino)cyclopentane-1-carboxylate (140 mg, 309 umol) and 4-isothiocyanato-2-(trifluoromethyl)benzonitrile (85 mg, 370 umol) in NMP (8 mL) was added isopropyl acetate (4 mL), the reaction mixture was stirred at 85° C. for 16 h. The reaction mixture was poured into water (80 mL) and extracted with DCM (20 mL×3), the combined organic layers were washed with water (100 mL) and brine (100 mL), then dried over $Na_2SO_4$ and concentrated under reduced pressure. The residue was purified by prep-HPLC to afford compound 38, 4-(1-(4-ethoxy-3-(5-methyl-4-oxo-7-propyl-3,4-dihydroimidazo[5,1-f][1,2,4]triazin-2-yl)phenyl)-4-oxo-2-thioxo-1,3-diazaspiro[4.4]nonan-3-yl)-2-(trifluoromethyl)benzonitrile (130 mg, 64.82% yield) as a white solid. $^1$H NMR (400 MHz, DMSO-$d_6$) δ 12.15 (s, 1H), 8.38 (d, 1H), 8.29 (d, 1H), 8.08 (dd, 1H), 7.65-7.60 (m, 2H), 7.36 (d, 1H), 4.19 (q, 2H), 2.95 (t, 2H), 2.58 (s, 3H), 2.32-2.27 (m, 2H), 2.23-2.18 (m, 2H), 1.81-1.72 (m, 4H), 1.46-1.42 (m, 2H), 1.35 (t, 3H), 0.93 (t, 3H); MS: m/z=650.4 (M+1, ESI+); HRMS: 650.2159.

Synthesis of Compound 47

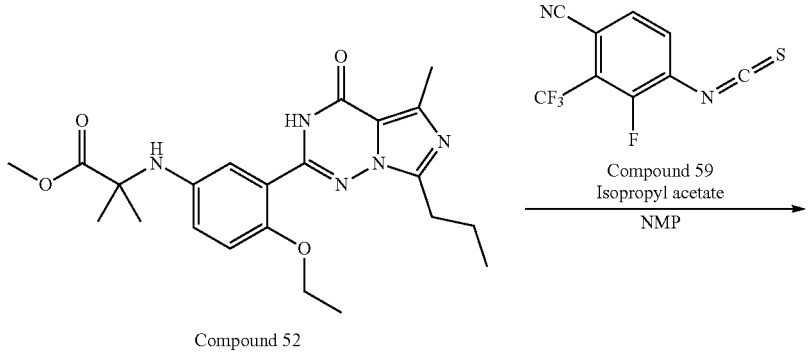

Compound 52

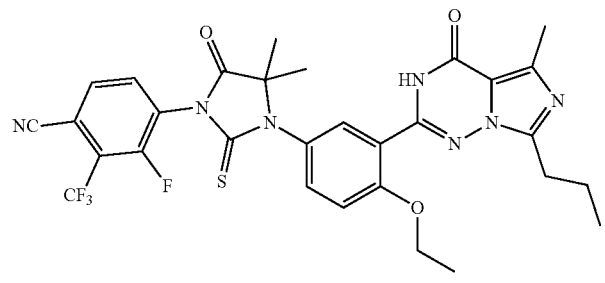

Compound 47

To a solution of compound 52, methyl 2-((4-ethoxy-3-(5-methyl-4-oxo-7-propyl-3,4-dihydroimidazo[5,1-f][1,2,4]triazin-2-yl)phenyl)amino)-2-methylpropanoate (540 mg, 1.26 mmol) and compound 59, 3-fluoro-4-isothiocyanato-2-(trifluoromethyl)benzonitrile (1.55 g, 6.3 mmol) in NMP (8 mL) was added isopropyl acetate (2 ml), the reaction mixture was stirred at 110° C. for 16 h. The reaction mixture was poured into water (80 mL) and extracted with DCM (20 mL×3), the combined organic layers were washed with water (80 mL) and brine (80 mL), then dried over $Na_2SO_4$ and concentrated under reduced pressure. The residue was purified by prep-HPLC to afford compound 47, 4-(3-(4-ethoxy-3-(5-methyl-4-oxo-7-propyl-3,4-dihydroimidazo[5,1-f][1,2,4]triazin-2-yl)phenyl)-4,4-dimethyl-5-oxo-2-thioxoimidazolidin-1-yl)-3-fluoro-2-(trifluoromethyl)benzonitrile (90 mg, 11% yield) as a pale yellow solid. $^1$H NMR (400 MHz, DMSO-$d_6$) δ 11.67 (s, 1H), 8.30-8.25 (m, 2H), 7.61-7.58 (m, 2H), 7.34 (d, 1H), 4.18 (q, 2H), 2.83 (t, 2H), 2.48 (s, 3H), 1.76-1.70 (m, 2H), 1.54 (dd, 6H), 1.33 (t, 3H), 0.91 (t, 3H); MS: m/z=642.4 (M+1, ESI+); HRMS: 642.1904.

Synthesis of Compound 48

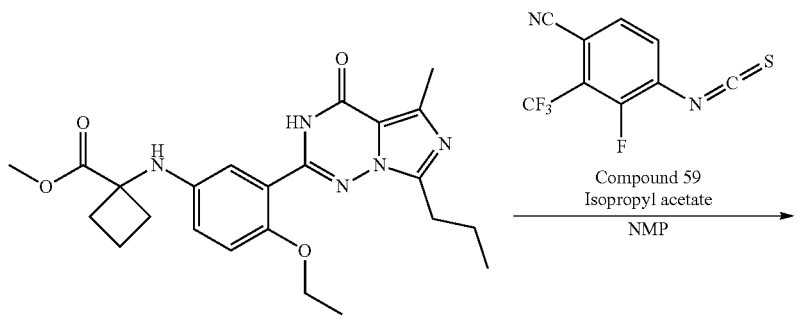

Compound 48

To a solution of compound 54, methyl 1-((4-ethoxy-3-(5-methyl-4-oxo-7-propyl-3,4-dihydroimidazo[5,1-f][1,2,4]triazin-2-yl)phenyl)amino)cyclobutane-1-carboxylate (600 mg, 1.36 mmol) and compound 59, 3-fluoro-4-isothiocyanato-2-(trifluoromethyl)benzonitrile (1.67 g, 6.8 mmol) in NMP (8 mL) was added isopropyl acetate (2 ml), the reaction mixture was stirred at 110° C. for 16 h. The reaction mixture was poured into water (80 mL) and extracted with DCM (20 mL×3), the combined organic layers were washed with water (80 mL) and brine (80 mL), then dried over $Na_2SO_4$ and concentrated under reduced pressure. The residue was purified by prep-HPLC to afford compound 48, 4-(5-(4-ethoxy-3-(5-methyl-4-oxo-7-propyl-3,4-dihydroimidazo[5,1-f][1,2,4]triazin-2-yl)phenyl)-8-oxo-6-thioxo-5,7-diazaspiro[3.4]octan-7-yl)-3-fluoro-2-(trifluoromethyl)benzonitrile (120 mg, 13.5% yield) as a pale yellow solid. $^1$H NMR (400 MHz, DMSO-$d_6$) δ 11.68 (s, 1H), 8.26-8.20 (m, 2H), 7.63-7.61 (m, 2H), 7.37 (dd, 1H), 4.19 (q, 2H), 2.82 (t, 2H), 2.68-2.62 (m, 1H), 2.58-2.52 (m, 2H), 2.49-2.44 (m, 4H), 2.02-1.95 (m, 1H), 1.78-1.69 (m, 2H), 1.60-1.56 (m, 1H), 1.35 (t, 3H), 0.91 (t, 3H); MS: m/z=654.4 (M+1, ESI+); HRMS: 654.1901.

Synthesis of Compound 49

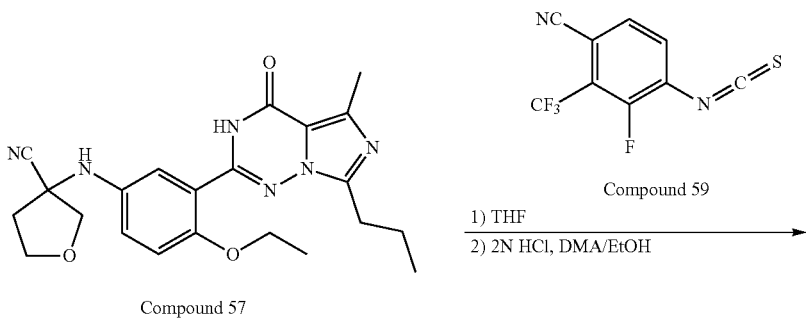

Compound 57

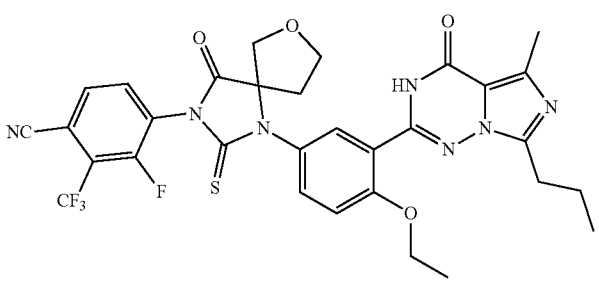

Compound 49

To a solution of Compound 57, 3-((4-ethoxy-3-(5-methyl-4-oxo-7-propyl-3,4-dihydroimidazo[5,1-f][1,2,4]triazin-2-yl)phenyl)amino)tetrahydrofuran-3-carbonitrile (900 mg, 2.13 mmol) in THF (50 mL) was added Compound 59, 3-fluoro-4-isothiocyanato-2-(trifluoromethyl)benzonitrile (1.57 g, 6.39 mmol), the reaction mixture was stirred at 70° C. for 16 h. The reaction mixture was cooled to room temperature and concentrated under reduced pressure, the residue was dissolved in EtOH (50 mL) and DMA (5 mL), then 2 N HCl (5 mL) was added to the above solution. The resulting mixture was stirred at 70° C. for 2 h. The reaction mixture was cooled to room temperature and concentrated under reduced pressure, the residue was poured into water (80 mL), extracted with EA (30 mL×3), washed by brine (80 mL), dried over $Na_2SO_4$ and concentrated. The residue was purified by Prep-HPLC to afford Compound 49, 4-(1-(4-ethoxy-3-(5-methyl-4-oxo-7-propyl-3,4-dihydroimidazo[5,1-f][1,2,4]triazin-2-yl)phenyl)-4-oxo-2-thioxo-7-oxa-1,3-diazaspiro[4.4]nonan-3-yl)-3-fluoro-2-(trifluoromethyl)benzonitrile (135 mg, 9.46% yield) as a pale yellow solid. $^1$H NMR (400 MHz, DMSO-$d_6$) δ 11.62 (s, 1H), 8.29-8.20 (m, 2H), 7.72-7.67 (m, 2H), 7.32 (d, 1H), 4.40 (dd, 1H), 4.18 (q, 2H), 4.03-3.96 (m, 1H), 3.80 (q, 1H), 3.61-3.51 (m, 1H), 2.83 (t, 2H), 2.72-2.52 (m, 2H), 2.48 (s, 3H), 1.78-1.69 (m, 2H), 1.34 (t, 3H), 0.92 (t, 3H); MS: m/z=670.4 (M+1, ESI+); HRMS: 670.1849.

Synthesis of Compound 50

$ZnCl_2$ (83 mg, 610.91 umol), the reaction mixture was stirred at 50° C. for 16 h. The reaction mixture was cooled to room temperature and poured into water (80 mL), extracted with EA (30 mL×3), washed by brine (80 mL), dried over $Na_2SO_4$ and concentrated. The residue was purified by column chromatography to afford 1-((4-ethoxy-3-(5-methyl-4-oxo-7-propyl-3,4-dihydroimidazo[5,1-f][1,2,4]triazin-2-yl)phenyl)amino)cyclopentane-1-carbonitrile (1.15 g, 89.53% yield) as a yellow solid. MS: m/z=421.3 (M+1, ESI+).

Step 2:

To a solution of 1-((4-ethoxy-3-(5-methyl-4-oxo-7-propyl-3,4-dihydroimidazo[5,1-f][1,2,4]triazin-2-yl)phenyl)amino)cyclopentane-1-carbonitrile (1 g, 2.38 mmol) in THF (50 mL) was added compound 59, 3-fluoro-4-isothiocyanato-2-(trifluoromethyl)benzonitrile (1.76 g, 7.13 mmol), the reaction mixture was stirred at 70° C. for 16 h. The reaction mixture was cooled to room temperature and concentrated under reduced pressure, the residue was dissolved in EtOH (50 mL) and DMA (5 mL), then 2 N HCl (5 mL) was added to the above solution. The resulting mixture was stirred at 70° C. for 2 h. The reaction mixture was cooled to room temperature and concentrated under reduced pressure, the residue was poured into water (80 mL), extracted with EA (30 mL×3), washed by brine (80 mL), dried over $Na_2SO_4$ and concentrated. The residue was purified by Prep-HPLC to afford compound 50, 4-(1-(4-ethoxy-3-(5-

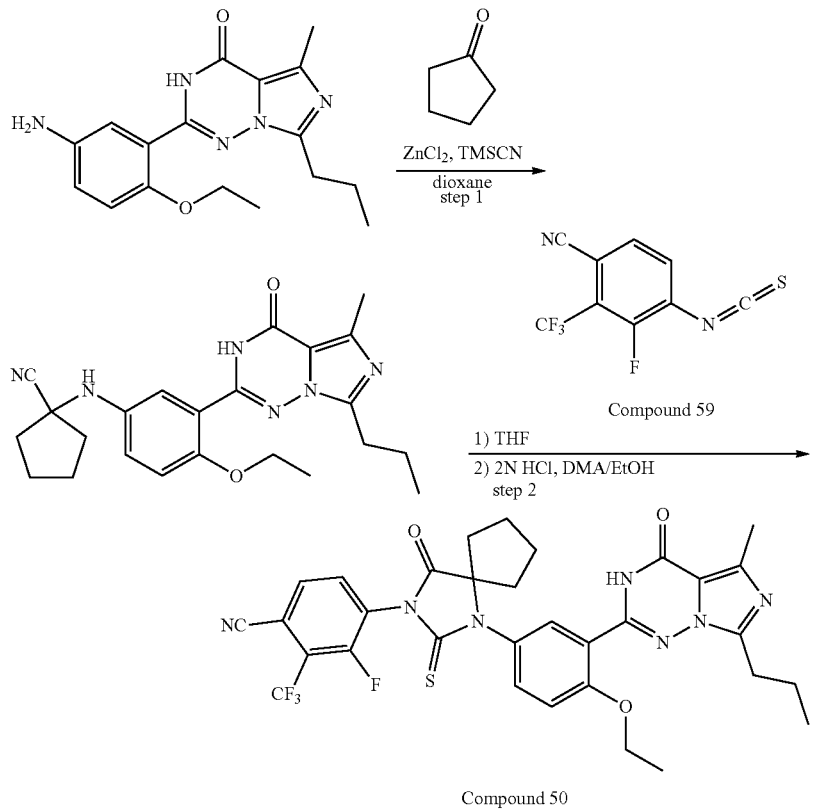

Compound 50

Step 1:

To a solution of 2-(5-amino-2-ethoxyphenyl)-5-methyl-7-propylimidazo[5,1-f][1,2,4]triazin-4(3H)-one (1 g, 3.05 mmol) and cyclopentanone (514 mg, 6.11 mmol) in dioxane (30 mL) was added TMSCN (454 mg, 4.58 mmol) and methyl-4-oxo-7-propyl-3,4-dihydroimidazo[5,1-f][1,2,4]triazin-2-yl)phenyl)-4-oxo-2-thioxo-1,3-diazaspiro[4.4]nonan-3-yl)-3-fluoro-2-(trifluoromethyl)benzonitrile (126 mg, 7.94% yield) as a yellow solid. $^1$H NMR (400 MHz, DMSO-$d_6$) δ 11.67 (s, 1H), 8.26 (s, 2H), 7.65 (s, 2H), 7.32

(d, 1H), 4.18 (q, 2H), 2.82 (t, 2H), 2.48 (s, 3H), 2.32-2.20 (m, 4H), 1.76-1.71 (m, 4H), 1.50-1.43 (m, 2H), 1.34 (t, 3H), 0.92 (t, 3H); MS: m/z=668.5 (M+1, ESI+); HRMS: 668.2057.

Example 3—Human PDE-5A1 Inhibition Assay

This example illustrates the in vitro inhibition of human PDE-5A1 by exemplary compounds of this disclosure (e.g., as described herein).

Materials

Sildenafil citrate (Catalog no. LKT-S3313, Axxora, San Diego, CA), Vardenafil hydrochloride trihydrate (Catalog no. SML2103, Sigma-Aldrich, St. Louis, MO), PDE Assay Buffer (Catalog no. 60393, BPS bioscience, San Diego, CA), PDE Binding Agent (Catalog no. 60390, BPS bioscience, San Diego, CA) and PDE Binding Agent Diluent (cGMP, Catalog no. 60392, BPS bioscience, San Diego, CA) were used for assays. Test compounds were supplied by Ildong Pharmaceuticals Co., Ltd.

Experimental Protocols

The enzymes and substrates used in this experiment are summarized in Table 2.

TABLE 2

Enzymes and Substrates

| Assay | Catalog # | Enzyme Lot # | Enzyme Used (ng/reaction) | Substrate |
|---|---|---|---|---|
| PDE5A1 | 60050 | 181008-G | 0.2 | 100 nM FAM-cGMP |

The serial dilution of the compounds was first performed in 100% DMSO with the highest concentration at 1 mM and 0.1 mM. Each intermediate compound dilution (in 100% DMSO) will then get directly diluted 10× fold into assay buffer for 10% DMSO and 5 µL of the dilution was added to a 50 µL reaction so that the final concentration of DMSO is 1% in all reactions.

The enzymatic reactions were conducted at room temperature for 60 minutes in a 50 µL mixture containing PDE assay buffer, 100 nM FAM-cGMP, a PDE enzyme (Table 2) and the test compounds.

After enzymatic reaction, 100 µL of a binding solution (1:100 dilution of the binding agent with the binding agent diluent) was added to each reaction and the reaction was performed at room temperature for 60 minutes.

Fluorescence intensity was measured at excitation of 485 nm and an emission of 528 nm using a Tecan Infinite M1000 microplate reader.

Data Analysis

PDE activity assays were performed in duplicate at each concentration. Fluorescence intensity is converted to fluorescence polarization using the Tecan Magellan6 software. The fluorescence polarization ($FP_t$) in absence of the compound in each data set was defined as 100% activity. In the absence of PDE and the compound, the value fluorescent polarization ($FP_b$) in each data set was defined as 0% activity. The percent activity in the presence of compound was calculated according to Equation 1:

$$\% \text{ activity} = \left(\frac{FP - FP_b}{FP_t - FP_b}\right) \times 100 \qquad \text{(eqn. 1)}$$

where FP=the fluorescence polarization in the presence of the compound.

The values of % activity versus a series of compound concentrations were then plotted using non-linear regression analysis of Sigmoidal dose-response curve generated with Equation 2:

$$Y = B + \left(\frac{T - B}{1 + 10^{(LogEC50 - X) \times HillSlope}}\right) \times 100 \qquad \text{(eqn. 2)}$$

where Y=percent activity, B=minimum percent activity, T=maximum percent activity, X=logarithm of compound, and Hill Slope=slope factor or Hill coefficient. The $IC_{50}$ value was determined by the concentration causing a half-maximal percent activity.

Results

The results are tabulated in Table 3 with $IC_{50}$ values shown as ranges.

TABLE 3

In Vitro Inhibition of Human PDE-5 Activities

| Cmpd No. | $IC_{50}$ (nM)<br>A: $IC_{50}$ ≤ 10 nM<br>B: 10 nM < $IC_{50}$ ≤ 100 nM<br>C: $IC_{50}$ > 100 nM<br>PDE-5 | Cmpd No. | $IC_{50}$ (nM)<br>A: $IC_{50}$ ≤ 10 nM<br>B: 10 nM < $IC_{50}$ ≤ 100 nM<br>C: $IC_{50}$ > 100 nM<br>PDE-5 |
|---|---|---|---|
| 1 | A | 2 | B |
| 3 | B | 4 | B |
| 5 | A | 6 | A |
| 7 | A | 8 | A |
| 9 | A | 10 | A |
| 11 | C | 13 | C |
| 18 | A | 19 | C |
| 20 | A | 21 | C |
| 22 | A | 23 | C |
| 24 | A | 25 | A |
| 26 | A | 27 | A |
| 28 | A | 29 | A |
| 30 | A | 31 | A |
| 32 | A | 33 | A |
| 34 | A | 38 | A |
| 47 | A | 48 | A |
| 49 | A | 50 | A |

As illustrated by this example, the tested compounds exhibited very good inhibitory activity against PDE-5.

Example 4—Androgen Receptor (AR) Reporter Assay

This example illustrates the in vitro antagonistic activity toward androgen receptor (AR) exhibited by exemplary compounds of this disclosure (e.g., as described herein). The protocols and results of this Example were carried out and obtained by Thermofisher Scientific.

Test Compounds

Test compounds were received at 1000× (or greater) of the desired starting concentration in 100% DMSO. If compounds were supplied at greater that 1000× concentration, an initial dilution is made in 100% DMSO to bring the compounds to 1000× concentration. The 1000× test compounds were serially diluted (10 point ½-log increments) in 100% DMSO.

Substrate Loading Solution

The Substrate Loading Solution consists of three Life Technologies reagents: Solution A (10 mM LiveBLAzer™-FRET B/G Substrate), Solution B and Solution C.

Androgen Receptor (AR)—Antagonist Screen, Activated by R1881

AR-UAS-bla GripTite™ 293 cells were thawed and resuspended in Assay Media (DMEM phenol red free, 2% CD-treated FBS, 0.1 mM NEAA, 1 mM Sodium Pyruvate, 100 U/mL/100 µg/mL Pen/Strep) to a concentration of 312,500 cells/mL. 4 µL of a 10× serial dilution of Cyproterone Acetate (control antagonist starting concentration, 3,160 nM) or compounds are added to appropriate wells of a Poly-D-Lysine assay plate. 32 µL of cell suspension was added to the wells and pre-incubated at 37° C./5% $CO_2$ in a humidified incubator with compounds and control antagonist titration for 30 minutes. 4 µL of 10× control agonist R1881 at the pre-determined EC80 concentration was added to wells containing the control antagonist or compounds. The plate was incubated for 16-24 hours at 37° C./5% $CO_2$ in a humidified incubator. 8 µL of 1 µM Substrate Loading Solution is added to each well and the plate was incubated for 2 hours at room temperature. The plate was read on a fluorescence plate reader (Tecan Safire²).

Results

The results are tabulated in Table 4 with $IC_{50}$ values shown as ranges.

TABLE 4

In Vitro Androgen Receptor (AR) Reporter Assay

| Cmpd No. | Concentration Range (nM)<br>A: $IC_{50} \leq 500$ nM<br>B: 500 nM < $IC_{50} \leq 1000$ nM<br>C: $IC_{50} > 100$ nM<br>$IC_{50}$ | Cmpd No. | Concentration Range(nM)<br>A: $IC_{50} \leq 500$ nM<br>B: 500 nM < $IC_{50} \leq 1000$ nM<br>C: $IC_{50} > 100$ nM<br>$IC_{50}$ |
|---|---|---|---|
| 13 | B | 18 | A |
| 19 | B | 20 | A |
| 21 | A | 22 | A |
| 23 | A | 25 | C |
| 26 | C | 27 | C |
| 28 | C | 29 | B |
| 30 | A | 31 | B |
| 32 | C | 33 | C |
| 34 | A | 38 | A |
| 47 | A | 48 | A |
| 49 | B | 50 | A |

Example 5—Androgen Receptor (AR) Radioligand Binding Assay

This example also illustrates the in vitro antagonistic activity toward androgen receptor (AR) exhibited by exemplary compounds of this disclosure (e.g., as described herein), and illustrates the binding affinity of the exemplary compounds.

Procedure

Methods employed in this study have been adapted from the following literature procedure.

Human androgen receptors obtained from human LNCaP cells are used in modified HEPES buffer pH 7.4. A 70 µg (adjusted if necessary) aliquot is incubated with 0.5 nM [³H]Methyltrienolone for 20 hours at 4° C. Non-specific binding is estimated in the presence of 1 µM testosterone. Receptors are filtered and washed, the filters are then counted to determine [³H]methyltrienolone specifically bound (Historic values: Kd=0.71 nM: Specific binding=75%; Bmax=0.25 pmole/mg protein). (See, e.g., Traish, A. M et al., Binding of 7α, 17α-dimethyl-19-nortestosterone (Mibolerone) to androgen and progesterone receptors in human and animal tissues. Endocrinology. 118(4): 1327-1333, 1986).

Compounds are screened at 10 µM.

Where presented, $IC_{50}$ values were determined by a non-linear, least squares regression analysis using MathIQ™ (ID Business Solutions Ltd., UK).

Results

The results are tabulated in Table 6 with the following values shown as ranges: $IC_{50}$ (nM) concentration ranges: (A) refers to $IC_{50} \leq 50$ nM; (B) refers to 50 nM<$IC_{50} \leq 200$; and (C) refers to $IC_{50} > 200$ nM.

TABLE 6

In Vitro Androgen Receptor (AR) Binding Assay

| Compound | AR $IC_{50}$ (nM) |
|---|---|
| 13 | C |
| 18 | A |
| 19 | C |
| 20 | B |
| 21 | C |
| 22 | B |
| 23 | C |
| 24 | B |
| 26 | C |
| 29 | B |
| 30 | A |
| 31 | B |
| 32 | C |
| 33 | C |
| 34 | B |
| 38 | A |
| 47 | A |
| 48 | A |
| 49 | A |
| 50 | A |

As illustrated by this example, exemplary compounds of this disclosure exhibit potent AR inhibitory activity and binding affinity

6. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are herein incorporated by reference in their entirety, for all purposes.

The invention claimed is:

1. A compound of formula (I):

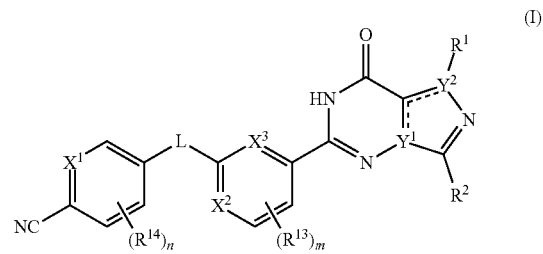

or a pharmaceutically acceptable salt or stereoisomer thereof, wherein:

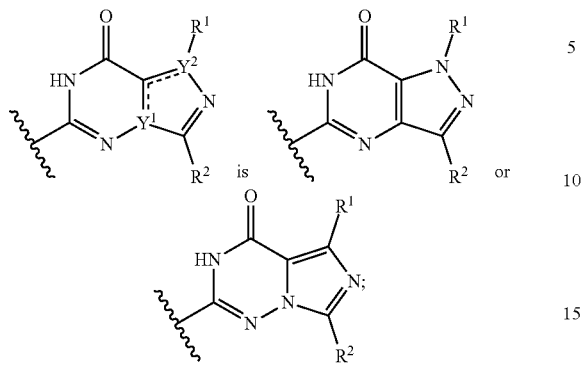

is

R[1] is H, $(C_1\text{-}C_6)$ alkyl, $(C_2\text{-}C_4)$ alkenyl, $O(C_1\text{-}C_6)$ alkyl, or $(C_3\text{-}C_6)$ cycloalkyl;

wherein the $(C_1\text{-}C_6)$ alkyl, $(C_2\text{-}C_4)$ alkenyl, or $O(C_1\text{-}C_6)$ alkyl is optionally substituted with one or more substituents independently selected from the group consisting of halogen, CN, $NO_2$, =NH, =$NNH_2$, =NOH, =OH, =O, =S, cycloalkyl, heterocycloalkyl, aryl, and heteroaryl; and wherein the $(C_3\text{-}C_6)$ cycloalkyl is optionally substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

R[2] is H, $(C_1\text{-}C_6)$ alkyl, $(C_2\text{-}C_4)$ alkenyl, $O(C_1\text{-}C_6)$ alkyl, or $(C_3\text{-}C_6)$ cycloalkyl;

wherein the $(C_1\text{-}C_6)$ alkyl, $(C_2\text{-}C_4)$ alkenyl, or $O(C_1\text{-}C_6)$ alkyl is optionally substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl; and wherein the $(C_3\text{-}C_6)$ cycloalkyl is optionally substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

L is -A-B—;

A is a covalent bond, —NHC(O)R[5]—, —NR[6]C(Z[1])NR[7]—, —NR[11]S(O)$_2$—, 3- to 6-membered heterocyclylene, $(C_6\text{-}C_{12})$ arylene, —$(C_3\text{-}C_{12})$ heteroarylene-$(C_1\text{-}C_5)$ alkylene-, or $(C_3\text{-}C_{12})$ heteroarylene;

wherein the 3- to 6-membered heterocyclylene is optionally substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

wherein each haloalkyl substituent of the 3- to 6-membered heterocyclylene is optionally and independently substituted with one or more OH substituents;

wherein the $(C_3\text{-}C_{12})$ heteroarylene portion of —$(C_3\text{-}C_{12})$ heteroarylene-$(C_1\text{-}C_5)$ alkylene- is optionally substituted with one or more substituents independently selected from the group consisting of halogen, CN, $NO_2$, alkyl, haloalkyl, alkenyl, haloalkenyl, alkynyl, haloalkynyl, OH, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

wherein the $(C_6\text{-}C_{12})$ arylene or $(C_3\text{-}C_{12})$ heteroarylene is optionally substituted with one or more substituents independently selected from the group consisting of halogen, CN, $NO_2$, alkyl, haloalkyl, alkenyl, haloalkenyl, alkynyl, haloalkynyl, OH, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$; and wherein A is bonded to the aromatic ring bearing $X^1$;

B is a covalent bond, —NHC(O)R[5]—, —NR[6]C(Z[1])NR[7]—, —NR[11]—, —NR[11]S(O)$_2$—, —O—, —S—, —S(O)$_2$—, or 3- to 6-membered heterocyclylene;

wherein the 3- to 6-membered heterocyclylene is optionally substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$; and wherein B is bonded to the aromatic ring bearing $X^2$ and $X^3$;

each R[5] is independently $(C_1\text{-}C_5)$ alkylene, $(C_1\text{-}C_5)$ haloalkylene, or —O;

wherein each $(C_1\text{-}C_5)$ alkylene is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl;

each R[6] is independently H or $(C_1\text{-}C_3)$ alkyl;

wherein each $(C_1\text{-}C_3)$ alkylene is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl;

each R[7] is independently H or $(C_1\text{-}C_3)$ alkyl;

wherein each $(C_1\text{-}C_3)$ alkylene is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl; or any $R^6$ and $R^7$, taken together with the nitrogen atoms to which they are attached, independently forms a 3- to 6-membered heterocyclylene;
- wherein each 3- to 6-membered heterocyclylene is optionally and independently substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$; or
- wherein each 3- to 6-membered heterocyclylene is optionally and independently substituted with one or more substituents independently selected from the group consisting of =O, =S, $R^8$, and $R^9$;

each $R^8$ is independently H or $(C_1-C_3)$ alkyl;
- wherein the $(C_1-C_3)$ alkyl is optionally substituted with one or more substituents independently selected from the group consisting of halogen, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, $S(O)_tR^a$, $S(O)_tN(R^a)_2$, and $S(O)_tOR^a$;

each $R^9$ is independently H or $(C_1-C_3)$ alkyl;
- wherein the $(C_1-C_3)$ alkyl is optionally substituted with one or more substituents independently selected from the group consisting of halogen, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, $S(O)_tR^a$, $S(O)_tN(R^a)_2$, and $S(O)_tOR^a$; or each $R^8$ and $R^9$, taken together with the carbon atom to which they are attached, independently forms a spirocyclic 3- to 6-membered carbocyclyl or a spirocyclic 3- to 6-membered heterocyclyl;
- wherein each spirocyclic 3- to 6-membered carbocyclyl or spirocyclic 3- to 6-membered heterocyclyl is optionally and independently substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

each $R^{11}$ is independently H or $(C_1-C_3)$ alkyl;
- wherein each $(C_1-C_3)$ alkylene is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl;

each $Z^1$ is independently O or S;

$X^1$ is C $R^{14}$ or N;

$X^2$ is C $R^{13}$ or N;

$X^3$ is C $R^{13}$ or N;

each $R^{13}$ is independently H, $(C_1-C_6)$ alkyl, or $O(C_1-C_6)$ alkyl;
- wherein each $(C_1-C_6)$ alkyl and $O(C_1-C_6)$ alkyl is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl;

each $R^{14}$ is independently H, halogen, CN, $NO_2$, $(C_1-C_5)$ alkyl, $(C_2-C_4)$ alkenyl, $NH_2$, OH, $O(C_1-C_5)$ alkyl, or $(C_3-C_6)$ cycloalkyl;
- wherein each $(C_1-C_5)$ alkyl, $(C_2-C_4)$ alkenyl, and $O(C_1-C_5)$ alkyl is optionally and independently substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl; and
- wherein each $(C_3-C_6)$ cycloalkyl is optionally and independently substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, =S, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR^aS(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$;

each $R^a$ is independently H, alkyl, alkyl(cycloalkyl), alkyl(heterocycloalkyl), aralkyl, alkyl(heteroaryl), cycloalkyl, heterocycloalkyl, aryl, or heteroaryl;
- wherein each alkyl, alkyl portion of alkyl(cycloalkyl), alkyl portion of alkyl(heterocycloalkyl), alkyl portion of aralkyl, and alkyl portion of alkyl(heteroaryl) is optionally and independently substituted with one or more substituents independently selected from the group consisting of halogen, CN, $NO_2$, =NH, =$NNH_2$, =NOH, OH, =O, and =S;
- wherein each cycloalkyl and heterocycloalkyl is optionally and independently substituted with one or more substituents independently selected from the group consisting of halogen, CN, $NO_2$, alkyl, haloalkyl, alkenyl, haloalkenyl, alkynyl, haloalkynyl, =NH, =$NNH_2$, =NOH, OH, =O, and =S; and
- wherein each aryl and heteroaryl is optionally and independently substituted with one or more substituents independently selected from the group consisting of halogen, CN, $NO_2$, alkyl, haloalkyl, alkenyl, haloalkenyl, alkynyl, haloalkynyl, and OH;

each $R^b$ is independently alkylene, alkylene(cycloalkyl), alkylene(heterocycloalkyl), aralkylene, alkylene(heteroaryl), cycloalkylene, heterocycloalkylene, arylene, or heteroarylene;
- wherein each alkylene, alkylene portion of alkylene(cycloalkyl), alkylene portion of alkylene(heterocycloalkyl), alkylene portion of aralkylene, and alkylene portion of alkylene(heteroaryl) is optionally and independently substituted with one or more substituents independently selected from the group consisting of halogen, CN, $NO_2$, =NH, =$NNH_2$, =NOH, OH, =O, and =S;
- wherein each cycloalkylene and heterocycloalkylene is optionally and independently substituted with one or more substituents independently selected from the group consisting of halogen, CN, $NO_2$, alkyl, haloalkyl, alkenyl, haloalkenyl, alkynyl, haloalkynyl, =NH, =NNH$_2$, =NOH, OH, =O, and =S; and wherein each arylene and heteroarylene is optionally and independently substituted with one or more substituents independently selected from the group consisting of halogen, CN, NO$_2$, alkyl, haloalkyl, alkenyl, haloalkenyl, alkynyl, haloalkynyl, and OH;

each R$^c$ is independently alkylene, alkylene(cycloalkyl), alkylene(heterocycloalkyl), aralkylene, alkylene(heteroaryl), cycloalkylene, heterocycloalkylene, arylene, or heteroarylene;

wherein each alkylene, alkylene portion of alkylene(cycloalkyl), alkylene portion of alkylene(heterocycloalkyl), alkylene portion of aralkylene, and alkylene portion of alkylene(heteroaryl) is optionally and independently substituted with one or more substituents independently selected from the group consisting of halogen, CN, NO$_2$, =NH, =NNH$_2$, =NOH, OH, =O, and =S;

wherein each cycloalkylene and heterocycloalkylene is optionally and independently substituted with one or more substituents independently selected from the group consisting of halogen, CN, NO$_2$, alkyl, haloalkyl, alkenyl, haloalkenyl, alkynyl, haloalkynyl, =NH, =NNH$_2$, =NOH, OH, =O, and =S; and wherein each arylene and heteroarylene is optionally and independently substituted with one or more substituents independently selected from the group consisting of halogen, CN, NO$_2$, alkyl, haloalkyl, alkenyl, haloalkenyl, alkynyl, haloalkynyl, and OH;

m is 0, 1, or 2;
n is 1, 2, 3, or 4; and
each t is independently 1 or 2;
with the provisos that:
(1) if A is a covalent bond, then B is not a covalent bond; and
(2) if B is a covalent bond, then A is not a covalent bond.

2. The compound of claim 1, or a pharmaceutically acceptable salt or stereoisomer thereof, wherein:
R$^1$ is (C$_1$-C$_6$) alkyl, wherein the (C$_1$-C$_6$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl;
R$^2$ is (C$_1$-C$_6$) alkyl, wherein the (C$_1$-C$_6$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl;
each R$^{13}$ is independently H or O(C$_1$-C$_6$) alkyl, wherein each O(C$_1$-C$_6$) alkyl is optionally and independently substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl; and
each R$^{14}$ is independently H, halogen, or (C$_1$-C$_5$) alkyl, wherein each (C$_1$-C$_5$) alkyl is substituted with one or more independently selected halogen substituents, and optionally further substituted with one or more additional substituents independently selected from the group consisting of CN, NO$_2$, =NH, =NNH$_2$, =NOH, OH, =O, =S, cycloalkyl, heterocycloalkyl, aryl, and heteroaryl.

3. The compound of claim 1, or a pharmaceutically acceptable salt or stereoisomer thereof, wherein:
(i) X$^1$ is CH;
   X$^2$ is CH; and
   X$^3$ is CH; or
(ii) X$^1$ is CH;
   X$^2$ is N; and
   X$^3$ is CH; or
(iii) X$^1$ is CH;
   X$^2$ is CH; and
   X$^3$ is N; or
(iv) X$^1$ is N;
   X$^2$ is CH; and
   X$^3$ is CH.

4. The compound of claim 1, wherein the compound is of formula (IIa) or formula (IIb):

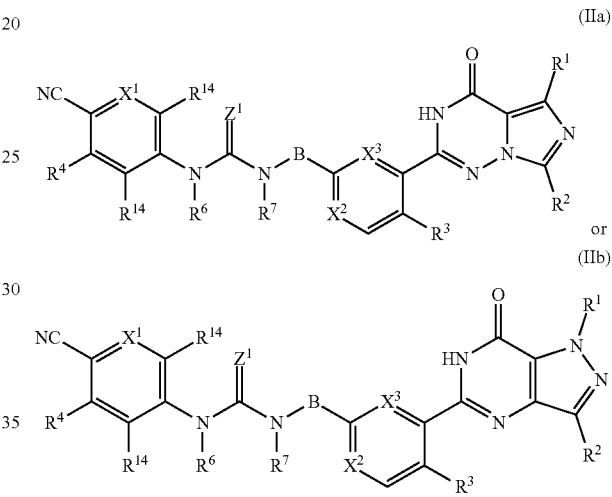

or a pharmaceutically acceptable salt or stereoisomer thereof,
wherein:
R$^3$ is H or O(C$_1$-C$_6$) alkyl, wherein the O(C$_1$-C$_6$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl;
R$^4$ is H, halogen, CN, NO$_2$, (C$_1$-C$_5$) alkyl, NH$_2$, or OH, wherein the (C$_1$-C$_5$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl; and
B is a covalent bond or 3- to 6-membered heterocyclylene, wherein the 3- to 6-membered heterocyclylene is optionally substituted with one or more substituents independently selected from the group consisting of halogen, CN, NO$_2$, alkyl, haloalkyl, alkenyl, haloalkenyl, alkynyl, haloalkynyl, =NH, =NNH$_2$, =NOH, OH, =O, =S, R$^b$C(O)R$^a$, R$^b$C(O)N(R$^a$)$_2$, R$^b$C(O)OR$^a$, R$^b$N(R$^a$)$_2$, R$^b$NR$^a$C(O)R$^a$, R$^b$NR$^a$C(O)OR$^a$, R$^b$NR$^a$S(O)$_t$R$^a$, R$^b$OR$^a$, R$^b$OC(O)R$^a$, R$^b$OC(O)N(R$^a$)$_2$, R$^b$OC(O)OR$^a$, R$^b$OR$^c$C(O)N(R$^a$)$_2$, R$^b$S(O)$_t$R$^a$, R$^b$S(O)$_t$N(R$^a$)$_2$, and R$^b$S(O)$_t$OR$^a$.

5. The compound of claim 4, wherein the compound is of formula (IIIa) or formula (IIIb):

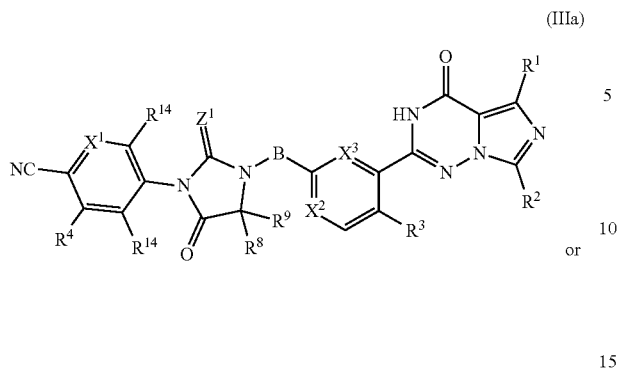

(IIIa)

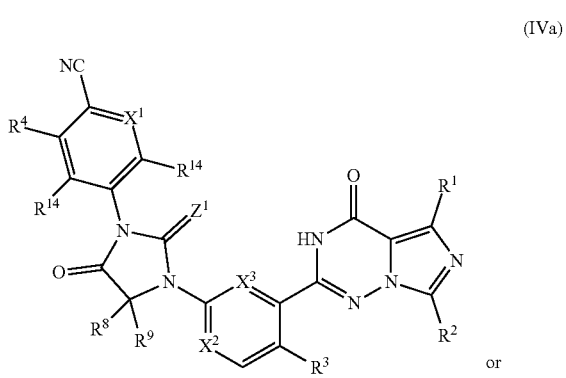

(IVa)

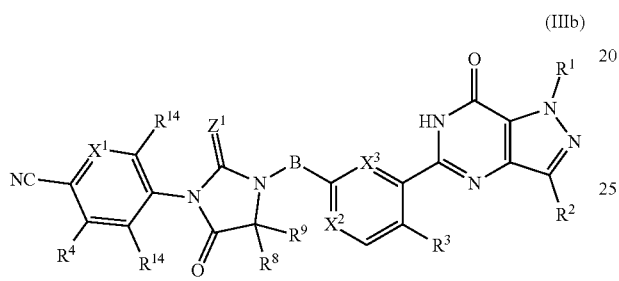

(IIIb)

or a pharmaceutically acceptable salt or stereoisomer thereof, wherein:

- $R^8$ is H or $(C_1-C_3)$ alkyl, wherein the $(C_1-C_3)$ alkyl is optionally substituted with one or more substituents independently selected from the group consisting of halogen, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, $S(O)_tR^a$, $S(O)_tN(R^a)_2$, and $S(O)_tOR^a$; and

- $R^9$ is H or $(C_1-C_3)$ alkyl, wherein the $(C_1-C_3)$ alkyl is optionally substituted with one or more substituents independently selected from the group consisting of halogen, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^t$, $OC(O)R^a$, $OC(O)N(R^a)_2$, $OC(O)OR^a$, $OR^c(O)N(R^a)_2$, $S(O)_tR^a$, $S(O)_tN(R^a)_2$, and $S(O)_tOR^a$; or

- $R^8$ and $R^9$, taken together with the carbon atom to which they are attached, form a spirocyclic 3- to 6-membered carbocyclyl or spirocyclic 3- to 6-membered heterocyclyl, wherein the spirocyclic 3- to 6-membered carbocyclyl or spirocyclic 3- to 6-membered heterocyclyl is optionally substituted with one or more substituents independently selected from the group consisting of halogen, CN, $NO_2$, alkyl, haloalkyl, alkenyl, haloalkenyl, alkynyl, haloalkynyl, $=NH$, $=NNH_2$, $=NOH$, OH, $=O$, $=S$, $R^bC(O)R^a$, $R^bC(O)N(R^a)_2$, $R^bC(O)OR^a$, $R^bN(R^a)_2$, $R^bNR^aC(O)R^a$, $R^bNR^aC(O)OR^a$, $R^bNR'S(O)_tR^a$, $R^bOR^a$, $R^bOC(O)R^a$, $R^bOC(O)N(R^a)_2$, $R^bOC(O)OR^a$, $R^bOR^cC(O)N(R^a)_2$, $R^bS(O)_tR^a$, $R^bS(O)_tN(R^a)_2$, and $R^bS(O)_tOR^a$.

6. The compound of claim 5, wherein the compound is of formula (IVa) or formula (IVb):

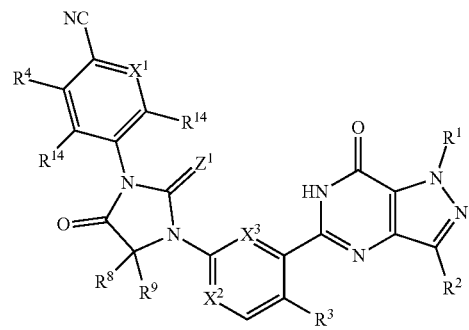

(IVb)

or a pharmaceutically acceptable salt or stereoisomer thereof.

7. The compound of claim 6, wherein the compound is of formula (IVc) or formula (IVd):

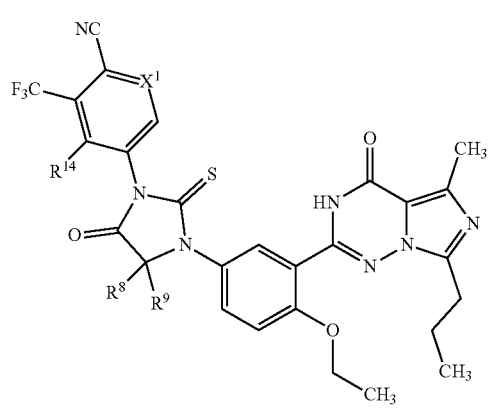

(IVc)

or

165

-continued (IVd)

[Chemical structure]

or a pharmaceutically acceptable salt or stereoisomer thereof, wherein:

$R^{14}$ is H or halogen.

8. The compound of claim 7, or a pharmaceutically acceptable salt or stereoisomer thereof, wherein:

$R^8$ is H or ($C_1$-$C_3$) alkyl, wherein the ($C_1$-$C_3$) alkyl is optionally substituted with one or more substituents independently selected from the group consisting of halogen, C(O)$R^a$, C(O)N($R^a$)$_2$, C(O)O$R^a$, N($R^a$)$_2$, N$R^a$C(O)$R^a$, N$R^a$C(O)O$R^a$, N$R^a$S(O)$_r$$R^a$, O$R^a$, OC(O)$R^a$, OC(O)N($R^a$)$_2$, OC(O)O$R^a$, O$R^c$C(O)N($R^a$)$_2$, S(O)$_r$$R^a$, S(O)$_r$N($R^a$)$_2$, and S(O)$_r$O$R^a$; and $R^9$ is H or ($C_1$-$C_3$) alkyl, wherein the ($C_1$-$C_3$) alkyl is optionally substituted with one or more substituents independently selected from the group consisting of halogen, C(O)$R^a$, C(O)N($R^a$)$_2$, C(O)O$R^a$, N($R^a$)$_2$, N$R^a$C(O)$R^a$, N$R^a$C(O)O$R^a$, N$R^a$S(O)$_r$$R^a$, O$R^a$, OC(O)$R^a$, OC(O)N($R^a$)$_2$, OC(O)O$R^a$, O$R^c$C(O)N($R^a$)$_2$, S(O)$_r$$R^a$, S(O)$_r$N($R^a$)$_2$, and S(O)$_r$O$R^a$.

9. The compound of claim 7, or a pharmaceutically acceptable salt or stereoisomer thereof, wherein:

$R^8$ is CH$_3$; and $R^9$ is CH$_3$.

10. The compound of claim 7, or a pharmaceutically acceptable salt or stereoisomer thereof, wherein $R^8$ and $R^9$, taken together with the carbon atom to which they are attached, form a spirocyclic cyclobutyl, a spirocyclic cyclopentyl, or a spirocyclic tetrahydrofuranyl.

11. The compound of claim 6, or a pharmaceutically acceptable salt or stereoisomer thereof, wherein:

(i) $X^2$ is CH; and
$X^3$ is N; or
(ii) $X^2$ is N; and
$X^3$ is CH;
$R^1$ is CH$_3$;
$R^2$ is CH$_2$CH$_2$CH$_3$;
$R^3$ is OCH$_2$CH$_3$;
$R^8$ is ($C_1$-$C_3$) alkyl, wherein the ($C_1$-$C_3$) alkyl is optionally substituted with one or more substituents independently selected from the group consisting of halogen, C(O)$R^a$, C(O)N($R^a$)$_2$, C(O)O$R^a$, N($R^a$)$_2$, N$R^a$C(O)$R^a$, N$R^a$C(O)O$R^a$, N$R^a$S(O)$_r$$R^a$, O$R^a$, OC(O)$R^a$, OC(O)N($R^a$)$_2$, OC(O)O$R^a$, O$R^c$C(O)N($R^a$)$_2$, S(O)$_r$$R^a$, S(O)$_r$N($R^a$)$_2$, and S(O)$_r$O$R^a$; and
$R^9$ is ($C_1$-$C_3$) alkyl, wherein the ($C_1$-$C_3$) alkyl is optionally substituted with one or more substituents independently selected from the group consisting of

166 halogen, C(O)$R^a$, C(O)N($R^a$)$_2$, C(O)O$R^a$, N($R^a$)$_2$, N$R^a$C(O)$R^a$, N$R^a$C(O)O$R^a$, N$R^a$S(O)$_r$$R^a$, O$R^a$, OC(O)$R^a$, OC(O)N($R^a$)$_2$, OC(O)O$R^a$, O$R^c$C(O)N($R^a$)$_2$, S(O)$_r$$R^a$, S(O)$_r$N($R^a$)$_2$, and S(O)$_r$O$R^a$; or $R^8$ and $R^9$, taken together with the carbon atom to which they are attached, form a spirocyclic cyclobutyl, a spirocyclic cyclopentyl, or a spirocyclic tetrahydrofuranyl.

12. The compound of claim 6, wherein the compound is of formula (IVc):

(IVc)

[Chemical structure]

or a pharmaceutically acceptable salt or stereoisomer thereof, wherein:

$X^1$ is CH or N;

$R^8$ is H or ($C_1$-$C_3$) alkyl;

$R^9$ is H or ($C_1$-$C_3$) alkyl; or $R^8$ and $R^9$, taken together with the carbon atom to which they are attached, form a spirocyclic 3- to 5-membered carbocyclyl or a spirocyclic 4- or 5-membered heterocyclyl; and $R^{14}$ is H or halogen.

13. The compound of claim 5, wherein the compound is of formula (Va) or formula (Vb):

(Va)

[Chemical structure]

or

-continued (Vb)

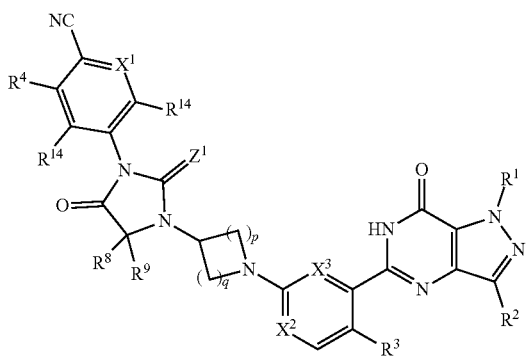

or a pharmaceutically acceptable salt or stereoisomer thereof,
wherein:
p is 1 or 2; and
q is 1 or 2.

14. The compound of claim 13, wherein the compound is of formula (Vc):

(Vc)

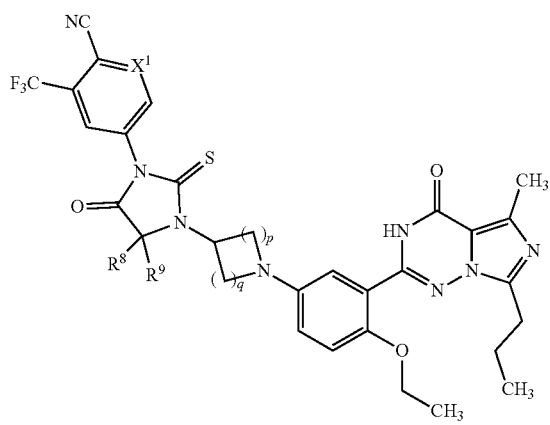

or a pharmaceutically acceptable salt or stereoisomer thereof,
wherein:
R$^8$ is (C$_1$-C$_3$) alkyl, wherein the (C$_1$-C$_3$) alkyl is optionally substituted with one or more substituents independently selected from the group consisting of halogen, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, and S(O)$_t$OR$^a$; and
R$^9$ is (C$_1$-C$_3$) alkyl, wherein the (C$_1$-C$_3$) alkyl is optionally substituted with one or more substituents independently selected from the group consisting of halogen, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, and S(O)$_t$OR$^a$; or
R$^8$ and R$^9$, taken together with the carbon atom to which they are attached, form a spirocyclic cyclobutyl, a spirocyclic cyclopentyl, or a spirocyclic tetrahydrofuranyl.

15. The compound of claim 4, wherein the compound is of formula (VIa) or formula (VIb):

(VIa)

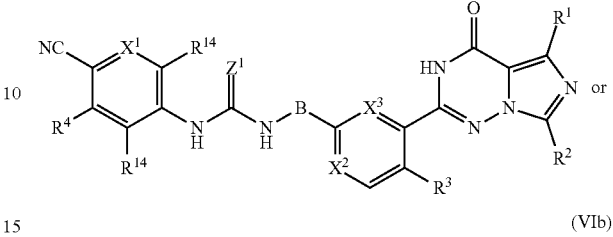

or (VIb)

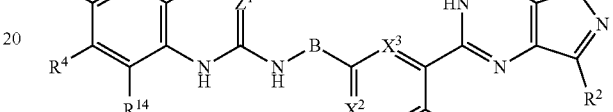

or a pharmaceutically acceptable salt or stereoisomer thereof.

16. The compound of claim 15, wherein the compound is of formula (VIIa) or formula (VIIb):

(VIIa)

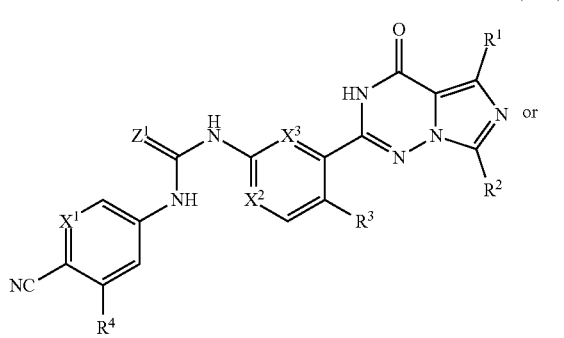

or (VIIb)

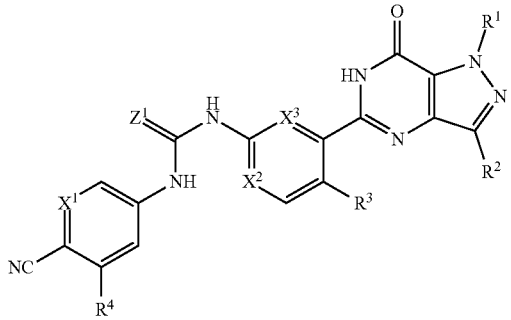

or a pharmaceutically acceptable salt or stereoisomer thereof.

17. The compound of claim 16, wherein the compound is of formula (VIIc):

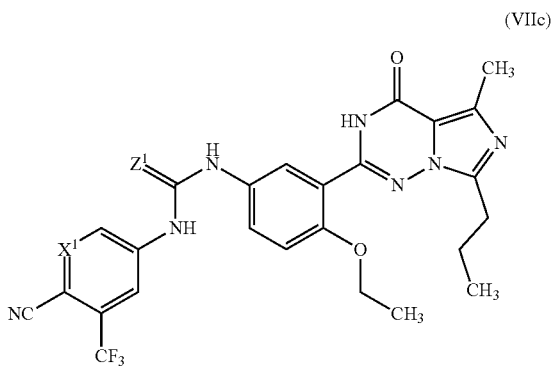

(VIIc)

or a pharmaceutically acceptable salt or stereoisomer thereof.

18. The compound of claim 1, wherein the compound is of formula (VIIIa) or formula (VIIIb):

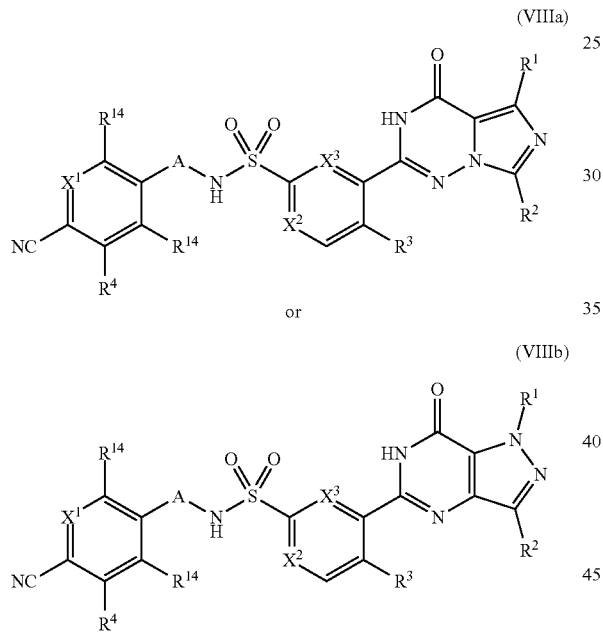

or a pharmaceutically acceptable salt or stereoisomer thereof, wherein:

$R^3$ is H or O($C_1$-$C_6$) alkyl, wherein the O($C_1$-$C_6$) alkyl is optionally substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl; and $R^4$ is H, halogen, CN, $NO_2$, ($C_1$-$C_5$) alkyl, $NH_2$, or OH, wherein the ($C_1$-$C_5$) alkyl is optionally substituted with one or more substituents independently selected from the group consisting of halogen, CN, $NO_2$, =NH, =$NNH_2$, =NOH, OH, =O, =S, cycloalkyl, heterocycloalkyl, aryl, and heteroaryl.

19. The compound of claim 18, wherein the compound is of formula (VIIIc):

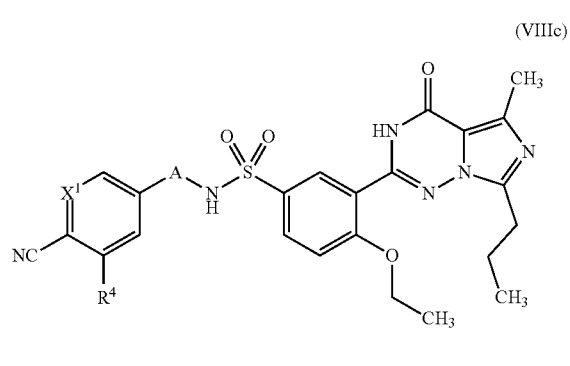

or a pharmaceutically acceptable salt or stereoisomer thereof.

20. The compound of claim 19, or a pharmaceutically acceptable salt or stereoisomer thereof, wherein:

A is

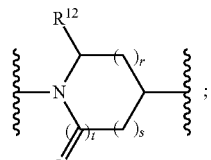

$R^{12}$ is H, ($C_1$-$C_5$) alkyl, or OH, wherein the ($C_1$-$C_5$) alkyl is optionally substituted with one or more substituents independently selected from the group consisting of halogen, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, S(O)$_t$ $R^a$, S(O)$_t$N($R^a$)$_2$, and S(O)$_t$O$R^a$;

r is 0 or 1;

s is 0 or 1; and t is 0 or 1.

21. The compound of claim 18, wherein the compound is of formula (VIIId):

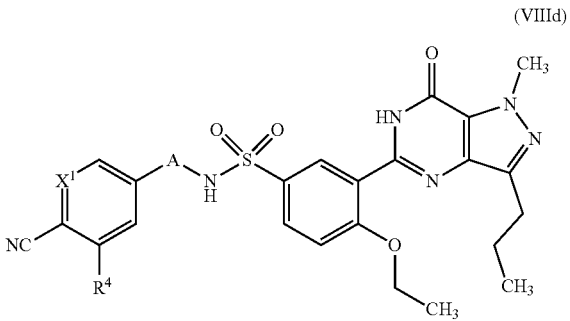

or a pharmaceutically acceptable salt or stereoisomer thereof.

22. The compound of claim 18, wherein the compound is of formula (IXa) or formula (IXb):

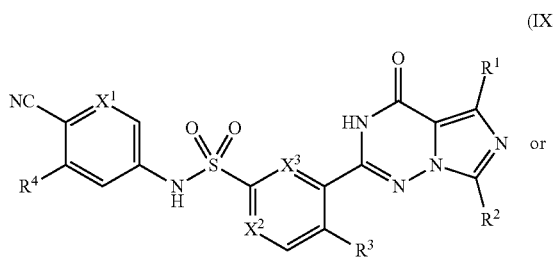

(IXa)

or (IXb)

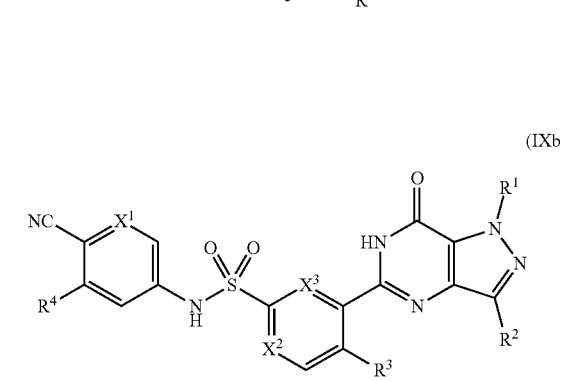

or a pharmaceutically acceptable salt or stereoisomer thereof.

23. The compound of claim 22, wherein the compound is of formula (IXc) or formula (IXd):

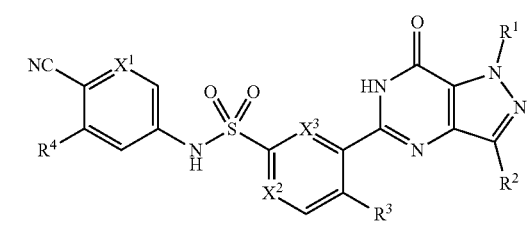

(IXc)

or (IXd)

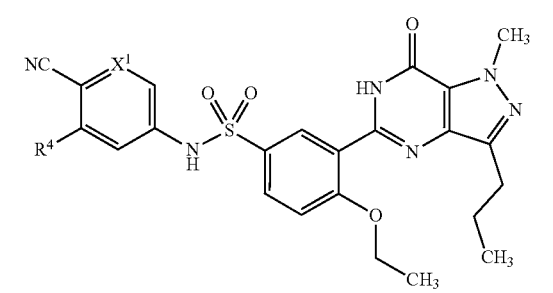

or a pharmaceutically acceptable salt or stereoisomer thereof.

24. The compound of claim 1, wherein the compound is of formula (Xa) or formula (Xb):

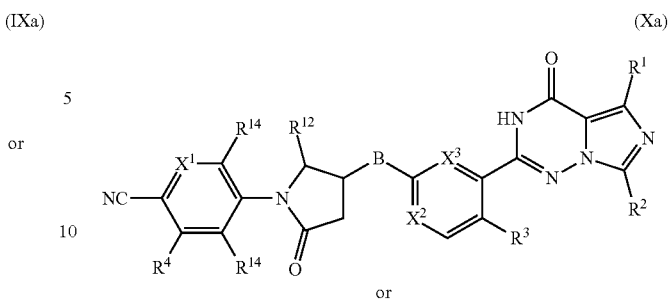

(Xa)

or (Xb)

or a pharmaceutically acceptable salt or stereoisomer thereof, wherein:

B is —NH—, —NHS(O)$_2$—, —O—, —S—, or —S(O)$_2$—;

$R^3$ is H or O(C$_1$-C$_6$) alkyl, wherein the O(C$_1$-C$_6$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl;

$R^4$ is H, halogen, CN, NO$_2$, (C$_1$-C$_5$) alkyl, NH$_2$, or OH, wherein the (C$_1$-C$_5$) alkyl is optionally substituted with one or more substituents independently selected from the group consisting of halogen, CN, NO$_2$, =NH, =NNH$_2$, =NOH, OH, =O, =S, cycloalkyl, heterocycloalkyl, aryl, and heteroaryl; and $R^{12}$ is H or (C$_1$-C$_3$) alkyl, wherein the (C$_1$-C$_3$) alkyl is optionally substituted with one or more substituents independently selected from the group consisting of halogen, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, and S(O)$_t$OR$^a$.

25. The compound of claim 24, wherein the compound is of formula (Xc):

(Xc)

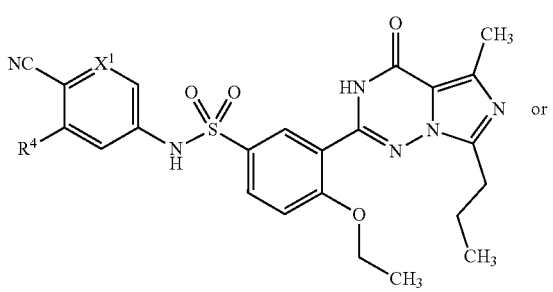

or a pharmaceutically acceptable salt or stereoisomer thereof, wherein:
B is —NH—, —O—, —S—, or —S(O)₂—.

26. The compound of claim 1, wherein the compound is of formula (XIa) or formula (XIb):

(XIa)

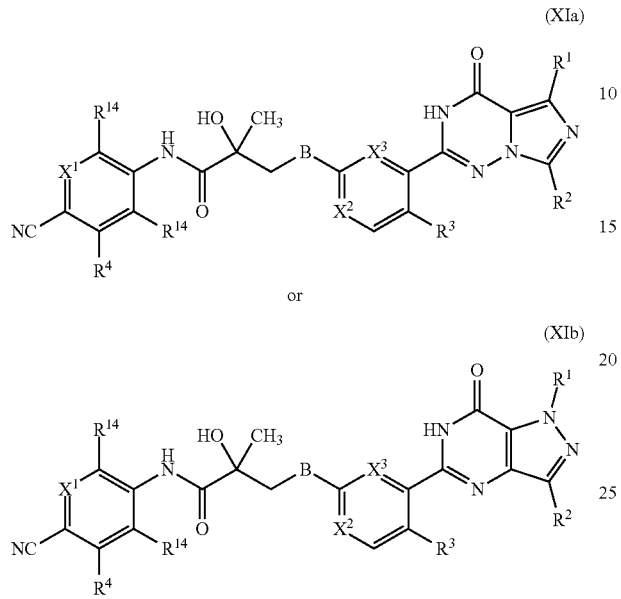

or (XIb)

or a pharmaceutically acceptable salt or stereoisomer thereof,
wherein:
B is —NHS(O)₂—, —O—, —S—, or —S(O)₂—; and
R³ is H or O(C₁-C₆) alkyl, wherein the O(C₁-C₆) alkyl is optionally substituted with one or more substituents independently selected from the group consisting of halogen, CN, NO₂, =NH, =NNH₂, =NOH, OH, =O, =S, cycloalkyl, heterocycloalkyl, aryl, and heteroaryl; and
R⁴ is H, halogen, CN, NO₂, (C₁-C₅) alkyl, NH₂, or OH, wherein the (C₁-C₅) alkyl is optionally substituted with one or more substituents independently selected from the group consisting of halogen, CN, NO₂, =NH, =NNH₂, =NOH, OH, =O, =S, cycloalkyl, heterocycloalkyl, aryl, and heteroaryl.

27. The compound of claim 26, wherein the compound is of formula (XIc):

(XIc)

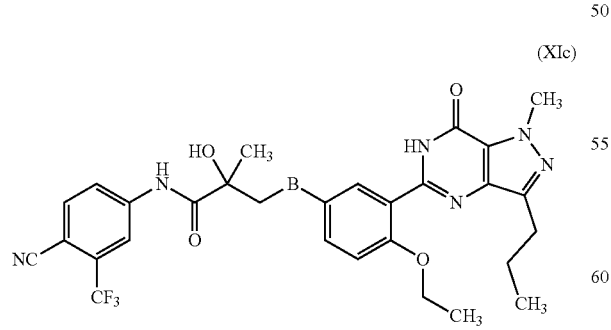

or a pharmaceutically acceptable salt or stereoisomer thereof.

28. The compound of claim 9, wherein the compound is selected from the group consisting of:

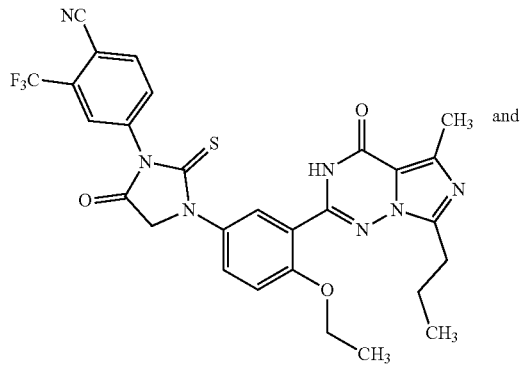

and

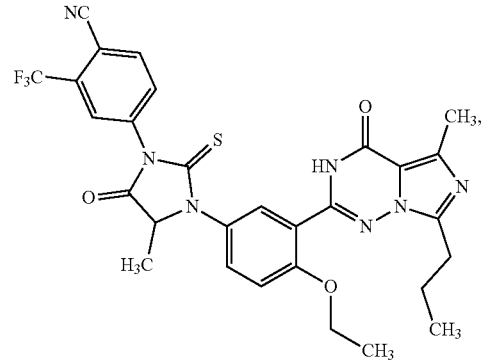

or a pharmaceutically acceptable salt or stereoisomer thereof.

29. The compound of claim 9, wherein the compound is selected from the group consisting of:

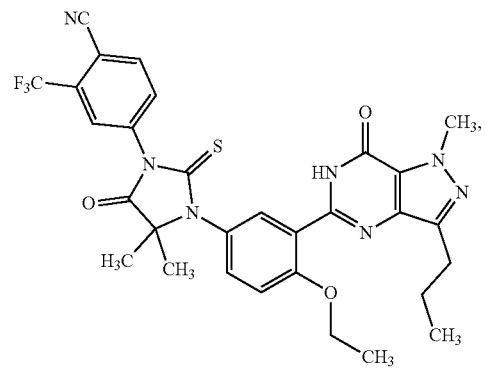

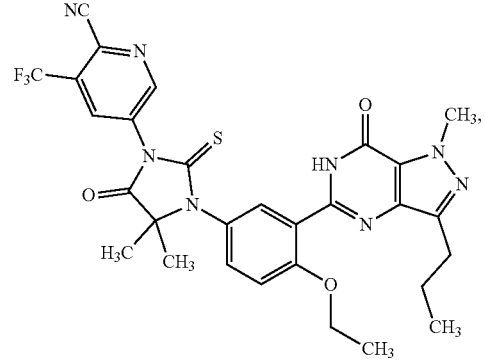

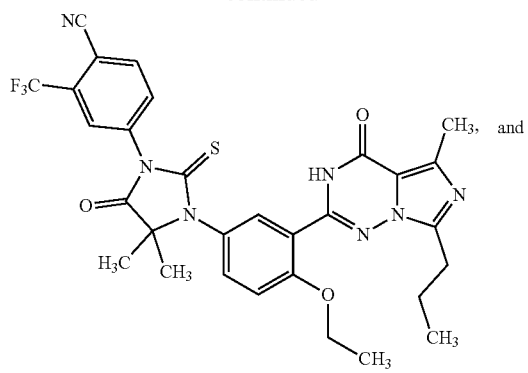
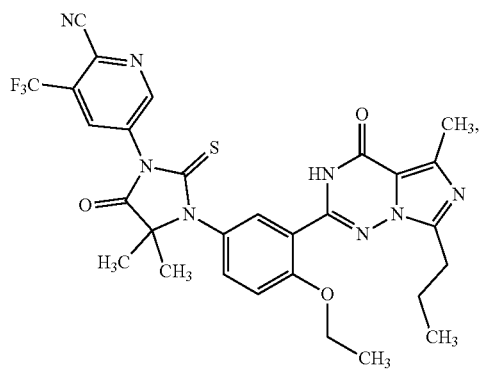
or a pharmaceutically acceptable salt thereof.
30. The compound of claim 10, wherein the compound is selected from the group consisting of:
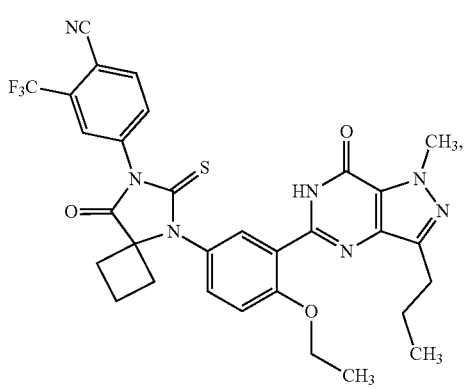
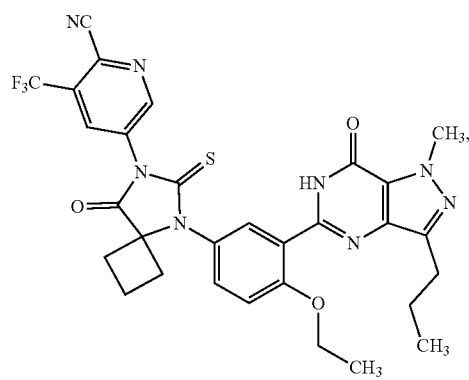
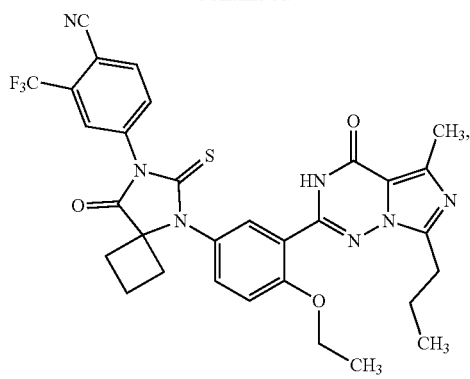
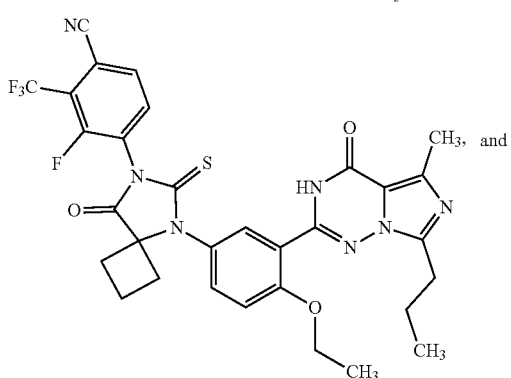
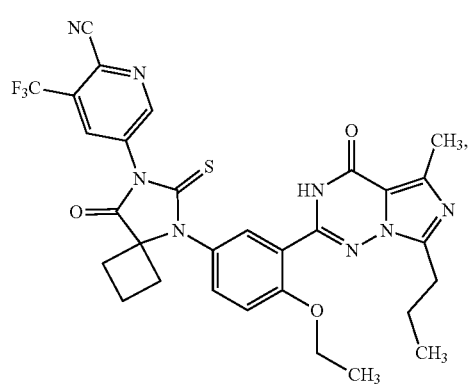 [SMILES: CCCc1nc(C)c2c(=O)[nH]c(-c3cc(N4C(=S)N(c5cnc(C#N)c(C(F)(F)F)c5)C(=O)C45CCC5)ccc3OCC)nn12]
or a pharmaceutically acceptable salt thereof.
31. The compound of claim 11, wherein the compound is selected from the group consisting of:
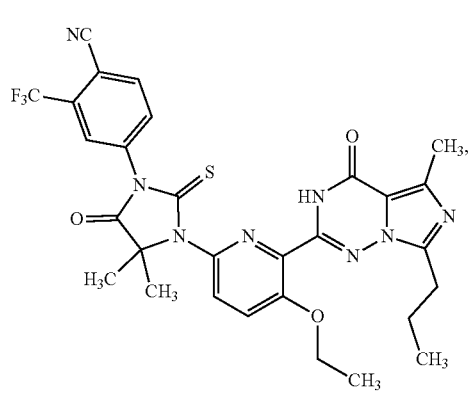

-continued
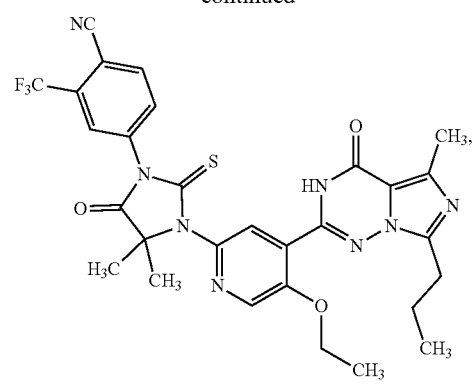
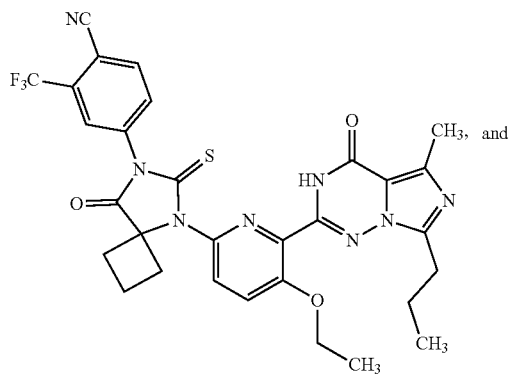, and
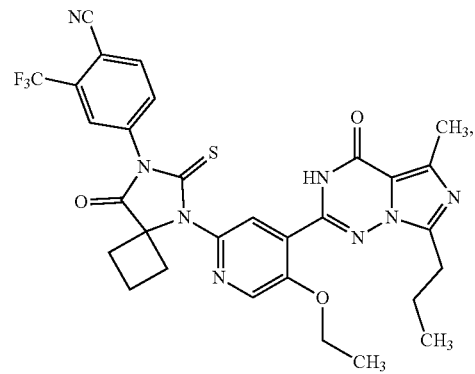
or a pharmaceutically acceptable salt thereof.
32. The compound of claim 12, wherein the compound is selected from the group consisting of:
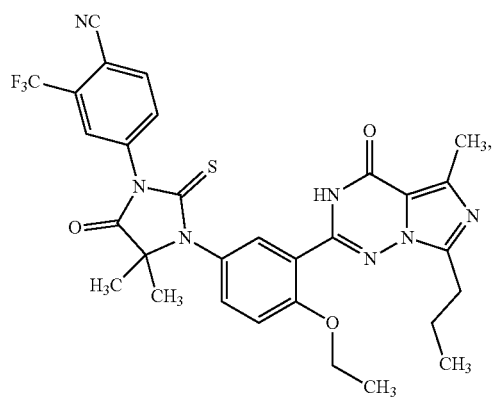
-continued
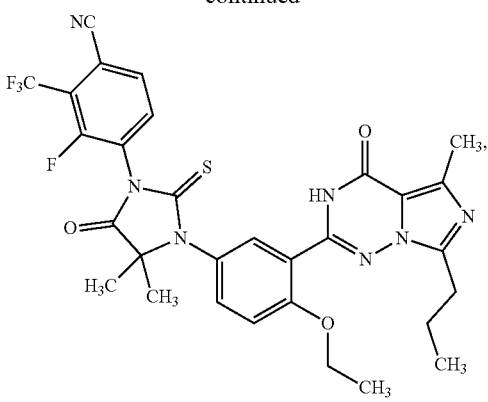
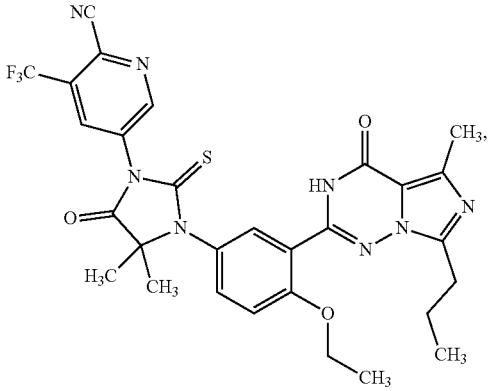
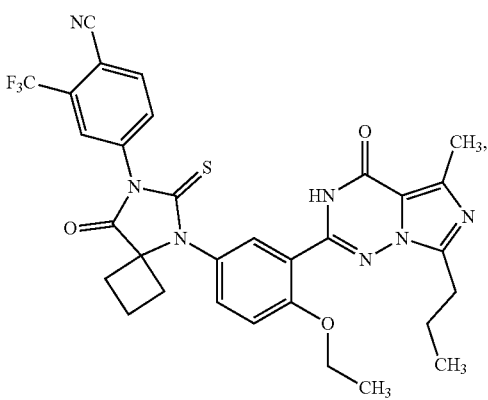
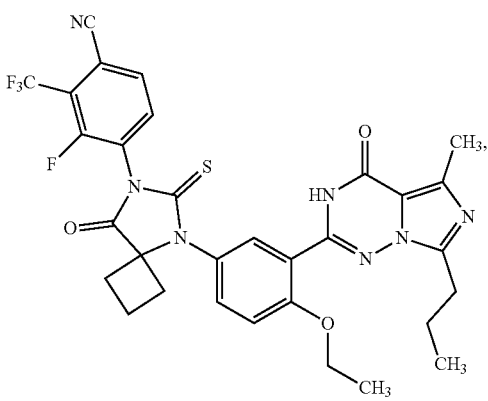

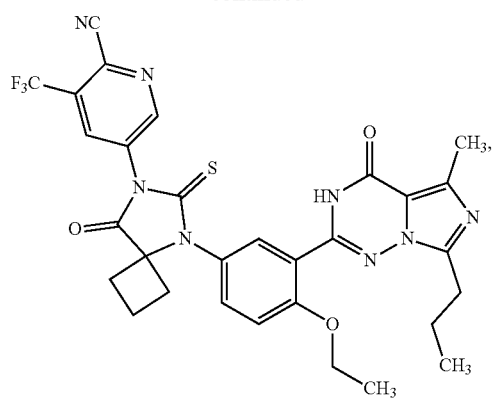
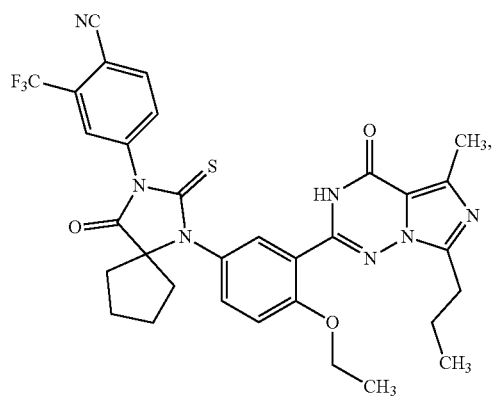
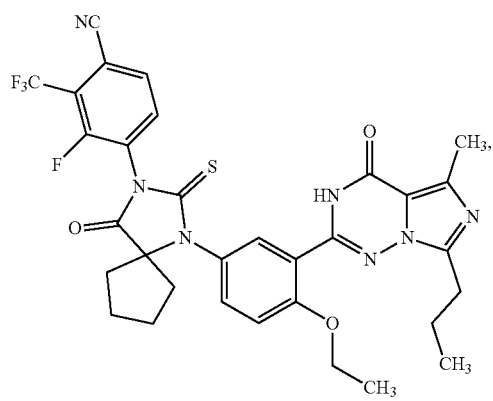
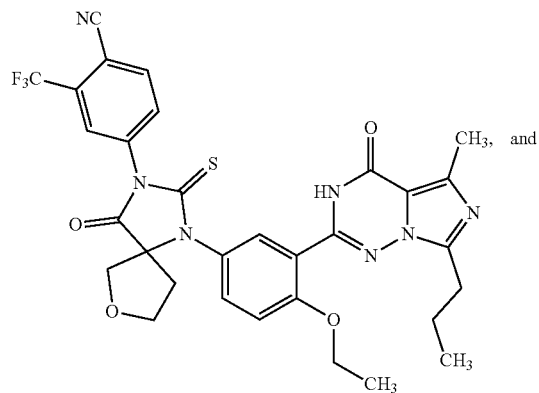
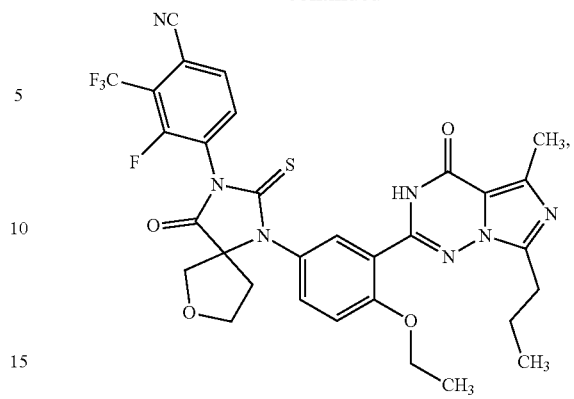
or a pharmaceutically acceptable salt or stereoisomer thereof.
33. The compound of claim 14, wherein the compound is selected from the group consisting of:
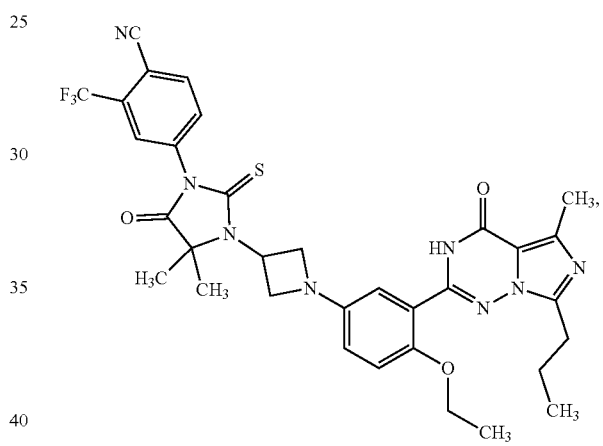
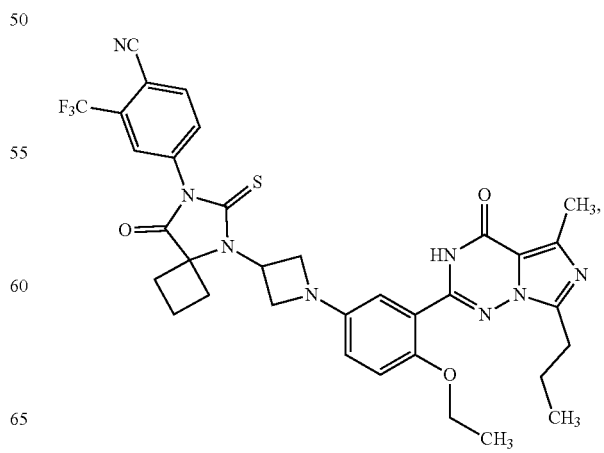

-continued
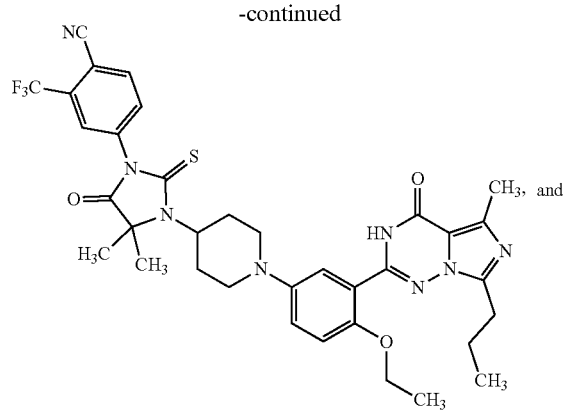
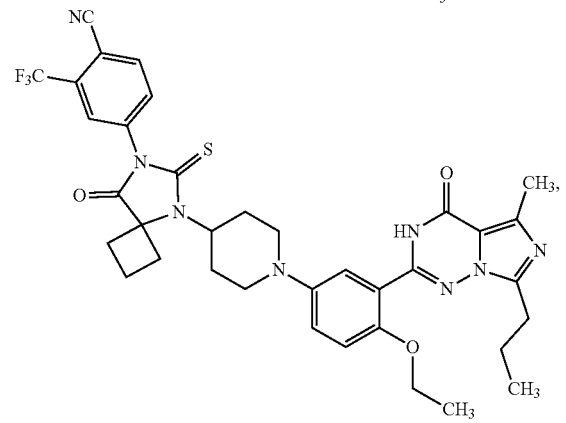
or a pharmaceutically acceptable salt thereof.
34. The compound of claim 17, wherein the compound is selected from the group consisting of:
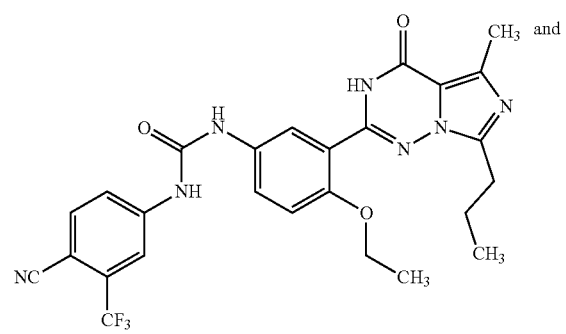
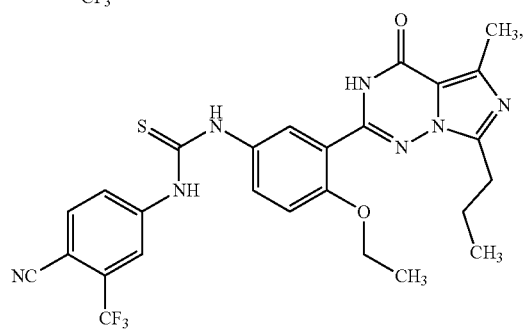
or a pharmaceutically acceptable salt thereof.
35. The compound of claim 20, wherein the compound is selected from the group consisting of:
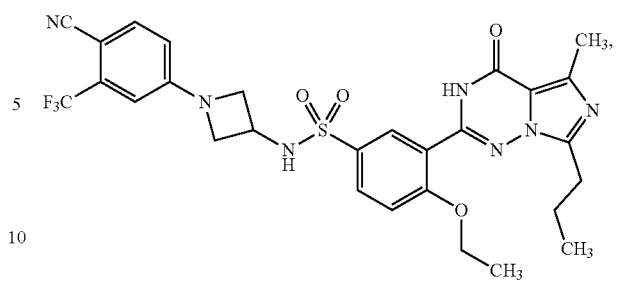
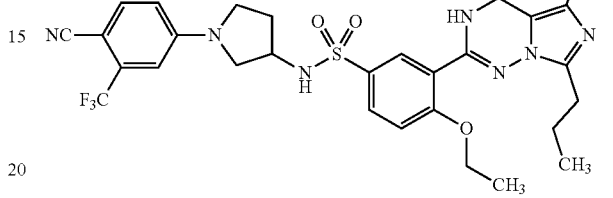
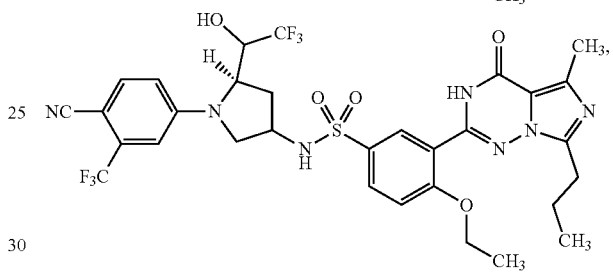
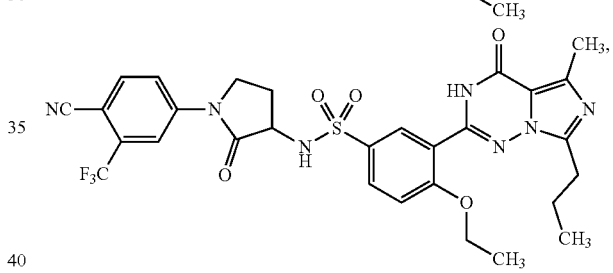
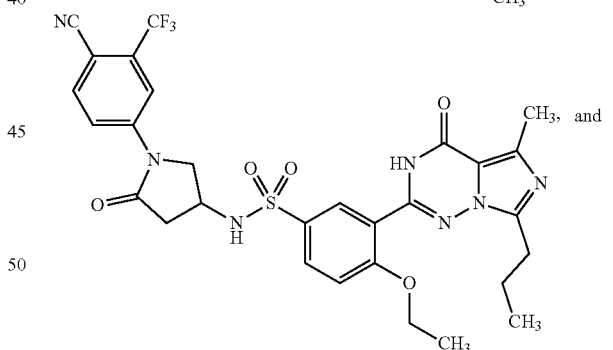
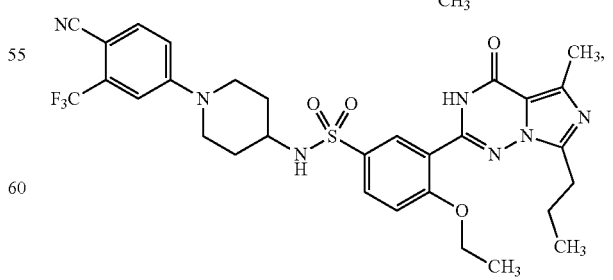
or a pharmaceutically acceptable salt or stereoisomer thereof.

36. The compound of claim 21, wherein the compound is:
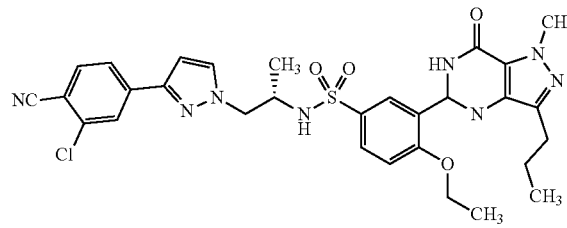
or a pharmaceutically acceptable salt thereof.
37. The compound of claim 23, wherein the compound is selected from the group consisting of:
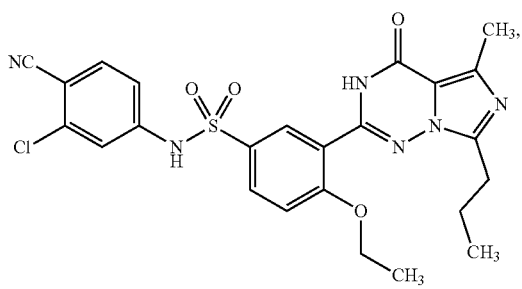
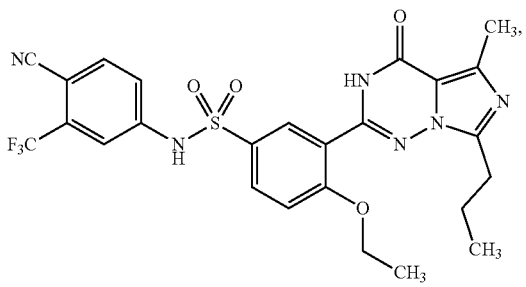
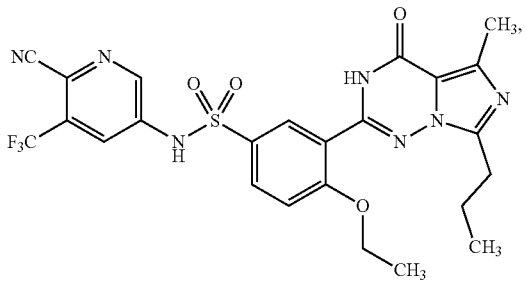
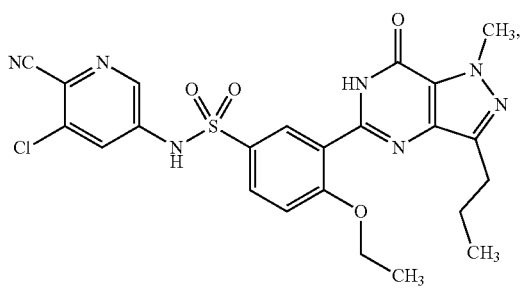
-continued
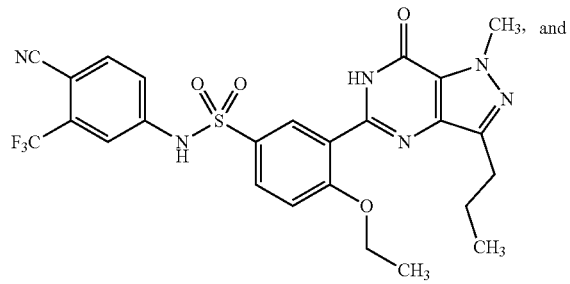
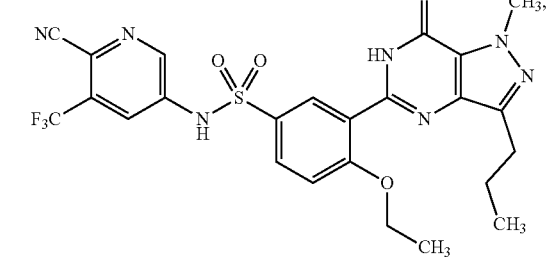
or a pharmaceutically acceptable salt thereof.
38. The compound of claim 25, wherein the compound is selected from the group consisting of:
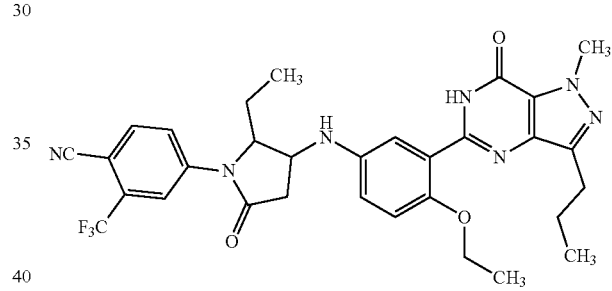
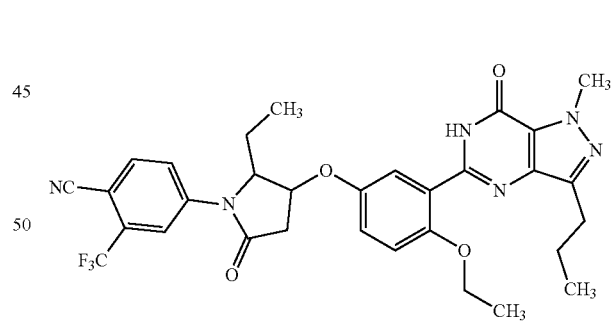
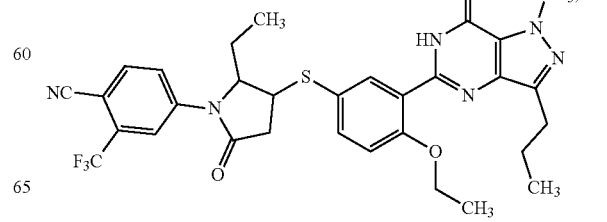

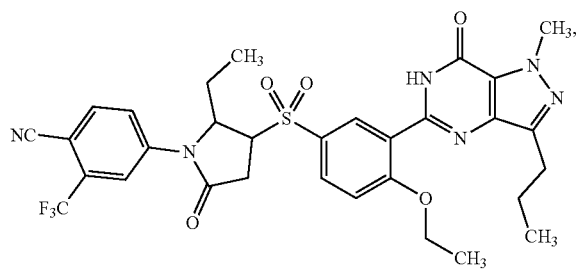

or a pharmaceutically acceptable salt or stereoisomer thereof.

39. The compound of claim 38, or a stereoisomer thereof, wherein the stereoisomer of the compound is selected from the group consisting of:

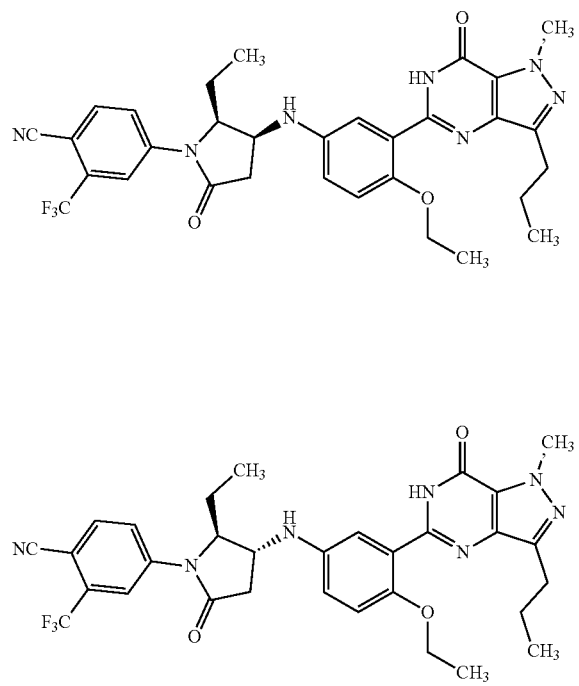

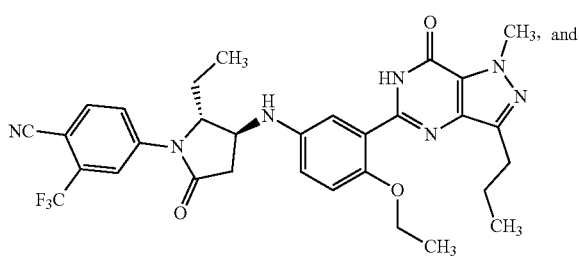

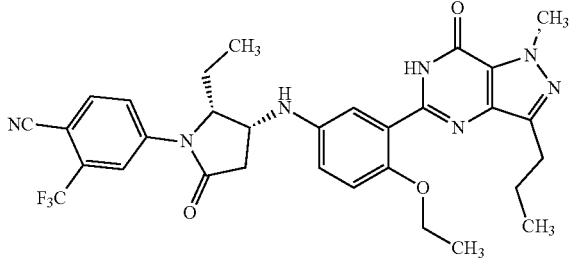

or a pharmaceutically acceptable salt thereof.

40. The compound of claim 27, wherein the compound is selected from the group consisting of:

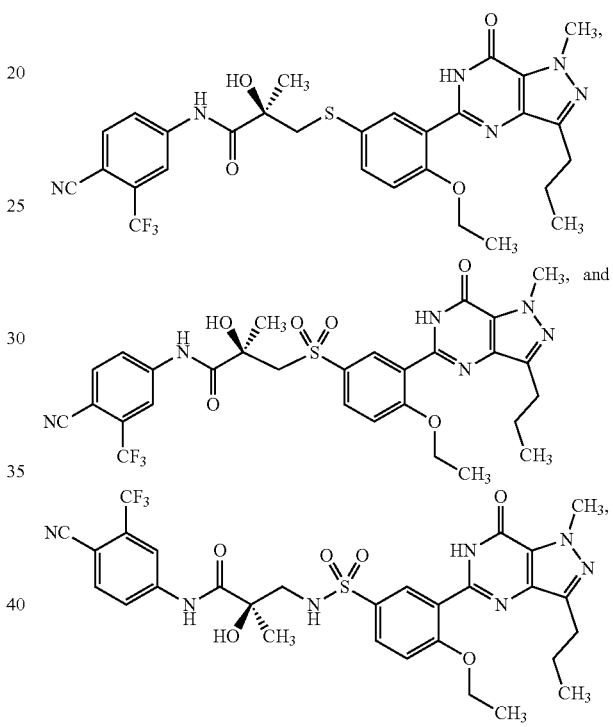

or a pharmaceutically acceptable salt thereof.

41. A pharmaceutical composition comprising at least one pharmaceutically acceptable excipient and a therapeutically effective amount of a compound of claim 1, or a pharmaceutically acceptable salt or stereoisomer thereof.

42. A method for modulating phosphodiesterase-5 (PDE-5) activity in a biological system, wherein the method comprises contacting the biological system with an effective amount of a compound of claim 1, or a pharmaceutically acceptable salt or stereoisomer thereof.

43. A method for modulating androgen receptor activity in a biological system, wherein the method comprises contacting the biological system with an effective amount of a compound of claim 1, or a pharmaceutically acceptable salt or stereoisomer thereof.

44. The method of claim 43, wherein the biological system is comprised within a sample in vitro.

* * * * *

UNITED STATES PATENT AND TRADEMARK OFFICE
CERTIFICATE OF CORRECTION

PATENT NO. : 11,787,812 B2
APPLICATION NO. : 17/548279
DATED : October 17, 2023
INVENTOR(S) : Lee et al.

It is certified that error appears in the above-identified patent and that said Letters Patent is hereby corrected as shown below:

On the Title Page

Item (54), in Column 1, in "Title", Line 3, delete "[5,1 -F]" and insert -- [5,1-F] --, therefor.

Item (57), in Column 2, under "Abstract", Line 4, delete "$(R^{13})n$" and insert -- $(R^{13})m$ --, therefor.

In the Specification

In Column 1, Line 3, delete "[5,1 -F]" and insert -- [5,1-F] --, therefor.

In the Claims

In Column 157, in Claim 1, Line 25, delete "=OH," and insert -- OH, --, therefor.

In Column 159, in Claim 1, Line 61, delete "C $R^{14}$" and insert -- $CR^{14}$ --, therefor.

In Column 159, in Claim 1, Line 62, delete "C $R^{13}$" and insert -- $CR^{13}$ --, therefor.

In Column 159, in Claim 1, Line 63, delete "C $R^{13}$" and insert -- $CR^{13}$ --, therefor.

In Column 163, in Claim 5, Line 46, delete "OR'," and insert -- $OR^a$, --, therefor.

In Column 163, in Claim 5, Lines 47-48, delete "$OR^cC(O)N(R^a)_2$," and insert -- $OR^cC(O)N(R^a)_2$, --, therefor.

In Column 163, in Claim 5, Line 61, delete "$R^bNR'S(O)_tR^a$," and insert -- $R^bNR^aS(O)_tR^a$, --, therefor.

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 11,787,812 B2

In Column 185, in Claim 39, Lines 21-22, delete "$\overset{CH_3}{\overset{|}{\cdot}}$" and insert --$\overset{CH_3}{\overset{|}{/}}$--, therefor.

In Column 185, in Claim 39, Lines 37-39, delete "$\overset{CH_3}{\overset{|}{\cdot}}$" and insert --$\overset{CH_3}{\overset{|}{/}}$--, therefor.

In Column 186, in Claim 39, Line 2, delete "$\overset{CH_3}{\overset{|}{\cdot}}$" and insert --$\overset{CH_3}{\overset{|}{/}}$--, therefor.